US009395369B2

(12) United States Patent
Schleiss

(10) Patent No.: US 9,395,369 B2
(45) Date of Patent: Jul. 19, 2016

(54) GUINEA PIG CYTOMEGALOVIRUS (CIDMTR STRAIN)

(71) Applicant: REGENTS OF THE UNIVERSITY OF MINNESOTA, St. Paul, MN (US)

(72) Inventor: Mark Schleiss, St. Paul, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 12 days.

(21) Appl. No.: 14/059,309

(22) Filed: Oct. 21, 2013

(65) Prior Publication Data

US 2014/0127265 A1 May 8, 2014

Related U.S. Application Data

(60) Provisional application No. 61/716,302, filed on Oct. 19, 2012.

(51) Int. Cl.

| | |
|---|---|
| ***A61K 39/245*** | (2006.01) |
| ***C12Q 1/70*** | (2006.01) |
| ***G01N 33/569*** | (2006.01) |
| ***C12N 7/00*** | (2006.01) |
| *A61K 39/00* | (2006.01) |

(52) U.S. Cl.

CPC ............ *G01N 33/56994* (2013.01); *C12N 7/00* (2013.01); *A61K 39/00* (2013.01); *C12N 2710/16121* (2013.01); *G01N 2500/00* (2013.01)

(58) Field of Classification Search

None

See application file for complete search history.

(56) References Cited

U.S. PATENT DOCUMENTS

| | | | | |
|---|---|---|---|---|
| 3,817,837 | A | 6/1974 | Rubenstein et al. | |
| 3,850,752 | A | 11/1974 | Schuurs | |
| 3,939,350 | A | 2/1976 | Kronick | |
| 3,996,345 | A | 12/1976 | Ullman | |
| 4,275,149 | A | 6/1981 | Litman | |
| 4,277,437 | A | 7/1981 | Maggio | |
| 4,366,241 | A | 12/1982 | Tom | |
| 4,683,195 | A | 7/1987 | Mullis | |
| 4,683,202 | A | 7/1987 | Mullis | |
| 4,800,159 | A | 1/1989 | Mullis | |
| 4,816,567 | A | 3/1989 | Cabilly | |
| 4,965,188 | A | 10/1990 | Mullis | |
| 7,501,129 | B2 | 3/2009 | Williams et al. | |
| 2003/0130264 | A1* | 7/2003 | Jaen | 514/217.06 |
| 2010/0285059 | A1 | 11/2010 | Shenk | |
| 2012/0237921 | A1 | 9/2012 | Lee et al. | |
| 2014/0127265 | A1* | 5/2014 | Schleiss | 424/230.1 |

OTHER PUBLICATIONS

Schleiss et al. (Viruses. 2014; 6: 448-475; doi: 10.3390/v6020448).*

Yang et al. (Antimicrobial Agents and Chemotherapy. Sep. 1989; 33 (9): 1563-1568).*

Bia et al. (Journal of Infectious Diseases. Mar. 1984; 149 (3): 3555-362).*

Nozawa et al. (Virology. 2008; 379: 45-54).*

SEQ ID No. 2 sequence alignment with UniProt access No. C6L6E7__9BETA by Yamada et al. in Virology 2009; 391; 99-106.*

SEQ ID No. 4 sequence alignment with UniProt access No. B7TPY__9BETA by Kanai et al. in J of Gen Virol. 2011; 92; 1005-1020.*

SEQ ID No. 5 sequence alignment with UniProt access No. GH__CPCMV by Brady in Arch of Virol. 1996; 141; 2409-2424.*

SEQ ID No. 6 sequence alignment with UniProt access No. GB__GPCMV by Schleiss et al (Virology. 1994; 202; 173-185).*

Clackson et al., "Making antibody fragments using phage display libraries", Nature 352, 624-628 (1991).

Crumpler et al., "A live guinea pig cytomegalovirus vaccine deleted of three putative immune evasion genes is highly attenuated but remains immunogenic in a vaccine/challenge model of congenital cytomegalovirus infection", Vaccine 27, 4209-4218 (2009).

Fong et al., "Ultrastructural development of guinea pig cytomegalovirus in cultured guinea pig embryo cells", J Gen Virol 42, 127-140 (1979).

Fong et al., "Ultrastructural development and persistence of guinea pig cytomegalovirus in duet cells of guinea pig submaxillary gland", Arch Virol 64, 97-108 (1980).

Fong et al., "Ultrastructural localization of viral antigen in nuclear inclusions of cytomegalovirus infected guinea pig cells", Arch Virol 74, 125-133 (1982).

Hartley et al., "Serial propagation of the guinea pig salivary gland virus in tissue culture", Proc Soc Exp Biol Med 96, 281-285 (1957).

Kanai et al., "Re-evaluation of the genome sequence of guinea pig cytomegalovirus", J. Gen Virol 92, 1005-1020 (2011).

Kohler et al., "Continuous cultures of fused cells secreting antibody of predefined specificity", Nature 256, 495 (1975).

Li et al., "The sequence alignment/map format and samtools", Bioinformatics 25, 2078-2079 (2009).

Marks et al., "By-passing immunization. Human antibodies from V-gene libraries displayed on phage", J. Mol. Biol. 222, 581-597 (1991).

Milne et al., "Tablet-next generation sequence assembly visualization", Bioinformatics 26, 401-402 (2010).

Morrison et al., "Chimeric human antibody molecules: mouse antigen-binding domains with human constant region domains", Proc. Natl. Acad. Sci, 81, 6851-6855 (1984).

Nozawa et al., "Identification of a 1.6 kb genome locus of guinea pig cytomegalovirus required for efficient viral growth in animals but not in cell culture", Virology 379, 45-54 (2008).

(Continued)

*Primary Examiner* — Shanon A Foley

(74) *Attorney, Agent, or Firm* — Viksnins Harris & Padys PLLP

(57) ABSTRACT

The present disclosure provides an isolated or purified guinea pig cytomegalovirus (GPCMV) Strain CIDMTR, glycoproteins from GPCMV Strain CIDMTR, and methods of use thereof.

29 Claims, 56 Drawing Sheets

(56) References Cited

OTHER PUBLICATIONS

Schleiss et al., "Protection against congenital cytomegalovirus infection and disease in guinea pigs, conferred by a purified recombinant glycoprotein b vaccine", *J. Infect. Dis 189*, 1374-1381 (2004).

Schleiss et al., "The non-nucleoside antiviral, bay 38-4766, protects against cytomegalovirus (cmv) disease and mortality in immunocompromised guinea pigs", *Antiviral Res 65*, 35-43 (2005).

Schleiss, "Nonprimate Models of Congenital Cytomegalovirus (CMV) Infection: Gaining Insight into Pathogenesis and Prevention of Disease in Newborns", *ILAR Journal 47*, 65-72 (2006).

Schleiss et al., "Analysis of the nucleotide sequence of the guinea pig cytomegalovirus (GPCMV) genome", Virology Journal 5, 139 (2008).

Schleiss et al., "Molecular and Biological Characterization of a New Isolate of Guinea Pig Cytomegalovirus", Viruses 6, 448-475 (2013).

Simpson et al., "A parallel assembler for short read sequence data", Genome Res 19, 1117-1123 (2009).

Waterhouse et al., "Jalview version 2—a multiple sequence alignment editor and analysis workbench", Bioinformatics 25, 1189-1191 (2009).

Yamada et al., "Characterization of the guinea pig cytomegalovirus genome locus that encodes homologs of human cytomegalovirus major immediate-early genes, ul128, and ul130", Virology 391, 99-106 (2009).

Yang et al., "Complete genome sequence of pathogenic guinea pig cytomegalovirus from salivary gland homogenates of infected animals", Genome Announc 1, e0005413 (2013).

Bia et al., "New Endogenous Herpesvirus of Guinea Pigs: Biological and Molecular Characterization", Journal of Virology, 36(1), 245-253 (1980).

Hsiung et al., "Viruses of Guinea Pigs: Considerations for Biomedical Research", Microbiological Reviews, 44(3), 468-490 (1980).

ATCC, Caviid herpesvirus 2 (ATCC VR-682), Product Sheet, 2 pages (2014).

ATCC, Caviid herpesvirus 2 (ATCC VR-682), General Information and History, 2 pages, http://www.atcc.org/Products/AII/VR-682.aspx (downloaded Feb. 1, 2016).

* cited by examiner

ENA_Validated_v0.0.CIDMTR.ann.embl Text View
Fri. Oct 18, 2013 6:09 PM

Sequence: ENA_Validated_v0.0.CIDMTR.ann.embl Range: 1 to 232778

```
                                                                                                    100                                                                                                   200
CTCGGAGTCCCGCCGTACCGGTTTTGCCACCCCCGGGGGGCCTTTCGGGC GGGGGGCCTTTTGTTGCGGTTGGGGGCGCGGCGCGGCGCTTCCCGAGC GGTTTCGGGGGTGGGCGCCGGAGCCTTTTGTTGCGGTTTAGGCCCGCGGC GCCGGCGCTTCTCTGGTGGTCACGGCGAGGTTTCGATGAGCTTTCGATGC
                                                  NOTE=LEFT TERMINAL REPEAT
                                                                                                    300                                                                                                   400
GACCGCAGCCGGGTTTCGATGAGCTTTCGCGGTCGCGGTCGGAGGTCGGC GGACGGGTCACAGCGGCTGCTCGGCGCGCCGCTTGCGCGCGCCGCGGCGG GACGCCGACGACGGACGCTGGCGGTGGTGCTGCTGTTGCTGCACTCGATG CGGCGGCTGCTGTTGCTGCTGCTGCGTGCGCTGCGCCGGCGGCCAGCGAG
                                                  NOTE=LEFT TERMINAL REPEAT
                                                                                                    500                                                                                                   600
GCCGGTCTCGCGCCCGGTCGCGGTCCAGCTGCATGCGGACGCACGGCCGC TCGCCCGTCTCCAGCGCGCGCCGCACGCCCGCCGCCTCCACCTCCGTGCG GCTCCAGCGCCGCTCGTCCGTCTCGATCTCGATCTCGACCTCCGTCCCGG GGCCGGCCTCGGCCATCTCGCCGCTCCACTCCACCACGCGCTCGCCTCCT
                                                  NOTE=LEFT TERMINAL REPEAT
                                                                                                    700                                                                                                   800
GCTCTTCCCCCGTTCTCGTGCCCGGAACCGCCGACTTCTGCCTCGTCCTC CTCTTTCTCCTCCTCCTCCGCCGACGAGCCCGTGCTCCAGTCGGGGCTCC AGTCCTCGTCCCACGCGTCCCAGTCCCCGCCAAAGCTCATCTCGCCGCCT CGCCTCGCCCGACTCCGGCCTTTAGCGCTCGCCCGGCGCCGCCGCGACGC
                                                  NOTE=LEFT TERMINAL REPEAT
                                                                                                    900                                                                                                   1000
CCCTTTTTCTCGAACCCAAGCACGCGGGTGCGCGACCAGCACTCCACCCT CGTGCCGGGAGCGCAGCGTCAGAGCGTCGGGGCGCGGGCGCGCGGGTGTT AATACTAAGGCGCGGCGTGTTGGCAGGCGTTTTGGGTGGTTCGTCAGCGC GCGTGGTTACGTGTATGCCCTGTGTTGTGTGCCGCATCGTGTGGTTACGT
NOTE=LEFT TERMINAL REPEAT
                                                                                                    1100                                                                                                  1200
CGCGCTGTTGGGGGCAACCGCTCGCGTATCCGGCGGAGGAGTCCGGTGCG GCGTTTTGGGACGGGTACCGAGGACGTTTCGGCTTCCGACGTGTTTCGTT TTTTAAACTGTGTGCTGCTCGGCTTTTGTTCCGTTAGTTATTTCTCGTTT GTCTCGGGTTGGCTTGTTTTGGTCTCGTTTTGTTTTTGGTATATTTCTGT
                                                                                                    1300                                                                                                  1400
GTTTCGGGTGAGGTGAAGTTTTGCTTCCGTGTAATTATTCGCGTTACGAT GTGACCCCGAGGCGGAGCCCGAGGCCGACAATGTCGTGGAGCCCGCAGAC GAAGCAGACGGCGTCTCACGAGAAACCCAAAGGCGAAGACCGATCAGAAG AAGACGAAGAAGAATTAGCCTCGTTTTTTAACCAGTTGTTGTATCTTTTC
                                                                                                    1500                                                                                                  1600
GTCGGTTTTTCCCTTTCTTGTTATCTACCATCTTATTATTTTTTCTTTGG TTCTTTTAAAACCCTGCGAAAGACCCCGGCTCGGCGGTTCCGTGCTGTTT TGGTTTGGGGTAATAATTAATTCATTTTTTGTTTTATTTTATCTTATCTT ATCCTATTGCTTCTTATTTGTATTATTTCTTCTTATCCCTACTGCTGTTT
                                                                                                    1700                                                                                                  1800
ATCATCTCTTTATCCACATCTATCTGATCCAACCTAATCTAATCTAATCT AATCTAATCTAATCTATCGATGTCTTTGCTAACTTTGCTTCGAGGTGAGG TCGAGGCCGGGAGCGCGCGGTCCAGCCGCGCGCGCGCACACACACGCCTC CCTACCGCTTTCGCTTTTCTGTACCCGTTTACCTACGTATCATCTCTAAT
                                                                                                    1900                                                                                                  2000
TTATCTGTTTATCCTTTCAGTCGACCAATTTTTCTTTCTTTCTTTTTTTT CCTTAGTTCGGTTTAAGTGTATACGATTACTTTTACATTCACTCGGCTTC CTACTTTTCGTAATTTCTTTCTTTCTCTTCGTTTTCTTTATTTTGGTCAA TGATGTACGAACACCAATCAATCTATCACTGTTCTTCAACCAGTTTGATT
                                                                                                    2100                                                                                                  2200
ATTTATTTTTTTCTGATCCTCCTAGTTATCTATCTATCTATGTAGGTACT TCTTTATTCATTTAAGTAATACCCATTCTTTTTTATTTTACTTTGTCACT TATCGTTTCTTCTTATTTTTGTATCTTGACTTCGACTTCTCTCCGGTTTC TTGCTATTTTTTCCTCGCTTATTATTACTGCTTTCGTTATCATCTATTAT
                                                                                                    2300                                                                                                  2400
TTTGCAAAAACGTTTATATTTTTCTCGTTTCTTTATTTTACATTTCGACT CCTCCCGTTTTCGTATTCATTTAATATCTTTTGCTTATTCGGTTCTCATC GCAAGTATTTCTTTCCTATATTGTTATCGTTTCTTTTCACTATATTCTCG CTTCTCTTCATCTTTGTTGTTTCTTTTTTATTATGTTTTTGATTTTTACT
                                                                                                    2500                                                                                                  2600
CTTACTTTTATCCTATAATTTCTTTTTTGATCAATTGGCCGGCATCGCCC GAACACACGGTTCCGTGAATAACGGTTTGAATTCGTATCTGCGCCACAAC TACAAGCTTCTTGCTCTTTTTCTTTCTCTATACTCGTATTTTTATTTTTC CTTTTAAAATATATATATATATTATTCATCATAGTTATTTATGATCGCGATT
                                                                                                    2700                                                                                                  2800
ATGATTATGATTAGGACTCGACATACAGAATGTCTTCTTAACTCTTTTCT GTTCGGTTTTTTTTTTTCTAACCCTCCCGAACGAGATCAGCTTGCTGGCC CCACGCGTAGGATATACGATGGATGGTAACGATGACGCGTACGACCCGAC CCAGACCGTCGTCTCGTCTGTTGATTCGTTGATTTATCTGCTTGCTTGCT
                                                                                                    2900                                                                                                  3000
AACTTGCTCGTTTGCGTGCTCGCTCGCTCGTTCGTTCGTTGTTAGTTCGT ACGTTTTCCATGATCGTTTCTTTCCTTTTTCATCGTTTCTTTCTTTCTTA AAAAATGTGATTAATACATCGTCGTTTCTTACTTTATTTTATTTGAGAAT TCTATTTTCTTAATCATTAGGATTGTTACCACTTAAAACTTTTCTTGTTT
                                                                                                    3100                                                                                                  3200
TTGCCTTGTATTGTATTTATCTTCTCGTTTCCCCATCGATGACATGTGTA TACGAAGAAATCGGGGAAAAAATAATACTTAAATCCCTCACCCCTTAAAA CCCTAACCTGTTAACCCTTACGCGAACCTTGACCTCAAATCCGAAGAAAA AGCAACACCGATGGTAAAAATCCCGACCCACCCACCCCGCCACCTCCCATT
                                                                                                    3300                                                                                                  3400
TCGGTCTTTTTTCTAGTTTTTCCCTTCCTTCTTCCCCAAGCTGAGATAAT CTGTTTTTGTTTTTAAATTCTCACTATCGCCACTACGATAAGATTCTCAT GATAATACTCATCACCCAAATTAACCATAGAGGGCAAAGAAACCAAATAT CATCACTGAAAAACAAACCTATACATCATCAACTATCTCGTCTATCTATT
                                                                                                    3500                                                                                                  3600
CTTATCTATCTTCCCTGACGGGGGGACAAAATGACCCAATCCTGTGGCGT CGCTACCAATATCAGACGCGCGTCTCCCTTTTTTCCCCTCTGACTTACGT CTTTTTTTTTGCTATCACTATTATCTTGTTATTTCTTGTTCTCGATACTA TTTTATGTGTCGCATCTACCATGTTATCATTAGTTAGTTACCTTTGTCCC
                                                                                                    3700                                                                                                  3800
TACTATATTACTATTATTTACTGTTAACAACAATGATAATTTTTCTTTCT CTTTTACATTTTTCTCTTTTTCTTTTCTTTAACTCCCCCTATTCACTGTT ACTCTTTCCTCTACGTCTTTCTCCGCTCCATCGGTTATCACCCTGGTCTT TTTTTTTTTCTTTTCTTTTATTCGACGAATAGAGGTTTGTCTCTTTTTTA
                                                                                                    3900                                                                                                  4000
CTTGTTTCCATTTGGGACCTCTCTTTGTAATAATAGACATTATTTTGACG ATTTTATTTCTTTCTTTTTTTTTTAAATGCATTCGTATTCGCATCTATAT TTCCCTTCTTCTTTTTATTTGTTTTTTCTATCTTCTTATGTTGTTTTCTT TTCTTTTTCGTGTCGTATCGTAAATCATCTTTTTTATACATGGATTTCTC
                                                                                                    4100                                                                                                  4200
TCACTAGATTATTATTTTCATTTGCAAAAACAGTTTTCTTTCTTCTGCGA CTATTACTTCTTCCTTTTTTCTAACATCATCATCGTTCGCTTTATGTATA TCTATCTATTTCCCTCGTCTATCTCGAGATCTCTTAATTATTATGTGTTT AATTCGTTTCGATATCTTTCCCATCGTTCACTTCTCTTTCCTTTTTGTCA
                                                                                                    4300                                                                                                  4400
TCGATCTCGTTTTTTTTTTAAAGTTTCACATTAAAGACCAGACTAGAATT GTCGGTGTTGGTGTTGGCGTTGGACTCGACGTATTCGTTTATTTATTTCT TTTCTTTTTTTTTTTCTTTTCGTTCTTTTTGTTTTTTTTTTGTTTGTCTTC GTTTAGAATTGCAAAACATTCTGACACCTACGCCGCAAAGAAAGCAGCTC
```

Figure 1B:
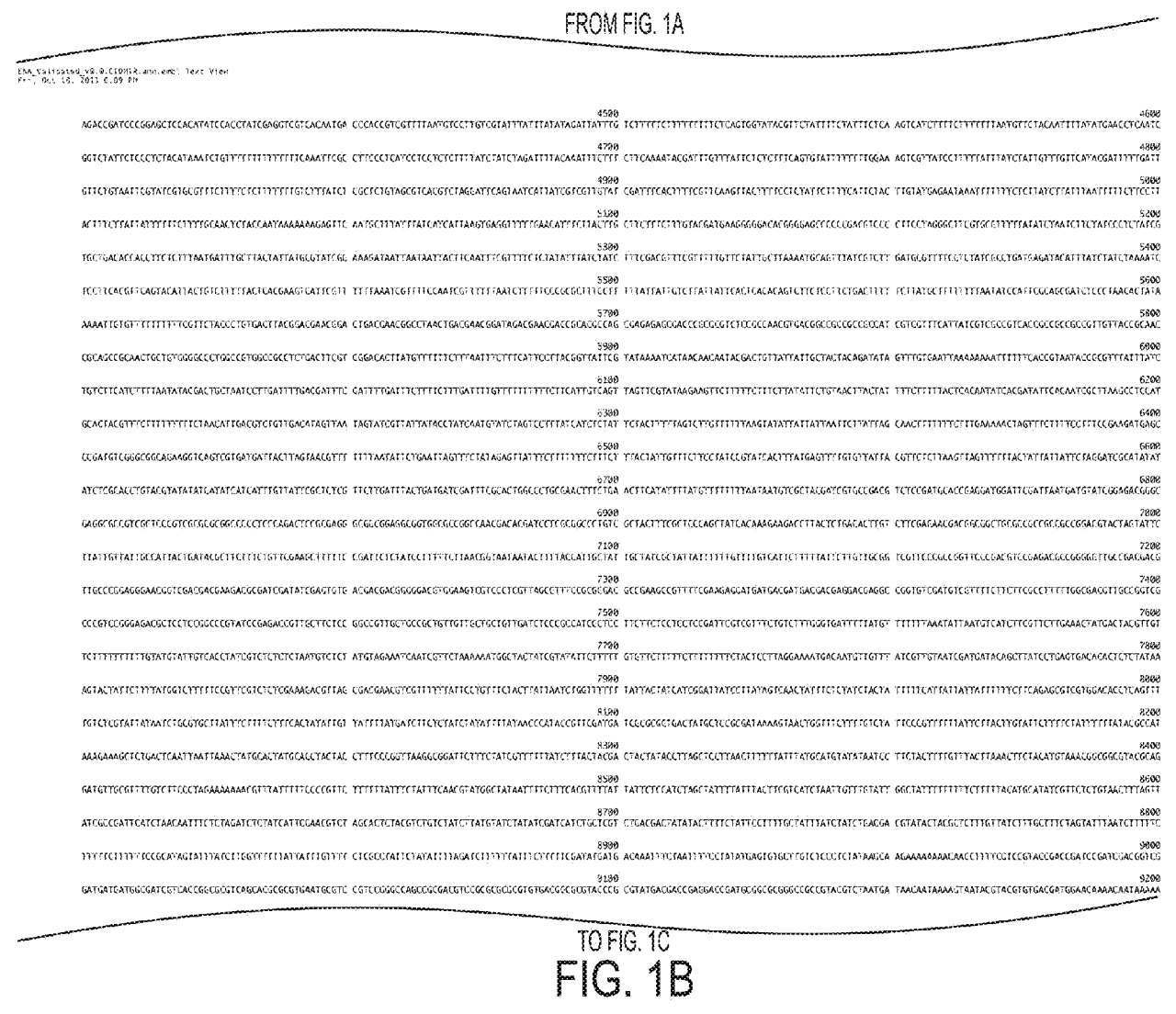

FROM FIG. 1A

EVA_Validated_v9.0.CIDMSR.and.embl Text View
Fri, Oct 18, 2013 6:09 PM 4500 4600 4700 4800 4900 5000 5100 5200 5300 5400 5500 5600 5700 5800 5900 6000 6100 6200 6300 6400 6500 6600 6700 6800 6900 7000 7100 7200 7300 7400 7500 7600 7700 7800 7900 8000 8100 8200 8300 8400 8500 8600 8700 8800 8900 9000 9100 9200

FROM FIG. 1B

FROM FIG. 1C

ENA_Validated_v3.0_CEOMFR.aco.esbl Text View
Fri Oct 18, 2013 6:09 PM

FROM FIG. 1D

DNA_Validated_v0.6.CIDMTR.aun embl text View
Fri, Oct 18, 2013 6:09 PM 18900 19000
ACAGACGTCCGGGTTCCCTGGATGCGGCGAACAGCATGGAGATGGTCCCC AACTGATCGGACGGAATGGACTCCGCATCGACCTGGGGCAGCAGCTGACG GCGGCGCTGCAGCGCTTCGCAGCCCATCGTTCTGTACATACCCGCCTCCT GCTCGAAAGTCTGCAGGAGCCACGACGGGTACTCCTGACTGGGCGAGTTC 19100 19200
TGCCTGAAACTCGCGCATCCGGCCAACGCGGCGACCTCGTACATCCATCC GCCGCTCGCCTCGGCCTCGCACGCCGCCGCGGTCCGAGACACGTTGGCCC TCGTGGAGTACGGTTCGTGGCGCTGCGCGACGTTCCTGCGGGCTTTCTTT CCGGCGCTGGAGCCGCCGCAGGCGCCGTCTTCCCGACGTTCTACGTCCAT 19300 19400
GTCGTTGTCGGCTCCGTCGCCGCTCCCGGACGCTCCGTTCTCGCCGTCGA TCGCGAGCTGTCTGGTCCGACTGGCCAATCTAGACACGGCCTGCGACGAG AGCCGCCGCTTGGAACCGGCCATCACGGGCGCCCGGCCCCCGGATCTCAC GGATCGCCTCTGATCCGAAGAGTCCGCCCGAGACGAAACGGACGCCGACT 19500 19600
CGTGGCCGTCCCGTCCGCATCCAGGACCCCCCGTTGGACGGGCCACGGAC CTCCTGATCCTCTCCTCATCCTCCGGACGACCGTCCACCTCCGGCCGCCG TTCGCGTATCGCCCTGGGACGAAGCTCGCGTCTAGCCTCGGCCCCGGCTT CCGATCGCTTCATAGCGCAGGCCGTATGATAAAAAAGACTTCGAGACGTG 19700 19800
GAACGGCGAACGTTTTTCTCCGTGAAGCGATGAGTCTTCCCGTACGACGT CCCGGTCGCAACGTTTTCACGGCGACATAGCGGATAAACTCATATATTCA CAAAGTACGAGCGTCCACTTAATCGAATCCTTTTTCACGACCATAAAAT CGATGTCCGGAGGAGCGATGCTCCGCGCTCCCCTCGGCCGAGCTATGTGAT 19900 20000
CCTCCATTTGCCGCGGGGACCTTTTATAGATCTGCGAGTGACTAACCCCA CAGCGGGAAAACAGCCAGACAGATTATTCAAATCCCCCCGAGAGGACTCA GTAATCGCCTTCCGGATGCTACCCGGCCGCGACTAACGGCGAACGTCCCT CCGACTTCCCGAAACAGACGTGACCGCAGACACCGAAATTATCATATCCG 20100 20200
TAATTTTATTGCAACGCTCGAGAAATTTACAGCCCATCCTATACACGTCC CCGGGCGGGATTTACCGTCAGTCCGACACCGCAGAGAAGATACGTCACCG TTTATAGACGCGGTTTACATCCAGAACGCGACCGGCGTCCGGTTCGCCGT GACGGTTTTCGAAACGGTGAATATAATGACGCATCCGTTCTAGGAGACAA 20300 20400
AACGTGGCCGCGAGGATGACGCACGCCACCAGGGCCGACGAACTCGAGGA GATGAAGTCTAGACCCCATACGCGGATCAGCTGTTGGATCGTCCACGTAT CCATGGGAGGTCTGCCGTCGGTCACGACCTCCATGTCTATCGTGGGCTCG TCCCCCACGTAGAGCTGAAAGGTGCACTTCAGCTGATGCCACGGCCGCCA 20500 20600
ATCGCCGGGGATGCGAACCCTGGCCTTCAAGACGTTCAGCGGCCGGTCGT CGGAATGAACGTACGTCTGGTCGTCCCACCGGCTGTATCGCACCGGATGT TCGGACACGAAATTGACGGACCCGCTTCCCAGTCGGCCCACCTACAGACC CGCGACGATCTCTAGCTTGTCTTCGGTGTCGTCCCAGAAGGTCGGGACGG 20700 20800
TCAGGGTCGTGAAGGGCTCGTGAGAGCTCCCGTCCTAGAAGTCGAGTATC AGGTTCTTAGCGTGCATGGTGTCGTAGCTTCGAACTTCGCATTGATGCAC CACCACGTTCTTATCCGCGAATATCTCTACGGAACCCGACGGCACCACGC CGGAGTGCCTGACGAACTTTCTGACACAATCCTTCCTCTCTCGCCTCCGC 20900 21000
TTCAGACTCGTGACGAAGAACATCCTGTTCAGATACAAGTTATCGCTGCG ACAACGCTCCGGCGGCTTAGGATCGCGATAGCACATGAAGGTACCGTTGT CGCAAGGCTCCTGCCGGAACCTCTCGTAGCACTCCGTCTTCCACCACCAC GTCCCCGAGCAACGAAGCACCTCGTTATCCTCCGCGAATCCGAGACACCG 21100 21200
ATAACACCTCTTGCCGTCGCCGTCGCCGACGACGGGTTCCATGAACGGCG AAGAGCCGCACTGCTGGCAGGCCGCGTCGTCCCGTCTCGACGCGTCGCCG TCGGACGCTTTCTTGACCTCGCGTAGGTGCCGAACCGTATGGTTGAGAAC ATCTACCATATTGGAGAGAGCCTGCAGGGCTTCCGCGGACCCCTCCTGTT 21300 21400
CGGCCGGTCGAGGCGCATCTCCCTCCGCATCCCCACCAACGGAGACCGAC ACCACATAGAAAACGCAAACGATCCTCGCTATGCGGCGAATTCCGTATCC GTCGGCCATGCCCGAGGGTCGCGATCCGATCTGTCCGGCACGCCAAACCT ATATGGACGCGCGTCGAGAGAGATCAGAAAATTTATCCGTCGCAGGCGGG 21500 21600
TGTCCGGCGTGGGATGACTCGGACGAGCGAGGAACAACCCGCTGGAGTGT TATCAAAGGAATGCGTTTATAAGCCAACCATGGAGGGGCGTGGACCCCGT CCCCCGCGATGCTCGGATGACGCCTCGTCTGATGTCATTGCAGAGAAGCC CCCTCGCATAGACCCGATCGAAGCACCATCTAGCGTCTGAACGAGAGACT 21700 21800
CTTCGCGATGCTGCCTATTCGTCTACGAATACGATCTCTCTTGGCGCTGG AGATCAGACAGACGTACCGCGCGCTCCCGACCAGGACGAACATCATGATG ATGAAAGCCACGACCATCAGACTGAAAGCCGGCAACACGTAGGCGATATA ATCCATCAACAGGACGTCGTATCTGAAATTATCGGGATGCAGCGACGACA 21900 22000
CGTACCTGAGCGTGCACGTCTTGCCGCCCTCCGCCATCCGCCGACGACCA GAGAAGCCTCTAGCGATATAAAATTTGTTATTTCTGTTGTCGTGCTCCGT GACCCAACCTCCGTCGTCAGAAGTATAAGGCACAGCCATCGTAAGCTTCG GAAGGCTGTAGTTCTCCGCGAAGGGCCCCAAAGACATCAATATGACATTA 22100 22200
TTTCTAGGCCTCATGGTCGAACTGCGAACGATAGCCAGTGCGGGCAGAAC GACGACGGAGTACGCTAACGATAAGCGCATGTCGGGATTTTTCCACCTGC GTAAAAGCACACGCCCGCGCGTAGAAACGCGTGCGTCCCCCACGCAGCTC GTATTCACAGACGTAACAAAGATTATCACGCGCCCCACACCGATGTTGAG 22300 22400
ACCCACGGATAGATTATTCCCCTTAATGTTGTAGTTCAGGACATTATCAA ACAACCGTAACCTATCACTCCTTATGGATATATTTCTAACGTCTCCCGTC GCGCAAAACTCATCCAAAACCTTTCGCCATAAACATCCTTGTACGTCCAA ATTCATAACAGTGTCCCCCACGTAGCAATGTACCCGCGAAAACACGTAT 22500 22600
CGTTACCCTCCCCCCTACAACACCACACGCTAAACCATTTCTCGCTCCCG TTCGTCACGGCCGCGGCTTCCCCGTGACTTTTGTCGCGGACAACGTTTC GATACACGTCAACGTCGAAACCGCCGCCGTGAATATGAATATTCTCAGCG CATTACGGATATCGAGCTTACTCATCACCCTCCCCGCACACCCACATGCCA 22700 22800
CAAATCTTGGCACTCGATCGATTCCCGTGAAACACCCACACGCGCATCTC TTTATAATGTCACTCAGACCTGTCTCTCCACCCATCTTTTCTCATGACGT GTGATACGTAAACGAGATTTCAACATAATACGTACACGATATAGATCAAT TCAATCATTTATCTTTATTCTATCGCACGTATTAGCAGTATTTTATCAAT 22900 23000
ATATCGATAACATCGTCAGCCGCGCACACACAGCAACCCCCGTCACCCCA TCCGCGCGCTCCGGGAAAACGTTACACCTTGGGGAACTTAGACGCGTAC GGTAGCAACGTGGTCTCAAAGCTGTCCAGCTGGCCGCAGAAGCCCAGCGT GCCGATCTCGAAAACTTTCTGCGCGCGTTGGGTAAATTTAAAAAGTAAA 23100 23200
TGTAGCCCACGATGTTCCTGTGCCGTTCCGCGCTGACCACCGCTTCCATC CACCCCATGACCCTGGGGGTTGCCGTTTTTGAGACCAGTTTACCGAGTCT GGCGTACAAGGCCTCCTGGTGACTGAACATGTGTATCTCGCTATTCGAG ACATGGCCATGAACCGCATCAGGGCCCTGTACTCGAAAGGGATGTCCCCG 23300 23400
GATTGCCACAGTCCGTCCGATATCAACCGCATGACGTCTCCGCGAAGGTA GCGGCGGCGAGCCGTCGGGTGAAACCCTCCGTCGAGGGCAGACACTCCG GGGGCGGCGTCTCCTGAATCCGAACCCTCTTGAGGGCCCCTTCCACGCTG AGACCCACGAGGTCATTGAGTTCTCTGCTGATCGTCACGTACAACAGAGG 23500 23600
GTCCATGGAGAACGTCGCGAAACCCAGACAGACGGAACAGGACGTCATTT CGCCGAACGGATAGCTCCCCTCCAGACCGGATCCGATGACTACCATGTAG TTGCCGTCAGGGATGTTCAAAGGCTCGTACGGGACCGTGCAGGGTCTATC GACGGACTGCAGATAACCCCCCGACATACACGGGGCGAGGAGTTCCGCCC

FROM FIG. 1E

ENA_Validated_v0.0.CIDMTN and embl Text View
Fri, Oct 35, 2013 5 59 PM 23700 23800
TGGTGAGGGGTTTCTTAAACTGCAGAACGCATTCGATCCCGTATCCGGGA GCGTGTCTGAAAACCACGGCGGCCCCTTTGTAATCCACGCGAACCTCCTC GTCCGGTCCGGCGCGCATCGTCCTCGCCCGTACCGGACAGTTCTCGT AACACAGAAAATGCAGACATTCGGCCTCCTCCAGGGTCATCGGGAACGG 23900 24000
ACTTTGAACCGCTCGAACTTACGGACAATCTCGTAGGAAAGACCTTTAC GTTTTTATCATCGTCGCCCATGCCGACCATGGCGTATCGGAACACCATCT CTCCGGACCACGAAAACACGTTCTTCACCGACATGTGCTCGAGCATCACT CCGTAGATCGTGGACGGCGGTAAAACGTACGGATCCATTTCCATGTCCCT 24100 24200
TTTGTACGCATCGTCCACCCACTTCGCAAAAACCTCGCCGTCATCGAAGC AGGACTCGTCTCTCGGGTTCATGTTCACGCGATATCGCGACAGATCGACC GGCGATACACTCCGACACCGGTCTCGCCTCCAGATGTGGTCTCACACTGC CCGGCGCATATTAATATGACTCCCGAAGGAGAGGATCAACCCATCGATCC 24300 24400
GCGTCATCTCTGACACATCTGTTCCGATCACCTGAGGCGGGATAACGTAT CCCATGGAGACGTTACAGATAGCGATAACATATCAGACGTATCGGCCGTA AGCACATGCACGCGACACACGTAACGGAAAACCGGTCACGGTCTCCTTTT TATAAAACGAGATTCGACGGATGGGACTTATCGGCCAACAGTCCGTTCAG 24500 24600
AACCTCCATGATCCCGTCGCAATACGTCAGCTCCACCACATGCTCCCCCG TAGCGGTTATTTTCGTGCAACGAAGACTGGTCGTTCGTTCGTCCACACCC CTGTAGCTCTCGCGGAAAGTCACCGTTCTAGAGATGTCGAACGCGCCGTC GACCACGCGGATCTTGTATACGGAATACCTCTGTACGCATTTGTGTCTGC 24700 24800
GGTCGCCAGCCGGCTTCGCGTGCAACAGACAGGACAGTCGGTTCGTCACG TCGGCGACCCGATCGTCGCCCGCCGCTCTATCCGCATCATCGTCGCTCCC GACGTCCATATATCTCGGCCTCTGCACCAACGGTACGACGGCCCTCGTTA CGACATCGAAGTCGAAGGAGACGAAGTACTCCCCGTCCCGCCACCGTAT 24900 25000
TTCATGCGCCATCCGTCTTTGCGAGTCCGCACGCAACACTCGTCGCGTCT ATCGACGAGATCGAGGTCCTCGAACATCTGGGACAGCTTAACGAGGTCGA ACAGGTGACGCTCGACGACCCTGATGAGATCGAATAGCCTCGTGCCCCTG GACACCTGGATCCGATGTTCGTGCGAGGCGGTGAAGAAACACCGCACGAA 25100 25200
AGGGAACTTCTTGAAGCTGACCGTAACGGTCGGATTCATCTCGTCGCGGA CAGCCTATAAACCGAACCGCGGACGCCCCGGGAATCGCCCTACTCGCAAT CGCAGTCTGGCCGCCAGACAGGACCAGGAGACCCTCGAGCCGCGTATAAG TACGAGATTTTCCCCTTCTTTACACGCCCCAGCCGCGAACATGTCACGTG 25300 25400
AATGTGGCCACGGGAAATGACACACGGGTACGGGTACCGCATCGAGCGTC GTACGTCGCGTCGCACAAGAAGTCGAGAGACGTTATCGTTGCACACACGT GTTTATTGATCGGCCGAACGCACGGGTCGATAAAGCACATATACAGCGAT CGGGAAAGCCGTCACGTTATCATCAGGGTAGTACTGCCCAAACTCTAGA 25500 25600
TACAGATCTCTGAAAAAGCCGCTCACGCCACGGTTATCTCTGTCCAGCGT GCCTATCTCGTAATTTCCGTGGGTATCCGAAACGGAACCGTGTACGTAAA TGTACGCGGCGGTCTTCCCGTAGAGTCCTTCGTCCTTGAGCCTCTCGATA GTTTTCATGATGGAGACGGACGCGGATCGGTTCAATAGATAATCCAGTCT 25700 25800
CTGAAATAGCTTTTCCTCACGGGTCATAAAAAAGGCATTGTTCTTCACGT AAAAACCGAGAAATTCGAATAAGGCTTGACACTCCACGGGAAGCGTGTCA TCGTCGGGCCCGACGTCGCGCCTTCGCCGTTTGGGGTATAGTGATCCGC CATGTATTCGGTAAATCCCTTTCGACAGACGCGTCGAAAACCCCCGGAA 25900 26000
GAGCGCGCGCCTCCATCTTCATCTTTTCGGACAGTCCGTCATCGTCGCTG CTATCCATATCCTCGGGCGCCAGGTCGCAGCCGCCGATGGGCGCGATATC GTACGATCTTATGTACGACTCCACGTACGCCGTCATCTTGTGATACAGCG CCTCATCGATACGGAACGTCGCGATTCCTCGACACACGTCGCATCTGGTC 26100 26200
ATCGTTCCGTTCGGAAAGCTCCCCGATATGCCCGGCCCTATCACCAGCAG GATCTGCTCATCGTCGGGAACGCGAGGCGTATCGCTAGTCCACATCTCCC TGGCTATCGAGTACCCGTTCTCGTAAGCAGGCGATGACCTCGTACCAG GTGCATCGTTTCTTGAACCTCAAACAACAATCCAGATGACCGTCGTCCAG 26300 26400
AACGCGTACGTCTAATCTGAACAGACTGGTGTCGATATTAGACGTGGTGC CCGTACCCATCTCCAAACCGAACTCGTACACCAGCCGATGTACGAACTTG GTCTCCACGGCCGTCGCCTCGCGCTCCTCGTCGTCCACCCCGTCACCCGC GTGAACCTCGAGGTTGTCGTCCAGCGAGGCGAGTTCGGACATCGAACGCC 26500 26600
ATTTATCCTCGTCATATTTCTGCATGGAGACATGCGGTCCCAGAACGACG CGGATGAGATTCTCTCCGACCTGAGCGTTGATGCACCATGGATACCGCGC GTTCAGCCCGGACGTACGGGAAGGGAGATCGTCAGAACTGTCATCCTCGC TAGACATGGCTATCTCGATTTTATTTAGTCCCTACTGCGAACGCACCTCC 26700 26800
GCACGACCGAACAGTCCAGGTGAGTGTCGGGGGGAACGATTCTTATACTT GCCTTAATCCTTATTGTGTTTTTGTTGGCGATCGATGATCGATCGATAGG TCGCGAGACCCAAATGGTGATCACGACGTTTCGTCGCTCCGTATCTCGAT CTCCTCCATATCCAACGTCGCGCCCTTGTTGTCAAATGCCGCCGGATACC 26900 27000
ACGGCGCGTCGCCTATGACCACGTCTGGCGGCTGCTCGTCCGTTTTCATC CGCGTCGTATCGTCGATCGATTTCCGCCGCGTCGATACGTATCTCCAAGA TACGTACGATACGACCCATATCACGAGGCACGCCGACGAGCAGATGCCCG CGATGCATATGATCAGAAAAACATGAGACCGGCCACTCTCCAGAAACGGT 27100 27200
GCGCGAATACTATGCGCCACCGGACGGTCGATAATCCCGCCGTCTACCGC TTCCACTACGCACGAGCCATGCCGCAACGTCGAACCACTAGTGTACGCGA ACAATCTGGCTTTGGACCGAAACAATCCATCACTACAGATATGATCTTCG TGAACTATCAGATCCATAATTGTAAATCCTGTCGAATTATCTGGATATGT 27300 27400
TATATAAATATATGCAGCCATATGTACGGATTCCGATATTCTAGCGTAAG GATTGATCATTCTAAAGTGATAGATTACCTCCCCGGCATCATCACTATAA TCCATGCCGAATGACGTGGCAAACTCGATCCGCTTTCAAAATCACAACC GCTCGTGATACCAACGAGGCTACTATCACCGCTTACGTCGATGTCTCCGA 27500 27600
TGGCGGTTAGACGGTCAGACACGTCTGGATCGCCACGAATCTGCTCAGGC AGTATCCACTCCATCCGTGTGTCCCTCATACGTACGGACATATTGAAAGC CACCACGACGGCCCTCTCCTCCGGATCGACGAACACTGGATCAGAATCTA TATGCTTGCATATCCATGTGTAGGACAACACGTGTCCGTCTCTCGCATCC 27700 27800
CTTACGGATCCAGAACAATTCAGAATTCCATCACGAGGGATTTTGGTTTG CGGTTCGGAGCAATCGGAGACGTTCGATATGCATCTGGATTCCATCCACA CCATTATATGATCGGTCGCGTTGATAGGAACATCGTTGGCACAGCAACCC GATGTGACAAAAAACGCCACAGACGCAATGGCCCAGTACGGTCCTCCGAA 27900 28000
ACGGTCTTTGCGTACCATGCTGGAAACACTCGGATCTTCTTCAAGCAAGC GGTCACCCACCCGATACGGTCAGATGACACACACCCTTTCTCGTATATCG AAACGTGTAGCGCATAGCACTTTACACCGCAAGTCTCTTCTTTTTATCCC GTGGTCAGATGTTCATGTTTCCGGAGCCAAACCCACCGGAAACAAGCAC 28100 28200
GCATGACGCCGCGCGGCCCCGTACACGCGAAAAGCAAGGCTCACCGGGCT CGTACCGTTCTATTCCAGCATACTGAATATGGCCCAAGCTATAGTCTGCG TCAAAAACTCGACACAGATCCCGATCAGCACGAACCAGACGATCACGCCG GAGAGATACACACGCTGTCCACCGTTACGTAGAAATCGCCAAACACCTG 28300 28400
ACGGATGTCGATCGCGCGGCATGGCTCCTCCGGCTCGGGTTCATCGGGAC CGTCGTTCTTCACGACATCACGTTTTCCTCCCAACATGAGGATATCGAAC CGTTTCTCTGAACCGTTGACGAAAGACATCAACTCTTCCCTGCCGACCCG CATCTCGTGCACGTTGCGCGGCGATGCCGCCGGCCGATCCCGCCTTCGTT

FROM FIG. 1F

RNA_Validated_v0.0:CLONER [illegible] Text View
Fri Oct 18 2013 6:09 PM

```
                                                                                                      28500                                                                                                       28600
TCGGCACGTCGACGGCCGGCACGGACAAAAGAGACGCCGATCTCTGAACC ACACGCAAGGCGCCTCCGGCGTTGCCCGCCGTCTCTTCACGTACATACA ATCGACGGGCAGAGAGATCGCCTCCTTGGCGCGAAACGTCGTCGAGACCT AAGATATCATCTCGCCGTCACCGTTAACCTCTTGACCGTACCGAATCTCT
                                                                                                      28700                                                                                                       28800
CGAATCGCGCAATGCGACCGCGCGCCCGAGGCCGTCTCGATATACATGGA GCCGAACTCGGTATACAGCCCGCTCTCAGCTTTGACCTAGTTCATCCTAA AAGAAAAATCGGCCGTGTACACTATTCCCAGTCCCTCCACGCGTTCGAAG TTCTTGCCCATCAGCAGACACGTCACCTGCATGGTTCCGTCTGACGCGAT
                                                                                                      28900                                                                                                       29000
CGTGACCGTGCCGCCCAAGCGCAGCTTGCCGTGGGACCTCGTCTCGGACG GTACGGGGAACGGAATCGCCTTCTTTTCGCGTTACGTTCAGACGCGCAT GTGGACGAGGACGCCGTAATATAAACGGTTCCCGACGCGCATCTATCCGG ACCGGTGTCGTAACTCACAGTCCCGAGACGGACGGGCCGTCGACGTCGC
                                                                                                      29100                                                                                                       29200
CCCACATCGAGTACCGCGTGACGAGAGACCTCACCGAATGAGGATCGTTC AGAGCGTCCCCGAAGACGGTCAGATTCACCTTCACCGAGTCGCGGACCG CATCCCGACAACGTCGGCGGTCCTCACCCTCGCGGAATTCAACTCCCTGT TGACGAACACTCGTACCGAAGCGGAGGAGTCCCCGAATCGCACGCACATC
                                                                                                      29300                                                                                                       29400
TGAGCTAACCACAGGACCAGACATAACCTTCCCCACGCGTACGGGACCGA CATATCGACGTGTCTAGTTTTTCCCTCGGCGATCCGGACGGAGGCCGGAG TCGTACGAGACCCAAACCGACGACAAACACCTCACGTGCGGACGATTCTA TTGGCACGGACACACAAAATCACTGCCAACACATTGTAATTGCATCAACC
                                                                                                      29500                                                                                                       29600
ATTGTTTATTTTATTCGGGAAAGTGATCCCACCCATCCCCGTGGTACGT CATCATTACGATTTCCGCGCGACAGATCTCGTTCACACGGACGAAGATCT GATCCGTCTTCTAACACGGCGACACGACCGCCGGTCCCCCGACGTCTCGC ACCGACGTCGCACGCGGTCATCGGGATAGGTCTCCGGAGTCGGGTCGGCG
                                                                                                      29700                                                                                                       29800
TCACCGTCGTCGTACGACCCGGAGATACATTCCGGTCGCCATATCATCAC GATGATCACGACCGAACAGATAAACGGCACGGACATCAGTAGCGCCACAC ACTGTCTATAGATCGCGTTGAAGACGATCGTGTCCATGATACTGCCATCC GCTTAAAAAAAGCGATCAATCCCTTTTCGCCCGTCTCGCCGTCGTTGTCG
                                                                                                      29900                                                                                                       30000
CCGCTCGTCTCGTCCTCAATATGTTTCTCGAAGAGCCGGGCGAGACGTTC TCCTCGGACGCGGCCGGCGCTCTACGAAGGATCGTCGAGCGCAACCTTCC CACGATATCCAGCTTGCGACCTATGACGTATATTACGCACGCGGCCACGG AGATCATCAGCATACCGTCGAAGCTCACGACGGAATCTCTAACCCAGGCT
                                                                                                      30100                                                                                                       30200
CCCCATCCGCCGCCCTTCGCTCCCCCGACGAAGTCATCGCTAAAGTAAAG AGCGTCGACGAGAGGATTGCCGTCGTGGGTGTACGTTACGTTTCTCGCGA ACCAGTGTATCAACGTCGGGTCATCTTGCCGAAAGCCTATGGAAAACTCG TACAGGCCGTTCTTCGACTCGTTCGCCGCACCTAGATGCCAAGAGGCGAC
                                                                                                      30300                                                                                                       30400
GAGAAAGTCCTTTACGTGATGCGCGCCGGGAATCTTGATACCCGCCAATC TGTCCACGGTGATGGTGATATACGTCTGCATGGTACCCGCTAACATGTAC TTTAGGGCGGTCGAGGACGTCAGAGGTATGTGTCCGGTCTCATATCTGGG TAGTTTTAATTCCGCGCGACTCTCCGCCGACGTATTCCCCATTCTGCAGTG
                                                                                                      30500                                                                                                       30600
TCATTCTGGTGAACCCCACGCGGATGGCCGCCACGACCGCGACCTGCATC GGCACTCCCCAGCGCACCACGAGTTTCCCCCGACGCCTCTCGACGTGCGG TTCGAGGCCTTCGTAGTTCGGATCCCGCTGATCTGCCGTGACGTTATACA GATACATGAAAAACAGACGCGTGTGTTCGTTATCCACGTACAGGGGACCT
                                                                                                      30700                                                                                                       30800
TCCTCCGTGAGATGGGGTATATCCTGATATTTTTCGATCCGGGACAAGAA AGCGAGATCGTTCAAAAGCCGACACGTCAACGCGTCCCCACGAACCCTAC TGTAATTTCGAAAGACGAAACCTCTGAGCGGCATAGTGCATCCCAAACCC TGTACGTTAATCACCATGTCGGTCGCGTTGACCTCGACCGCGCCTTCCGG
                                                                                                      30900                                                                                                       31000
CTCTTCTTTACATACTCCCTCACTCTCGCACGAGACGTAGTAAGGCTCGG TAGTCATGTTCTGACTGAGATCGGGTCCGCTGGGTCCGGGATTGGCGGAT GGCGAATGTATGCTGAACCTGGAGTATATGCTTCGGAGTCGGTCGCGCTC ATCCCGTTCCCCCACTCGTTTGATATCGCACGCGTCGACACATACGGCCG
                                                                                                      31100                                                                                                       31200
ACCCGAGAACGACGCACGCCAGGATCGCCGAACGGACACCCATACCGACA ATCGAGCGAGGCGCGCTCCCTCGCGTCGATAAGCAGCGACTACCCTTCGC GCCAGATTATATACACAAGCGTACCCACAGCCCACATCCCCACATCCCAT TTCCCGCATTCCACATCCCCGCCTCTCCTCGCGACGATCTATCGACACCC
                                                                                                      31300                                                                                                       31400
AGAGAGCCAATAAGATGAAAGACACTGCATTCCAAGAAAGGAATGGTCGT CCGTTCTTTATTTAATCATGTATACGTATAAGATATACGTAAGGAACGCC TTCGCTTCAATTATAAATAGAATCGTCGCACGGTCGACGAGAACACTGCT CGAAAGGCCCTCTCGTCGCGGTAGTCGTCACGCTGAGGTTGCGTCTCGAA
                                                                                                      31500                                                                                                       31600
GTATACGCTGTCGATCGAACCGGAATCCACACGAAGTCGGAACTACATTC TTCCACACCGCCACCGATCGAGCCGACGGCGTCCTTTCTGACGCGTTTAT AGCACTTCTTGTCGAACCACTTGACGATGGAGCTCGTGCGATGCCGAGCC CCCGCGGCCGACTTGCACTTGCTGCTCACGCGAGGCATGTCGACGGTCTG
                                                                                                      31700                                                                                                       31800
AAAATCGTCTCGGGCAACGCGGTCCTGCAACGGAGAATCACACCCGTGAG AACATGTCCTCCCCGGAGGAGGTCGCAGCGCGCGCCCGCGACCGACATGAA ACCACACCCCCACAGATCCCAAACGTACGTTTAATAATCAGCCTTCGTC TGGCAGGCCGCGGCAGGAGACCAGCTACCCCGCGTGCCACAATGACAGGC
                                                                                                      31900                                                                                                       32000
GACGTACAGCTTTTTAAACCTTTTGCGCACGCTTAAGAACCAATCCATAA TAAGCTCGTCCCACGCAAATCCAGGACCCTCCGGCCGGCCAATCTGGG AAATGACCTCTCGGCCATGGGATAGCAATTTCTCCCCAGAGAGATTCC GGATAATACGTCTCATCACCGATAGTTGCATAATCACACAACATATTACC
                                                                                                      32100                                                                                                       32200
GGAAAGTCCTTTATTTCTATACACTTTATGTCTAAAAATAACATCCCGGC ATCCCACCGACCCGCCGCGGACGCGACAGTCTATATAACGCGTCAGCTGA CGAAAAGACGGTTTATAACAACGTTGGCCGCGGTACGTTACGCGGATACG TCCGTCGCGGTAGTCCGAAGTCCATTAAATGGCACCAGTTACCATTTCGC
                                                                                                      32300                                                                                                       32400
CGGTATACGTAACGTTGAAGCACGAACACAACACAGCATCCCGCGTAATC TCCTCCCGAACCCCTTCGTCTCCCTCCATACGCCAAACCTTTTTCCCGAT ACACCACACCATCGACCGATTCGTCCCGCGAGTCCCGTTACCCATCGATG CGTGCGAACTTTTAATACACGTAAACGCTCGACGCCCGCGCGCCGATACA
                                                                                                      32500                                                                                                       32600
TCTCTCCCAGTAACCGTCACAAACCGACTAGCGGCCCACAGATTCTTTACC CTCCACAACGATCAAACACCCAACGCGAATCCCCACACCGCTACGTCGACC TATCGATACCACGATCCGAAAATATGTAGATGGACGCCGCGCATCGTGCGC CTCTCAGAGATAATAGGTGCCGTCTATCCCTGAAGATAAGTGTCCCGGGT
                                                                                                      32700                                                                                                       32800
CTCATCATGGCCGCTATGACGGTCGACACATTATATCTCGCGGTCCCGGT CGTCCCCGACGAACCATTCACGACGCCGACATCGCGTCTCGCGCTCGCGC CGTGCGACCGCGCGGTCGACAGCAGCGTGATCAGGCCGAGCGACGTGACG ATAACGATGACGATGACGTGCACCACGGCGATGAACCTGCTTTCTTTCAG
                                                                                                      32900                                                                                                       33000
GCCGCATATGATCTCCTCGTCCGAAAACGCGGACACGCCTTTATCAGAAA CGTTGTCCGCGTCCGGAGACTGTCCGTACCAGCGTGTCCTAGCTACGTCG AGATTAACGGCCTCGGTCGGTCCGCTCGAGTCGCTCATCTTGGGCTTCTC ATCGCTCTCCGCGTACAATTTCATGCGAGTGGACTCTCTCCCCGTCGTAC
                                                                                                      33100                                                                                                       33200
GTTTCCCGCCGCACATGTCCCATACGTTTTTCTTACCGTAACGTTCGATC GACCGTATCGATCCGTTATATATTGCCCACGGTCTCGTACGCATCCCAT AGAGAATCCCACGGGCGACAGACGACGTAAAACACACGGTAGTCAGGAGT AACATCACAGAACTGTTTACTTTCGATTTCATGTACAACGGATTATCGAA
```

FROM FIG. 1G

DNA_Validated_v0.0.CIDNTS.ann.embl Text View
Fri, Oct 18, 2013 6:09 PM

```
                                                                                                    33300                                                                                                 33400
GATTTCATATATGTACAACGTAAATCATCGTAATCACACACCAATAATAA ACCCGATACACGCTTTCGTACCCAAAAAACAAACACAACCCATCCCGTT AGTTCACGGCTGCGCCACGTCCGGTGACAGGCATCGCTCACGTCGACC AGCTCCACGTCTTCCTCGTCGCCGGTGTCCATCGTCCTCACGCTCGACCG
                                                                                                    33500                                                                                                 33600
GCTCATCATGCTCGTGCTGTTCGTCTCGCTACTGGCGCTGACGAAACTGC CGGTGCTGAAAACGCTGTTGGTGCTGACGACGCTACTGGTACTGACGACG CTGCTGGTGCTCATCACGCTGTCTCTCCGTCTTCGATCCTTCAGGCTCGG CCTCCACGAGAACAACCCTTTCTTCTCTCTGCGCACCGGGTCGAACGACT
                                                                                                    33700                                                                                                 33800
CGATGTACCCGCACGAACCGTGACTCACGTCGCACGGGCACGTCGGACGA AAACACAGGGACCGGCATTTTTCCCCGCCGTAGTAAAATTTCTCGTTCGA CCTGTAGCGCTGCAGGCCCAACGCGGCCATCTCCCGAGGGTCGTCTCCGA CCAGTACCACCCTGCTTCTATCCGCGGCGAACAGACGCATCTTGCCGTCT
                                                                                                    33900                                                                                                 34000
ATCAAGATGGTCAACTGAGTCGTTTTCAAGTCGCAGCCGCCTCCCGCCAG GTACCTGACCGTGGCCAGGACCGCGAGCATCCTCACGCCCGCTATGACGC TCCAAGACTCTATGTCGTCTTCGCACAACCCGGCGGACAACATGTTGCAC ACCGCTATGAAGGAACCGTCTTCCAGGCGCAGCAGCTGCCCCAACCTCTC
                                                                                                    34100                                                                                                 34200
GTCCCTCCACCCGATCACATCATCTAGATCCTGCAATCTGGAAAACGCGG ACATGGACGGTTCCCCGCACGTCGTGTGATACAGGAGCGCGCGGTACGCG TACGTGGCGAACCCTTTGTTCCGAAACTGCGCACGCTGTGCGTCACGAT CGACATGCTGGAGGTGTACAGCCCGGGCATATACACGTATATCCCCCCGC
                                                                                                    34300                                                                                                 34400
TCCTCCCGATGTACAGTTCCGGGTACCAGCTGGCCATGATGGGTTCCCAG TGAAACGCGTTCGGACCGGACGAGCAGACGCTGCCGATCAACTTCAGCGG TTCGGGGCAGCACAGAAGCCCGGACAGCCTGACGTTCTCCCGTTCCCGAAG ACTGACACATGGGTCTCCAGCGTCTTCCCACGCATATCACCAGATGCTTG
                                                                                                    34500                                                                                                 34600
GGCCAGGCCAGGCGCACGCGGCGATCCAAGTGCACCGAGACCCGCCGATC GACCTCGTCAAACTTTTTCAGTAAACTCTTTAGAAACCTCGGAGGCGCCA TAGCGGCCCAGGACCTACGTGCGCCGCACGTTCCAACCCGATTCCCGGGT CACGGACGATACTCAACCCGACCGCCAATCTTTCACGTCCAGGTGCCACG
                                                                                                    34700                                                                                                 34800
GTGCGACTTTTTATCGGGCGAAGAGGCGCGTCAATTTCCGGAGGGCAGGT CCCAAAAACGCGTTCTTGTGAAACAAAACGTATGTCCTCCATCGCCGGTG CGCGCCGTAGCCCGTATTCCCCCCTCCCCGCGTGCGAACTAGCCGCGTAG CTTATCCGACACCGTGCCACACGCGGGGAACGAGGGACATCCCGGCGCGC
                                                                                                    34900                                                                                                 35000
GATCGAAATAGCTACGTTTCCCGTCTCTCGCGTGGCGATCGTTTCGGTAG AAATACGTGAGCCCCAGACCCACGAACCCCGGCAGGTTGTCGCCGAGACG TACGCACGTATTGACCGACGTGTCGTAGGCCAAGACGTATCCTTGCTCCG TTATGAAAATGGGCACGTCGCTGGGCTGTATGCCGCGAGAGAACGTCAGG
                                                                                                    35100                                                                                                 35200
TGAAAAGTCGATTTCCTCACGGCTATTCCTATCGGAACCATCCTCTTGCG GAGAGTCGTAACGATAGCCTTCCAGAAGCGACCCGTATCTCGATTACGGG AAAAACACTCCAACCCGCACACCTAAGGACCCAGTTCTCCGGGTGCGCG ATGGGAAAGAGACAGCCGTGTCTCGGGATCAAAAACCGCATGAGTCCGGG
                                                                                                    35300                                                                                                 35400
CACGCCTCTCTTCTCGAAAGACGTGATCCATTCCCTATACCTGCCGATACG TCCTGATGTCGTTGTAGACTATACCGGAATAGATGGTGTCCACGGTCTGC AACCCGCCGATACGAATTCGTCCACGCCGGCCGCCACGCGGTAGACGGT CTCTTTGGGTTCTCCCGGCGTAGCAGAACACGCTCCGTTATCGAGCGACA
                                                                                                    35500                                                                                                 35600
CCAGTAGAACGAACTGTTCGACGTTCATCTCATCGAGCACGCGACCCACG GGCACCAGGTTGCACCGGCAACACAGATACTCCTCGTTCATCCTGCGCGA AAACGCTTCGTCTCTACATAGATCGGCGTCGACGCGTACGCACCAGCCGA CGGGCCAGGCTAACCGGAGGACGCTGTCGTGTCTGTCGGCGATATATTCC
                                                                                                    35700                                                                                                 35800
AGCGGCCCGCGTTCCGACTCCCGGTCCTGCAACGCCTCTTTCAACCATTG AAAATCCTGAGACGAGAAGGTAATGTAGACGGCCCGCATCAACGGATACA ACTCTTCGCCGATAGACCGCTGCACGTCCCTGATCGATCGCCGTTCGCCC ATGATGACGGAGGCCGGCGCCTCCTGATCAGGTTCCCCCTTCTTCGACG
                                                                                                    35900                                                                                                 36000
AGAATCGTCCTGAGAAACGACCCTCTCGACGAGCCGTTTACCCTCCACAA TCCCCGCCTCCGCGTAACAAGAAAGCCATTCGCACAGAGGATCCGAAAAA TCGCTGCTCTCCGCAGAGGCGGCGCGATCCGCGCGAGAGCGTTCGAACGA CTCCATGTCACGCGACGCCGCTTTTACCTCCGAATAATATATGTATCCGC
                                                                                                    36100                                                                                                 36200
TGCGAGGATAACCGTACGGCGAACGACGTATAAGTATTGGGATCAAGCTG CTGCAATATAAGAATATCGTCACGATAATCGAGACGTATCGCGGTCGACA ATCGAGGTTCTAGACAGACAAACACGGGTCACCGCGTCGGCGAACAGGAGT CAGATCGGAGAATCTCTCGCTGTCGTTCGAGTCGACACAGCTTCTAAAAA
                                                                                                    36300                                                                                                 36400
AGGCGGACGTCAAACAAAGCATGGCGTCTACAAATAGCGACGACCCCAGG CAAAGTAAACAAAAACCCATAAAGCAGGCAAGCGCGTCCGCCTCCAGCGG TATGTCTGGCATTAAAAGACAGTTCGGCTTTTTCATGGGAAACAAAAAGA ACGGAGACACGCATCGTAACTCGGACGATCGAAACCATCGCAGCGCGCC
                                                                                                    36500                                                                                                 36600
GTAGCCGCGGACGACGGTTTTCAATACAGACACTACACGCACGGAGACGA CGGGGAAGAGATATACGGAGCCGTCGGTGCCGGCCGACACGGCCGAAGAG ACGCATCGCAGTCCAAAGTCGTTCCCAAAAAGCCTCCCAGGATGGGACGC TCCGAGTCGATGAACCGAGAGCTCGAACACGTCACTAGGTATAGATCTCA
                                                                                                    36700                                                                                                 36800
AGACGAACACGGCGCTTCGGGAAACGTACTCCCCGTTACGAGAAACGCGTT CGACATCCTTCAGCGGAAACAGGAGCAGCTCGATGGATCAAAGTCCGACC GAAACGGTGTACTCGCTTCTCAAACAAGGAGGCGCAGACCGAAACTCAA GACATCATCGAAATCGGTCGATCACGGGAACCGGTCTCCGGAAGACGAGG
                                                                                                    36900                                                                                                 37000
ACGACGAGTCCGGAATAATATACTCGGACTTAAAGATAGTAGCGACGGCT CCAAAGACTTACAGAGAAGAGATATACGTCAATTCTCACGCCGTGCGGGC ATGGGCCTCCGAATCCCGCGATCAGATGAACCAACTCGGCTTCAACCCAA ATATATTCGATAGTGCGATGGTGGACATCATCAAAGACTGCCTGAGTCCG
                                                                                                    37100                                                                                                 37200
TCTTACCTCAAAACGCTCATCAAATTCAACACCACGAGAGCGGCACCGAT GAGCGTCGTCGTGACTACCCTAGACCCGATGTGTTCCGTAGCCGCGGCTA GAGCGTTGCCTATCGTCAAACCCGTACTCAAACTCATGCTATGGATAAAC TGCTATCAAACGGGGTAGCCGCAGCCAACAACATGCGTTCTCACATGAG
                                                                                                    37300                                                                                                 37400
GGACGTGATGCGTTCATCAGAAGTGAATCTCATCAGGCTTCGTATGGAAC AAGCCCCCAAGGGACGGCTCGGAACTCATACGCGTACTACTGAACAACTTT CATACGGAAGACCTCTACGACCGAAAGCATCTCCGTTCCCTGACGGCCGC CAAGATGCACCTGCTCTCCATGAACACATCCTGTCTGTATTTCTCATCGG
                                                                                                    37500                                                                                                 37600
GAAAAATAAGCGCGCTACGGGGGATCTGTCCCTTGTTCCGTCCGGGTGAC AATCTCTGCGAACAGGCATACGGAATATACAGGAAATCTCTGCAAAATAT CACTCTGGCCCGTGAAACACCCATACAGCTCATATGCCAAGGCAAAAACC ACCCCATGAACGAAGTACTATCTGACTTCTGTTTCTCGCGGCCATCAGA
                                                                                                    37700                                                                                                 37800
AACATGTTGCACAACTACAACCGCGCCCTCGGCGACCTTCGTTCGTTTAT CTTTTATCAACTGGAAGCCCTTCTCGAAACACTGTACCTGGCCTACGTGC AGCTGCCACACATGAAGCAGGAGCTGCTCACCGTAGTCGGATGCGTACAA GACGTGATATCGCAACACAACCCGTCGGACATGGCCCTGCACGGTTTGTG
                                                                                                    37900                                                                                                 38000
TAAGAGCATCCTAGTGTTCGTCCGCGACGCCCTAGCCTGCGAGATATTGA TCAATCCGGACCTGACGAGACACGCTCTCCGGCAGCTGTGTAACGGCGGG AACACGCGCGGCGGGGCGAACCTCACGCGCGCGATCTGTCTAATGAACTC ACCTCTCACGTACAGACCCATGGTATCCCCAGATGAATGTAGAAACATAG
```

FROM FIG. 1H

FROM FIG. 1I

FROM FIG. 1J

ERA_Validated_v0.0.CIDMTR.ann.embl Text View
Fri, Oct 18, 2013 6:09 PM 47700 47800
CCCCATGTCGGCGACGCGGCCGATCGTCCCGAACACGACGAGCTTGGACA CGTTTAGACGATTGGCGAAGTCCTTCAGATCTTTCTTCGAATACATAGAT TCGTCCACCGTACATAAACGCAACAGACAATCGTTCGGCCATAACAACGC GATCTCCCCGTAACAGTGATCTGCTGCGTATCTCTCTACAGCGTTTAGAT 47900 48000
CTGTCTCTATCGCCATCATATCTCTCAAACGGGTCAACGAAAAAATACAC GCCGCCGTCATCGAAACGCCACGGTAACCGTTAACATCGACGCTCCCCAC CCCTTCGACACAACTTCTCGCCGCCCGTCCGCCCGCGAACCCCGATGGTT ACAGCGGAGGCCACTGGATCGTCGGAACGCCGGCCTCAGGTCATAAATCG 48100 48200
CACGACCGCGAGACACCGAACGAAATGTTTTAAAACACGCGTCACAGAAG CACCCGTTCCCTACCAGACCTCCAAATCATACCGTTCAGTTTATAACCA TCGTGATTTGTCAGTCAAAATCGATAAGGTCTTGGAGTTCCGTGATTTCT GCGGTCAGGGCGGCCAGTTCCTCGTCATCGACGCGAGACGTAACCACGGG 48300 48400
CCCGCAGTCCTCGCCCGTCCCGCAACACGAGTCCATCTCATCCTCTCCGC AGTCCGATAACGAGAAGGGGTCCTTCTCACAATCCATTTGTATCACAGCC GTATCGTCGTCCAATTGCGTATACGCATACGACACGTCCGCACAACCGCA AGCCTCGTTTAGGACATCGTTGATCCAACACGTCGCCTTCAAAACGTCGT 48500 48600
CGAAATCCACCAACGTTACCGAAGCCATCCTCGCGAGTTTAAACGCGACG TCTCGGAGCGAGCTCCTAGACATAAAGATGGCCACACACCACGAGACCCG AAACGGCCCGACCGCCACGAACACAGATTTTTGCCACCCAATGCGCCGCG TGTTCCTTATATATGTACGATTGACATAACTCACGTGATCCAGATACATG 48700 48800
ACATAATCGAACATAATTACTCACCCCGGGAGAAACGGAGCCCGATCACA GCAGATAACGATATCGCCTCGCCTGCGTTTCCAGCAGACTCTTCTCGCTC TGACACAACGTGTCGTAATAAGCGCAGAACAGCTTCATATCCCTGACCAG AAGACGTCTGCGATCCAACACCATGGCCCGAATCTGACGTGCCTCATCC 48900 49000
ACTCGTCACAATCCCTATCGTTCGGCGCGCTGAACATGATCGAGCCCCGT GCGCGAAACCGCCGAGACCCGTGTCACGCGAAACCCCGGAACATTTAACT CTATGAAGAGATGTCACATCCGGGCATTTATGGATCCGGACGTCGACGAC GCAGACGCCCGCGCATCTCACGGCGACCGCGAATATGTCACCCACCCGCA 49100 49200
CACGTTATCGCCGTTCTTCGACACGTCGCGGATCCCCACACCCCCGTTTC CCCTCCCCTTACAATCATCGCCGGCCACGACTTACGCCGTCACCAGAAAC GTGTTATCGTATCGGCGCCTCCGACGTATCCGTTCCCTGAGAGCGTTCTC TTCGGAAGCGCTTCGCGCACGGTGCCTGTCTGCGGCACGCGATACGACAT 49300 49400
CGCTCACCACGTCGGACCCGGGACCGTAAGCGAACCACAGGGGAGACTTG AACATCATCATGCCGTCCGACGCGCACAGGATGACCTCCGTGATCATGGA TAGCTCGGGCCGCTCACGAAGACGACTGAAATCTACCACACCGTACTCCG ACAGTACCAGATGTCTGAGCTGCTGCGCGAGCACTATCTCGAACCTGCGT 49500 49600
CTCACGCACCGTCTCGAGCTCATCAGATACAGGTGCTCCAGAATCACCCG AGCCCTGTTGCTTCCGGACCGACTCGAGTCCGTGGAGTAATTCCGAAGTA ACCGAATAGCCAGATTCGCCATACCCGGCAGTTCGTTAGGTCTATTCCTG ACCCTATCGACCATGCAACGCAGAGTAATTCCGGGTTCGTGTATTCGTC 49700 49800
CAGTATTCGACACATCCTCACCCCTGTAACACGAACTCCTGCGCCAACA GGTCGATCTCGAACGCTATGAGACGCCTGACCGTGATATCAGAACACAC ACAAAACACACGTTGTACACCAGGTTGAGGACTATCCTCTCCAGGAGCCC TCTGCCGGCGCTATCGTTATCCAGACTGATGAGCAGCCTGCCGCTATCCA 49900 50000
CGGCGCCGTACACATACGACTGCATGAGGTCCGTCGACAATTCCCGCAAC ATCACGTCCCGGGATGTATCGTCGACATGAACTATATTCGGCAGATACAT GGGAGGAAACGAGGGAGACTCACTGAGATACGCCACGGAACCGTGGAGAC CGTAGCCGCGCCGATACGTTCGAGCGATACGCTATATCTGATCCCATAGCA 50100 50200
CCGATACGTCTCGCGCGACGTATCCCGCTGACGTTAAGACCATCTGGGGT ATCCGTAACGGCCGTCCCGCATCGTCTCCGTCGCCGGACGCGTCCCGCGG ACTCCGCGCCCGCCGTCGCCGTAACGCTATAGTTACCATAAAGCCAAGGC ATGCGCGTCCCCGCTATGGCGTCCGGGATCACGCGGGCGCACTTGTGACA 50300 50400
GTCGCACAACGCTTTCGACACAAAACCCACCCTGGAGCAGTAATGTTCGT ACAGATCTTCCGTAGAATAAGCGTTCTTAACCGTTCCCTCGCTTATCGGG TTACGCAACATATCGAACACCACCCGCAGATTGACGTTATCGTGACATTC TCCCATGTGACGCAGCATCAAGAGTTGCTCGAATACGGAGTTTGCCATTC 50500 50600
TACACAGCAATCTGACGTATCCTATCAGGGTGTTCCTCTTTTGACTGAAC GAAGCGTAATACGCGATCAGATAGTGACACCTCGCCAGGAGCCTCGAGGC CGTCTCCGCATCCGGGTGGAACCCGTCCACGAATTCACGGGTCCTAAGAA ACGTCAAAAACTGTTCGGCCTTCATCACCGGCCGCGTGATGGACTGATCT 50700 50800
AGCTCCAGATAACCGTTTATCAGAACGCTCCATATCACGGAATCGTCGTC AAACGATAGGCCGTGAACGGAAAACGCACCTTCCGAGGTCAATAACATAT TTCGAACCGTTCCCGTATCCCTGATCAACCAAAAATCCATATCAGACCAA GCGATATCATCTATCTCGTCGACGTGCGAATCCAAATCCTGTGACAGCAT 50900 51000
ATCGCATGCACGAGATGCGATACTATAGACGGAACTCAGATCCACCGGAG ACCGTATCTAGACACACACGATGCAGATCGATTTCAATAAACATGAAAAC AACTCAGCCTGTCACGAGAACGCGTCTCTTATCACTTTAATGAGGGAAAT GAGATATAAGATCTCGCGTCACAGATGCTACAAGAACCCGCGGATGACAC 51100 51200
ATTCGAGGGGCAATCGGCTGCCAGTCACCGTCGGCGCCACCAGAATCCA TCCCCGACTCAGCGAAGACTCGCGAGATTACCCAATCGTCGACATGGACT GTCCGCTGGACAACATCTACGACGATATGGACCTGGCGGATATATGTCCG TTCGATCCGGTAAATAGCTCTGAGCAACTGTATACGGACGCGGAACACGA 51300 51400
AACTGACGAGCCACAGCATCCGGAACCGGTGAATACGCAAAAAATAAATT TAAAACCATTTAAATTCTACGAGAGCAGGATGAGACAAGCGATCGACTCG TACAACGGGCAAGAGACCGTATCGTTCGAGGCCAGATACTACAACGATCG CATCTATTTCACGGCACCCATATTGGACCACAACTACGGAGCGAAGGCGC 51500 51600
CGAAGCTGTACGGATGGGCCAACATCGTAACCCCGAGCGTACACACCGAC GACCTGTTTTTCCTTCTCGTGAGCGCGGACGGTAAAGGCGTAACGTGTCA ACCCACCATAACCCGGGGAGGACTGGTCTCCATATTGATGGTCTACACGA CCGGCAATACCCCGCGCCATAATCCGGAGTCCTTCATCATCCTCAGCGAG 51700 51800
CTGGTGATGCTCCCGTTCATCCCTTTCCACGTACCAGAACACGTGTCGTG CTTCAGTCTGCAAGAGGAACCGTGCCGATCCGATCGTCGAGAAATTAACCC GCATGCCGGGATGGGGAACGTTCACGCAAGAAAACGGGGGCATCCTCATT CACGCGCATAACTTGTTCTGGAAGATCCAGAGAGTATATTCGCTCGGCAA 51900 52000
GAGGAGACTCACGTATTACAGCGCCGGCTTCATCGCGGATCCGCAAGGAT GCGACGTAAGCCCGGGCACCAGATGGCTCACGCCGAACAACATCACGTTT GACTCCGGCGCGTTCAAGTTCTCCATGAACCTCGACTCCCTGTCTATCAC CAAGCACTGTTACCCACGAGTGGTAGGTATCGTCTCTACCACGTGTTGCG 52100 52200
ATCCCCCGGAAGACTACAAGTCGCCGTTCGTCTTTCCCAAATCCGTTAAA TTTCGCATCGTCATACCGGAACTCCCATCACCGTGGCAGATCGTATTCAC GCGCAACCCGAAACTGTTCCTCAGCGGAGACTCCTTGAACATGAACACGC GTCTCCTTAACGAGCCGAACCTCAAGACCATCACCGTACACGCGCCGTAC 52300 52400
GATATATACTTTGTGGACAGCGGCAGGAGATGCGTCAGATACGACATCTG CTACACGTCGCCGAACGGCATGTTCATCGTCTCTTCCCCAACAACCAGA GCGCGCACGCCTTTCACACGGCCATGGACCTCTGGAAGAGAGACACTCCC CTGAAAGTGACGCTGTGGTCCAATAACGATCACCTGGTGGTTCCTCACGG

Figure 1L:
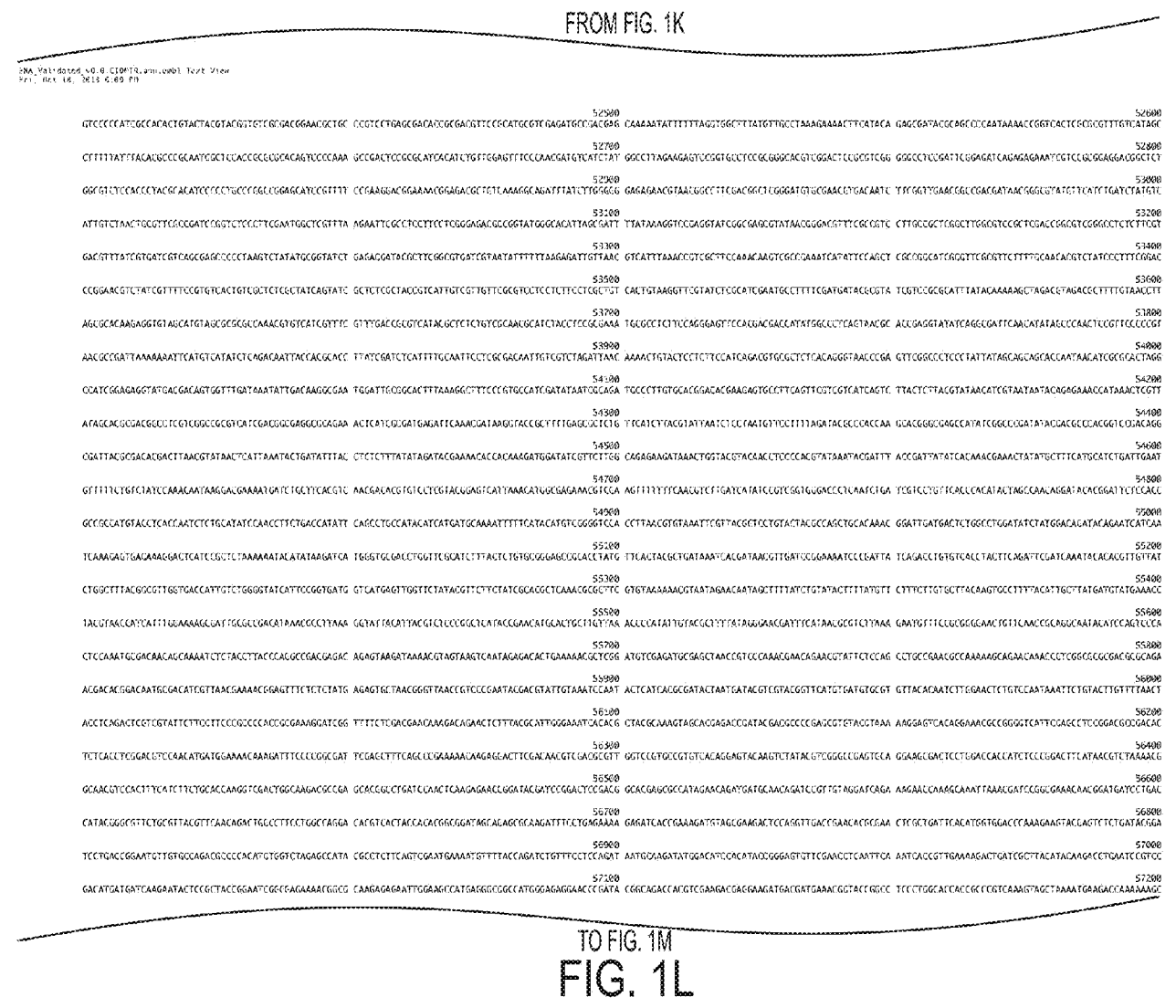

FROM FIG. 1K

DNA_Validated_v0.0_CIOMTR.ann.embl Text View
Fri, Oct 18, 2013 6:09 PM 52500 52600
52700 52800
52900 53000
53100 53200
53300 53400
53500 53600
53700 53800
53900 54000
54100 54200
54300 54400
54500 54600
54700 54800
54900 55000
55100 55200
55300 55400
55500 55600
55700 55800
55900 56000
56100 56200
56300 56400
56500 56600
56700 56800
56900 57000
57100 57200

FROM FIG. 1L

FROM FIG. 1M

FROM FIG. 1N 66900 67000

FROM FIG. 1O

FROM FIG. 1P

FROM FIG. 1Q

FROM FIG. 1R

FROM FIG. 1S

FROM FIG. 1T

FROM FIG. 1U

FROM FIG. 1V

ENA_Validated_v0.0.CIDMTR.ann.embl Text View
Fri Oct 18, 2013 6:09 PM

```
                                                                                                    105300                                                                                                      105400
TATATGCAAATGATAATAAACAACGCCGAATCAGGTTACCCTAACGTATC CGTTTTATCCGAATGCAAGTTAATACGGGACGTTTCTATTTAACCAACGC TTTCCTGTAACACCCCCAATAAACAAACAGGTCCTTGTATTTGCATATGC AAACGAACCGTTTTCACGGCACGTTACTTTCCACGGGTTACGAATATTCA
                                                                                                    105500                                                                                                      105600
TTGGTGGGCGTAACCTAATTTGCATACGTATCCGGTGCAATTCCGTATCC ATCCAATGGGACGTACTCCCCCCTACGTATAGGTTCCAAACCTATAAATA CAAAACCTATAAATACAAAACCTATAAATACACTAGGTACGTATATATGC TCCCTAACGAATATACACCCCCTAACGGATATACACACCCCCTACGTAAC
                                                                                                    105700                                                                                                      105800
CACACCCACCTACGTACACACCCACCTACGTATACCCACCCCCTACGAAT ATACAAGGTTTACGGGGGCGTAATTCGGGTCTACGTATAGGACCTACCA ACCCTATCCTTACTTCCCCCTTACTACCCCCCCCCCTAACCCCCCCCCT TCATCCCCCTCATCCCTCCCCTTCCTCCCTAGCCCGAAAATTCGGCGGC
                                                                                                    105900                                                                                                      106000
CGGCCGCCGATGACGTCCAAGCTGGCGGGCTGCCAGGCCACCTGGCTGCG TGTGGGACTGGCTTTGGGACCACGTGACGGTGGGTATAAGAGGCCGCGCA CAGCAGTCCCCGCCCGGCATTCGGCGGGCGGACGGACCACAGCGGACGGG TAGGTGCTGCGCCGCGGAGCCCCGGGATCGGGTGGCGGGGGATGGGCCG
                                                                                                    106100                                                                                                      106200
CCGGGTGGGGGGGGGGATGGGACGGCTATACCCCCCGTTCCACAGGCTC GGAGCCGCCGCGAGCAGCGCAGGATCCCGGACCCGGACCCGGACCCGGAC CCGGACCCGGACCCGGCCGCCGCCGCTGGAACCCGCGCCACCCCCACCCG GCTGGATCGGCACCCCACCCCCACCCCGGTAAGCGACCTGCACCCCCAC
                                                                                                    106300                                                                                                      106400
CCGGCTCGGCCTGCACCCCCACCCGGCTCGGCCTGCACCCCCACCCGGCT CGGCCTGCACCCCCACCCGGCTCGGCCTGCACCCCCACCCGGCTCGGCCT GCACCCCCACCCGGCTCGGCCTGCACCCCCACCCGGCTCGGCCTGCACCC CCACCCGGCTCGGCCTGCACCCCCACCCGGCTCGGCCTGCACCCCCACCC
                                                                                                    106500                                                                                                      106600
GGCTCGGCCTGCACCCCCACCCGGCTCGGCCTGCACCCCCACGCGCAGCT CCTGCATCCCTCACCGGTAAGCGTCCCCTCCCCCACCACCCAGGATCCGC ATCGCCGACCGTCGGAACCGCACCGCAGCAAGCCGCATCCGCATCGTGAG CCGTTGGATCTGCACCCCCGTCGGTGAGCACCCCCTCCCCTCAGCTACCG
                                                                                                    106700                                                                                                      106800
TACCCCCACCCGGCTCGGCCTGCACCCCCTCCCCTCAGCTACTGTACCCC CACCCGGCTCGGCCTGCACCCCCACCCGGCTCGGCCTGCACCCCCACCCG GCTCGGCCTGCACCCCCACCCGGCTCGGCCTGCACCCCCACCCGGCTCGG CCTGCACCCCCACCCGGCTCGGCCTGCACCCCCACCCGGCTCGGCCTGCA
                                                                                                    106900                                                                                                      107000
CCCCCACCCGGCTCGGCCTGCACCCCCACCCGGCTCGGCCTGCACCCCCA CCCGGCTCGGCCTGCACCCCCACCCGGCTCGGCCTGCACCCCCACCCGGC TCGGCCTGCACCCCCACCCGGCTCGGCCTGCACCCCCACCCGGCTCGGCC TGCACCCCCACCCGGCTCGGCCTGCACCCCCACCCGGCTCGGCCTGCACC
                                                                                                    107100                                                                                                      107200
CCCACCCGGCTCGGCCTGCACCCCCACCCGGCTCGGCCTGCACCCCCACC CGGCTCGGCCTGCACCCCCACCACCCCTCCCCCAACACGCATCCAGACCG ACCTCGGCCCTGCAGTGGCCGGGCCCGGAACACGTTACGTATTGAAAAGC CGTATCGCGACCGAAACCCGTGGCCCATCCCCCACCGCGGGCGAGGCCAA
                                                                                                    107300                                                                                                      107400
GCCGGGTTGCGGCCCACGGCTCCCACTGTGGGCGAGGCTGTCACCGTGCC GCCACAGGCCCCTCCCACATCTAGGTGTGGCTGTCGCGTCACCGTCATCA GCCACACCCACAAGCCTCGTCACGATAGGGCCAGACGTTACGCACAAGCA CATCCCCCGAGAAGCCACGCCCACCGCCAAACACGCCCGGGCGGCTCTCA
                                                                                                    107500                                                                                                      107600
CAGACCCAGAAGCAGCAGCCGCTGTCGGCAGTAGCTTCTTCGTCTGCCCT CGAACGCTACCAGCCTTTTTCGTACCCAGGCGTCTTTTTCACACAAAAAA GGCAAAATTTTACCCTTTCTTGTTTTCCTCCCAATAAAAAAGCTCGTCCG AGAGCACTCGGCAACGTTTCCATATGGTGAGCTTTCCGGTACGCGGCGTG
                                                                                                    107700                                                                                                      107800
ACCGTATCGAAACGCTTAGGAAACGTACGTCCGCGACCCACGTTTCTCAG CCCAGGCCTTTTCTGTCCGTTTGAAAGGCCCGCACGCGGCATCAGTGCC ATCGAGCTCGCGCTCGGCAGTCGACGCATCGCGTGTCTCCCCCTTCGGTG AGAGAAAAAGCACGGGTGCGGCCGGCCGGTCTGACACCGTATTGCGGCGGA
                                                                                                    107900                                                                                                      108000
CGAGGTTCGTTCGCCGGTTTTTTATGAGCTAACATCGTCCGATTTAGGCT CGTAGCAGGTTGCCAGGTCTGCCCACAAAAAGCTACGCTCAGCATGGGCC TCGCCGAGCTGGTAACATTCATCGAAAGCCTCTTCATCACGGTCGACGCC GCTGAGCCGGAGGGTCCGTAGTCCGGCGGGAACGCTCGACGCAAACCCCT
                                                                                                    108100                                                                                                      108200
TCGAGAAGAAAAAACCCGCAGTCGTAATATAAGCATGCATAAAAACTTAA AAAAACCATGGACGATGAGCCATGGGTAGATCGCGAGTCATGCCCCGTAC ACGAAGGAGCCCCGTCACAGTCACACAAGCAGCACACGAACACGGCCCAC TTTGTTATCTGTTGAGAAACCGTTAGCGATACAATGCGAGTAACGATAGA
                                                                                                    108300                                                                                                      108400
AAATGAGTAAACCGTTTGAAGAGTCAGTATCTTTTATTTGTTACGCGTTC TCGCTGCCCTCAATCCCGCTCATCATCGTCTTCGATGATGTCCACATCTA AATCCTCATCGTCTTCCTCATCAAAGTCCCTCTCGTCCTCACTGTAACAC AAGTCGTCGCAGTCCATCAGTTGATGCGACTGAAAGTCCAAGTCCTCGGC
                                                                                                    108500                                                                                                      108600
GTCGTGCTTCACGACTCCGTTTTCCATACCGTCGTTCTCGTCCTCGCTCA CCGGGTCGCCGTCGGCGACCCCGGGGGTCAGTACCACGTCCATGGTGCCG GCGCGCAGGGCGTCGGGCGCGAAGGACGATAGCGCGTTTTGGGGTACGAG ACCGAAAGGGAAAACGGGAGAGGAACCGCACTCGCGCTCGGCCTCCGTCT
                                                                                                    108700                                                                                                      108800
GCGGAGACGATACGGCCTTCGTCACGGAGGCCGTCTGCTGGGAAGGCTGT TGATACCTAGAGATACTGCCCGGCCCGGGAGTCGCGGCTTGGATGATAGG CCACGCGGTCGATATCGACGTCGGGACGGACGTCGGCAGGGACAACGGCG GCGGGGATAGGGCCGTGGGAGACGTCGGCTCGACGGATGCGGCGGTCTGG
                                                                                                    108900                                                                                                      109000
GCCTGGATCGGAAAGACGACGGCGGCGACGCCGGCGCCAGAAGACGACTG TCGCTGGGGCTTCTGTTGGTGCTGCTGCTGGTGCTGCTGCTGGTATTGCG GCTGTTGCTGACGACGGACGGTCTCGTGATACCGTCTGGCGCCGATCCGAC GATCTGTTCAACGGACTGCGGTGCTTCGTGGGCGACGCGGTGTCGACGTC
                                                                                                    109100                                                                                                      109200
GCGACGCGCCGTCTCTCTGCCGACGTCTCCGGCGGTCCGTTGCGGCTCGC GCTCGCCGCGTCTCGGCCTCTTGGGTATCACGTAGCCGTCCAGCGTCGAG GTAACACACGCGGAGGCCCTCTTCGCGGCCGTCCTGGGGTCTCTGGACGA TATCTTGCCGGTGCCGTCATCTCCTCTCAGAGAACGACGATGACGATAAG
                                                                                                    109300                                                                                                      109400
CGTCGGACTCCAGGGGACAACCACACGTCGCGGCCTGGGCTCCCGATCCG GTCTGCGCATGCAGCCGCCGTTTCTTCTCGAGGCGCGTGTCCGAGGGAGG TTCCGACGCCGTCGCTGAGACGCGCTTCTCTTCGCGTGCAGGGACGACGT CGTCCCGTCGCGGAGAAAACTGTAGGGTGGACACGGAAGCGAGGTCGGAG
                                                                                                    109500                                                                                                      109600
AGGAAATCTCCGTCGTCCGCGCCCTCGCCGACGCCATCCGTCTTCGCGAG CGCCAAGTCGGGACGGCCGTGGGCGCCGTCCAGATAGGGATAGTACATCA GGGTGAGGCCGTAGGGACTCAAGAGGCGCGTAATGCGGAACTGGCACACC TCGTCGTCACACTCATGCGTCTTGAGGGCCCGCAGGACGACGTCGGCCAG
                                                                                                    109700                                                                                                      109800
CATACCGCATCGGTAGTGTCGCAAAGCCCCGTTGGCGTCGTAGTCGGACA GCACGTGCAGGCGCTGGGGTTGCTGTCTCATCCGGCGACGCAGGGATCCG ATGCTGCGGTTGAAGTAGGTGAGCATAGCCAGGGCGCGATGTAACGGCTG GTCGAAACGCGCGATATGCTTGCACTGCGCCGCGGGTTGGAAGCCCTTGC
                                                                                                    109900                                                                                                      110000
CGCCGACGACGCCTTCGACCGCGCCGTTGCCGGCCATCTGTCCCAGGGGC AGTTTATTGGCCAGCTGCCGGAAGATCTGGTAGTCGTTCTGCGACCTGTT GGGACCGCAGGCGCCACGCATGATGCACATCAGGTTCGCCATGTTCAACT TATTGAACAGAGCGTATCTCAGCGGGCTCAGAGTGGTGAGGTACGGGTCG
```

FROM FIG. 1W 110100 110200 110300 110400 110500 110600 110700 110800 110900 111000 111100 111200 111300 111400 111500 111600 111700 111800 111900 112000 112100 112200 112300 112400 112500 112600 112700 112800 112900 113000 113100 113200 113300 113400 113500 113600 113700 113800 113900 114000 114100 114200 114300 114400 114500 114600 114700 114800

FROM FIG. 1X

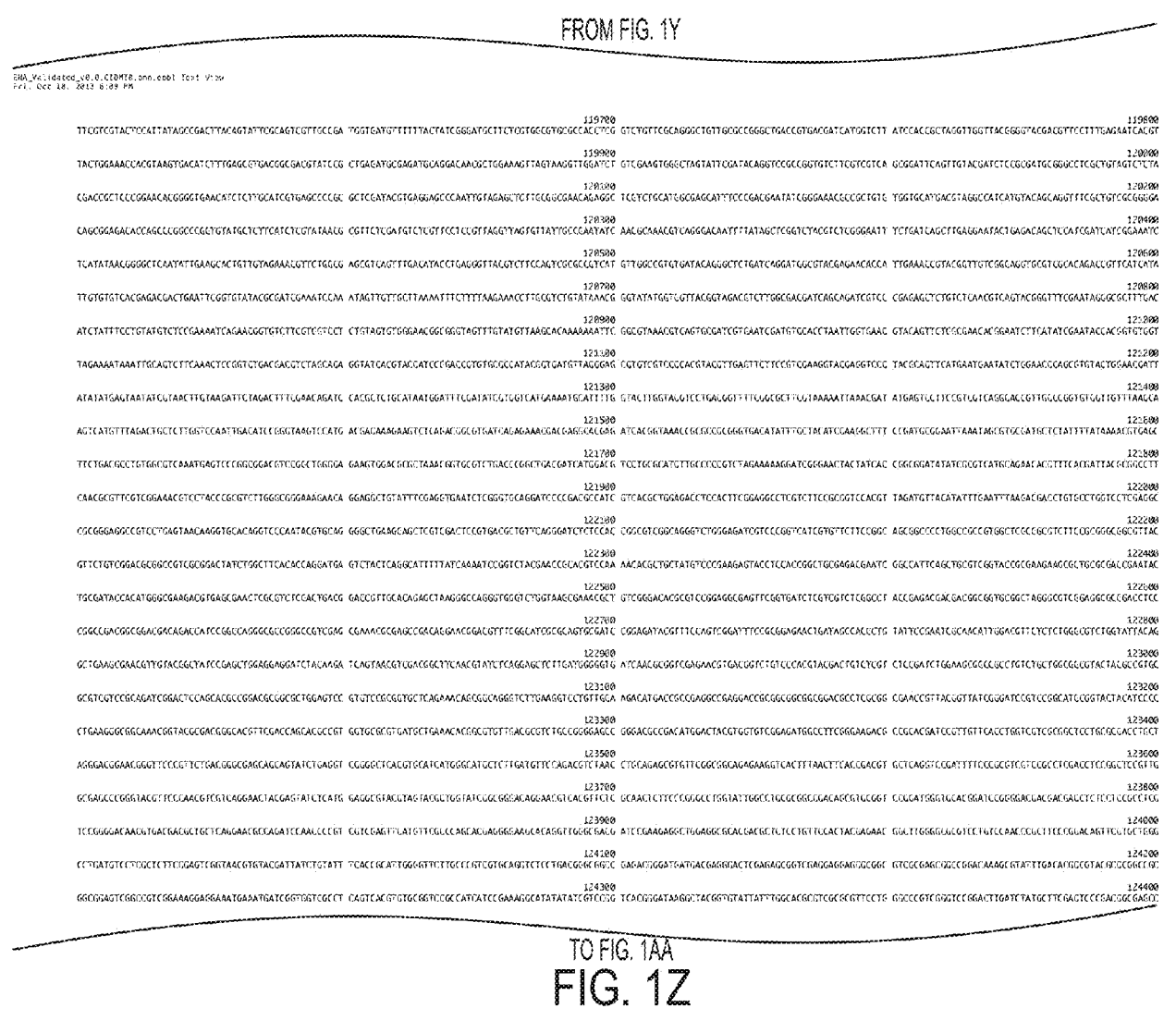

FROM FIG. 1Y

ERA_Validated_v0.0.CIDMIR.snn.embl Text View
Fri. Oct 18, 2013 6:09 PM

FROM FIG. 1Z

ENA_Validated_v8.0.CIOMTR.ann.embl Text View
Fri, Oct 18, 2013 6:09 PM

```
                                                  124500                                                124600
GGCCGCGCGGCGAGGTCGCGGGATAGCGATCGTCATCCGGGCGAAAGGAT ATAGAGAGAAGACGGGTCGATCATGGCGACGACGGCGGCGACGACGACGG TGTTGACCGTCGTCCATCGGCTCAGCCTGGCCGAGACCCTGGCCAGGAAC TACAGTTACTTCTACATTCCCATAGTGCCCCAGTCGTTTCAGATCTGGGT
                                                  124700                                                124800
GGTGCCCTCGGCCGTCTTCTTCTCCGTGTTGTACGTTATCACCCTGTACA AGAGGAGGTTCAGCGACGCCGGCAGCGTCGTCAGCATCGGCATCATGGCC CGCTGGTTCACGTCCTTGCTGGCCAACGCGGTTCTGCAGGTACCCGTGTA CAGGGATTTCGGGTTCAGCGACAAGACGTGCAAGACGCTGCTCTTCATGG
                                                  124900                                                125000
ACGACATCGGCAGCTACGCGTGCGTGTTGCAGTTCATCTACATGATCGTG GACATGATCTACGCGACGATCCATCCGCGCTTCGACAGGAAGACCTTCAC CGCCGTTACCACCATGCAGGCGTGCGCCCTGTGCTGGGTGACCGCCGCGT TCCTGGCCGCCCCGTCCGGGATCGTGTCCGTCTCGACGCGCCAGCTCGGC
                                                  125100                                                125200
AGTCGCGCCGCGTGCACGGTCCCCCTGACGCACAGCACGCTGGTCATGAC CATCAAGATCTCCTTCGCCGGCTGCGTCCCCCTGCTACTGACCATACCGT TGTGCGCCGAGGTCGCGTACGCCGAGAGGCGCTCCGACAGGTACCCGCAG CTCGCCGTGGCGGTGCTGCACCACATCCTCATGTTCCTGTTTCACGCGCC
                                                  125300                                                125400
GTACCCCATAGTCAGGGCCCTGCGAGCCGTGTACGGCGATTTCAGGGATC CCCCCGGGATTCTGGACTATGCCGAGACCGTGTCGGAAGGTCTGCAGCTC GCCAGACTCGCCGTGATTCCCATGATCGTGACCCTGTTCGCCGAGCCCCG CTCCCTGGGGAAGGCGATGCGAGACGGCTCGTCCTTCGTTCTGGGGCTGT
                                                  125500                                                125600
TGAGATGGTTGGTTTCTCTCGTCCGCGAAAAGCGCCCGGACGTCGTCGCA AAAGTGGTGCACGCCGTCAAGGCCCTCCTGTTGAAACAGCTCCTCGGATG CGAATCGAGGAAATGGCCGACGGGGCATGATAAGTGTTTCGTGCATTACG AAGTACCCAGTAACTCGCCCTCGATCGTCGACGAACAAGAAGGAGAAGAA
                                                  125700                                                125800
GAGGGTTCTCGGTGCGATTCCGTCGTGACCGCGGACTGCGGGATCTCTGA CCAGACCGAAACGGCGCCCAGCCCAGACGTATCGGTAGCGTTCGAGCCCG ATTGCGTTAAGCCGTGACGGCGCCGTCGGGCGGCCGGGAGACGCGCAACC GATACGGCCGGTGACGTGCGTGCGAGCGTGCAATAAAGACGCGATCGGTA
                                                  125900                                                126000
CAGAACAAAAAAAAAAACACGAGACGACGTGTGTGTGCGCGTGGTTATTT CGATACGTGTCAGTTTTTATTCAAACACCCCGTGCGGTCCAGATGTCTCC CTCCCGTCCGCCCTCAACACAACGTGGGTATCCGGCTCGCGTTGGTCAGG TCGTTCACCTCGGGGTACGTCACCGGAGGTAGCGGTGGGGGGTTTCGGTA
                                                  126100                                                126200
CAGGGTCCCAGTGAACGTCCTCCAGTCCTGTATCAGAAAGTTATAGAGTC CGAGCTCGTGATCGAAACGCTGATCCCGGAACGCCCGACGGGAGACGCGC AGTTTCCCGTCCGACAGCAGGGACAGCATCCACATCTTCTGACACAGGAG CCGCATCGCGGGCTCGTACTGATCTTCCCCCCAGTGTTTCGTGAAGAACC
                                                  126300                                                126400
TGGCCATCCTGAAAAAGCGGTGGCAGTAGACCGTCCCCAGTGAGAACAGA AAGTTCCCGTCCTGCGTCATGTCCCGCGGCAGCCGGATGGCGATGCCGCA CTGGTCCCTGACGAAGTCGCACAACAGTCCGTGCGCCGTGGGCATGCTCG CCAGCGAGGCGGACAGCTGCGCCGCGCGCGTCTCGTTGAAAATGCCCTCG
                                                  126500                                                126600
ATCTGGGCGTCGCGCAAGACGCGGGTGATGTAGCGGTACAGCTGCTGCCA GTACTGAAAGGAGATCTTGCGGTTCAAGATCCCGTTGTCCCCCACGCCGG AGTTGTGCAGCGTCTCCCTGAGCAGTAGGGTCTCCACCCCCCTCTGAAAC AGCAACACGCATCGCAGTCGGAGGACCTTGAGCTCTTCCAGCCTCATCCT
                                                  126700                                                126800
GGACAGGGGTCTCCCGGATAGCATCTTTTCGGTGATTTGTATTATTAGAT CGTTCTGGGGATCTATGTCCACGAACCTCCCTATCTGAAATCCGGGCCGG TCCTCGTCCTCCCGCGGGTCCATGGAGACCGACAGGCTTTTCGTGAGCGG TTTCCTGGCGCTGTACCGGGAGCAGCCGCAGGAGGACTGTCTCCGGCTAT
                                                  126900                                                127000
CCCGAGACGTGGTCGCTGCGAATCTACCCGGCGTGGATCCGTCCTCGATA GCGATCAACATCAATCACGACGACAACGCCGTCGTCGGTCGCCTGCACGG CCTGTTCGATCTACCGAACGGGCTGTTCTGTTTCGGGGAGATCAGCTCCC CGTCTTTCCTGGATATCGTGCGGCGCAGCGCCGAGAAGTCCCAGCTGCTG
                                                  127100                                                127200
TCTCGGGGTCCGGGGAACGGGCTGAAGCCCGACGCCGTCGTGGAGTACCT CAGCACGGGGTACCCCGGCCTCTCCCTGTCCAGCCGTTCCACCGACGAGC GCCGCTGTGACGCGCCGTCCGGGCCCGCGCGCGCTCATATAGACGGCGAG ACGACGGACGAGGGTACGTTTTTCAGGCACGTCGCCATATGCGGCGTCGG
                                                  127300                                                127400
TCGGAGGCGAGGCACGCTGGCGATCTACGGTCGGGACCCCGGGTGGATGC TGGACAGGTTTCCCGGCATCTCGAACGAGGACAAACTCCGGATGGTCACC CGGGTCGTCTCCGCCGTCTTCGCTCCGGGCGCGAGGACGGGCGCGGACGC GCGGGATCCGTTCCGTTCCGATCCGTACGGCCTGCTGGCCAATTCCGTGG
                                                  127500                                                127600
ATACATCGTACATTCGCGAGAGGTTCCCGAAACTGGATTACGATAAGAGG GTCCTGCGGATACCTCCCGACACGTACGTGAAGGCCAGCGAGAGTCCGAC GGCGTCTCGGGCCGAAGGCGACTGTATTATTAAAAGGAGTGAGCCTTTTC TCGTCTGGGAACGTCGCGCCGAGGAGAGCGGCCCGTCGTGCGGCGCGGCC
                                                  127700                                                127800
GACACCGACATGTCCGCTCAGCCGCAGGTCGTCCCCACAGTCGTCCCGGC CGCCTCCGCGCCCGCCGTGCCCGCCGCCGCCGTCGTCTCGGCCTCGCCCG CGCCGCTCGCCCTGTCTAACGATTGCGTCTATCTTCCCAAGGATACGTTC CTGTCGCTGGTGAACGCGTCCAGGCGAGAGGCGACGTTTCCCGACGTCGG
                                                  127900                                                128000
CAGGCCGAAAGACGCGGACGGCGCGGCCACCCTGACTTCGCTGCCCTCGT TCGTGGCTCAGACCGCACCCCGTCCAACGCTTCGTCCTGCCCGAGTCGGTC ACGTCGACGACGCGTCTGCAGCCGGCGCCGTACGGGTACGCGGGCATGGA GGGCCGGTCTCGGTCGTCCGTCTCAGATCGCCTCGTTTCAGACTCCGTACG
                                                  128100                                                128200
ATACGTCTCAGTACGGCGGGCCCGCGGGGTCCGGCTACTTCGGACCCCTG CCGGGACCGTCGCCGCAGGTCCTCGCGCCCATTTCCCAGGCGTCCCCCGC GTCCCAGGTCCATCCGGCCGTCGTGCCGCATCACGTACCGTCGGCCGCTC CGCCCTATCAGTTCCCGAGCGCGGTGCCCGCCGCGGCGCCGGGCACTCTT
                                                  128300                                                128400
CATCCTGGCGGTACGTATCCGCAGTTCTATCCGCACCCGACGTATTACGG TCATCGGGGGTACTACGGAGCGTCGCCGCCGCCACCGCCGCCGTTGGCCG GAGAGCGTTACGGGCCCTACGATCCTCGCTGGCCCGCGGACGCGACGGAT CCTTATTCCAGATATCCTCGGGATCCCGTCGCGAGTAGGGAGCGGGAGCA
                                                  128500                                                128600
CGTCGGGCGAAAGAGACGCGCGGAGGCGGACGACGGGGACGACCAGCAAG TCGCCAGAGAGGATCTCAGTCTGCCCGGTGACGCCGACTATCCCCGCTCC AAGAGGCCCGCCGTCGACGCTCGAGACGTGCGGCAGTCCGGACGCGCGCG CGAGCACCCGGAGTACGCGGAACTCAGGAACGTGATACACGACCTCAGGA
                                                  128700                                                128800
GGGACATCGCGGTCATACGCAGCCTGAGCGGCTCGCGTTCCGACGCCAAC GGTTCTCCCGCCCCGGTGCAGTCGTCGTCTTCTCCGTCCTCGGCGCCCCC GACGGTCGGGGACGAGGAAGACGCCTCGGTCCCGAGCGCCGCGACGACCG GCGTCCCGGCGGTCATCCCCACCGCACACGGTCTGCCCGTCACGACGGCC
                                                  128900                                                129000
CCGTCGGCGCCCGCGCAGCCGACGGACGTCGCGCGGAAGGCGGGCAAGGC CGGACTCCCCGTCTCCGGCGGTCAGCACCACGCTCATCAGCCCGTCAGGG CGAAACCTCCCCTGGTGGTGAACGCCTCGTGCGTCCCCGAGGCGCAGCCC GGCACGTCCCGAGACGCCCAGATGTCCATTCTGGACATTAACCGACAACG
                                                  129100                                                129200
TTTCGTGGACGCTCTGCGGAACATGGAATGACGACTCCACGGTCGCGGGG TCGGAAAACGGGTAGAGAGAGAGAGGACCGGGCTGGGATGGGAAAAGTGG GACCGAACCCCGGGCGGCCAGAAAGAACCGTGCGTGTATCGATTAAAGAT AACGTGACGACGTGTACGTGTGGTCTGGTGCGTTTTATTAATACGCCCGG
```

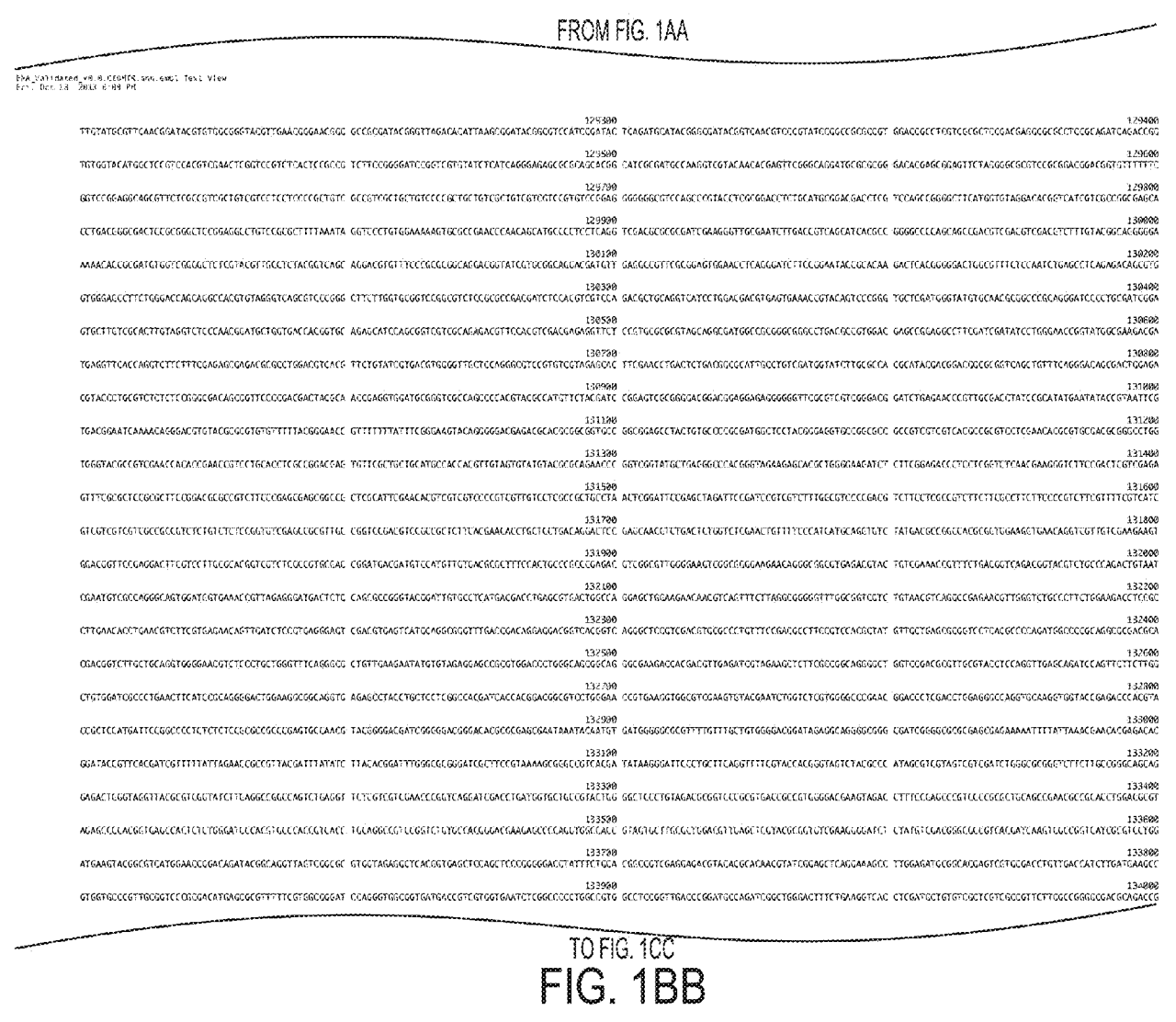

FROM FIG. 1AA

FAA_Validated_v8.8.CEOHIS.ann.xml Text View
Fri Dec 18 2013 6:09 PM 129300 129400
[illegible]

129500 129600
[illegible]

129700 129800
[illegible]

129900 130000
[illegible]

130100 130200
[illegible]

130300 130400
[illegible]

130500 130600
[illegible]

130700 130800
[illegible]

130900 131000
[illegible]

131100 131200
[illegible]

131300 131400
[illegible]

131500 131600
[illegible]

131700 131800
[illegible]

131900 132000
[illegible]

132100 132200
[illegible]

132300 132400
[illegible]

132500 132600
[illegible]

132700 132800
[illegible]

132900 133000
[illegible]

133100 133200
[illegible]

133300 133400
[illegible]

133500 133600
[illegible]

133700 133800
[illegible]

133900 134000
[illegible]

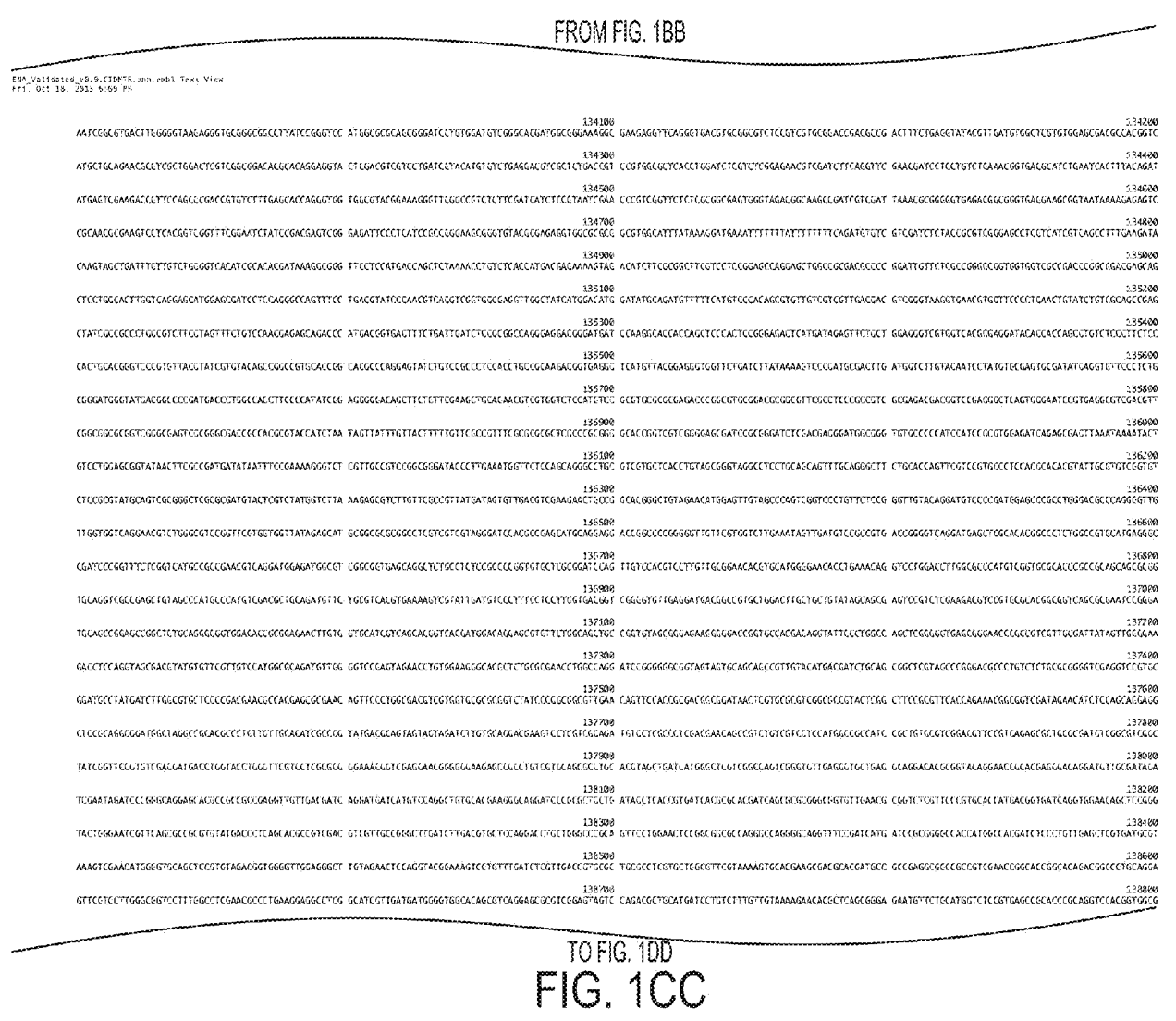

FROM FIG. 1BB

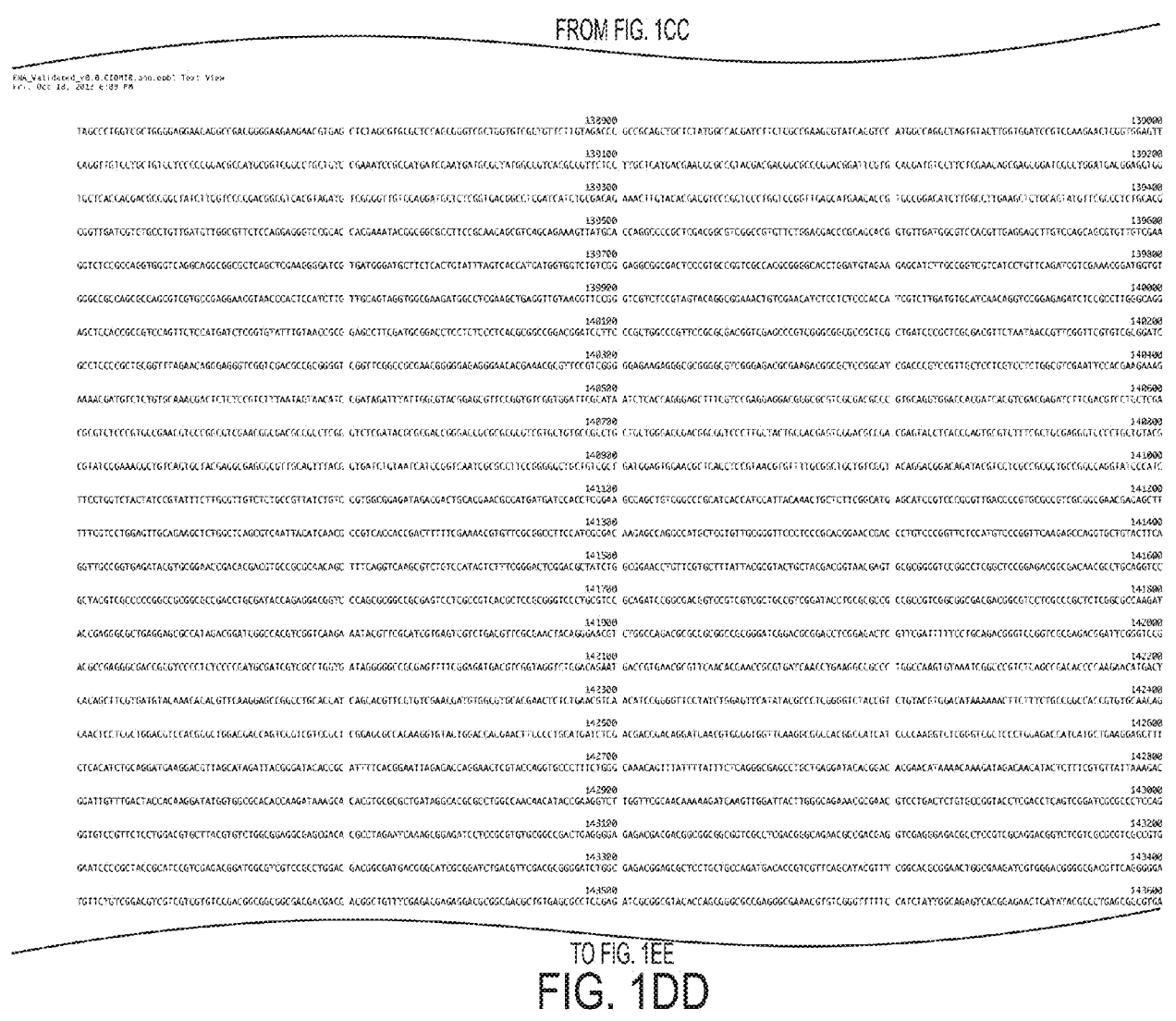

FROM FIG. 1CC

FROM FIG. 1DD 143700 143800 143900 144000 144100 144200 144300 144400 144500 144600 144700 144800 144900 145000 145100 145200 145300 145400 145500 145600 145700 145800 145900 146000 146100 146200 146300 146400 146500 146600 146700 146800 146900 147000 147100 147200 147300 147400 147500 147600 147700 147800 147900 148000 148100 148200 148300 148400

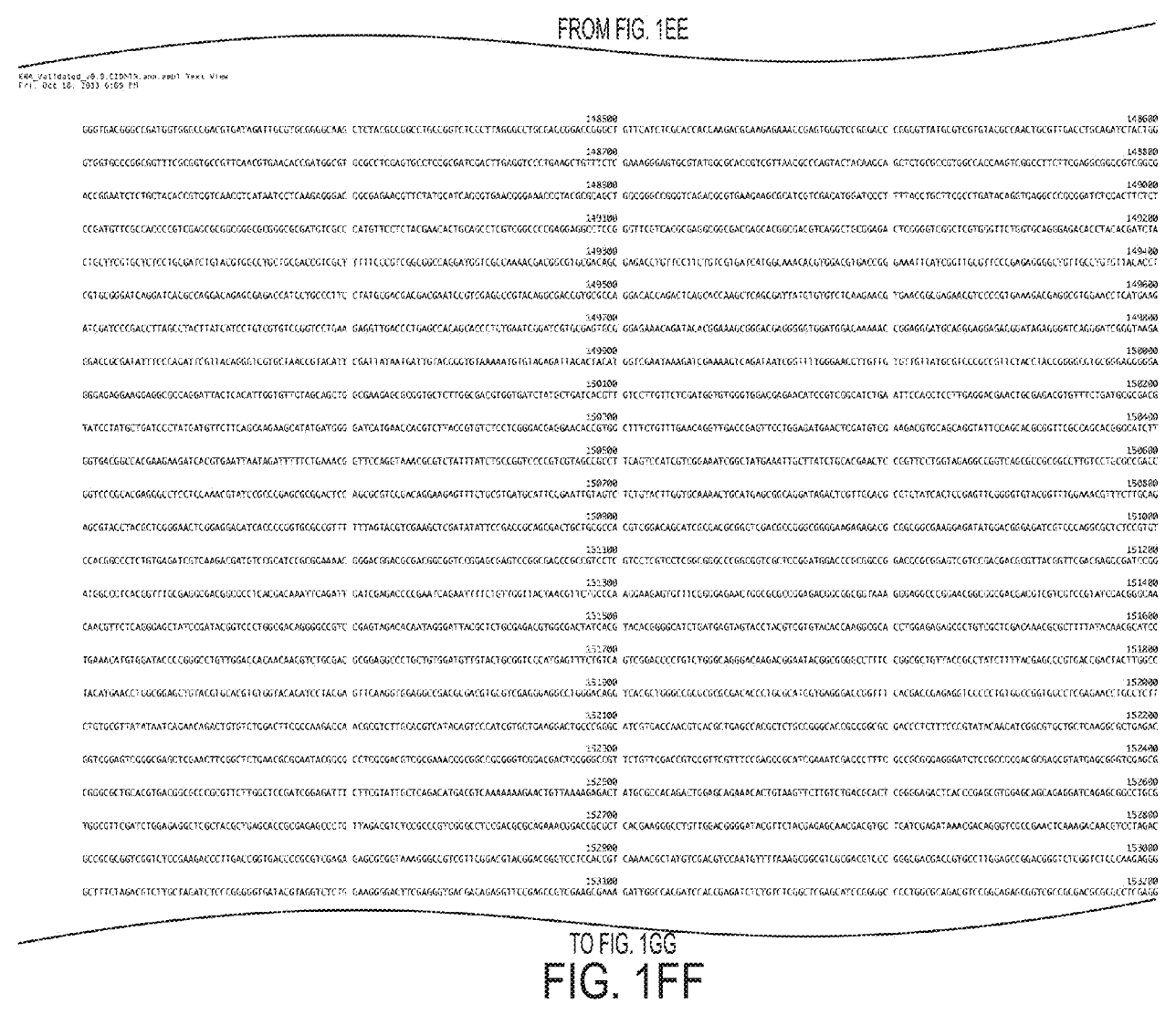

FROM FIG. 1EE

KHA_Validated_v0.9_CIDN13.ann.embl Text View
Fri Oct 18, 2013 6:09 PM

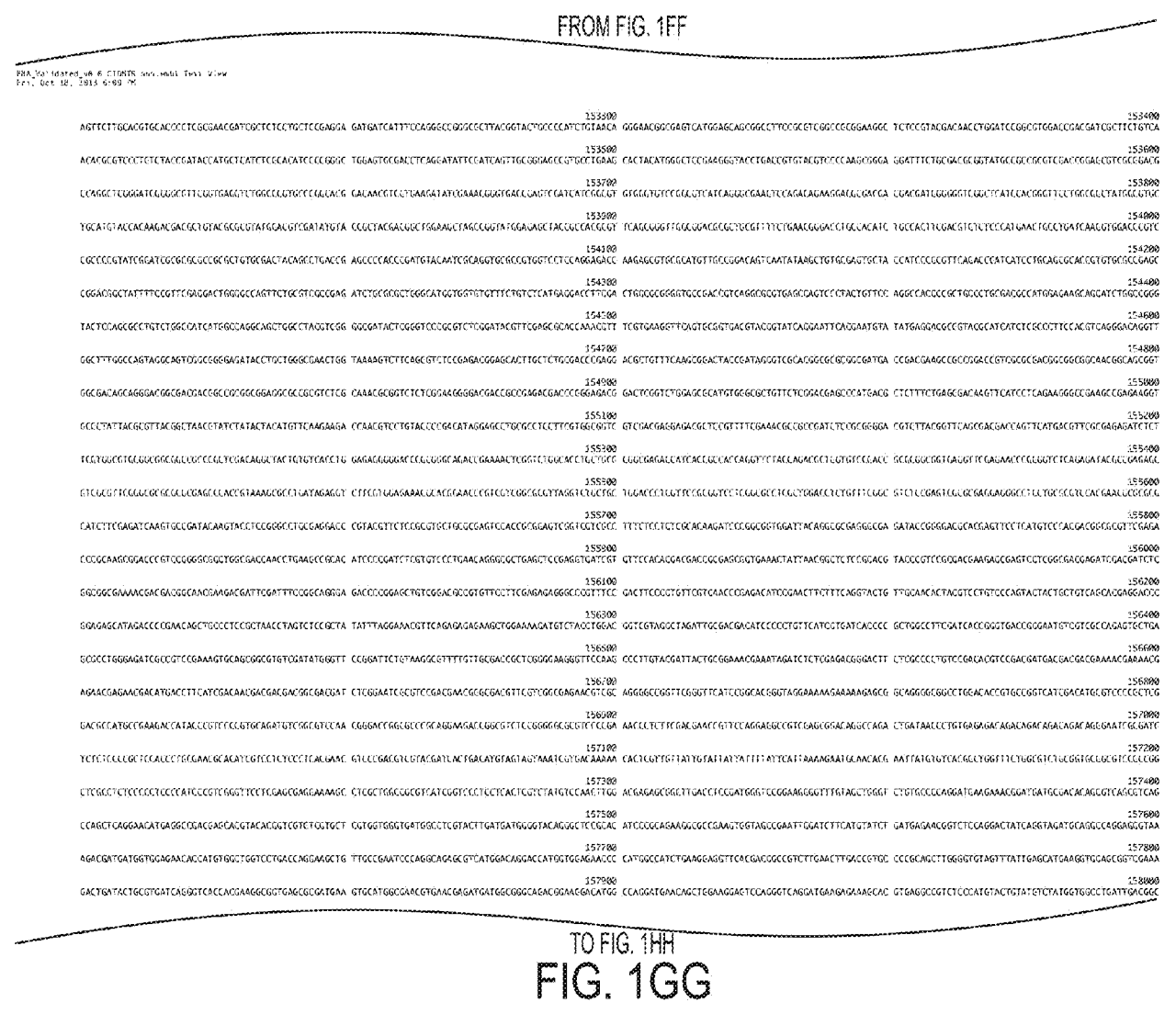

FROM FIG. 1FF

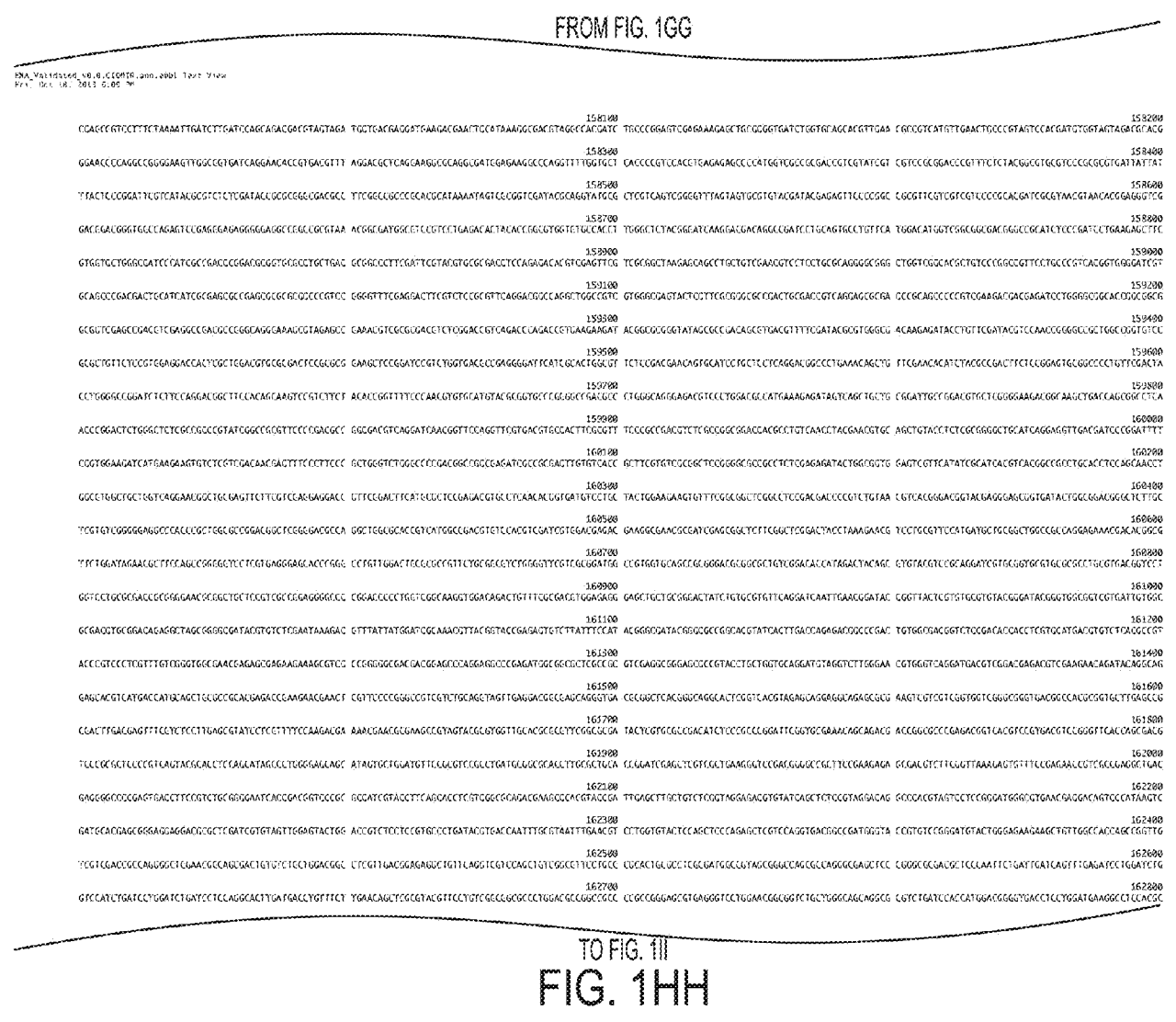

FROM FIG. 1GG

FROM FIG. 1HH

DNA_Validated_v8.0 CODMFR ... Text View
Fri, Oct 19, 2012 6:09 PM 162900 163000 163100 163200 163300 163400 163500 163600 163700 163800 163900 164000 164100 164200 164300 164400 164500 164600 164700 164800 164900 165000 165100 165200 165300 165400 165500 165600 165700 165800 165900 166000 166100 166200 166300 166400 166500 166600 166700 166800 166900 167000 167100 167200 167300 167400 167500 167600

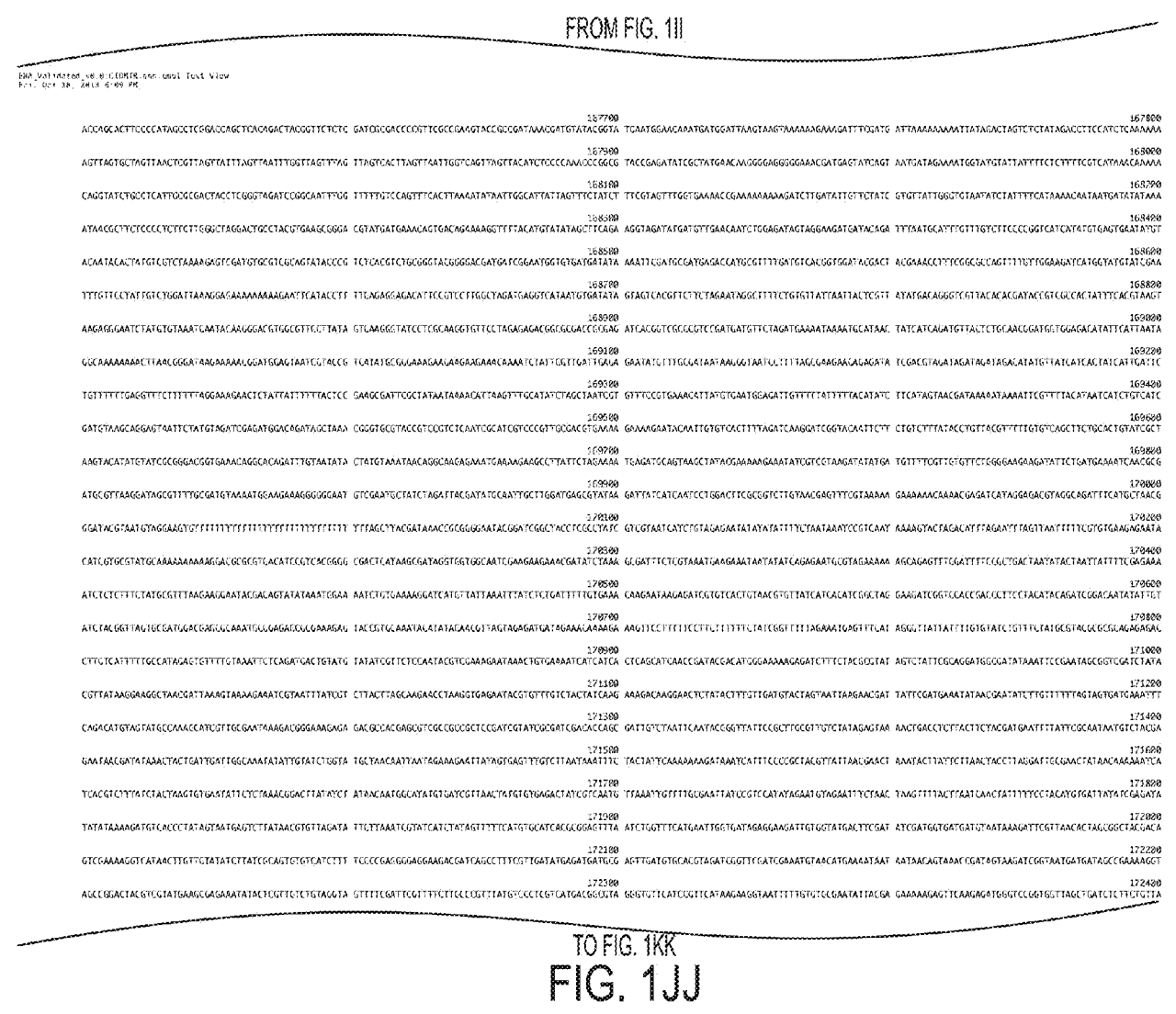

FROM FIG. 1II 167700 167800
167900 168000
168100 168200
168300 168400
168500 168600
168700 168800
168900 169000
169100 169200
169300 169400
169500 169600
169700 169800
169900 170000
170100 170200
170300 170400
170500 170600
170700 170800
170900 171000
171100 171200
171300 171400
171500 171600
171700 171800
171900 172000
172100 172200
172300 172400

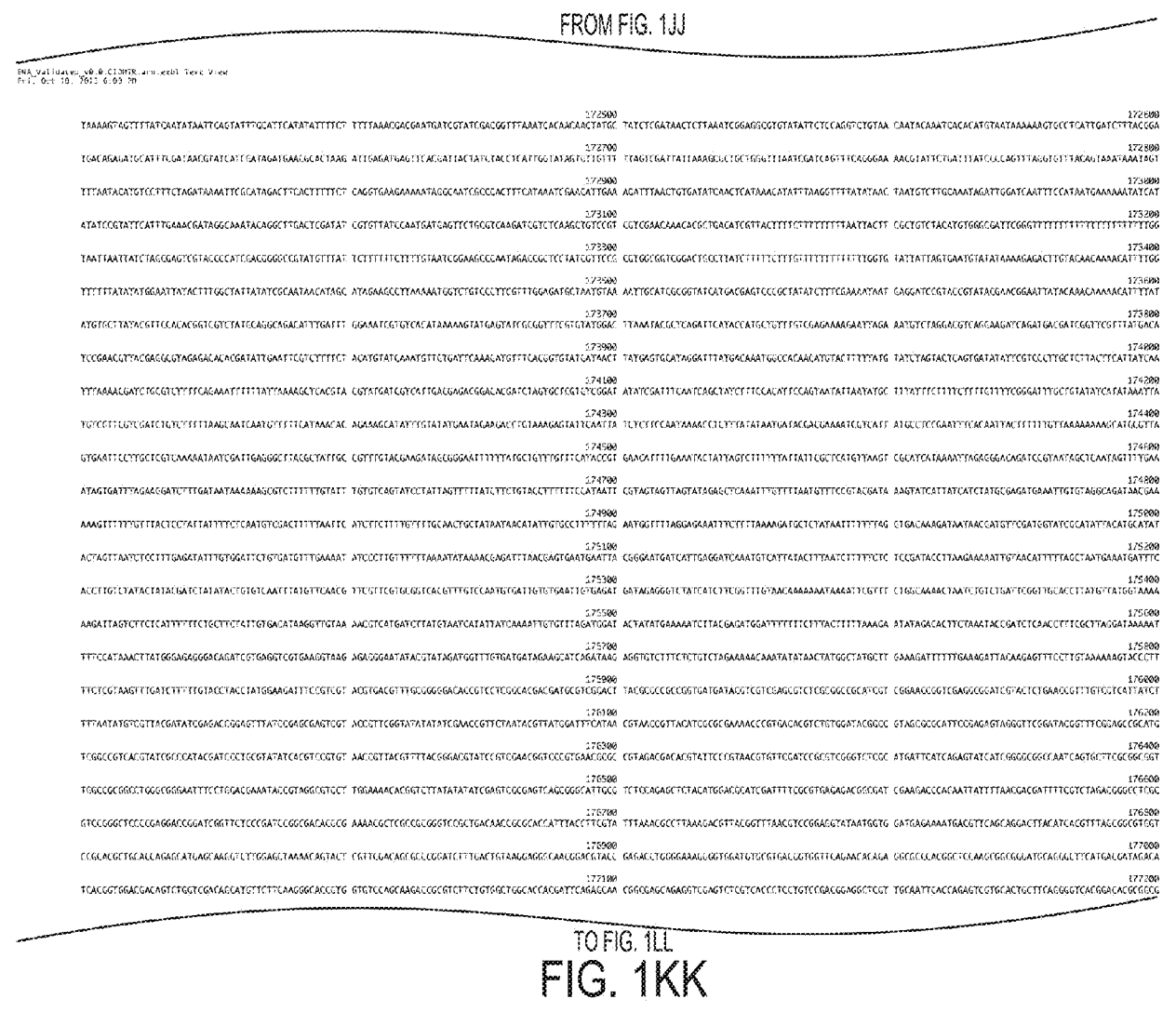

FROM FIG. 1JJ

ENA_Validates_v0.0.C120TR.arn.embl Text View
Fri Oct 10, 2011 6:03 PM 172500 172600 172700 172800 172900 173000 173100 173200 173300 173400 173500 173600 173700 173800 173900 174000 174100 174200 174300 174400 174500 174600 174700 174800 174900 175000 175100 175200 175300 175400 175500 175600 175700 175800 175900 176000 176100 176200 176300 176400 176500 176600 176700 176800 176900 177000 177100 177200

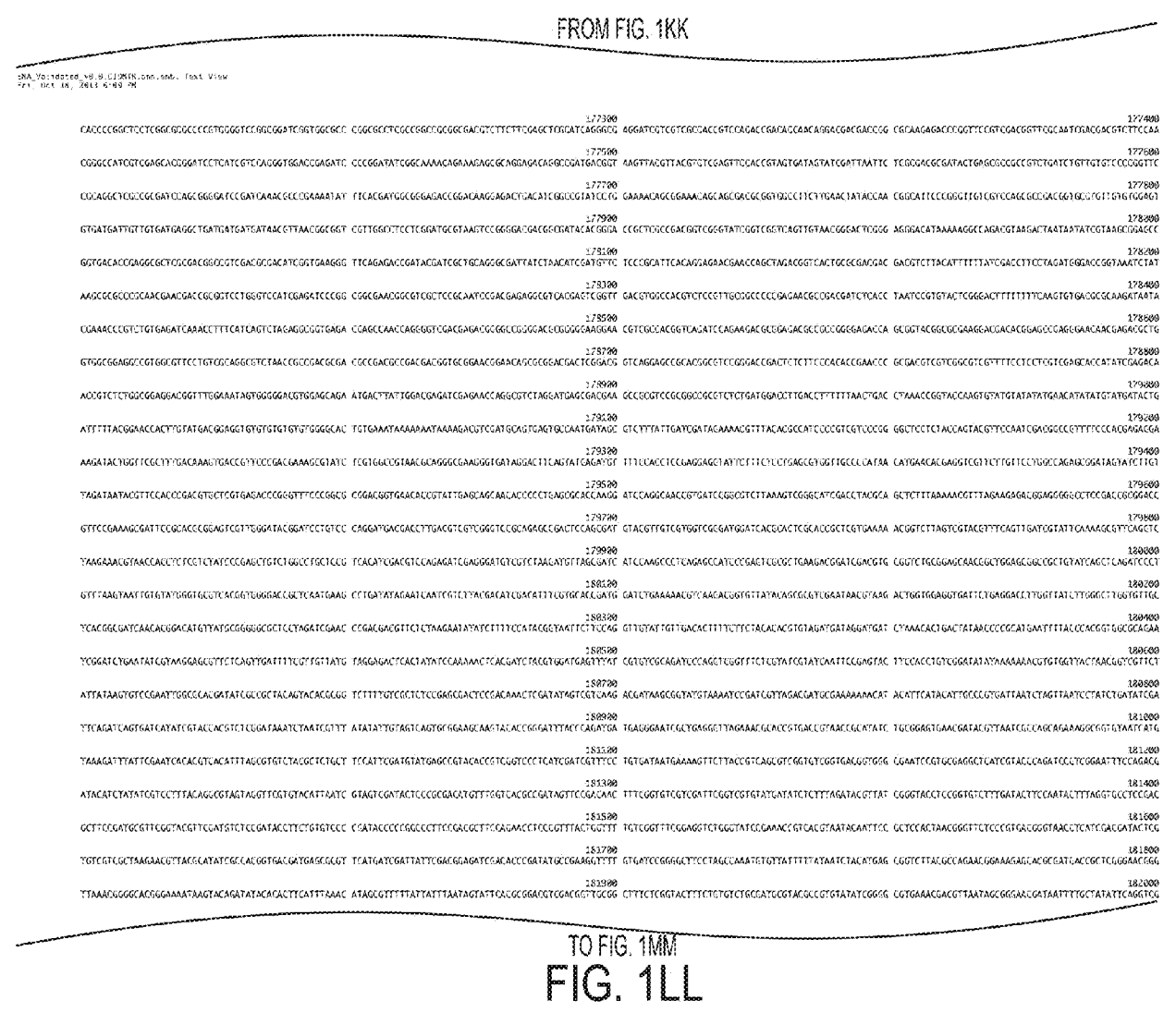

FROM FIG. 1KK

FROM FIG. 1LL 182100 182200 182300 182400 182500 182600 182700 182800 182900 183000 183100 183200 183300 183400 183500 183600 183700 183800 183900 184000 184100 184200 184300 184400 184500 184600 184700 184800 184900 185000 185100 185200 185300 185400 185500 185600 185700 185800 185900 186000 186100 186200 186300 186400 186500 186600 186700 186800

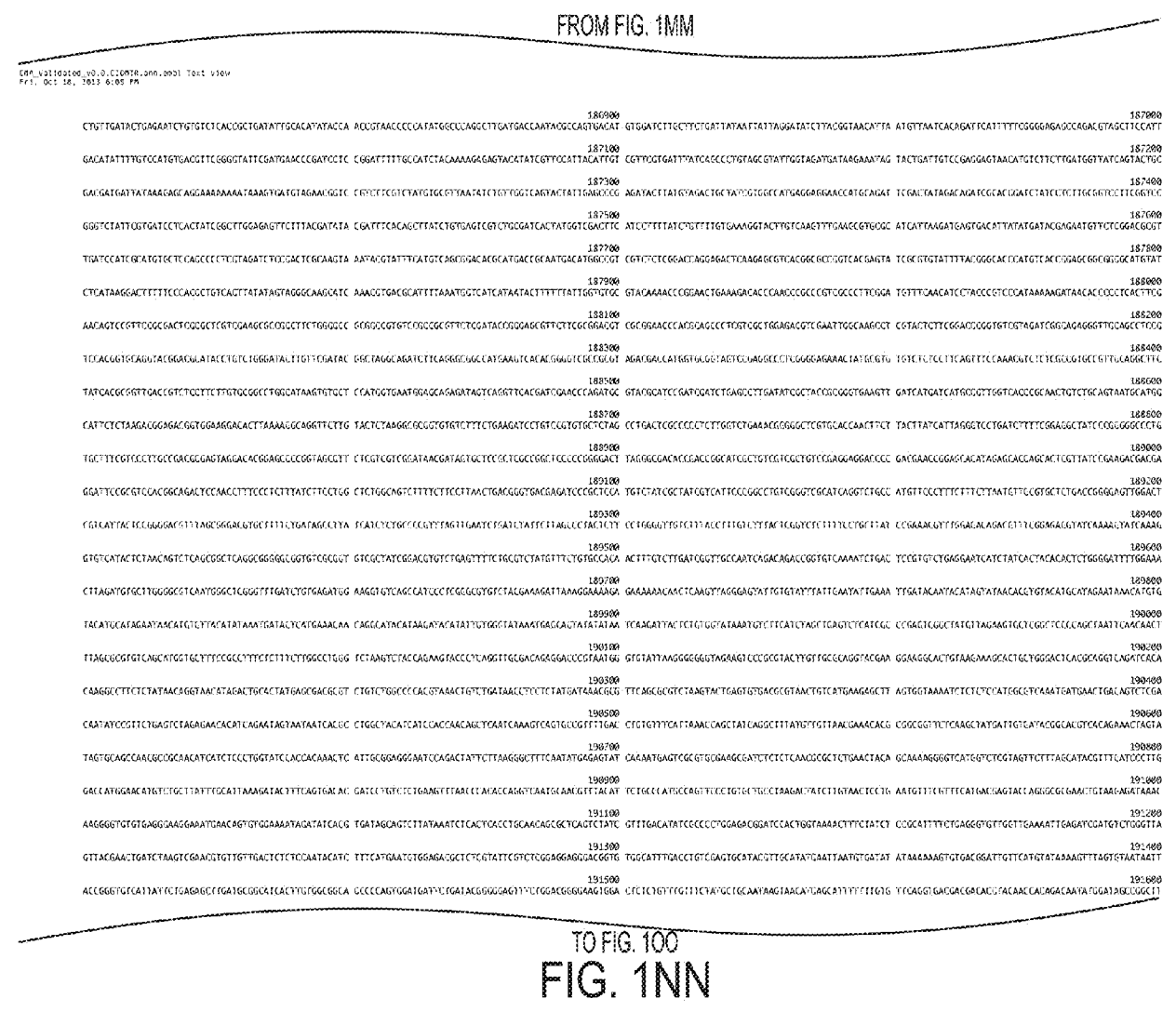

FROM FIG. 1MM

FROM FIG. 1NN 191700 191800 191900 192000 192100 192200 192300 192400 192500 192600 192700 192800 192900 193000 193100 193200 193300 193400 193500 193600 193700 193800 193900 194000 194100 194200 194300 194400 194500 194600 194700 194800 194900 195000 195100 195200 195300 195400 195500 195600 195700 195800 195900 196000 196100 196200 196300 196400

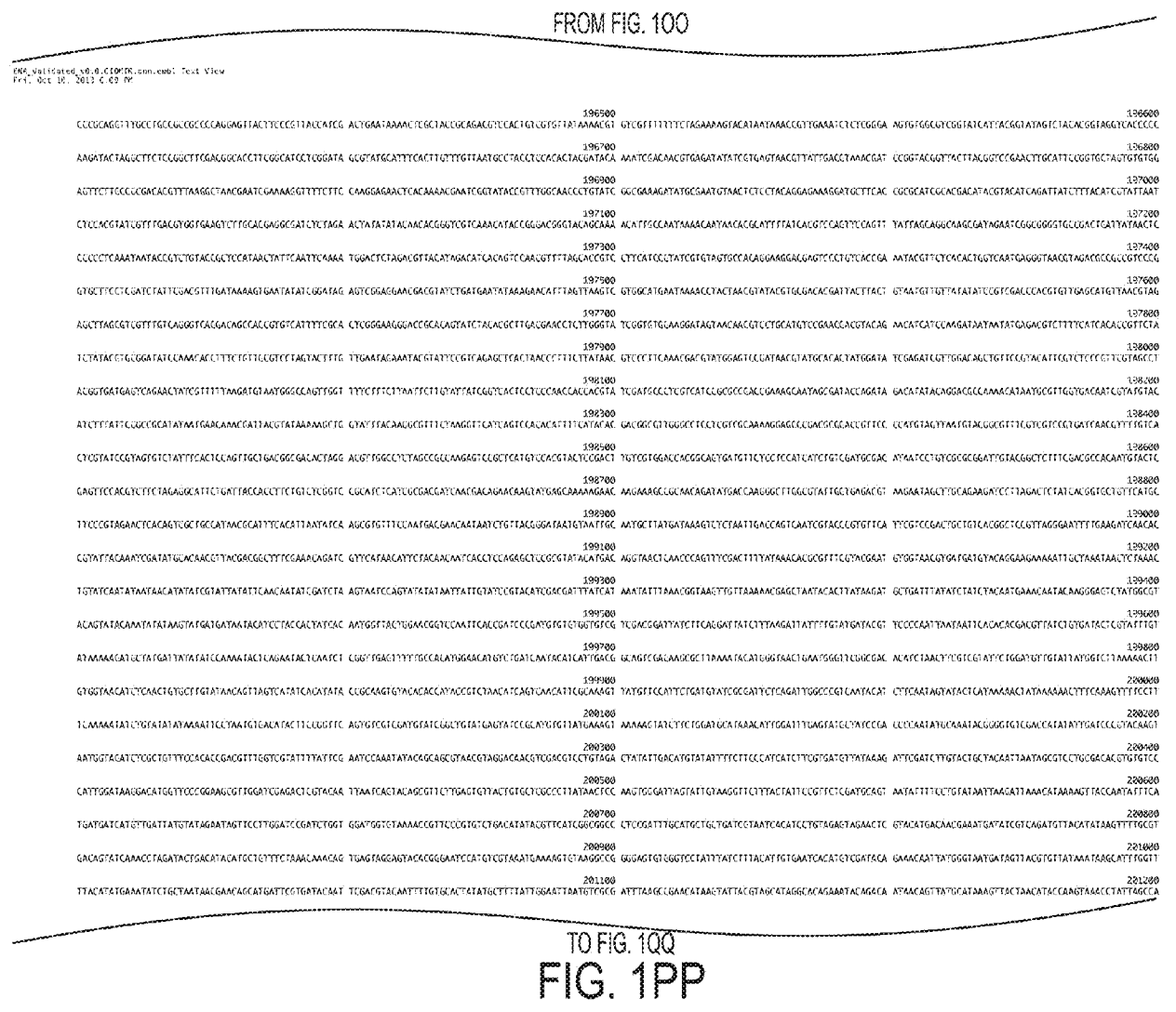

FROM FIG. 1OO

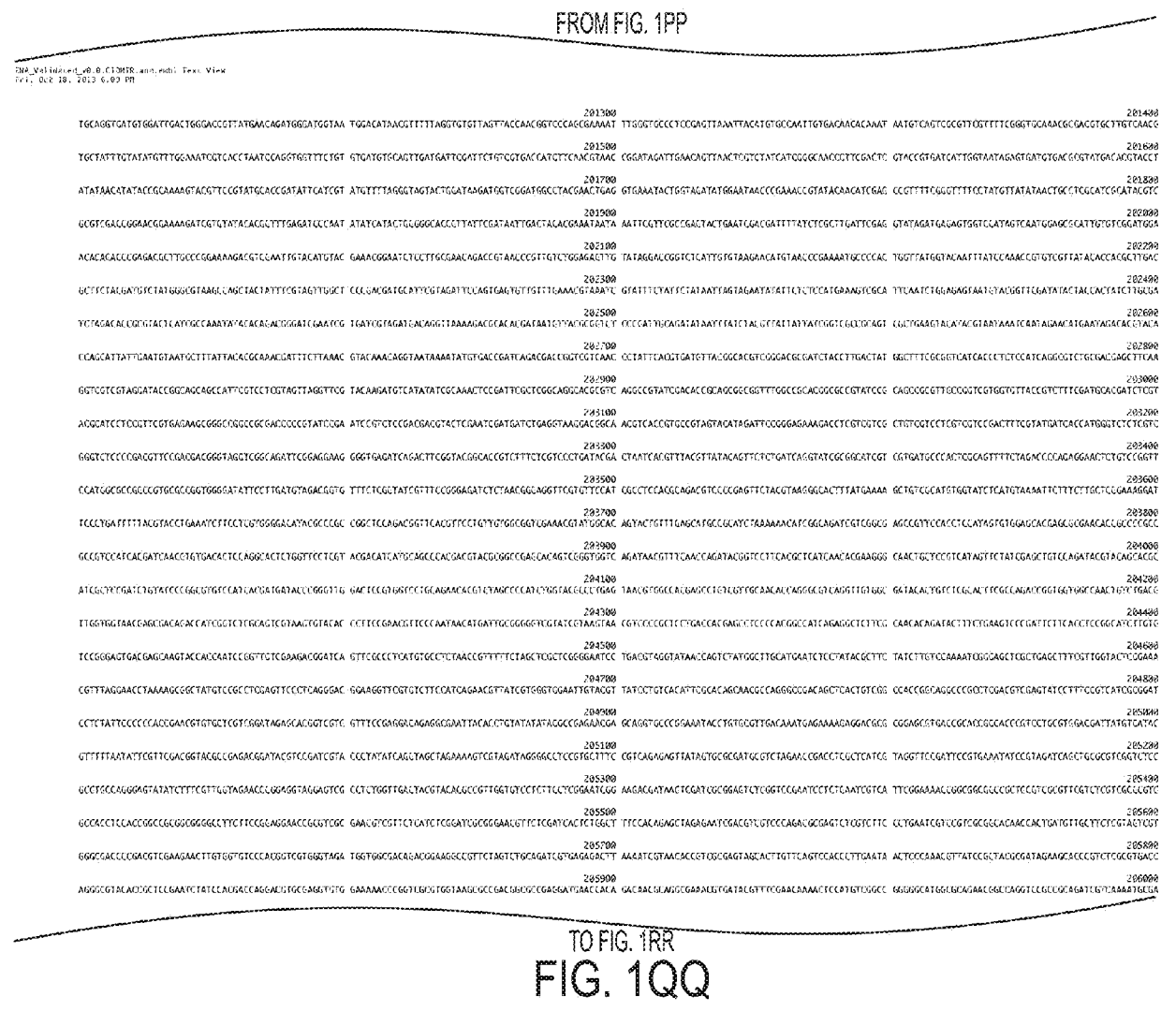

FROM FIG. 1PP

FROM FIG. 1QQ 206100 206200

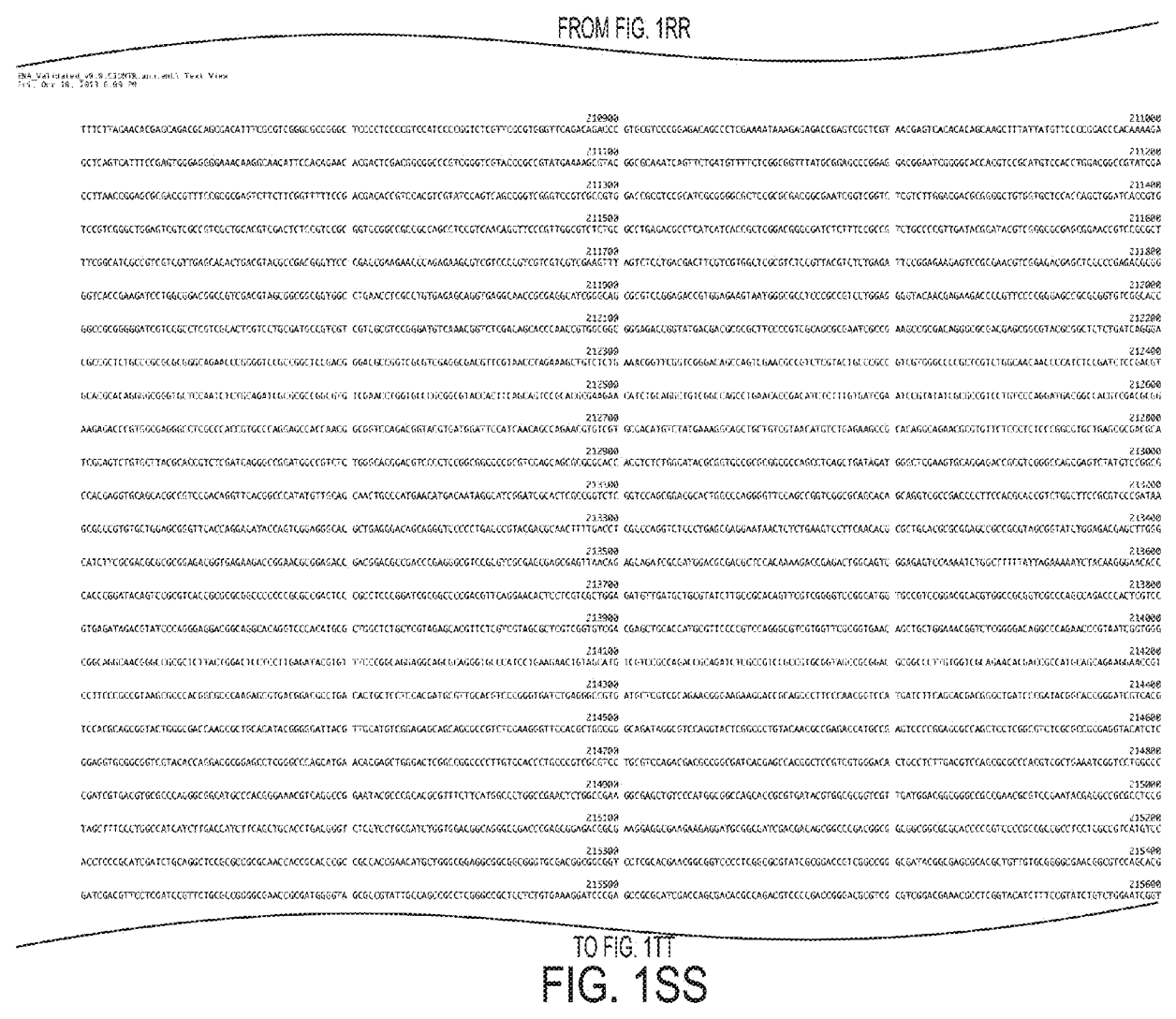

FROM FIG. 1RR

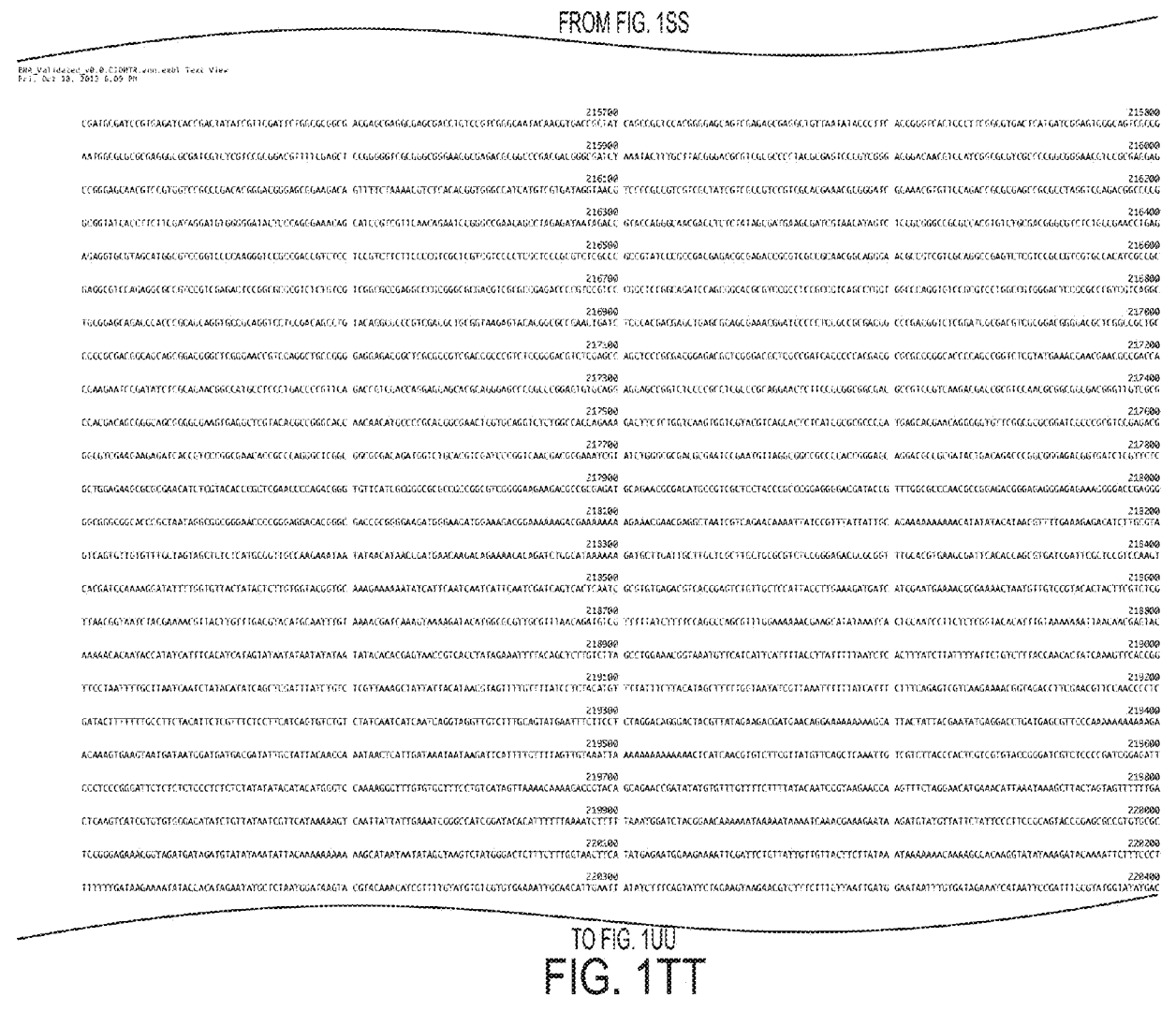

FROM FIG. 1SS

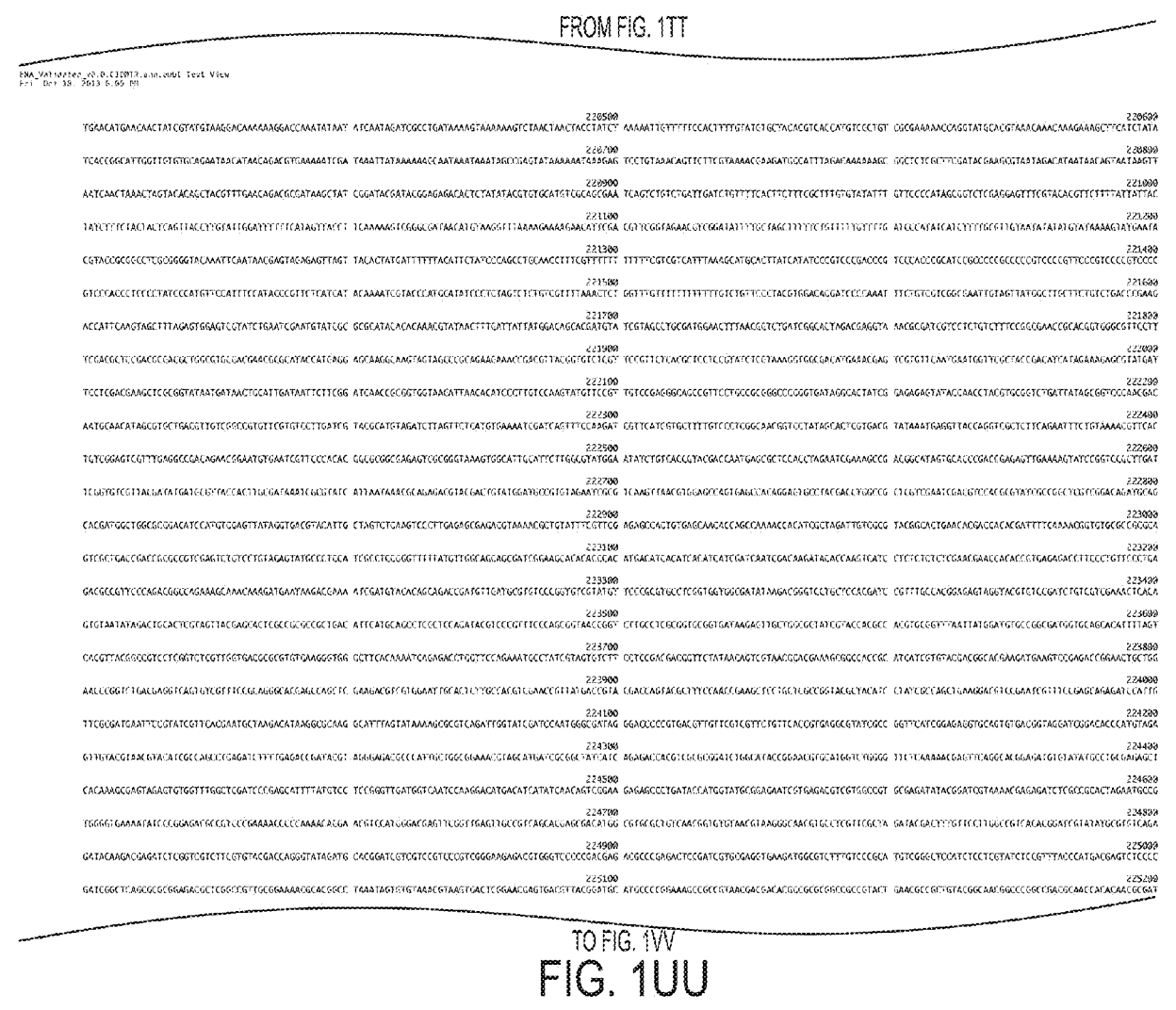

FROM FIG. 1TT

FROM FIG. 1UU 225300 225400 225500 225600 225700 225800 225900 226000 226100 226200 226300 226400 226500 226600 226700 226800 226900 227000 227100 227200 227300 227400 227500 227600 227700 227800 227900 228000 228100 228200 228300 228400 228500 228600 228700 228800 228900 229000 229100 229200 229300 229400 229500 229600 229700 229800 229900 230000

FROM FIG. 1VV

```
EMA_validated_v0.0.C1DMFR.ann.embl Text View
Fri, Oct 18, 2013 6:09 PM

                                                   230100                                                 230200
GCGGTCGTGGCGGCCGATGGCACTGCGCTTGGGGCGGCCGCGCTCGTGTC CGCGCCGTTCGAGCCCGTCGCGGACGGACTGCGGTCGCTTACTGTGGTGT CTACAGGCGACGTCTCAAGCGTCGTGGCGAGCGTCGTGTTTGCCACAGCT CTCGTCGAGAGCATGAGGATCGCGACGCCTGTAAAAGCAGCGACATGTC
                                                   230300                                                 230400
TCGATCCATGTCCCGTGGGACGATCTCGGCTCAGGAATGGGTCGTGCAGC GTGGTGGGCCTAACACGAGCGTCGCCGAGTGGGCGTCCTTCGGTGGCGGG ATCTCGCAGGAAGAGTGTTCGAGCTGTGCTAATATACTCTCGTCTCGAAG GAGTGGTCTCGCGTCGTTGAGGCGGCGCTTCCGCGAGCGGGGGCGATTGT
                                                   230500                                                 230600
GGGACCGGCCCCGTCGGTTCACAGGGACTCCGGGGCCGGCTGGTTCCGAG GCAGGGTGTCGGTGAGGCGCGCGAGCAGACGTCGGCGGCGGGCACGACAC GATGATGCGGCGTTCCGCGCGTCACGGTTCCGTGATGGTGTGCTGGCTGT GGGCGCACCACGGGGTGACGAAGTCCACCGCGTTAGCCGGATCGAGTGTA
                                                   230700                                                 230800
TAACTGGGCACCCTGATTTCAACGGAAGGCGTCCTCCATGTTAGCGCCTG CGAACAATGTGACGGCAGCATCAACAATATCAGCAGCGATAACGGGATAG CGAGTCTCCCGCCGTAGTATGCGTTCATGCTCGTGGCGTCGGCGGCAGCT CGCGTGCGGGGTCTGTGGCGTCGAGGTGGTTTCGGCGAGACGGGGACCGA
                                                   230900                                                 231000
ACGAGGGAGTCTCGGGCGAGTCTCGGGTTGGTTATACCCGGCCGGGATCG GGCGGCCGGGATCGGAGCCGCGGACGGAGACTCTCACGAGGTGAGGGCTG GTAGTTGTCATGACAGCGATGTGAACGGGGTGCTGCCATATAAAGGCGGG CGGCCGCTGCCCTCCTGACCCACGTGGAGAAAAAGCAACAGAAAAAAAAG
                                                   231100                                                 231200
CAAAAGCGGACACCAAAACGGAGCGCAATGGTCGGCGGACCGGCGAGCGA CGCCCGCGGCGGCACGATGGAAACGTGCCGGCCGCACCGCCGCAACGGGA AACGGCCGGAAGCATTGTCGCCACCGCCGCCGCCCACGCACCGGCACGTC AGATCGACCCGCGTCGACGGCGCCCCGAGTGACAGCGGCAGCGACAGCGA
                                                   231300                                                 231400
CATCCGTGTCCGTGACCGTGACGGAGCGACCACGGCCCGTCAGGGCCGAA CAGCGAACCGTAGCCCCACGTCAAAAAGGGTCGAACAGCAACAGCAGGG ACGCGCACAGCAGCAGCGCCAGCATGCACGCCAACAGGAGCAGCACCGCC GGCGCCAGCCTGACGGACTACGCGGACGCAAAAACACACACGGACACACA
                                                   231500                                                 231600
CGGCGCCCAAGCGCCACACAGACACACGTTACGGAAGCGCGCGGAACACG CGCGTAAACAGCTCGCTACAGACACGTGCCTCCTCACCCACCAACGGCCA CGCCGTCTCCGCCACCCGCAGCAGGGTGCCGGAGTCCAACACGCACAGAA CGAACACACAAACGAACGAAAAGCTTAGCGCCGCCGCCAGGCAGCAACAA
                                                   231700                                                 231800
CAACCCATCCCCCGACGCAGACACATAGCCACCGACGGGCACAAACACCA CTTTTAAGCCCGCACACGCCCTCCCGGCGTCTCACACGCACACATCAGAC ACAACGCACCACACACACCGCCTACCCCGCGTCGCGCAAAACACGCCAGC ACAAAAGCGCATACCCGAGACGCGCACAATGCGCCCAAAAAAACAGCACC
                                                   231900                                                 232000
CCGCCACCCAATGCGACCGCTCCGCGCTACGATTTTCCCCTCTCCACATC TATCCACACGTCACACACACAGCGCGACCACACACACGCTTCCAAACCCT CGATCTCACCCGCTCCCTAAACCCTGCGCGTAAAAGCCTCGGAGTCCCGC CGTACCGGTTTTGCCACCCCCGGGGGGCCTTTCGGGCGGGGGGCCTTTTG
                                                                                                                                    ...............b..NOTE=RTR; RIGHT TERMINAL REPEAT....................>
                                                   232100                                                 232200
TTGCGGTTTGGGGGCGCGGCGCCGGCGCTTCCCGAGCGGTTTCGGGGGTG GGCGCCGGAGCCTTTTGTTGCGGTTTACGCCCGCGGCGCCGGCGCTTCTC TGGTGGTCACGGCGAGGTTTCGATGAGCTTTCGATGCGACCGCAGGCGGG TTTCGATGAGCTTTCGCGGTCGCGGTCGGAGGTCGGCGGACGGGTCACAG
__________________________________________________b______________________________NOTE=RTR; RIGHT TERMINAL REPEAT_______________________________b_________________________________________________>
                                                   232300                                                 232400
CGGCTGCTCGGCGCGCCGCTTGCGCGCGCGCCGGCGGGACGCCGACGACG GACGCTGGCGGTGGTGCTGCTGTTGCTGCACTCGATGCGGCGGCTGCTGT TGCTGCTGCTGCGTGCGCTGCGCCGGCGGCCAGCGAGGCCGGTCTCGCGC CCGGTCGCGGTCCAGCTGCATGCGGACGCACGGCCGCTCGCCCGTCTCCA
__________________________________________________b______________________________NOTE=RTR; RIGHT TERMINAL REPEAT_______________________________b_________________________________________________>
                                                   232500                                                 232600
GCGCGCGCCGCACGCCCGCCGCCTCCACCTCCGTGCGGCTCCAGCGCCGC TCGTCCGTCTCGATCTCGATCTCGACCTCGGTCCCGGGGCCGGCCTCGGC CATCTCGCCGCTCCACTCCACCACGCGCTCGCCTCCTGCTCTTCCCCCGT TCTCGTGCCCGGAACCGCCGACTTCTGCCTCGTCCTCCTCTTTCTCCTCC
__________________________________________________b______________________________NOTE=RTR; RIGHT TERMINAL REPEAT_______________________________b_________________________________________________>
                                                   232700
TCCTCCGCCGACGAGCCCGTGCTCCAGTCGGGGCTCCAGTCCTCGTCCCA CGCGTCCCAGTCCCCGCCAAAGCTCATCTCGCCGCCTCGCCTCGCCCGAC TCCGGCCTTTAGCGCTCGCCCGGCGCCGCCGCGACGCCCCTTTTTCTCGA ACCCAAGCACGCGGGTGCGCGACCAGCA
__________________________________________________b_____________________NOTE=RTR; RIGHT TERMINAL REPEAT______________________________________b______________________________>
```

FIG. 1WW

| GPCMV Open Reading Frames (ORFs): CIDMTR Strain | | | | | |
|---|---|---|---|---|---|
| **ORF** | **Strand** | **Begin** | **End** | **Codons** | **Notes** |
| gp1 | C | 12,464 | 12,769 | 101 | GPCMV MIP 1α; homology to CC chemokines |
| gp2 | | 14,840 | 15,685 | 281 | Homology to MCMV M69[a] |
| gp3 | C | 17,197 | 19,563 | 788 | Homology to THV T5[b]; US22 superfamily |
| gp4 | C | 20,829 | 21,152 | 107 | Homology to RCMV r136[d] |
| gp5 | C | 26,721 | 27,818 | 370 | Homology to MCMV m32[a] |
| **GP23** | C | 33,299 | 34,501 | 400 | UL23 homolog; US22 gene superfamily |
| **GP24** | C | 34,739 | 35,956 | 405 | UL24 homolog; US22 superfamily |
| **GP25** | | 36,542 | 38,194 | 550 | UL25 homolog; tegument protein |
| **GP26** | C | 38,360 | 39,043 | 227 | UL26 homolog |
| **GP27** | C | 39,166 | 41,211 | 681 | UL27 homolog |
| **GP28** | C | 41,311 | 42,378 | 355 | UL28 homolog; US22 superfamily |
| **GP28.1** | C | 42,866 | 44,287 | 473 | UL28 homolog; US22 superfamily |
| **GP29** | C | 44,653 | 46,623 | 656 | UL29 homolog; US22 superfamily |
| gp29.1 | C | 47,247 | 47,861 | 204 | US22 superfamily |
| **GP30** | C | 49,082 | 50,800 | 572 | UL30 homolog |
| **GP31** | | 51,094 | 52,572 | 492 | UL31 homolog |
| **GP32** | C | 52,665 | 54,365 | 566 | UL32 homolog |
| **GP33** | | 54,585 | 55,868 | 427 | UL33 homolog; 7-TMR GPCR superfamily |
| **GP34** | | 56,221 | 57,804 | 527 | UL34 homolog |
| **GP35** | | 58,008 | 59,666 | 552 | UL35 homolog |
| **GP37** | C | 59,788 | 60,711 | 307 | UL37 homolog |
| **GP38** | C | 61,068 | 61,988 | 306 | UL38 homolog |
| gp38.1 | C | 62,705 | 63,262 | 185 | Positional homolog of HCMV UL40 |
| gp38.2 | C | 63,620 | 64,933 | 437 | Positional homolog of HCMV UL41a |
| gp38.3 | C | 65,624 | 66,478 | 284 | Positional homolog of HCMV UL42 |
| gp38.4 | C | 66,997 | 67,362 | 121 | Homology to RCMV r42[d] |
| **GP43** | C | 67,951 | 68,964 | 337 | UL43 homolog |
| **GP44** | C | 68,952 | 70,175 | 407 | UL44 homolog |
| **GP45** | C | 70,887 | 73,673 | 928 | UL45 homolog |
| **GP46** | C | 73,779 | 74,867 | 362 | UL46 homolog |
| **GP47** | | 74,674 | 77,787 | 1037 | UL47 homolog |

FROM FIG. 2A

| | | | | | |
|---|---|---|---|---|---|
| **GP48** | | 77,784 | 84,155 | 2123 | UL48 homolog |
| **GP48.2** | C | 84,238 | 84,468 | 76 | UL48a homolog |
| **GP49** | C | 84,479 | 86,119 | 546 | UL49 homolog |
| **GP50** | C | 86,088 | 87,158 | 356 | UL50 homolog |
| **GP51** | C | 87,281 | 87,580 | 99 | UL51 homolog; terminase subunit |
| **GP52** | | 87,900 | 89,480 | 526 | UL52 homolog |
| **GP53** | | 89,473 | 90,459 | 328 | UL53 homolog |
| gp53.1 | C | 90,196 | 90,537 | 113 | Homology to RhCMV rh86; YP_068179.1 |
| **GP54** | C | 90,551 | 93,904 | 1117 | UL54 homolog; DNA polymerase |
| **GP55** | C | 93,947 | 96,652 | 901 | UL55 homolog; glycoprotein B |
| **GP56** | C | 96,549 | 98,816 | 755 | UL56 homolog; terminase subunit |
| **GP57** | C | 98,967 | 102,650 | 1227 | UL57 homolog |
| gp57.1 | C | 104,411 | 104,926 | 171 | Homolog to RCMV r23.1[d] |
| **GP69** | C | 108,260 | 111,430 | 1056 | UL69 homolog |
| **GP70** | C | 112,136 | 115,339 | 1067 | UL70 homolog; helicase-primase |
| **GP71** | | 115,338 | 116,114 | 258 | UL71 homolog |
| **GP72** | C | 116,277 | 117,350 | 357 | UL72 homolog; dUTPase |
| **GP73** | | 117,432 | 117,833 | 133 | UL73 homolog; glycoprotein N |
| GP73.5ex1 | | 117,860 | 117,869 | 3 | |
| GP73.5ex2 | | 119,005 | 119,198 | 64 | |
| **GP74** | C | 117,780 | 118,904 | 374 | UL74 homolog; glycoprotein O |
| **GP75** | C | 119,349 | 121,529 | 726 | UL75 homolog; glycoprotein H |
| **GP76** | | 121,694 | 122,533 | 279 | UL76 homolog |
| **GP77** | | 122,247 | 124,091 | 614 | UL77 homolog |
| **GP78** | | 124,473 | 125,717 | 414 | UL78 homolog; 7-TMR GPCR superfamily |
| **GP79** | C | 125,914 | 126,861 | 315 | UL79 homolog |
| **GP80** | | 126,722 | 129,031 | 769 | UL80 homolog; CMV protease |
| **GP80.5** | | 127,610 | 129,031 | 473 | UL80.5 |
| **GP82** | C | 129,324 | 130,889 | 521 | UL82 homolog; pp71 |
| **GP83** | C | 131,109 | 132,809 | 566 | UL83 homolog; pp65 |
| **GP84** | C | 133,051 | 134,487 | 478 | UL84 homolog |
| **GP85** | C | 134,785 | 135,696 | 303 | UL85 homolog |
| **GP86** | C | 135,977 | 140,026 | 1349 | UL86 homolog |
| **GP87** | | 140,407 | 143,328 | 973 | UL87 homolog |
| **GP88** | | 143,231 | 144,499 | 422 | UL88 homolog |
| **GP89ex2** | C | 144,545 | 145,675 | 376 | UL89 homolog; terminase subunit, exon 2 |
| **GP91** | | 146,102 | 146,365 | 87 | UL91 homolog |
| **GP92** | | 146,362 | 146,991 | 209 | UL92 homolog |

FROM FIG. 2B

| | | | | | |
|---|---|---|---|---|---|
| **GP93** | | 146,957 | 148,732 | 591 | UL93 homolog |
| **GP94** | | 148,644 | 149,681 | 345 | UL94 homolog |
| **GP89ex1** | C | 150,032 | 150,913 | 291 | UL89 homolog; terminase subunit, exon 1 |
| **GP95** | | 150,967 | 152,235 | 422 | UL95 homolog |
| **GP96** | | 152,468 | 152,830 | 120 | UL96 homolog |
| **GP97** | | 152,910 | 154,727 | 605 | UL97 homolog; protein kinase |
| **GP98** | | 154,747 | 156,531 | 594 | UL98 homolog; alkaline nuclease |
| **GP99** | | 156,444 | 156,965 | 173 | UL99 homolog; pp28 |
| gp99.1 | | 157,155 | 157,769 | 204 | Homology to RCMV r4[d] |
| **GP100** | C | 157,278 | 158,327 | 349 | UL100 homolog; glycoprotein M |
| **GP102** | | 158,657 | 160,942 | 761 | UL102 homolog |
| **GP103** | C | 161,127 | 161,852 | 241 | UL103 homolog |
| **GP104** | C | 161,815 | 163,908 | 697 | UL104 homolog; portal |
| **GP105** | | 163,748 | 166,531 | 927 | UL105 homolog; helicase-primase |
| **GP112ex1** | | 176,745 | 177,498 | 315 | UL112 homolog; replication accessory, ex 1 |
| **GP112ex2** | | 177,606 | 177,782 | | UL112 homolog; replication accessory, ex 2 |
| **GP112ex3** | | 178,115 | 178,131 | | UL122 homolog; replication accessory, ex 3 |
| **GP114** | C | 179,126 | 179,920 | 264 | UL114 homolog; uracil glycosylase |
| **GP115** | C | 179,986 | 180,762 | 258 | UL115 homolog; glycoprotein L |
| **GP116** | C | 180,755 | 181,654 | 299 | Homology to THV t116[b]; Fc receptor//Ig |
| **GP117** | C | 181,877 | 183,262 | 461 | UL117 homolog |
| gp119.1 | C | 184,418 | 185,167 | 249 | Similar to MCMV in ACE95619.1 |
| **GP121.2** | C | 185,160 | 185,834 | 224 | Betaherpesvirus B7D8, accession AFK83957 |
| **GP121.4** | C | 186,299 | 187,174 | 291 | UL121 homolog; Tupaia t121.4, NP_116476 |
| **GP122ex3** | C | 187,993 | 189,677 | 677 | UL122 homolog; HCMV IE2 |
| **GP122ex2** | C | 191,079 | 191,311 | | |
| **GP122ex1** | C | 191,403 | 191,518 | | |
| **GP123ex3** | C | 189,907 | 190,985 | 475 | UL123 homolog; HCMV IE1 |
| **GP123ex2** | C | 191,079 | 191,311 | | |
| **GP123ex1** | C | 191,403 | 191,518 | | |
| **GP128** | | 195,400 | 196,455 | 351 | Similar to Bat herpesvirus B126; US22 Family |
| gp130 | | 196,655 | 196,999 | 114 | |
| GP129ex3 | C | 196,432 | 196,690 | 178 | Homolog of HCMV UL128 |
| GP129ex2 | | 196,768 | 196,890 | | |
| GP129ex1 | C | 196,974 | 197,128 | | |
| GP131ex2 | C | 197,133 | 197,469 | 191 | Homolog of HCMV UL130 |
| GP131ex1 | C | 197,550 | 197,788 | | |
| GP133 | C | 197,788 | 198,174 | 128 | Homolog of HCMV UL131 |

FROM FIG. 2C

| | | | | | |
|---|---|---|---|---|---|
| GP134 | C | 198,268 | 198,951 | 227 | |
| gp138.2 | C | 199,367 | 200,875 | 502 | |
| gp138.3 | C | 201,090 | 202,607 | 505 | |
| gp139 | C | 202,706 | 204,793 | 695 | THV T5; US22 superfamily |
| gp140 | | 204,522 | 204,929 | 135 | Homology to CCMV UL132 |
| gp141 | C | 205,053 | 206,660 | 535 | HCMV US23; US22 superfamily |
| gp142 | C | 206,928 | 208,622 | 564 | HCMV US24; US22 superfamily |
| gp143 | C | 208,875 | 210,866 | 663 | THV T5; US22 superfamily |
| gp144 | C | 211,109 | 213,403 | 764 | US26; US22 gene superfamily |
| gp145 | C | 213,677 | 215,575 | 632 | HCMV IRS1/TRS1; US22 superfamily |
| gp146 | C | 215,932 | 217,914 | 660 | HCMV IRS1/TRS1; US22 superfamily |
| gp147.1 | C | 221,739 | 222,935 | 398 | MHC class I homolog |
| gp147 | C | 223,124 | 224,218 | 364 | MHC class I homolog |
| gp148 | C | 225,379 | 226,560 | 393 | MHC class I homolog |
| gp149 | C | 228,236 | 230,209 | 657 | MHC class I homolog |
| gp149.1 | | 230,163 | 230,465 | 100 | Unique ORF sequence in CIDMTR |

| | Primer Sequences | SEQ ID NO. |
|---|---|---|
| Mismatch 1 F1 | 5'-GTGAGACGTAAGAATAGCTTGC-3' | SEQ ID NO: 11 |
| Mismatch 1 F2 | 5'-GATCCTTAGACTCTATCACGG-3' | SEQ ID NO: 12 |
| Mismatch 1 R1 | 5'-GTGTTGTCACAATTGGCACATG-3' | SEQ ID NO: 13 |
| Mismatch 1 R2 | 5'-ACATGGTCACGACAGAATC-3' | SEQ ID NO: 14 |
| Mismatch 2 F1 | 5'-GTGGACAGGATCCCCAAATT-3' | SEQ ID NO: 15 |
| Mismatch 2 F2 | 5'-CCAAATTTCTGTCGTCGGCG-3' | SEQ ID NO: 16 |
| Mismatch 2 R1 | 5'-TGTTTCCGTGTCTGTCTCCGT-3' | SEQ ID NO: 17 |
| Mismatch 2 R2 | 5'-GTCTTAGCCCGAGACCTTC-3' | SEQ ID NO: 18 |

Figure 5

CTTGCAGAGCCTCCTCGCTCTGCCCGGCTTCTAAACCGGAGCCCCTTATATACTCATAAACCACTCCCC
CATAGGGTACGTGGACCAATAGTGGAGTGGGGCGTGCTCTCCAAAAATGCAAAGTCACCATGATACA
GTACTTGAGCGGTTTCCAGGGACTTTCCAGAGGACGGTCAAATGTCAGTGAATCACCCAGTATGTACT
GCCAATTTGGCAGTAATTGGATACCGCATGACTAAGGAAAAAGTTATAATTGACAGGGAAAATCCCCT
TTGTGGCTGATTTGCATAAAACTAAGTGTAATTTACTGGAATATTGGCCCTGGAAAGATGTACTTAACT
CTGAGTGACCCTTTCCCTCTGCCAAGTGACTATAATGCTGCCCGGGACTTTCCAGATGCTCTTTGCCAA
AAAGAACATGACTAAATATGGCTGTGCTTTGTCCCCGTATCAGTTTACTGTAAATGGCCCGGGACTTTC
CACGTTTCCTTTGCCAAAAGAACACTGTTAACTCTGGCTGACCCTATCCCATGCCAATCAAACGTCCCA
TAACCGTATCCCTTTGCCAAAAAGGACACAGCTACCTCTGGCTGACCTTCTTTCATATTAATCAGACGT
CCCACGTCCAGGGACTTTCCATAGACCCTCTGCCAAGCAATACATGACTAAATATGGCTGTGCTTTGTC
CCCGTATCAGTTTACTGTAAATGGCCCGGGACTTTCCACGTTTCCTTTGCCAAAAGAACACTGTTAACT
CTGGCTGACCCTATCCCATGCCAATCAAACGTCCCATAACCGTATCCCTTTGCCAAAAAGGACATGAC
TAATTCTGGCTGACCTTTCCCCATATCACTCAAACGTCCCATGACCGTATCCCTTTGCCAAAAAGGACA
TGGCTAACTCTGGCTGACCTTTCCCCATATCACTCAAACGTCCCATGACCGTATCCCTTTGCCAAAAAG
GACATGACTAACTTTGGCTGACCTTTCCCCATATCACTCAAACGTCCTATGACCGTATCCCTTTGCCAA
AAAGGACATGACTAACTCTGGCTGACCTGTCTCCATATCAATCAAACGTCCCGTGACCGTATCCACCG
TGCCAAAAAGGACATGAGTAATCATGACCGTACTTCGTCCCCGTATTAGTTTACTGTAATTTGGCCAGG
GACTTTCCACATCATCCAAATTAATCAATAATGATTACAAGTGGACAGGTTGTTGGCATCTACTTATTC
AGAAAAATCCATATGCGTGCTGCCAGCATCAAAACAATGTAATATATTCATGAGATCATGATTAATTT
AATGGAAAACACCTAAAAAATCCAGTCATCATCTGGAAAGCACCTAACGTTACGTAAAATTTTAATAT
GATTCAGAGATGGGCCGGGTTATACGGAATACGCCTATAAAAGAGGAGGAGTTCGCTGGTTTAGAATC
AGTATTGTGCCAGACTCCGAAGAGGACACATCTCCCGTGCTCGGAATGCTGCCAATATATTAAAAGAA
TAGGTGCGTATGGTTATCTTTGATATAGCACAGGTAGAATACGCGTATAGAGGTGACCTTTACCTGTG
AGAGTAGGTTAGTAAACAAAGAATCGTGCCAGACTGAAGGTACAGCAAGTCAATTTATATGTGATAGT
TAATAATATAGATTACATTGATCTGATATTGTATAGTTTGACGTGGAATGTAGGTTTGCTTACTAGATG
ATCGATAGCGCAGGCTTATAGCGTAAGAGATGTGATAGATGCGATGGTATGCATCGGCAGTTTCCGAC
AGATGTTCGTACTGAATTGT (SEQ ID NO: 10)

SEQUENCE LISTING

```
<160> NUMBER OF SEQ ID NOS: 29

<210> SEQ ID NO 1
<211> LENGTH: 232778
<212> TYPE: DNA
<213> ORGANISM: Caviid herpesvirus
<220> FEATURE:
<223> OTHER INFORMATION: Guinea pig cytomegalovirus strain CIDMTR

<400> SEQUENCE: 1

ctcggagtcc cgccgtaccg gttttgccac ccccgggggg cctttcgggc ggggggcctt      60

ttgttgcggt ttgggggcgc ggcgccggcg cttcccgagc ggtttcgggg gtgggcgccg     120

gagccttttg ttgcggttta ggcccgcggc gccggcgctt ctctggtggt cacggcgagg     180

tttcgatgag ctttcgatgc gaccgcaggc gggtttcgat gagctttcgc ggtcgcggtc     240

ggaggtcggc ggacgggtca cagcggctgc tcggcgcgcc gcttgcgcgc gcgccggcgg     300

gacgccgacg acggacgctg gcggtggtgc tgctgttgct gcactcgatg cggcggctgc     360

tgttgctgct gctgcgtgcg ctgcgccggc ggccagcgag gccggtctcg cgcccggtcg     420

cggtccagct gcatgcggac gcacggccgc tcgcccgtct ccagcgcgcg ccgcacgccc     480

gccgcctcca cctccgtgcg gctccagcgc cgctcgtccg tctcgatctc gatctcgacc     540

tcggtcccgg ggccggcctc ggccatctcg ccgctccact ccaccacgcg ctcgcctcct     600

gctcttcccc cgttctcgtg cccggaaccg ccgacttctg cctcgtcctc ctctttctcc     660

tcctcctccg ccgacgagcc cgtgctccag tcggggctcc agtcctcgtc ccacgcgtcc     720

cagtccccgc caaagctcat ctcgccgcct cgcctcgccc gactccggcc tttagcgctc     780

gcccggcgcc gccgcgacgc ccctttttct cgaacccaag cacgcgggtg cgcgaccagc     840

actccaccct cgtgccggga gcgcagcgtc agagcgtcgg ggcgcgggcg cgcgggtgtt     900

aatactaagg cgcggcgtgt tggcaggcgt tttgggtggt tcgtcagcgc gcgtggttac     960
```

```
gtgtatgccc tgtgttgtgt gccgcatcgt gtggttacgt cgcgctgttg ggggcaaccg   1020
ctcgcgtatc cggcggagga gtccggtgcg gcgttttggg acgggtaccg aggacgtttc   1080
ggcttccgac gtgtttcgtt ttttaaactg tgtgctgctc ggcttttgtt ccgttagtta   1140
tttctcgttt gtctcgggtt gggttgtttt ggtctcgttt tgtttttggt atatttctgt   1200
gtttcgggtg aggtgaagtt ttgcttccgt gtaattattc gcgttacgat gtgagcccga   1260
ggcggagccc gaggccgaca atgtcgtgga gcccgcagac gaagcagacg gcgtctcacg   1320
agaaacccaa aggcgaagac cgatcagaag aagacgaaga agaattagcc tcgtttttta   1380
accagttgtt gtatcttttc gtcggttttt ccctttcttg ttatctacca tcttattatt   1440
ttttctttgg ttcttttaaa accctgcgaa agaccccggc tcggcggttc cgtgctgttt   1500
tggtttgggg taataattaa ttcatttttt gttttatttt atcttatctt atcctattgc   1560
ttcttatttg tattatttct tcttatccct actgctgttt atcatctctt tatccacatc   1620
tatctgatcc aacctaatct aatctaatct aatctaatct aatctatcga tgtctttgct   1680
aactttgctt cgaggtgagg tcgaggccgg gagcgcgcgg tccagccgcg cgcgcgcaca   1740
cacacgcctc cctaccgctt tcgcttttct gtacccgttt acctacgtat catctctaat   1800
ttatctgttt atcctttcag tcgaccaatt tttctttctt tcttttttt ccttagttcg   1860
gtttaagtgt atacgattac ttttacattc actcggcttc ctacttttcg taatttcttt   1920
ctttctcttc gttttcttta ttttggtcaa tgatgtacga acaccaatca atctatcact   1980
gttcttcaac cagtttgatt atttattttt ttctgatcct cctagttatc tatctatcta   2040
tgtaggtact tctttattca tttaagtaat acccattctt ttttatttta ctttgtcact   2100
tatcgtttgt tcttattttt gtatcttgac ttcgacttct ctccggtttc ttgctatttt   2160
ttcctcgctt attattactg ctttcgttat catctattat tttgcaaaaa cgtttatatt   2220
tttctcgttt ctttatttta catttcgact cctcccgttt tcgtattcat ttaatatctt   2280
ttgcttattc ggttctcatc gcaagtattt ctttcctata ttgttatcgt ttcttttcac   2340
tatattctcg cttctcttca tctttgttgt ttcttttta ttatgttttt gatttttact   2400
cttactttta tcctataatt tctttttga tcaattggcc ggcatcgccc gaacacacgg   2460
ttccgtgaat aacggtttga attcgtatct gcgccacaac tacaagcttc ttgctctttt   2520
tctttctcta tactcgtatt tttatttttc cttttaaaat atatatatat tattcatcat   2580
agttatttat gatcgcgatt atgattatga ttaggactcg acatacagaa tgtcttctta   2640
actcttttct gttcggtttt ttttttcta accctcccga acgagatcag cttgctggcc   2700
ccacgcgtag gatatacgat ggatggtaac gatgacgcgt acgacccgac ccagaccgtc   2760
gtctcgtctg ttgattcgtt gatttatctg cttgcttgct aacttgctcg tttgcgtgct   2820
cgctcgctcg ttcgttcgtt gttagttcgt acgttttcca tgatcgtttc tttcctttt   2880
catcgtttct ttctttctta aaaaatgtga ttaatacatc gtcgtttctt actttatttt   2940
atttgagaat tctattttct taatcattag gattgttacc acttaaaact tttcttgttt   3000
ttgccttgta ttgtatttat cttctcgttt ccccatcgat gacatgtgta tacgaagaaa   3060
tcggggaaaa aataatactt aaatccctca cccttaaaa ccctaacctg ttaaccctta   3120
cgcgaacctt gacctcaaat ccgaagaaaa agcaacaccg atggtaaaaa tcccgaccca   3180
cccacccgcc acctcccatt tcggtctttt ttctagtttt tcccttcctt cttccccaag   3240
ctgagataat ctgtttttgt ttttaaattc tcactatcgc cactacgata agattctcat   3300
```

-continued

```
gataatactc atcacccaaa ttaaccatag agggcaaaga aaccaaatat catcactgaa   3360
aaacaaacct atacatcatc aactatctcg tctatctatt cttatctatc ttccctgacg   3420
gggggacaaa atgacccaat cctgtggcgt cgctaccaat atcagacgcg cgtctccctt   3480
ttttcccctc tgacttacgt cttttttttt gctatcacta ttatcttgtt atttcttgtt   3540
ctcgatacta ttttatgtgt cgcatctacc atgttatcat tagttagtta cctttgtccc   3600
tactatatta ctattattta ctgttaacaa caatgataat ttttctttct cttttacatt   3660
tttctctttt tcttttcttt aactccccct attcactgtt actctttcct ctacgtcttt   3720
ctccgctcca tcggttatca ccgtggtctt ttttttttc ttttctttta ttcgacgaat   3780
agaggtttgt ctctttttta cttgtttcca tttgggacct ctctttgtaa taatagacat   3840
tattttgacg attttatttc tttctttttt ttttaaatgc attcgtattc gcatctatat   3900
ttcccttctt ctttttattt gtttttctta tcttcttatg ttgttttctt ttctttttcg   3960
tgtcgtatcg taaatcatct tttttataca tggatttctc tcactagatt attattttca   4020
tttgcaaaaa cagttttctt tcttctgcga ctattacttc ttcctttttt ctaacatcat   4080
catcgttcgc tttatgtata tctatctatt tccctcgtct atctcgagat ctcttaatta   4140
ttatgtgttt aattcgtttc gatatctttc ccatcgttca cttgtctttc ctttttgtca   4200
tcgatctcgt ttttttttta aagtttcaca ttaaagacca gactagaatt gtcggtgttg   4260
gtgttggcgt tggactcgac gtattcgttt atttatttct tttctttttt ttttcttttc   4320
gttctttttg tttttttttt gtttgtcttc gtttagaatt gcaaaacatt ctgacaccta   4380
cgccgcaaag aaagcagctc agaccgatcc cggagctcca catatccacc tatcgaggtc   4440
gtcacaatga cccaccgtcg ttttaatgtc cttgtcgtat ttatttatat agattatttg   4500
tctttttctt tttttttctc agtggtatac gttctatttt ctatttctca agtcatcttt   4560
tcttttttta atgttctaca attttatatg aacctcaatc ggtctattct ccctctacat   4620
aaatctgttt tttttttttt tcaaattcgc cttccctcat cctcctctct tttatctatc   4680
tagattttac aaatttcttt cttcaaaata cgatttgttt attctctctt tcagtgtatt   4740
tttttggaa agtcgttatc ctttttattt atctattgtt tgttcatacg atttttgatt   4800
gttctgtaat tcgtatcgtg cgtttctttt ctcttttttt gtctttatct cgctctgtag   4860
cgtcacgtct aggattcagt aatcattatc gtcgttgtat cgatttcact tttcgttcaa   4920
gttacttttc ctctattctt ttcattctac ttgtatgaga ataaattttt ttctcttatc   4980
ttatttaatt tttcttcctt actttcttat tattttttct tttgcaactc taccaataaa   5040
aaaagagttc aatgctttat ttatcatcat taagtgaggt ttttgaacat ttcttacttg   5100
cttctttctt tgtacgatga agggggacac ggggagcccc ccgacgtccc cttcctaggg   5160
cttcgtgcgt ttttatatct aatcttctat ccctctatcg tgctgacacc accttctctt   5220
taatgatttg cttactatta tgcgtatcgg aaagataatt aataattact tcaatttcgt   5280
tttctctata tttatctatc tttcgacgtt tcgtttttgt tctattgctt aaaatgcagt   5340
ttatcgtctt gatgcgtttt cgtctatcgc ctgatgagat acatttatct atctaaaatc   5400
tccttcacgt tcagtacatt actgtctttt tactcacgaa gtcattcgtt ttttaaatcg   5460
ttttccaatc gtttttaat cttttcccg cgctttcctt tttattattg tcttattatt   5520
cactcacaca gtcttctcct tctgactttt tcttatgctt ttttttaata tccattcgca   5580
gcgatctccc taacactata aaaattgtgt ttttttttc gttctaccct gtgacttacg   5640
gacgaacgga ctgacgaacg gcctaactga cgaacggata gacgaacgac cgcacgccag   5700
```

```
cgagagagcg acccgcgcgt ctccgccaac gtgacggccg ccgccgccat cgtcgtttca   5760
ttatcgtcgc cgtcaccgcc gccgccgttg ttaccgcaac cgcagccgca actgctgtgg   5820
ggccctggcc gtggccgcct ctgacttcgt cggacactta tgttttttct ttaatttctt   5880
tcattcctta cggttattcg tataaaatca taacaacaat acgactgtta ttattgctac   5940
tacagatata gtttgtgaat taaaaaaaat tttttcaccg taataccgcg tttatttatc   6000
tgtcttcatc ttttaatata cgactgctaa tccttgattt tgacgatttc gattttgatt   6060
tcttttcttt gattttgttt ttttttcttt cattgtcagt tagttcgtat aagaagttct   6120
ttttctttct tatattctgt aacttactat tttcttttta ctcacaatat cacgatattc   6180
acaatcgctt aagcctccat gcactacgtt tctttttttt tctaacattg acgtctgttg   6240
acatagttaa tagtatcgtt attataccta tcaatgtatc tagtccttta tcatctctat   6300
tctacttttt agtcttgttt tttaagtata ttattattaa ttcttattag caactttttt   6360
tctttgaaaa actagtttct tttcctttcc gaagatgagc ccgatgtcgg gcggcagaag   6420
gtcagtcgtg atgattactt agtaacgttt ttttaatatt ctgaattagt ttctatagag   6480
ttatttcttt ttttctttct ttactattgt ttcttcctat ccgtatcact ttatgagttt   6540
tgtgttatta cgttctctta agttagtttt ttactattat tattctagga tcgcatatat   6600
atctcgcacc tgtacgtata tatgatatca tcatttgtta ttcgctctcg ttcttgattt   6660
actgatgatc gatttcgcac tggccctgcg aactttctga acttcatatt ttatgttttt   6720
tttaataatg tcgctacgat cgtgccgacg tctccgatgc accgaggatg gattcgatta   6780
atgatgtatc ggagacgggc gaggcgccgt cgctcccgtc gcgcgcggcc ccctcccaga   6840
ctccgcgagg gcggcggagg cggtggcgcc ggccaacgac acgatcctcg cggccctgtc   6900
gctactttcg ctcccagcta tcacaaagaa gaccttactc tgacacttgt cttcgagaac   6960
gacggcggct gcgccgccgc cgccggacgt actagtattc ttattgttat tgccattact   7020
gatacgcttc tttctgttcg aagctttttc cgattctcta tcctttttct taacggtaat   7080
aatactttta ccattgctat tgctatcgct attatttttt gttttgtcat tctttttatt   7140
cttgttgcgg tcgttcccgc cggttcccga cgtccgagac gccgggggtt gccgacgacg   7200
ttgcccggag ggaacggtcg acgacgaaga cgcgatcgat atcgagtgtg acgacgacgg   7260
gggacgtgga agtcgtccct cgttagcctt tccgcgcgac gccgaagccg ttttcgaaga   7320
ggatgatgac gatgacgacg aggacgaggc cggtgtcgat gtcgttttct tcttcgcctt   7380
tttggcgacg ttgccggtcg cccgtccggg agacgctcct ccggcccgta tccgagaccg   7440
ttgcttctcc ggccgttgct gccgctgttg ttgctgctgt tgatctcccg ccatccctcc   7500
ttcttctcct cctccgattc gtcgtttctg tctttgggtg atttttatgt ttttttaaat   7560
attaatgtca tcttcgttct tgaaactatg actacgttgt tctttttttt ttgtatgtat   7620
tgtcacctat cgtctctctc taatgtctct atgtagaaat caatcgttct aaaaaatggc   7680
tactatcgta tattcttttt gtgttctttt tcttttttttt ctactcctta ggaaaatgac   7740
aatgttgttt atcgttgtaa tcgatgatac agcttatcct gagtgacaca ctctctataa   7800
agtactattc ttttatggtc tttttccgtt cgtctctcga aagacgttag cgacgaacgt   7860
cgttttttat tcctgtttct acttattaat ctggtttttt tattactatc atcggattat   7920
ccttatagtc aactatttct ctatctacta tttttcatta ttattatttt ttcttcagag   7980
cgtcgtggac acctcagttt tgtctcgtat tataatctgc gtgcttattt cttttctttc   8040
```

```
actatattgt tattttatga tcttctctat ctatatttta taacccatac cgttcgatga   8100
tcgcgcggtg actatgctcc gcgataaaag taactggttt cttttgtcta ttcccgtttt   8160
ttattcttac ttgtattctt ttctattttt tatacgccat aaagaaagct ctgactcaat   8220
taattaaact atgcactatg cagctactac ctttcccggt taaggcggat tctttctatc   8280
gtttttatc tttactacga ctactatacc ttagctcctt aactttttta tttatgcatg   8340
tatataatcc ttctactttt gtttacttaa acttctacat gtaaacggcg gcgtacgcag   8400
gatgttgcgt tttgtcttcc ctagaaaaaa acgtttattt ttccccgttc tttttattt   8460
ctatttcaac gtatggctat aattttcttt cacgttttat tattctccat ctagctattt   8520
tatttacttc gtcatctaat tgtttgtatt ggctattttt ttttcttttt acatgcatat   8580
cgttctctgt aactttagtt atcgccgatt catctaacaa tttctctaga tctctatcat   8640
tcgaacgtct agcactctac gtctgtctat cttatgtatc tatatcgatc atctgctcgt   8700
ctgacgacta tatacttttc tattcctttt gctatttatc tatctgacga cgtatactac   8760
gctctttgtt atctttgctt tctagtattt aatctttttc tttttctttt ttccgcatag   8820
tatttatctt ggtttttat tatttgtttt ctcgcctatt ctatatttta gatcttttt   8880
atttcttttt cgatatgatg acaaatttct aattttccta tatgagtgtg cttgtctccc   8940
tctataagca agaaaaaaaa caaccttttc gtccgtaccg accgatccga tcgacggtcg   9000
gatgatgatg gcgatcgtca ccggcgcgtc agcacgcgcg tgaatgcgtc cgtccgggcc   9060
agccgcgacg tccgcgcgcg cgtgtgacgg cgcgtacccg cgtatgacga ccgaggaccg   9120
atgcggcgcg ggccgccgta cgtctaatga taacaataaa agtaatacgt acgtgtgacg   9180
atggaacaaa acaataaaaa atcggccatc cgatcggggg tagtagacgt ttgtgtcttt   9240
tttttaaatt cttttttac ctatagctat ctgcctactt atctaataat tatgtttatc   9300
atctatcggc aaaagtgatt tataagcctt gtagcgaaca gagtaagcta taacggttgc   9360
tttatcgcaa tgaaaaataa acggcacaaa aaatcagtga cgactcaaac ccactgaatt   9420
ataattccct ctaaaataaa agcaaagcta ttctttcgtt acacaagtac taaatagtaa   9480
tgatacacac tacacaaaag atcttttttc tatgcaaaac atacgtactc aagcggtatt   9540
tatctggttt tcgatatatt tttttcgtat aagatgtcaa caaatgatta tgttcatcta   9600
gctatagagt tatcgtctaa caggtcaaga gaattttatt cttttttcct tcgttaaaga   9660
ctgtttcgga gccgtaagat aatacggtga tgaatctcat ttatcatcgt aagctacttc   9720
gtttttaaaa attttaaaaa gatacattcc atccttaaga aaacactaaa gtaagtacat   9780
tctattctat tttactctat tctatatcat ttttcccgta tcgcgctact actaccttaa   9840
atgttgttgt tatatttctg atttcgtaaa gttatatagc ttccacataa agagaaagga   9900
cgttaacata aaagatggtg agaattactc aagtaactga ataggtaatg atttatggaa   9960
aatgataaat gtaaagaaga agggaatctg cgcacctgcg aagcgtcgga cgccggacgt  10020
cggacggtga cggtgtcctc actcacacgc gaccagcgct ctgcgagtgt gtcccgcgcg  10080
tcctctccct tctcagcgag aggtcgacaa tgagcgcaga cgcgcgcgcg ctctcgataa  10140
aacctttctc agggccgatc ctatgccctt ccgcttgcct cgcccctctc gctctccggc  10200
cctcgcgtcg ccgttgccgt cgtcattgtc atcatcatcg ctgccgatat cgctatcgct  10260
atcgctaccg ccgtcaccgc tatcgtcatc atcgtcatca tcgagacggt agcggtaaca  10320
gcgacgacag tatcgggggc gtccggccgg acgcctaccc gtcgcgtcgt atcccttctt  10380
tctgccgttg tttttccttc tcctcgttct ctcttcccag tctgaatcta acccttcttc  10440
```

```
ctcgtcctcc ctcctctcgt ctccgcgacc gcgcgaaggt ccgacgtcgt gatcgtcgga  10500
gtctgagtcg cggcgaaatc cgccgttgtc cttgccgagg ttgacgaaga cgttgtcggc  10560
gcgtccccgg ccggccgcaa cggttctacc gggcgcgatg ccgtatccgc gtcccggcct  10620
ctcttcggcg atgatgtcga cgtcgtcctc gaacaggacg cgacgcgccg ggaacccgga  10680
tcccaacctc cggcccgagt ccgggttcgg ggtcgaaacg gtggaaggag tcggatccgg  10740
gtccggctct acggacagca gcagcgctcg tgactcttgg cctcctctcg cgcgtcgccg  10800
aggatcgacg gcgagtcggg agagacggcg acgcgtatcg cggaacagcg gaggacggcg  10860
acggaggccg ctccgacccc ggtcgaaggg ggtacatcgt ggttgttcca actctccttc  10920
ctcctctccc tctcctcggc acggggacga ggggcccgat ccccgtcgct tcggccacat  10980
gtcgcggcgg gagacggacg gactagcgaa cggaccgcgg gacggcggcg cgccctccgc  11040
cggccgcggg ggcccgaacg gagggcgcgc cgcccgctcg gaaagcgccg ctccctttta  11100
ttatccgctc ggcgtctttt cggagccccg aagcccgaaa agggtttccg aaacctcacc  11160
ttttataggt ttcagagccg gcgcgccgcc cggacgtgca tacgtcaccg gcgggaaagg  11220
attccgaaat ccttgtccct ggaatcactt ccccttttcc gtgcggatgc ttttcgagag  11280
ggcaaaaagc cgcgcgagac ccgctccccc gtcaccccgg ccggcgtcgg acgccgtagg  11340
tcggagtaac ggtaaaacga tgaagcggtc cccacggttt gcctccgtcc cccgacgcgg  11400
aacctcccga tccgtccgat gcctcccagc ttcgtctctc gacaccctcc gcgccccacg  11460
tttccatccg agagcgtgga tttatcgcgc cccatccgcg ccctcggatg ccgtcgacac  11520
ggctcggccc catcttctct cttcaggtct ggggatccga acgcagcgat gatacgtttt  11580
cattgccgta accgcgcgat tatgttttct ttactaacta ggcatcgaga cacagacaca  11640
cacacgtacg acgcatcgat cgggacgagg acgtcacgat acaccatcag acacgggtaa  11700
cgtacatcta gaacataaag aaaaaaaaat aaagtcttta attcagaaat gcaaacaagt  11760
agtgcgtatc gtgcgttcct ttttattgta ctcttcccac atccccaccg ggtatccttt  11820
tctcatccgg tttatctccg acgatcttcg gccgtcacgc cgtctcggac agaaccgcta  11880
tcatgttgcg tctccgctgc ggggtcatga acactctgta tactccgctg atgaccctgg  11940
tcgcgggttg ggaacccgcg gcggtggcgg ccgccgccgc cacattcgcg gaattcatgg  12000
cctgttgtcg catcatcaga cgaagcgccc gcccggggtg atgcaaacgg cacgacggat  12060
cgtctatcgt gtcgcgatga tcttccacgt gatcgcaggt cagcgcgcga ccgaacccag  12120
atctgtccag gtcgtccggc gtcatgccgt ctaccatcag aaactcgacg tacgtggcgg  12180
tctctctctt cttcctctcc tcctcctctc gtccattctc cagctcacgg ggcaccttca  12240
ccatcgcgcc gtcgagacga tccgatctcc cgcgcgcgaa tggcgccgac ggcgggcgag  12300
tcgcaattta tggaccgcga cgtcgaccct ctaacatatc agagacgccg gaattgatcg  12360
acgcgccgtt cgttctctca cgttgagcgc atcgccttcg cggcacgcga tttcttccgc  12420
gacggggagc gatcccgagc ggctaggggc gcacgagtcg tatctaggcc tgctgcacgc  12480
tcggtgattt atccagacgc tcgacgtaat ccttcaccca cggatccgag ggattggcgc  12540
acaccatctg tcccttctta gtgataaaaa taacacccgg aaacgcacaa ttactactgg  12600
ataccgagac gtacgtgagg atcctgttga actttaaggc tttggtcgca tattgggtac  12660
aacacgtcgc tggaacatgc ggcatcgcgt ccgtcctcat cacctccagg ccgacgacga  12720
ggatcgcgat gagtacggct gtaccaagat aagctctcat ctttctcatt acgctcgttc  12780
```

```
accccaggcc taccgatccg tacgccctcg ccccggatta cgtgccgccg aaacagatct  12840
ggagtaccgc ggcgtctagc ggacagccat gttcttataa cgtcgttggt gacggcgttt  12900
agctaatgtc gccataacgc ccgcagacgt cccgtctccg agccgtcacc gctcctgtac  12960
ccgagacgtc cgtggacgtg accggcgttg cgcctgcatc gcaacgtttt acgcgtcgga  13020
gcgcgtatcc acgtatcgat atgaaaacgt ttcccgtggc catcgcccgt gtcacgcccc  13080
atatcgtcga tacggtcatc gcgccgtatc ggcgaaacgt aacagacaca catgttacag  13140
ctcggtcgtg aagcatgacg tctttattga atgtgatcag aacaccgtaa tgaacgtaca  13200
ctatcagatc cccgtaataa tataccttcg cctacgctac gccccatccc cgagcaacgg  13260
tcacacgcgc gagagagaaa gtccgggatc gtccgccgag accgcggaat ccgcggagcc  13320
gtctcagaga tgtctcctcc cgcgtcgatc gatcatggta cggagagcga aacatctcta  13380
agatgacacc gcggtcccac cgaaaccgac gttatacggt cgacctcttc ccattcccgg  13440
tcctcctcct cttcctcctc ccatagcaga catgcccccc gttcccagtc ctccgtacat  13500
cgcgggcccg ccgacgggcg gcgaagacaa catgccgttg ttgcgatgtc cgggaaatga  13560
tccccgctga gacgggaacg gcccgcagat gggttgctgc tggcccggat tcctcaaggc  13620
atccatatcg ggcggcgacg acatcatcca actctgaggc cgatacgtac cgccgccggc  13680
gcccatcgcg cctctacctc gtctcggagg gtactgaccc tgctgcgact gttggccctg  13740
ctgatgataa ggctgctgct gatgcgacgg atattgctgt tgttgctgct gttgctgaca  13800
gtacgggggc cgcggagacc ctccgcgacc gccgccaccg ccactaccgc ctcctctgta  13860
ttggaaagga cccgtgggcc gattcgagaa tcctccacga tctgcatcga acggtttatc  13920
tccggatccc cggccccccct gaaacgtgca aaacggcgac attttattga tatcaccgcc  13980
ggatccgtcg acggacccgt aatctccccg accccggcct cctcctctgc caccgccgcc  14040
gcggcctcct cctctgccgc caccacggcc tcccatgccg cctcggggac cgggtctcgt  14100
catcccgacg gacatcatca cgccgtcctc cgagcgatcg tactccgcgc cgacggaact  14160
ctcgccgcct cggcctcggc cccggccccg tccaccgcta ccaccaccac caccgcctcc  14220
tcctctggcc gccaagacgc tcttggggta gaacgggatc gaattcgcgg acaggttgct  14280
cgacatcaac agcgacgacg cggtaggaca ggcgctcgcc gacgagatct gacagccgtt  14340
catgtcgtct atcaacttac tcaccgcggt cacggtactc atgatgctat tttcggtgga  14400
tacgccgatc ggaacgccgt ccgagacctc cggtccgtct cgacggcact gctcgggcgg  14460
cctgggtctg aggtccggag cgacaaccac gggagaggtg acggcgtctc tgccgtcgtc  14520
gtgcggagac ggcacggaga gaccgccgcg tccgcctcgt ccgccgcgtc cgcctcgtcc  14580
tccgcccctg taggatcccc gacggggtct tctcccggcg acttcggacg cgacgcccaa  14640
aaaagtcgcg gagaccgtta ggttcgttcg acacgcacca cggcctcccg gaatcaggcc  14700
gaggttctga tcgcgcccgt ccgcgccggg ggcgcagagc gcgagctggc cggacggatc  14760
actgccgtct tcggcgacgg tgacgatccc gacggcgtcg cgcgcgccgt caccaccgcc  14820
gtgctgtcgg ccacgaccga tgccagcggc gtccgataga cacgcggcgg gtacggcggg  14880
cgccgcggag ttagccgacg cgtttctgcc gccgccgccg ccgccacctc gccgacgccg  14940
ccgctgctcc ccgggtcgac cggtcggcgc cgccgtcgtc gtcagcgtcg tcgtcgcgct  15000
cgtcccagac gttaccatcg tctcggcgga cggcaacgcc gcgccggata cggagtccgc  15060
ggcccctcgc gtctcgacgg gactcccgat catagcgccg gtcgggaccc cccgatccag  15120
agagaagaac tgcgatcctc gagcgcctag cagaggcgga ggaggcccga agcgttccaa  15180
```

```
ctcttgtcgc tgttggtccg gccgcgtccc gcatgactcg ccatacaccg tcccccgatc  15240
gatctggccc gagacgtgtc gatttatagc gcagaagggc ggcacggacg tgggagggca  15300
gggcgagagc gcggacgaag acaacgacga cgcggatgac gaggacgaca acgcatcgcc  15360
gacgaaagac accggcggcg cgggctgcgg gcggacgcag ccgcggtcgg taggatccgg  15420
acacataaat aacctgtcgg tcgctaatac ggatccgggg ttgactcccg cggcgacggc  15480
ggaatacgac gcggcgaagc cgcacttgat cgggccggag accggcgggg acggagacgg  15540
aggggacgcg gtcggcggcg tcctcggcag ggacgggggc gaagaacacc tagtcacgtc  15600
cgcgaacgac agcccggact cggcgtctcg gacatcttca ctagcgctat cgttatcgcc  15660
gccggccgaa ttcatcttag actgatctcc gattgttact ccgagaggcc tatccgacag  15720
cacataggag gcgaatgtcc tatgcgccga ggaggagaag cagccccaat aactattatt  15780
ctgcgcgtac gagtaggatg ctgggaacga tgacgccgag gagcaggaag acgccgaaga  15840
ggaagaagag gaagtcgcgg gcgttatgaa acactcagtg gagggcccgc actggaacgg  15900
gaccatcggc gtgcgcacgg gaccgccggg cagacccaat cgcgttggaa ttaaaaccgg  15960
gaagaggacg gcggcggcgg ccgaggcggt cgcgacaccg ccggcactag cagcggtcgc  16020
cccgacggga tgactcccga cggcgcccac tccgacgggt accagcacca cgccgcatcc  16080
cacaggtaaa gataccacga ggggacacgc gccgcccagg gaggcgggtg cgggcgaagt  16140
cgagggtctc ctccaaggca ccagactgtc cgtagtcacg acgggaacag agccgccgga  16200
gaaggacgga gagcaagagg agacggacgg aggggaccag atgccgccgc cgccaccgcc  16260
accgcctccg gattcgccgc cgcctccgcc gaacacggtg ccggacgtct gaataacgct  16320
cctgatcgga ggcgacgcca tcgccggagc aggacaagcc tccctcgaag gacaagatgg  16380
aagactgtca ctcatgacat cgatcgagat ttatcgaggc ctgcaaaagg tacattctga  16440
cggaacatcc ggggaaccaa tcatcaaacg acaggaatcg gccaccccgga gtgacgatac  16500
cgattgtaaa attatctcga tgacgaggcc tcgcggcgag acgcacccga ggcgctacgg  16560
aaaaccgtcg tgctccaata cggagcgcgg tttcccgcga acgagcgcgc gcttatggcc  16620
cctcaccgcc tccccgcgac gtcgcgcacg ccgacccggg gcctccgcga acccagacgc  16680
agccgtccgg agcggcgatg ttacgtacgc aaaagcacat cccacacgtt tcccataaaa  16740
taaagcgata cgggcccgtc gcgacgcgcg gaaggagcta agtttcattc gcgcgggcgc  16800
tcccggcccg acggaagccc ccgcgacgct ccgtcctcac gtatacgcgt ataagcccat  16860
agtcccgaaa accccgagac ggccaccgtc gtgactcccg ttacgatcac ggaacgttat  16920
gctttaaata aaccgatgac cctagcgagt agatacgtgt gtctcgcggc ctcggacaca  16980
tagggccgag acggcggggc gtcgcgcgat aaaccagatc cgaacgatac gtctgcgata  17040
tcacaaaata cttttattgt cattaaaacg taaggcgaac ccacacccgc gtgccacgag  17100
tgcggcaacc gcgaaaagcc cagaaaaccg accatacaga ggaaaaaccg tgcaatgtct  17160
cccacccctc cccacacaga gtccaagatc acacgttcaa tcgagatcca gttcgaacgt  17220
ggggaccttg agcgcccttc tggaccgtat caccctggag aagaacatca gacggaggta  17280
ctcgagcgac tcggcgtcta tgcagccctt ggtaccgctg gtcgccatct cgtgcgactg  17340
atcgtacagt acgtactcca ccctgggtcc ggcggactct tcgtcatcat cctcgcactc  17400
gtcgtcctcg ccgtcgccga tctcctccgc ggttccgacc gaaccgtcgt cctcccgctc  17460
cgactcttcc tcgaggagtt cctgggagtc ttccatgtat tcgtgttcct cccgggcgga  17520
```

-continued

```
ggcggcagcg gcggcgcccg acacgcgtcg gtcatcgccg tcgtcgccgc cgtcgtcgtc  17580

gccgccgtca tcgtcggccc tcctgagctt gacgttgtaa tatctgcgag cttcggccag  17640

gggcatggtg gacagaacca cccgagcgtt gcggtcgaac accaacttcg ggcactcgtc  17700

cgcgaacaac ggctcccggt gacagtcgac gttacggatg atcgcgtgcc cgacctgcac  17760

ggtctcgtcc atctcgggta tcttaccgca gggaacggta cataccgaga ccggatccgc  17820

ctgatccgtg agcttgctga gctgcagctt tcgaaggttg gcggcatagt cgaacgactg  17880

acagaaaggc gtcagctccc gcgagcggtt ggcgcacacc gatcgccacg acctgtgaga  17940

ccgaggtacg gcctccagtc tggccgcgcc gcgatttccg agatcgaaac gcgtgccggg  18000

atccagcatc tttagaaacc cgcacctgaa gaacgccgtc accgagtcgg cgagtctcag  18060

gaaatcccct ccgtacacgc gcatggcgta cacggccgcg ctggcgtcga tgaggaccag  18120

atgcttcgcc ctgggctcgt gcctgtcgtc cagctgcacc tccacaccca cgaccacgaa  18180

cggcccttgc atcatgaggt gaacgtaacg gtgcagggcg acgagcgtgt aatcgtcggc  18240

gcggttaaac gggaagaagg acttcaggtt accccagtga cccacgggga tcatgagctt  18300

gttgggaaag cccggggtgg acaccacgac gatctccgac cgctggaaaa actcctcgcc  18360

gactttctga acccgctcga ggatggtgcc ctctccggac tgagtgaggc cgtagtagta  18420

cgacgtcgta gcgtcgtgta tgccgtcgaa cgcgttcggg gtcaagcggt ggttgtagac  18480

ggagcccagg gcgacgagcc cgtccgtggt cagcgaacgc agatcgtcgg ccaggaggta  18540

caccgctctc tccttccagt cgtaggcgta cacctgcgcg gactcgccga ccatcacgac  18600

gaccgacgtc tcgtcgaacg tcacggtgcc gagtcggatc accagccgac cgatcatggt  18660

cggcttcatg tcttcctcca gaccgtaggc caggtgatcg aatttctgga agtgaggatc  18720

cctgctgcac acttccatgt accagtgatc cggtctccgc atcctgatga ggcagccgtt  18780

gaggctctcc agtaccgcgc acagacgtcc gggttccctg gatgcggcga acagcatgga  18840

gatggtcccc aactgatcgg acggaatgga ctccgcatcg acctggggca gcagctgacg  18900

gcggcgctgc agcgcttcgc agcccatcgt tctgtacata cgcgcctcct gctcgaaagt  18960

ctgcaggagc cacgacgggt actcgtgact gggcgagttc tgcctgaaac tcgcgcatcc  19020

ggccaacgcg gcgagctcgt acatccatcc gccggtcgcc tcggcctcgc acgccgcggc  19080

ggtccgagac acgttggccc tcgtggagta cggttcgtgg cgctgcgcga cgttcctgcg  19140

ggctttcttt ccggcgctgg agccgccgca ggcgccgtct tcccgacgtt ctacgtccat  19200

gtcgttgtcg gctccgtcgc cgctcccgga cgctccgttc tcgccgtcga tcgcgagctg  19260

tctggtccga ctggccaatc tagacacggc ctgcgacgag agccgccgct tggaaccggc  19320

catcacgggc gcccggcccc cggatctcac ggatcgcctc tgatccgaag agtccgcccg  19380

agacgaaacg gacgccgact cgtggccgtc ccgtccgcat ccaggacccc ccgttggacg  19440

ggccacggac ctcctgatcc tctcctcatc ctccggacga ccgtccacct ccggccgccg  19500

ttcgcgtatc gccctgggac gaagctcgcg tctagcctcg gccccggctt ccgatcgctt  19560

catagcgcag gccgtatgat aaaaaagact tcgagacgtg gaacggcgaa cgtttttctc  19620

cgtgaagcga tgagtcttcc cgtacgacgt cccggtcgca acgttttcac ggcgacatag  19680

cggataaact catatattca caaagtacga gcgtccactt aatcgaaatc ctttttcacg  19740

accataaaat cgatgtccgg aggagcgatg ctccgcgctc ccctcggcga gctatgtgat  19800

cctccatttg ccgcggggac cttttataga tctgcgagtg actaacccca cagcgggaaa  19860

acagccagac agattattca aatccccccg agaggactca gtaatcgcct tccggatgct  19920
```

```
acccggccgc gactaacggc gaacgtccct ccgacttccc gaaacagacg tgaccgcaga  19980
caccgaaatt atcatatccg taatttttatt gcaacgctcg agaaatttac agcccatcct  20040
atacacgtcc ccgggcggga tttaccgtca gtccgacacc gcagagaaga tacgtcaccg  20100
tttatagacg cggtttacat ccagaacgcg accggcgtcc ggttcgccgt gacggttttc  20160
gaaacggtga atataatgac gcatccgttc taggagacaa aacgtggccg cgaggatgac  20220
gcacgccacc agggccgacg aactcgagga gatgaagtct agaccccata cgcggatcag  20280
ctgttggatc gtccacgtat ccatgggagg tctgccgtcg gtcacgacct ccatgtctat  20340
cgtgggctcg tcccccacgt agagctgaaa ggtgcacttc agctgatgcc acggccgcca  20400
atcgccgggg atgcgaaccg tggccttcaa gacgttcagc ggccggtcgt cggaatgaac  20460
gtacgtctgg tcgtcgcacc ggctgtatcg caccggatgt tcggacacga aattgacgga  20520
cccgcttccc agtcggccca cgtacagacc cgcgacgatc tctagcttgt cttcggtgtc  20580
gtcccagaag gtcgggacgg tcagggtcgt gaagggctcg tgagagctcc cgtcgtagaa  20640
gtcgagtatc aggttcttag cgtgcatggt gtcgtagctt cgaacttcgc attgatgcac  20700
caccacgttc ttatccgcga atatctctac ggaacccgac ggcaccacgc cggagtgcct  20760
gacgaacttt ctgacacaat ccttcctctc tcgcctccgc ttcagactcg tgacgaagaa  20820
catcctgttc agatacaagt tatcgctgcg acaacgctcc ggcggcttag gatcgcgata  20880
gcacatgaag gtaccgttgt cgcaaggctc ctgccggaac ctctcgtagc actccgtctt  20940
ccaccaccac gtccccgagc aacgaagcac ctcgttatcc tccgcgaatc cgagacaccg  21000
ataacacctc ttgccgtcgc cgtcgccgac gacgggttcc atgaacggcg aagagccgca  21060
ctgctggcag gccgcgtcgt cccgtctcga cgcgtcgccg tcggacgctt tcttgacctc  21120
gcgtaggtgc cgaaccgtat ggttgagaac atctaccata ttggagagag cctgcagggc  21180
ttccgcggac ccctcctgtt cggccggtcg aggcgcatct ccctccgcat ccccacgaac  21240
ggagaccgac accacataga aaacgcaaac gatcctcgct atgcggcgaa ttccgtatcc  21300
gtcggccatg cccgagggtc gcgatccgat ctgtccggca cgcgaaacct atatggacgc  21360
gcgtcgagag agatcagaaa atttatccgt cgcaggcggg tgtccggcgt gggatgactc  21420
ggacgagcga ggaacaacgc gctggagtgt tatcaaagga atgcgtttat aagccaacca  21480
tggaggggcg tggaccccgt cccccgcgat gctcggatga cgcctcgtct gatgtcattg  21540
cagagaagcc ccctcgcata gacccgatcg aagcaccatc tagcgtctga acgagagact  21600
cttcgcgatg ctgcctattc gtctacgaat acgatctctc ttggcgctgg agatcagaca  21660
gacgtaccgc gcgctcccga ccaggacgaa catcatgatg atgaaagcca cgaccatcag  21720
actgaaagcc ggcaacacgt aggcgatata atccatcaac aggacgtcgt atctgaaatt  21780
atcgggatgc agcgacgaca cgtacctgag cgtgcacgtc ttgccgccct ccgccatccg  21840
ccgacgacca gagaagcctc tagcgatata aaatttgtta tttctgttgt cgtgctccgt  21900
gacccaacct ccgtcgtcag aagtataagg cacagccatc gtaaggttcg gaaggctgta  21960
gttctccgcg aagggcccca aagacatcaa tatgacatta tttctaggcc tcatggtcga  22020
actgcgaacg atagccagtg cgggcagaac gacgacggag tacgctaacg ataagcgcat  22080
gtcgggattt ttccacctgc gtaaaagcac acgcccgcgc gtagaaacgc gtgcgtcccc  22140
cacgcagctc gtattcacag acgtaacaaa gattatcacg cgccccacac cgatgttgag  22200
acccacggat agattattcg ccttaatgtt gtagttcagg acattatcaa acaaccgtaa  22260
```

```
cctatcactc cttatggata tatttctaac gtctcccgtc gcgcaaaact catccaaaac  22320
ctttcgccat aaacatcctt gtacgtcgaa attcataaca gtgtcccccc acgtagcaat  22380
gtacccgcga aaacacgtat cgttaccctc cgccctacaa caccacacgc taaagcattt  22440
ctcgctcccg ttcgtcacgg cccgcggctt ccccgtgact tttgtcgcgg acaacgtttc  22500
gatacacgtc aacgtcgaaa ccgccgccgt gaatatgaat attctcagcg cattacggat  22560
atcgagctta ctcatcaccc tcccggacac ccacatgcca caaatcttgg cactcgatcg  22620
attcccgtga aacacccaca cgcgcatctc tttataatgt cactcagacc tgtctctcca  22680
cccatctttt ctcatgacgt gtgatacgta aacgagattt caacataata cgtacacgat  22740
atagatcaat tcaatcattt atctttattc tatcgcacgt attagcagta ttttatcaat  22800
atatcgataa catcgtcagc cgcgcacaca cagcaagccc cgtcacccca tccgcgcggt  22860
ccggggaaaa cgttacacct tggggaactt agacgcgtac ggtagcaacg tggtctcaaa  22920
gctgtccagc tggccgcaga agcccagcgt gccgatctcg aaaaactttc tgcgcgcgtt  22980
gggtaaattt aaaaagtaaa tgtagcccac gatgttcctg tgccgttccg cgctgaccac  23040
cgcttccatc caccccatga ccctgggggt tgccgttttt gagaccagtt taccgagtct  23100
ggcgtacaag gcctcctggt gactgaacat gtgtatctcg ctattgcgag acatggccat  23160
gaaccgcatc agggccctgt actcgaaagg gatgtccccg gattgccaca gtccgtccga  23220
tatcaaccgc atgacgtctc cgcgaaggta gcggcgggag cccgtcgggt gaaaaccctc  23280
cgtcgagggc agacactccg gggggcggcgt ctcctgaatc cgaaccctct tgagggcccc  23340
ttccacgctg agacccacga ggtcattgag ttctctgctg atcgtcacgt acaacagagg  23400
gtccatggag aacgtcgcga aacccagaca gacggaacag gacgtcattt cgccgaacgg  23460
atagctcccc tccagaccgg atccgatgac taccatgtag ttgccgtcag ggatgttcaa  23520
aggctcgtac gggaccgtgc agggtctatc gacggactgc agataacccc ccgacataca  23580
cggggcgagg agttccgccc tggtgagggg tttcttaaac tgcagaacgc attcgatccc  23640
gtatccggga gcgtgtctga aaaccacggc ggcccctttg taatccacgc gaacctcctc  23700
gtccggtccg gcgcgcgcat cgtccctcgc ccgtaccgga cagttctcgt aacacagaaa  23760
atgcagacat tcggcctcct ccagggtcat cggggaacgg actttgaacc gctcgaactt  23820
acgcgacaat ctcgtaggaa agacctttac gtttttatca tcgtcgccca tgccgaccat  23880
ggcgtatcgg aacaccatct ctccggacca cgaaaacacg ttcttcaccg acatgtgctc  23940
gagcatcact ccgtagatcg tggacggcgg taaaacgtac ggatccattt ccatgtccct  24000
tttgtacgca tcgtccaccc acttcgcaaa aacctcgccg tcatcgaagc aggactcgtc  24060
tctcgggttc atgttcacgc gatatcgcga cagatcgacc ggcgatacac tccgacaccg  24120
gtctcgcctc cagatgtggt ctcacactgc ccggcgcata ttaatatgac tcccgaagga  24180
gaggatcaac ccatcgatcc gcgtcatctc tgacacatct gttccgatca cccgaggcgg  24240
gataacgtat cccatggaga cgttacagat agcgataaca tatcagacgt atcggccgta  24300
agcacatgca cgcgacacac gtaacggaaa accggtcacg gtctcctttt tataaaacga  24360
gattcgacgg atgggactta tcggccaaca gtccgttcag aacctccatg atcccgtcgc  24420
aatacgtcag ctccaccaca tgctcccccg tagcggttat tttcgtgcaa cgaagactgg  24480
tcgttcgttc gtccacaccc ctgtagctct cgcggaaagt caccgttcta gagatgtcga  24540
acgcgccgtc gaccacgcgg atcttgtata cggaatacct ctgtacgcat ttgtgtctgc  24600
ggtcgccagc cggcttcgcg tgcaacagac aggacagtcg gttcgtcacg tcggcgaccc  24660
```

```
gatcgtcgcc cgccgctcta tccgcatcat cgtcgctccc gacgtccata tatctcggcc  24720
tctgcaccaa cggtacgacg gccctcgtta cgacatcgaa gtcgaaggag acgaagtact  24780
ccccgtcccg ccacccgtat ttcatgcgcc atccgtcttt gcgagtccgc acgcaacact  24840
cgtcgcgtct atcgacgaga tcgaggtcct cgaacatctg ggacagctta acgaggtcga  24900
acaggtgacg ctcgacgacc ctgatgagat cgaatagcct cgtgcccctg gacacctgga  24960
tccgatgttc gtgcgaggcg gtgaagaaac accgcacgaa agggaacttc ttgaagctga  25020
ccgtaacggt cggattcatc tcgtcgcgga cagcctataa accgaaccgc ggacgccccg  25080
ggaatcgccc tactcgcaat cgcagtctgc ccgccagaca ggaccaggag accctcgagc  25140
cgcgtataag tacgagattt tccccttctt tacacgcccc agccgcgaac atgtcacgtg  25200
aatgtggcca cgggaaatga cacacgggta cgggtaccgc atcgagcgtc gtacgtcgcg  25260
tcgcacaaga agtcgagaga cgttatcgtt gcacacacgt gtttattgat cggccgaacg  25320
cacgggtcga taaagcacat atacagcgat cgggaaagcc gtcacgttat catcaggggt  25380
agtactgccc aaactctaga tacagatctc tgaaaaagcc gctcacgcca cggttatctc  25440
tgtccagcgt gcctatctcg taatttccgt gggtatccga aacggaaccg tgtacgtaaa  25500
tgtacgcggc ggtcttcccg tagagtcctt cgtccttgag cctctcgata gttttcatga  25560
tggagacgga cgcggatcgg ttcaatagat aatccagtct ctgaaatagc ttttcctcac  25620
gggtcataaa aaaggcattg ttcttcacgt aaaaaccgag aaattcgaat aaggcttgac  25680
actccacggg aagcgtgtca tcgtcgggcc cgacgtcgcg cctttcgccg tttggggtat  25740
agtgatccgc catgtattcg gtaaatccct ttcgacagac gcgtcgaaaa cccccgggaa  25800
gagcgcgcgc ctccatcttc atcttttcgg acagtccgtc atcgtcgctg ctatccatat  25860
cctcgggcgc caggtcgcag ccgccgatgg gcgcgatatc gtacgatctt atgtacgact  25920
ccacgtacgc cgtcatcttg tgatacagcg cctcatcgat acggaacgtc gcgattcctc  25980
gacacacgtc gcatctggtc atcgttccgt tcggaaagct ccccgatatg cccgcgccta  26040
tcaccagcag gatctgctca tcgtcgggaa cgcgaggcgt atcgctagtc cacatctccc  26100
tgggtatcga gtacccgttc tcgtaacagc aggccatgac ctcgtaccag gtgcatcgtt  26160
tcttgaacct caaacaacaa tccagatgac cgtcgtccag aacgcgtacg tctaatctga  26220
acagactggt gtcgatatta gacgtggtgc ccgtacccat ctccaaaccg aactcgtaca  26280
ccagccgatg tacgaacttg gtctccacgg ccgtcgcctc gcgctcctcg tcgtccaccc  26340
cgtcacccgc gtgaacctcg acgttgtcgt ccagcgaggc gagttcggac atcgaacgcc  26400
atttatcctc gtcatatttc tgcatggaga catgcggtcc cagaacgacg cggatgagat  26460
tctctccgac ctgagcgttg atgcaccatg gataccgcgc gttcagcccg gacgtagcgg  26520
aagggagatc gtcagaactg tcatcctcgc tagacatggc tatctcgatt ttatttagtc  26580
cctactgcga acgcagctcc gcacgaccga acagtccagg tgagtgtcgg ggggaacgat  26640
tcttatactt gccttaatcc ttattgtgtt tttgttggcg atcgatgatc gatcgatagg  26700
tcgcgagacc caaatggtga tcacgacgtt tcgtcgctcc gtatctcgat ctcctccata  26760
tccaacgtcg cgcccttgtt gtcaaatgcc gccggatacc acggcgcgtc gcctatgacc  26820
acgtctggcg gctgctcgtc cgttttcatc cgcgtcgtat cgtcgatcga tttccgccgc  26880
gtcgatacgt atctccaaga tacgtacgat acgacccata tcacgaggca cgccgacgag  26940
cagatgcccg cgatgcatat gatcagaaaa acatgagacc ggccactctc cagaaacggt  27000
```

```
gcgcgaatac tatgcgccac cggacggtcg ataatcccgc cgtctaccgc ttccactacg  27060
cacgagccat gccgcaacgt cgaaccacta gtgtacgcga acaatctggc tttggaccga  27120
aacaatccat cactagagat atgatcttcg tgaactatca gatccataat tgtaaatcct  27180
gtcgaattat ctggatatgt tatataaata tatgcagcca tatgtacgga ttccgatatt  27240
ctagcgtaag gattgatcat tctaaagtga tagattacct ccccggcatc atcactataa  27300
tccatgccga atagacgtgg caaactcgat ccgctttcaa aatcacaacc gctcgtgata  27360
ccaacgaggc tactatcacc gcttacgtcg atgtctccga tggcggttag acggtcagac  27420
acgtctggat cgccacgaat ctgctcaggc agtatccact ccatccgtgt gtccctcata  27480
cgtacggaca tattgaaagc caccacgacg gccctctcct ccggatcgac gaacactgga  27540
tcagaatcta tatgcttgca tatccatgtg taggacaaca cgtgtccgtc tctcgcatcc  27600
gttacggatc cagaacaatt cagaattcca tcacgaggga ttttggtttg cggttcggag  27660
caatcggaga cgttcgatat gcatctggat tccatccaca ccattatatg atcggtcgcg  27720
ttgataggaa catcgttggc acagcgaacc gatgtgacaa aaaacgccac agacgcaatg  27780
gcccagtacg gtcctccgaa acggtctttg cgtaccatgc tggaaacact cggatgttct  27840
tcaagcaagc ggtcacccac gcgatacggt cagatgacac acaccgtttc tcgtatatcg  27900
aaacgtgtag cgcatagcac tttacaccgc aagtctcttc tttttatccc gtgggtcaga  27960
tgttcatgtt tccggagcca aacccaccgg aaacaagcac gcatgacgcc gcgcggcccc  28020
gtacacgcga aaagcaaggc tcaccgggct cgtaccgttc tattccagca tactgaatat  28080
ggcccaagct atagtctgcg tcaaaaactc gacacagatc ccgatcagca cgaaccagac  28140
gatcacgccg gagagataca acacgctgtc caccgttacg tagaaatcgc caaacacctg  28200
acggatgtcg atcgcggggg atggctcctc cggctcgggt tcatcgggac cgtcgttctt  28260
cacgacatca cgttttcctc ccaacatgag gatatcgaac cgtttctctg aaccgttgac  28320
gaaagacatc aactcttccc tgccgacccg catctcgtgc acgttgcgcg cgatgccgcc  28380
cggccgatcc cgccttcgtt tcggcacgtc gacggccggc acggacaaaa gagacgccga  28440
tctctgaacc acacgcaagg cgcctccggc gttgcccgcg cgtctcttca cgtacataca  28500
atcgacgggc agagagatcg cctccttggc gcgaaacgtc gtcgagacgt aagatatcat  28560
ctcgccgtca ccgttaacct cttgaccgta ccgaatctct cgaatcgcgc aatgcgaccg  28620
cgcgcccgag gccgtctcga tatacatgga gccgaactcg gtatacagcc cgctctcagg  28680
tttgacgtag ttcatcctaa aagaaaaatc ggccgtgtac actattccca gtccctccac  28740
gcgttcgaag ttcttgccca tcagcagaca cgtcacctgc atggttccgt ctgacgcgat  28800
cgtgaccgtg ccgcccaagc gcagcttgcc gtgggacgtc gtctcggacg gtacggggaa  28860
cggaatcgcg ttctttttcg cgttacgttc agacgcgcat gtggacgagg aggccgtaat  28920
ataaacggtt cccgacgcgc atctatccgg accggtgtcg taactcacag tcccgagacg  28980
ggacgggccg tcgacgtcgc cccacatcga gtaccgcgtg acgagagacc tcaccgaatg  29040
aggatcgttc agagcgtccc cgaagacggt cagattcacc ttcaccggag tcgcggaccg  29100
catcccgaca acgtcggcgg tcctcaccct cgcggaattc aactccctgt tgacgaacac  29160
tcgtaccgaa gcggaggagt ccccgaatcg cacgcacatc tgagctaacc acaggaccag  29220
acataacctt ccccacgcgt acgggaccga catatcgacg tgtctagttt ttccctcggc  29280
gatccggacg gaggccggag tcgtacgaga cgcaaaccga cgacaaacac ctcacgtgcg  29340
gacgattcta ttggcacgga cacacaaaat cactgccaac acattgtaat tgcatcaacc  29400
```

```
attgtttatt ttattcggga aagtgatccc acccatcccc cgtggtacgt catcattacg  29460
atttccgcgc gacagatctc gttcacacgg acgaagatct gatccgtctt ctaacacggc  29520
gacacgaccg ccggtccccc gacgtctcgc accgacgtcg cacgcggtca tcgggatagg  29580
tctccggagt cgggtcggcg tcaccgtcgt cgtacgaccc ggagatacat tccggtcgcc  29640
atatcatcac gatgatcacg accgaacaga taaacggcac ggacatcagt agcgccacac  29700
actgtctata gatcgcgttg aagacgatcg tgtccatgat actgccatcc gcttaaaaaa  29760
agcgatcaat ccccttttcgc ccgtctcgcc gtcgttgtcg ccgctcgtct cgtcctcaat  29820
atgtttctcg aagagccggg cgagacgttc tcctcggacg cggccggcgc tctacgaagg  29880
atcgtcgagc gcaaccttcc cacgatatcc agcttgcgac ctatgacgta tattacgcac  29940
gcggccacgg agatcatcag cataccgtcg aagctcacga cggaatctct aacccaggct  30000
ccccatccgc cgcccttcgc tcccccgacg aagtcatcgc taaagtaaag agcgtcgacg  30060
agaggattgc cgtcgtgggt gtacgttacg tttctcgcga accagtgtat caacgtcggg  30120
tcatcttgcc gaaagcctat ggaaaactcg tacaggccgt tcttcgactc gttcgccgca  30180
cctagatgcc aagaggcgac gagaaagtcc tttacgtgat gcgcgccggg aatcttgata  30240
cccgccaatc tgtccacggt gatggtgata tacgtctgca tggtacccgc taacatgtac  30300
tttagggcgg tcgaggacgt cagaggtatg tgtccggtct catatctggg tagttttaat  30360
tccgcgcgac tctccgcgac gtattcccca ttctgcagtg tcattctggt gaaccccacg  30420
cggatggccg ccacgaccgc gacctgcatc ggcactcccc agcgcaccac gagtttcccc  30480
cgacgcctct cgacgtgcgg ttcgaggcct tcgtagttcg gatcccgctg atctgccgtg  30540
acgttataca gatacatgaa aaacagacgc gtgtgttcgt tatccacgta caggggacct  30600
tcctccgtga gatggggtat atcctgatat ttttcgatcc gggacaagaa agcgagatcg  30660
ttcaaaagcc gacacgtcaa cgcgtcccca cgaaccctac tgtaatttcg aaagacgaaa  30720
cctctgagcg gcatagtgca tcccaaaccc tgtacgttaa tcaccatgtc ggtcgcgttg  30780
acctcgaccg cgccttccgg ctcttcttta catactccct cactctcgca cgagacgtag  30840
taaggctcgg tagtcatgtt ctgactgaga tcgggtccgc tgggtccggg attggcggat  30900
ggcgaatgta tgctgaacct ggagtatatg cttcggagtc ggtcgcgctc atcccgttcc  30960
gccactcgtt tgatatcgca cgcgtcgaca catacggccg acccgagaac gacgcacgcc  31020
aggatcgccg aacggacacc cataccgaca atcgagcgag gcgcgctccc tcgcgtcgat  31080
aagcagcgac taccccttcgc gccagattat atacacaagc gtacccacag cccacatccc  31140
cacatcccat ttcccgcatt ccacatcccc gcctctcctc gcgacgatct atcgacaccc  31200
agagagccaa taagatgaaa gacagtgcat tccaagaaag gaatggtcgt ccgttcttta  31260
tttaatcatg tatacgtata agatatacgt aaggaacgcc ttcgcttcaa ttataaatag  31320
aatcgtcgca cggtcgacga gaacactgct cgaaaggccc tctcgtcgcg gtagtcgtca  31380
cgctgaggtt gcgtctcgaa gtatacggtg tcgatcgaac cggaatccac acgaagtcgg  31440
aactacattc ttccacaccg ccaccgatcg agccgacggc gtcctttctg acgcgtttat  31500
agcacttctt gtcgaaccac ttgacgatgg agctcgtgcg atgccgagcc gccgcggccg  31560
acttgcactt gctgctcacg cgaggcatgt cgacggtctg aaaatcgtct cgggcaacgc  31620
ggtcctgcaa cggagaatca cacccgtgag aacatgtcct ccccggagga ggtcgcagcg  31680
cgcgccgcga ccgacatgaa accacacccc cacagatccc aaacgtacgt ttaataaatc  31740
```

```
agccttcgtc tcgcaggccg cggcaggaga ccagctaccc cgcgtgccac aatgacaggc  31800
gacgtacagc tttttaaacc ttttgcgcac gcttaagaac caatccataa taagctcgtc  31860
ccacgcaaat tccaggaccc tccgcccggc caattctggg aaatgacctc tcggccatgg  31920
gacagccaat ttctccccca gagagattcc ggataatacg tctcatcacc gatagttgca  31980
taatcacaca acatattacc ggaaagtcct ttatttctat acactttatg tctaaaaata  32040
acatcccggc atcccaccga cccgccgcgg acgcgacagt ctatataacg cgtcagctga  32100
cgaaaagacg gtttataaca acgttggccg cggtacgtta cgcggatacg tccgtcgcgg  32160
tagtccgaag tccattaaat ggcaccagtt accatttcgc cggtatacgt aacgttgaag  32220
cacgaacaca acacagcatc ccgcgtaatc tcctcccgaa ccccttcgtc tccctccata  32280
cgccaaacct ttttcccgat acaccacacc atcgaccgat tcgtcccgcg agtcccgtta  32340
cccatcgatg cgtgcgaact tttaatacac gtaaacgctc gacgcccgcg cgccgataca  32400
tctctcccag taaccgtgac aaacggacta gggcccacag attctttacc ctcacaacga  32460
tcaaacaccc aacgcgaatc ccgacaccgg tacgtcgacg tatcgatagc acgatccgaa  32520
atatgtagat ggacgccgcg catcgtgcgc gtctcagaga taataggtgc cgtctatccc  32580
tgaagataag tgtcccgggt ctcatcatgg ccgctatgac ggtcgacaca ttatatctcg  32640
cggtcccggt cgtcccggac gaaccattca cgacgccgac atcgcgtctc gcgctcgcgg  32700
cgtgcgacgc ggcggtcgac agcagcgtga tcaggccgag cgacgtgacg ataacgatga  32760
cgatgacgtg caccacggcg atgaacctgc tttctttcag gccgcatatg atctcctcgt  32820
ccgaaaacgc ggacacgcct ttatcagaaa cgttgtccgc gtccggagac tgtccgtacc  32880
agcgtgtcct agctacgtcg agattaacgg cctcggtcgg tccgctcgag tcgctcatct  32940
tgggcttctc atcgctctcc gcgtacaatt tcatgcgagt ggactctcct cccgtcgtac  33000
gtttcccgcc gcacatgtcc catacgtttt tcttaccgta acgttcgatc gaccgtatcg  33060
atccgttata tattgcccac ggtctccgta cgcatcccat agagaatccc acgggcgaca  33120
gacgacgtaa aacacacggt agtcaggagt aacatcacag aactgtttac tttcgatttc  33180
atgtacaacg gattatcgaa gatttcatat atgtacaacg taaatcatcg taatcacaca  33240
ccaataataa acccgataca cgctttcgta cccaaaaaaa gaaacacaac ccatcccgtt  33300
agttcacgtg ctgcgccacg tcccggtgac aggcatcgct cacgtcgacg agctccacgt  33360
cttcctcgtc ggcggtgtcc atcgtgctca cgctggaccg gctcatcatg ctcgtgctgt  33420
tcgtctcgct actggcgctg acgaaactgc cggtgctgaa aacgctgttg gtgctgacga  33480
cgctactggt actgacgacg ctgctggtgc tcatcacgct gtctctccgt cttcgatcct  33540
tcaggctcgg cctccacgag aacaaccctt tcttctctct gcgcaccggg tcgaacgact  33600
cgatgtaccc gcacgaaccg tgactcacgt cgcacgggca cgtcggacga aaacacaggg  33660
accggcattt ttccccgccg tagtaaaatt tctcgttcga cctgtagcgc tgcaggccca  33720
acgcggccat ctcccgaggg tcgtctccga ccagtaccac cctgcttcta tccgcggcga  33780
acagacgcat cttgccgtct atcaagatgg tcaactgagt cgttttcaag tcgcagccgc  33840
ctcccgccag gtacctgacc gtggccagga ccgcgagcat cctcacgccc gctatgacgc  33900
tccaagactc tatgtcgtct tcgcacaacc cggcggacaa catgttgcac accgctatga  33960
aggaaccgtc ttccaggcgc agcagctgcc ccaacctctc gtccctccac ccgatcacat  34020
catctagatc ctgcaatctg gaaaacgcgg acatggacgg ttccccgcac gtcgtgtgat  34080
acaggagcgc gcggtacgcg tacgtggcga accctttgtt cgcaaaactg cgcacgctgt  34140
```

```
gcgtcacgat cgacatgctg gaggtgtaca gcccgggcat atacacgtat atccgcccgc  34200
tcctcccgat gtacagttcc gggtaccagc tggccatgat gggttcccag tgaaacgcgt  34260
tcggaccgga cgagcagacg ctgccgatca acttcagcgg ttcggggcag cacaagaagc  34320
cggacagcct gacgttctcc cgttccgaag actgacacat gggtctccag cgtcttccca  34380
cgcatatcac cagatgcttg ggccaggcca ggcgcacgcg gcgatccaag tgcaccgaga  34440
cccgccgatc gacctcgtca aacttttca gtaaactctt tagaaacctc ggaggcgcca  34500
tagcggccca ggacctacgt gcgccgcacg ttccaacccg attcccgggt cacggacgat  34560
actcaacccg accgccaatc tttcacgtcc aggtgccacg gtgcgacttt ttatcgggcg  34620
aagaggcgcg tcaatttccg gagggcaggt cccaaaaacg cgttcttgtg aaacaaaacg  34680
tatgtcctcc atcgccggtg cgcgccgtag cccgtattcc cccctccccg cgtgcgaact  34740
agccgcgtag cttatccgac accgtgccac acgcggggaa cgagggacat cccggcgcgc  34800
gatcgaaata gctacgtttc ccgtctctcg cgtggcgatc gtttcggtag aaatacgtga  34860
gccccagacc cacgaacccc ggcaggttgt cggcgagacg tacgcacgta ttgagcgacg  34920
tgtcgtaggc caagacgtat ccttgctccg ttatgaaaat gggcacgtcg ctgggctgta  34980
tgccgcgaga caacgtcagg tgaaaagtcg atttcctcac ggctattcct atcggaacca  35040
tcctcttgcg gagagtcgta acgatagcct tccagaagcg acccgtatct cgattacggg  35100
aaaaacactc caacccgcac accctaagga cccagttctc cgggtgcgcg atgggaaaga  35160
gacagccgtg tctccggatc aaaaaccgca tgagtccggg cacgcctctc ttctcgaaag  35220
acgtgatcca ttccctatac ctgcgatacg tcctgatgtc gttgtagact ataccggaat  35280
agatggtgtc cacggtctgc aacccgcgtg atacgaattc gtccacgccg gccgccacgc  35340
ggtagacggt gtctttgggt tctcccgcgt agcagaacac gctcccgtta tcgagcgaca  35400
ccagtagaac gaactgttcg acgttcatct catcgagcac gcgacccacg ggcaccaggt  35460
tgcaccggca acacagatac tcctcgttca tcctgcgcga aaacgcttcg tctctacata  35520
gatcggcgtc gacgcgtacg caccagccga cgggccaggc taaccggagg acgctgtcgt  35580
gtctgtcggc gatatattcc agcggcccgc gttccgactc ccggtcctgc aacgcctctt  35640
tcaaccattg aaaatcctga gacgagaagg taatgtagac ggcccgcatc aacggataca  35700
actcttcgcc gatagaccgc tgcacgtccc tgatcgatcg ccgttcgccc atgatgacgg  35760
aggcccggcg cctcctgatc aggttccccc ttcttcgacg agaatcgtcc tgagaaacga  35820
ccctctcgac gagccgttta ccctccacaa tccccgcgtc cgcgtaacaa gaaagccatt  35880
cgcacagagg atccgaaaaa tcgctgctct ccgcagaggc ggcgcgatcc gcgcgagagc  35940
gttcgaacga ctccatgtca cgcgacgccg cttttacctc cgaataatat atgtatccgc  36000
tgcgaggata accgtacggc gaacgacgta taagtattgg gatcaagctg ctgcaatata  36060
agaatatcgt cacgataatc gagacgtatc gcggtcgaca atcgaggtct agacagacaa  36120
acacgggtca ccgcgtcggc gaacaggagt cagatcggag aatctctcgc tgtcgtccga  36180
gtcgacacag cttctaaaaa aggcggacgt caaacaaagc atggcgtcta gaaatagcga  36240
cgaccccagg caaagtaaac aaaaacccat aaagcaggca agcgcgtccg cctccagcgg  36300
tatgtctggc attaaaagac agttcggctt tttcatggga aacaaaaaga acggagacac  36360
gcatggtaac tcgggacgat cgaaaccatc gcagggcgcc gtagccgcgg acgacggttt  36420
tcaatacaga gactacacgc acggagacga cggggaagag atatacggag ccgtcggtgc  36480
```

```
cggccgacac ggccgaagag acgcatcgca gtccaaagtc gttcccaaaa agcctcccag  36540
gatgggacgc tccgagtcga tgaaccgaga ggtcgaacac gtcactaggt atagatctca  36600
agacgaacac ggcgcttcgg gaaacgtact ccccgttacg agaaagcgtt cgacatcctt  36660
cagcggaaac aggagcagct cgatggatca aagtccgacc gaaacggtgt actcgcttct  36720
caaacaagga ggcgcgagac cgaaactcaa gacatcatcg aaatcggtcg atcacgggaa  36780
ccggtctccg gaagacgagg acgacgagtc cggaataata tactcggact taaagatagt  36840
agcgacggct ccaaagactt acagagaaga gatatacgtc aattctcacg ccgtgcgggc  36900
atgggcctcc gaatcccgcg atcagatgaa ccaactcggc ttcaacccaa atatattcga  36960
tagtgcgatg gtggacatca tcaaagactg cctgagtccg tcttacctca aaacgctcat  37020
caaattcaac accacgagag cggcaccgat gagcgtcgtc gtgactaccc tagacccgat  37080
gtgttccgta gccgcggcta gagcgttgcc tatcgtcaaa cccgtactga aactcatgct  37140
atggataaac tgctatcaaa acggggtagc cgcagccaac aacatgcgtt ctcacatgag  37200
ggacgtgatg cgttcatcag aagtgaatct catcaggctt cgtatggaac aagccgcaag  37260
ggacggctcg gaactcatac gcgtactact gaacaacttt gatacggaag acctgtacga  37320
cggaaagcat ctccgttgcc tgacggccgc gaagatgcac ctgctctcca tgaacacatc  37380
ctgtctgtat ttctcatcgg gaaaaataag cgcgctacgg gggatctgtc ccttgttccg  37440
tccgggtgac aatctgtgcg aacaggcata cggaatatac aggaaatctc tggaaaatat  37500
gactctggcc gtgaaacacc cgatacagct catatgccaa ggcaaaaacc accccatgaa  37560
cgaagtacta tctgactttc tgtttctcgc gggcatcaga aacatgttgc acaactacaa  37620
ccgcgccctc ggcgaccttc gttcgtttat cttttatcaa ctggaagccc ttctcgaaac  37680
actgtacctg gcctacgtgc agctgccaca catgaagcag gagctgctca ccgtagtgcg  37740
atgcgtacaa gacgtgatat cgcaacacaa cccgtcggac atggccctcc acggtttgtg  37800
taagagcatc ctagtgttcg tccgcgacgc cctagcctgc gagatattga tcaatccgga  37860
cctgacgaga cacgctctcc ggcagctgtg taacggcggg aacacgcgcg gcggggcgaa  37920
cctgacgcgc gcgatctgtc taatgaactc acctctcacg tacagaccca tggtatcccc  37980
agatgaatgt agaaacatag ttaagcagaa cgtcgtcatc cccacttata cgggagaact  38040
gaccgagcag actatcccac taatctatac ccaggtggaa aacgtggctc ccctagcgac  38100
gtcgctctgt aaagcggcct cggcggaatg cgcgagcgag gaatcgggat atctgcaaga  38160
ggaggctcgc gatatcgtac gccacataca atgacgttac gtggtttttt ctttgtgata  38220
caatcgagat ggataaataa aaaatccgat gcccgatttt cgcgttcgta ttctttattt  38280
atcaaaccta tgtacaaaat ttacacgccc ggatccgtcc gatcgtgtcc gaccgacgcg  38340
gtacgtcaca cgatcgagct catccgcaga ataagatcga cgagctctcc atcacttccg  38400
tgtctgtgat cgggcagtcg ttgtctttcc cggtccctat cttgagtctg gccccgtgga  38460
ctcgcatgac gtccccggga gtgagttcgg tgtcagagtc catgtgcagt ccccgggccc  38520
gggccagtct cttagatatc cgtcgcacgg tcgcctccgt gatattctcg tcgagcacta  38580
tcttacgcat ggtctccagg taatgctggt tcggaccttt caccaacagt tcgcatatat  38640
tgtcggccac gcgtatcacg tagttggccg cgttcatcac ttcgtatccc atcacggagc  38700
cgtcctccgc tatgcctatc acgcatcggt cccacagata acacgtgcga tggccgatcg  38760
tcccgacaat caggaccgag cctcccatga cgggcatggc gcgccaggcc aggatatcgg  38820
ccggggtcag gatcgtgtcc tcggagggcc caactataaa tacgtagtta tcgggatgcg  38880
```

```
gaagatctat ccattttccc ctcagcgctt ccaccgcttc tcgcaattgt ctgctgcggc  38940
gactcgccga tatcaattct agagcgatcg ggtcgacctg ccccgcgcga tcgagcgcgg  39000
gcgaccggga cgcgggtaaa aggttccgct cttccgtggt catctcgcgc gcgtctccct  39060
acgcacccga gtcgggtcgg cgccgaccac ttcctctccc ttttgcgatg cgacgcagca  39120
cctgcgcccg agctcccata tatacacgcg agtatgctcc ctttttata gctcgtcggc  39180
cacttccgcg acgatgtccg gatcgaatcc actcccggaa atagtaaagt ccggcggtcc  39240
accgtgacta tggtcttccc ccgatgacgt atcggtcgaa cggctagatc ccgccgtatc  39300
gtcgctgccg ctttctctct ttacttgttt tcgcggaaca gacaccggcg caccggcacg  39360
acgacgttcg cgggcgcgct cgccgtcgga tcccgagcga cccttcgcgg caccgccctc  39420
cgacccacag gatgtgtaat cgagaggcaa cgcgtcgtag gcccaaacac acatatccgt  39480
caccgcgttg cgtctcttga acatgttagc gaaagtccac acgtagctct gacaggtagg  39540
gccgatacgg aactctctta tcttcacctc aggccacgtc gtctgcggat cctccaggtt  39600
acacaactcg ttctccccga cgaccgtcac cgtgcgactc acgtcttgag ggtgtacgg  39660
cgacccgcag ccgtgtctca gggcgaactg caccagacgc tccgctctat acatatcttc  39720
ggacgtatca tcgtacatgc gccgtaggaa cattacgtgt aacaacagtt cctcgcgcgt  39780
ctgtatctca ttgatctcgg agtactcgct gaccatagtg ctcaacttca acagctcacc  39840
catggccggt aggaagatca ggccggaccc gcctccgaaa ttcaggccgc gcaacctcgc  39900
gctcagccgt cggagggcct tgtgttgcga cctcgccgcc ttgctctcca cgagtccccc  39960
tccggcgaac aggtcagact gccgcgtgac gatctccgag acctcttgcg tcagttcttt  40020
caccgccacg acacacctac atatctcgca cttcaacacg gccgcggcca actgcgtcat  40080
ctgacacagg acaatgaaat tggccaccat cgtcagaaac ctggcgcgct ccgacaacag  40140
atgactataa tccggcttca cgggaagggt atccggatcc aggacgtctt tccagacctt  40200
gatcttcttg gcgtagctgc acagacaatc accgcgcacg ccctcgcagt acgctatctg  40260
ttcgtcgacg gacatgtgtt tgatcgtagg cacgttcacg ggacccatct ctgggtagtt  40320
tagcacgaag aggtgcggtt ccacgacgtt ctgtcgcccc acggcacgcg tcgtcatgtg  40380
cctcgacccc gacgtgcatt cgtcacaccc acatagagcg atctgcgccc tctcgaacat  40440
gacgttcacc ctgctcacgt attctttatc cataacggct ttctgcagag ggccgctccg  40500
tcctttcttc tttcgtgaat tcaggcaatt catcaacgaa cgacacgcgt acgcgtctcc  40560
gttactcagc gagctccacg cgtcttccac ctcccggtac gtgagacacg ctacgtagtt  40620
aagaaacctt acgtatccgg acaacgagcc gggattacga tacttgaaat ggtgttccat  40680
acagaacgcc gccgtcgcca gcgccttaca catgaccttc acgacgtccg tcgcctccgg  40740
acgaaactcc actcgatcca acaacctcgc gaattcgcgg tgctgagact ccagcaccgg  40800
gttcgtcgcg gacgttaaga cgggcgccat cagccgactc cacaccatca ggtcggacgg  40860
caacgtcata cccttcaccc cgtattttcc ggcgacggtg caggagcatg agttcgtaaa  40920
gtaccggtga gctatctgga tgaccttaca cgggttcatg aagacggatc gttccgatac  40980
ggacggctgc agctcggtaa acaagggctc gtcctcgtcg tcgtcggcat cgctctccga  41040
atcgttgcac tccggcctga cctgcaaaac cccgatggac atggcatcct gaagcgtatc  41100
gatgggagac agatgcgttt cgataaacgc tctgctaaac gggttacggg tattcggaca  41160
caacacatga tacaggacgg cgctctgctc gtacagcgta gaatcggcca tatcgccgtc  41220
```

```
cacgagacgt caacgtcgcg gcgaacgaga cggagcgttt ctgaaaaacc cgatccggga  41280
gccgctcagt tttatttcca cgttacgacg tcaatccgaa atcaccagcg tcgtgatctc  41340
tttgggatga gtcgcgtctt tcaaatccgc ggtcacggtc ttcaatttat cgtaaaacca  41400
tccgtcatct tgcagcacat acttgacatc gcagtcgaaa gatacgcatt cccctacgca  41460
aatatgattt ttagcgcgcc cagatttgaa aacgagcttc cgaacgccgg cggtgttcaa  41520
gagtcgatcc cgtataaacc cgacgatggt gttggcgacc tttaagagca tggcgttctg  41580
cagcagaacg aagacctcgc attctctgtt caccacgacg atggccatcc tgtatccctg  41640
acccagtacg tgatacccgg cggtgttcag acactcgaaa aggcgccccg ggtagaactg  41700
gtgcaggttc aggtggtgac aatccccgaa catgaaataa ccctctaaca tgtgcgcgga  41760
ctcgcacgtg aatctggggt gcgcgacctg gaacgttatg atcctcggca gcgtgatccc  41820
gtgacgcatc gcgtcgaaca gcacgggcga gcaggagaac tcgaagaaag tggcctcccg  41880
atagggggtg gtgggtgaga tatcgtaaag ttcgaacacg ttacgcatcc cgcgtccgtg  41940
ctgcaacaga ctctcgatgc cctcgtcgtc cagtatgtac agcagcttcg tgcgagtgct  42000
gaaagcgtac acccggccgc cgtaggaact caagatggca aacgttctcg gggcgatcgg  42060
ctcgaagacc tccagccgga cggtgccgac gagcgcgata tcgaataaag gagacacgca  42120
ctcgtaatcc ccgaactcta cctcttctat gtcaaactcg accgcgtctt tattgggccc  42180
tatgaccaat ctatctccgg gaggccatcc gatgggcacc atggacccga tgtgagatgt  42240
cacgaatctg tcgaaagaca tccacctgcc gtcgcccggt ttcttgggac acgtgttcac  42300
cagctccatc gcgagtaagt tcttagaggg gtaagattca tcgacccgag tgcgcgagat  42360
gaccgccgcg ctagtcatcg tagagagaaa aagcccacga cgagcagcag gacagactcg  42420
aagtttccag actatataac cgcgtgaaga atgcacgccc accgcacgca aaagaccgac  42480
cagtccgtgc ctcccaaact tggcaccaga cggatactgg cggtccccgg gcagatgtgg  42540
tccttatgta cgcgggtcga ccgccaattt tcatcggtgc gcaccgaaac actgctcaca  42600
tcacccgatg tgacctctcc acacacaaga tcccacgtga aaacgcgaca cgatatttag  42660
taccaaaaat aattctttat ttatacagcg atgagagaat aaatacatac gtcgacattg  42720
agtttgacat cctaacgaca ctttctaatg cgtacgatac gtacataact ttccatatac  42780
acgttacgtc tatgctaaac gtttagctgc gtccgatgat aacgggttac ttagagcaca  42840
gtctatatat acatgatacg tcatgctagt tcatacgatc cgcggagtcg gttacgttct  42900
ccgtctcggc gacgtcctgc tccgcggggt cggtcgcgtt ctccgactcg gcggcatcct  42960
gctccacgga gtcggtcgcg ctctgtgtct cggcgacgtc ctgctccgcg gagccggtcg  43020
cgccctccgc cgtttcggaa atatcgcgct ccgcggaccc ggtcgcctcc tcctcctctt  43080
ccgtctcgac gacgttctgc tccgttgagt cggtcacgct ctccgtctca gtgacatccc  43140
gccccacgtc caacatttcc gacacggagg tgtagctgta aagtctcccg ccggtccact  43200
ggttcaatat ctcgtcgtct ccggggaatt tgtataattc cgcacagctg tagcctatct  43260
gcttccccac cggaatgtac gaagtggatc ttcccttatc cgagatgtaa gacttctcgc  43320
acgcttgttt caggggggctc aggcgtctcc gtatgaactc cttgagggtg tccgcgactt  43380
tgatcacgca gcagttcggc ccctgcacgt atatgccgga ttcgtcacgg gcgacgagca  43440
ccagccggtt cagctccgtg gtgatgccga tgagatggaa tccggattgg tgcaaggatt  43500
ccaagacgca cttgggaacg gtatcggacg tactgaaaaa cgccgcatct cccatgatga  43560
acgcgaactg cccggatgcg tcctcgaaaa tcgtgccccg attcgtcagg gccaaggaca  43620
```

```
tgacgtccag ggaatacatg tcggtgctca gtatgagcga cgttatcccg acgggctcgt  43680
atccgaaaca cgcctgttcg tagacggatc cgcgaaacgg gatctgatag tatcggctga  43740
cgttccgcag ggacgcggag atgaactccg tcagtttgcg accgaatacg tagaccagat  43800
ccgcggacgg gtcgtatcct atgatccgtc cgtcgtccgt cgctatgacc cacagatcgt  43860
ctcggttacc ttctcggtcg cattcgcaca ccacaccgat aaagcagaac caggtgcaga  43920
tcttgacggg agcgaacttg cggagacgcg cgacgtatcc gcttatctcg aaacgtcgct  43980
gagaccccaa ctcgacgctg aagagaggcg gccaggccag caagatgcgt tctcccgagt  44040
gcttctgaac gaagtgcaga agcttgttcc tgggcctctc cagcgatccg gcctcccact  44100
tgtcgaacat agacatgatg tgaacgagcg aagactcgct cactttgacg taattgaaag  44160
cggatctggg agtacgtctg acggtcccgg cgttctccgc catggccaga aagatcgagg  44220
tgtcggtgat cccggcatcc agtatagcgt gagcgtacgt ggaatccaga tgttccggca  44280
gagacatcct gtgaccgccg accgggaggg agcgaccgac ccgatccgaa caggtaagtg  44340
gacaaataac cggtcgaacg gatgagtgaa tgaataaata aataaataaa taattaagcc  44400
agtctccgcg tgtcctttat accgattcaa gccaatagat gcgttacgct ctgaaacaaa  44460
gccgatcgcg ggcccccgcag gtgaaaagat cagggacgga gtctctcgag cggtccccga  44520
ttcttcacct ttctcatttc ccagttatgt ccaagtatat ctcacgcaga ccgagcccat  44580
caggtacctt ctctcgttct cttaacctct tcgcgctctc ctttatatcg cctgccgata  44640
caaatctctt agtcattcta cactgttccg gcccaattcc tttcccaatt cggcgcactt  44700
cttcctctgc gcgacgggga tattgagctg gccgctcacc gttatgacgg tggacgctcg  44760
cgggcaaaag cagtatcgcc tcttacgggc gaaccacacg catccgtgtc tgaagaagcc  44820
tcgcacgctc tccgccaatt tgacgacacg cgcccccgag accaacgcgt agaccctgca  44880
tccgtcgtcc aagaacagag gggcgttgat gccgatcacg cgcccgaaca agaaataacc  44940
ggccacctcg atgttccgta tgatttcctt gacctccttc ttgttgccga cggtgtcgac  45000
ggtaccgaac tctatctcgc actgcacggg tccgcccgag ttcatgatca tcccggaatg  45060
atcgcaggaa aaacggagca ttcgacgtct gtccctggag cactccagca tctcccgcag  45120
cgccgaggga gagatgttat accacatgga ctccgtctgc gggtcgtcga aatcccgttc  45180
gaagaagctg tacaccaaga tagccccgat cctactgaac tcgtcgatgg acgtcgccag  45240
gtcgtacatg cgatgctccg cgggcatata gcccaggacg cgtccggagt ccgtcatcag  45300
gacctccatg tccgaggacg tgtccggggc ggttccgtat tcgcagatca tgccgatgaa  45360
gtacaacatc ccgctccggt ccgtgcacgt gaactgtcga tactgtgcca tattgctggc  45420
gagcagaaag tgactcgccg tccccatggc cagaccgtac ttcggcggcc acaccagagg  45480
gagccacgcg cccgcgttgt tctccagaaa cctctgcagc ttagatctgt cccgcatctc  45540
gtaccgcttt ccgttcccgg gcgacgtatc cctcaaggac caccaccgaa agtcgaattt  45600
ggggactccg ttcggaccgt agatgctgga gagctcggcg aagggctgca tgacgatctt  45660
gcgtttcttg aggggcagac ggctgttatc taacacggtg acctccgtgg aggcctcgtc  45720
ggcgcgcagg tccgcgacgc tcccggagac gactccgacg cgctccaaac gatattcctc  45780
caccagtcgg cagaacccga ccctgacgaa ggtcctcatg gagtccgcga cgtccagcat  45840
caggacggag tccacgacgc tggcgtacac cttaccggaa tcgcccagga ggaccatcaa  45900
tcctccgaag agggtcccga gacctttgct cctcaccagg ccgagaaacg tcaacggctc  45960
```

```
cggaacggcg agcttacccc gcagtttcat catgtgggcg ttagtgacac cggcggcgtt  46020
ctggtccatg atgatcaatt tgtgattctc gggccacgtg agcgccagat tcttcccgca  46080
gttctgcttc acgtagccgg ccacgccgca gacgtcccgt aatttcagca actcctcgaa  46140
gtcctgcctc gaccggagat accgtatgcg ctccatcccg gcccggtgtc gattcacgct  46200
atgattgacg ccagtatccc tgtgtcccat gtgaaacggg tcgtagcgta tcatccctat  46260
actgaccagc tcggccacgt taccggccac ctcgtacaga caatcggtct gaaaatcgta  46320
cgcgtacaac agacccgtat cagcgcgtat gaggggacaa tatcgaccct cgcttcccgc  46380
ccacccgata agggtcatat tggtatcgat cccgaggaac tgcgtctcgc aaaccttgag  46440
atcggcctcg ttaaacttca ccggcgcgtc aaggccggag gacttcaata tcaggctaca  46500
atctttgggc cacggtaacg gtatcggacc ctgttcgcac tttttggcat acgaactcgc  46560
cgacacgatg tttccgccat cacagagttc gacgaacata ctgagatcga actcctccgc  46620
catggtcctc acgacctcgg ttctcggagc cagtttccgt aagcaaacgg cccgcgagaa  46680
agtcctcgcc tttacgtgtt tcatacacac agaacgacgc ggactaccgg acctcgcggc  46740
gatcctcgga gatctgcgat cgcccatctc tcgccgcgtc gcacgataca atgatagagc  46800
tgttccgcgt tcacagctaa ctcttttata ttccctgcgg gttggtttca aatctccacc  46860
caccgcccat ccgacagcga acagctcgtc tcgagaactg ccgcccgacg aggaacccgc  46920
gggaacgata aacgacaggg actgtgacgt ttattatctc atcgtcagcg tttattgtgg  46980
gcgagctcta acagatcgca ccggaaattc ggtcattaca tcacgatcat cgatggatga  47040
tcaatatata ttttaatcgc aaagttttta tcatagacga tctatattca gtagatcgcg  47100
tcgtatcgta cgctccacga ccggcgtggc tctgaatgcg gtcaggtgat cgatcccgaa  47160
cgtcagcaat aacctaaacg tcgccgttct ccgtcgaaaa gtatcgcacg tcttcatctg  47220
tgcgtctgaa atacaaaaaa aaaacatcac atcgcgtcac gatcgcgtct cataagtcgt  47280
ctgcgcgtcc cgcggaccgc atcgtcgtac ttacatacgc tcctacatac acagactcct  47340
ccaccgcagg cgtatatgtc atccagagga tcgacggcgc cgcggccttc cgtggaccgg  47400
cacacgttgt tcgcgggcgt cgcgtttacg gaacgcgact cggcggcgat cccgagcacg  47460
ttaccgtccc tctcgttaaa ccgtatcaga cccaacctcg caaaagatct aaaggtgtcc  47520
gagagcttga cgaaacagtc agagtacacg tcgtgtacga acacgccccc gtgacacaag  47580
aacgctgtca ggcgcgacat ccccatgtcg gcgacgcggc cgatcgtccc gaacacgacg  47640
agcttggaca cgtttagacg attggcgaag tccttcagat ctttcttcga atacatagat  47700
tcgtccaccg tacataaacg caacagacaa tcgttcggcc ataacaacgc gatctccccg  47760
taacagtgat ctgctgcgta tctctctaca gcgtttagat ctgtctctat cgccatcata  47820
tctctcaaac gggtcaacga aaaaatacac gccgccgtca tcgaaacgcc acggtaaccg  47880
ttaacatcga cgctccccac cccttcgaca caacttctcg ccgcccgtcc gcccgcgaac  47940
cccgatggtt acagcggagg ccactggatc gtcggaacgc cggcctcagg tcataaatcg  48000
cacgaccgcg agacaccgaa cgaaatgttt taaaacacgc gtcacagaag cacccgttcc  48060
ctaccagacc tccaaatcat accgttcagt tttataacca tcgtgatttg tcagtcaaaa  48120
tcgataaggt cttggagttc cgtgatttct gcggtcaggg cggccagttc ctcgtcatcg  48180
acgcgagacg taaccacggg cccgcagtcc tcgcccgtcc cgcaacacga gtccatctca  48240
tcctctccgc agtccgataa cgagaagggg tccttctcac aatccatttg tatcacagcc  48300
gtatcgtcgt ccaattgcgt atacgcatac gacacgtccg cacaaccgca agcctcgttt  48360
```

```
aggacatcgt tgatccaaca cgtcgccttc aaaacgtcgt cgaaatccac caacgttacc  48420

gaagccatcc tcgcgagttt aaacgcgacg tctcggagcg aggtcctaga gataaagatg  48480

gccacacacc acgagacccg aaacggcccg accgccacga acacagattt ttgccaccca  48540

atgcgccgcg tgttccttat atatgtacga ttgacataac tcacgtgatc cagatacatg  48600

acataatcga acataattac tcaccccggg agaaacggag cccgatcaca gcagataacg  48660

atatcgcctc gcctgcgttt ccagcagact cttctcgctc tgacacaacg tgtcgtaata  48720

agcgcagaac agcttcatat ccctgaccag aagacgtctg cgatccaaca ccatggcccg  48780

aaatctgacg tgcctcatcc actcgtcaca atccctatcg ttcggcgcgc tgaacatgat  48840

cgagcgccgt gcgcgaaacc gccgagaccc gtgtcacgcg aaaccccgga acatttaact  48900

ctatgaagag atgtcacatc cgggcattta tggatccgga cgtcgacgac gcagacgccc  48960

gcgcatctca cggcgaccgc gaatatgtca cccacccgca cacgttatcg ccgttcttcg  49020

acacgtcgcg gatccccaca cccccgtttc ccctcccctt acaatcatcg gcggccacga  49080

cttacgccgt cacgagaaac gtgttatcgt atcggcgcct ccgacgtatc cgttccctga  49140

gagcgttctc ttcggaagcg cttcgcgcac ggtgcctgtc tgcggcacgc gatacgacat  49200

cgctcaccac gtcggacccg ggaccgtaag cgaaccacag gggagacttg aacatcatca  49260

tgccgtccga cgcgcacagg atgacctccg tgatcatgga tagctcgggc cgctcacgaa  49320

gacgactgaa atctaccaca ccgtactccg acagtaccag atgtctgagc tgctgcgcga  49380

gcactatctc gaacctgcgt ctcacgcacc gtctcgagct catcagacac aggtgctcca  49440

gaatcacccg agccctgttg cttccggacc gactcgagtc cgtggagtaa ttccgaagta  49500

accgaatagc cagattcgcc atacccggca gttcgttagg tctattcctg accctatcga  49560

ccatgcaacg cagagtaatt ccggggttcg tgtattcgtc cagtatccga cacatcctca  49620

ccccctgtaa cacgaactcc tgcgccaaca ggtcgatctc gaacgctatg agacgcctga  49680

ccgtggatat cagaaacagc acaaaacaca cgttgtacac caggttgagg actatcctct  49740

ccaggagccc tctgccggcg ctatcgttat ccagactgat gagcagcctg ccgctatcca  49800

cggcgccgta cacatacgac tgcatgaggt ccgtcgacaa ttcccgcaac atcacgtccc  49860

gggatgtatc gtcgacatga actatattcg gcagatacat gggaggaaac gagggagact  49920

cactgagata cgccacggaa ccgtggagac cgtagcgcgc cgatacgttc gagcgatacg  49980

ctatatctga tcccatagca ccgatacgtc tcgcgcgacg tatcccgctg acgttaagac  50040

catctggggt atccgtaacg gccgtcccgc atcgtctccg tcgccggacg cgtcccgcgg  50100

actccgcgcc cgccgtcgcc gtaacgctat agttaccata aagccaaggc atgcgcgtcc  50160

ccgctatggc gtccgggatc acgcgggcgc acttgtgaca gtcgcacaac gctttcgaca  50220

caaaacccac cctggagcag taatgttcgt acagatcttc cgtagaataa gcgttcttaa  50280

ccgttccctc gcttatcggg ttacgcaaca tatcgaacac cacccgcaga ttgacgttat  50340

cgtgacattc tcccatgtga cgcagcatca agagttgctc gaatacggag tttgccattc  50400

tacacagcaa tctgacgtat cctatcaggg tgttcctctt ttgactgaac gaagcgtaat  50460

acgcgatcag atagtgacac gtcgccagga gcctcgaggc cgtctccgca tccgggtgga  50520

acccgtccac gaattcacgg gtcctaagaa acgtcaaaaa ctgttcggcc ttcatcaccg  50580

gccgcgtgat ggactgatct agctccagat aaccgtttat cagaacgctc catatcacgg  50640

aatcgtcgtc aaacgatagg ccgtgaacgg aaaacgcacc ttccgaggtc aataacatat  50700
```

```
ttcgaaccgt tcccgtatcc ctgatcaacc aaaaatccat atcagaccaa gcgatatcat  50760
ctatctcgtc gacgtgcgaa tccaaatcct gtgacagcat atcgcatgca cgagatgcga  50820
tactatagac ggaactcaga tccaccggag accgtatcta gacacacacg atgcagatcg  50880
atttcaataa acatgaaaac aactcagcct gtcacgagaa cgcgtctctt atcactttaa  50940
tgagggaaat gagatataag atctcgcgtc acagatgcta caagaacccg cggatgacac  51000
attcgagggg caatcggctc gccagtcacc gtcggcgcca ccagaatcca tccccgagtc  51060
agcgaagact cgcgagatta cccaatcgtc gacatggact gtccgctgga caacatctac  51120
gacgatatgg acctggcgga tatatgtccg ttcgatccgg taaatagctc tgagcaactg  51180
tatacggacg cggaacacga aactgacgag ccacagcatc cggaaccggt gaatacgcaa  51240
aaaataaatt taaaaccatt taaattctac gagagcagga tgagacaagc gatcgactcg  51300
tacaacgggc aagagaccgt atcgttcgag gccagatact acaacgatcg catctatttc  51360
acggcaccca tattggacca caactacgga gcgaaggcgc cgaagctgta cggatgggcc  51420
aacatcgtaa ccccgagcgt acacaccgac gacctgtttt tccttctcgt gagcgcggac  51480
ggtaaaggcg taacgtgtca acccaccata acccggggag gactggtctc catattgatg  51540
gtctacacga ccggcaatac cccgcgccat aatccggagt ccttcatcat cctcagcgag  51600
ctggtgatgc tcccgttcat ccctttcgac gtaccagaac acgtgtcgtg cttcagtctg  51660
caagaggaac cgtgcgatcc gatcgtcgag aaattaacgc gcatggcggg atggggaacg  51720
ttcacgcaag aaaacggggg catcgtcatt cacgcgcata acttgttctg gaagatccag  51780
agagtatatt cgctcggcaa gaggagactc acgtattaca gcgccgcctt catcgcggat  51840
ccgcaaggat gcgacgtaag cccgggcacc agatggctca cgccgaacaa catcacgttt  51900
gactccggcg cgttcaagtt ctccatgaac ctcgactccc tgtctatcac caagcactgt  51960
tacccacgag tggtaggtat cgtctctacc acgtgttgcg atccccccgga agactacaag  52020
tcgccgttcg tctttcccaa atccgttaaa tttcgcatcg tcataccgga actcccatca  52080
ccgtggcaga tcgtattcac gcgcaacccg aaactgttcc tcagcggaga ctccttgaac  52140
atgaacacgc gtctccttaa cgagccgaac ctcaagacca tcaccgtaca cgcgccgtac  52200
gatatatact ttgtggacag cggcaggaga tgcgtcagat acgacatctg ctacacgtcg  52260
ccgaacggca tgttcatcgt ctcttccccc aacaaccaga gcgcgcacgc ctttcacacg  52320
gccatggacc tctggaagag agacactccc ctgaaagtga cgctgtggtc caataacgat  52380
cacctggtgg ttcctcacgg gtcccccatc gccacactgt actacgtacg gtgtcgcgac  52440
ggaacgctgc ccgtcctgag cgacaccgcg acgttccgca tgcgtcgaga tgccgacgag  52500
caaaaatatt ttttaggtgg ctttatgttg cctaaagaaa acttcataca gagcgatacg  52560
cagccccaat aaaaccggtc actcgcgcgt ttgtcatagc ctttttattt acacgcccgc  52620
aatcgctcca ccgcgcgcac agtccccaaa gccgactccg cgcatcacat ctgttggagt  52680
ttcccaacga tgtcatctat ggccttagaa gagtccggtg cctccgcggg cacgtcggac  52740
tccgcgtcgg gggcctccga ttcggagatc agagagaaat cgtccgcgga ggacggctct  52800
ggcgtctcca ccctacgcac atccccctgc ccggccggag catccgtttt ccgaaggacg  52860
gaaaacggag acgctgtcaa aggcagattt atcttggggg gagagaacgt aacggccttc  52920
gacggctcgg gatgtgcgaa cgtgacaatc ttcggttgaa cggccgacga taacgggcgt  52980
atgttcatct gatctatgtc attgtctaac tgcgttcgcc gatccggtct cccttcgaat  53040
ggctcgttta agaattcgcc tccttcctcg ggagacggcg gtatgggcac attagcgatt  53100
```

```
ttataaaggt ccgaggtatc ggcgagcgta taacgggacg tttcgccgtc cttgccgctc  53160
ggcttggcgt ccgctcgacc ggcgtcgggc ctctcttcgt gacgtttatc gtgatcgtca  53220
gcgagccccc taagtctata tgcggtatct gagaggatac gcttcggcgt gatcgtaata  53280
ttttttaaga gattgttaac gtcatttaaa ccgtcgcttc caaacaagtc gccgaaatca  53340
tattccagct cgccggcatc gggttcgcgt tcttttgcaa cacgtctatc cctttcggac  53400
ccggaacgtc tatcgttttc cgtgtcactg tcgctctcgc tatcagtatc gctctcgcta  53460
ccgtcattgt cgttgttcgc gtcctcctct tcctcgctgt cactgtaagg ttcgtatctc  53520
gcatcgaatg ccttttcgat gatacgcgta tcgtccgcgc atttatacaa aaagctagac  53580
gtagacgctt ttgtaacctt agcgcacaag aggtgtagca tgtagcgcgc gccaaacgtg  53640
tcatcgtttc gtttgaccgc gtcatacgct ctctgtcgca acgcatctac ctccgcgaaa  53700
tgcgcctctt ccagggagtt ccacgacgac catatggccc tcagtaacgc accgaggtat  53760
atcaggcgat tcaacatata gcccaactcc gttccccgt aacgccgatt aaaaaaattc  53820
atgtcatatc tcagacaatt accacgcacc ttatcgatct cattttgcaa ttcctcgcga  53880
caattgtcgt ctagattaac aaaactgtac tcctcttcca tcagacgtgc gctctcacag  53940
ggtaacccga gttcggccct ccctattata gcagcagcac caataacatc gcgcactagg  54000
ccatcggaga ggtatgacga cagtggtttg ataaatattg acaaggcgaa tggattgcgg  54060
cactttaaag gctttcccgt gccatcgata taatcgcaga tgcccttgtg cacggacacg  54120
aagagtgcct tcagttcgtc gtcatcagtc ttactcttac gtataacatc gtaataatac  54180
agagaaacca taaactcgtt atagcacgcg acggcctcgt cggccgcgtc atcgacggcg  54240
aggcgcagaa actcatcgcg atgagattca aacgataagg taccgctttt gagcgctctg  54300
ttcatcttac gtattaatct cctaatgttc cttttagata cgcccaccaa gcacgggcga  54360
gccatatcgg cccgatatac gacgcccacg gtccgacagg cgattacgcg acacgactta  54420
acgtataact cattaaatac tgatatttac ctctctttat atagatacga aaacaccaca  54480
aagatggata tcgttcttgg cagagaagat aaactggtac gtacaacctc cccacgtata  54540
aatacgattt accgattata tcacaaacga aactatatgc tttcatgcat ctgattgaat  54600
gtttttctgt ctatccaaac aataaggacg aaaatgatct gcttcacgtc aacgacacgt  54660
gtcctcgtac ggagtcatta aacatggcga gaaacgtcga agttttttc aacgtcttga  54720
tcatatccgt cggtgggacc ctcaatctga tcgtcctgtt cacccacata ctagccaaca  54780
ggatacacgg attctccacc gccgccatgt acctcaccaa tctctgcata tccaaccttc  54840
tgaccatatt cagcctgcca tacatcatga tgcaaaattt ttcatacatg tcggggtcca  54900
ccttaacgtg taaattcgtt acgctcctgt actacgccag ctgcacaaac ggattgatga  54960
ctctggcctg gatatctatg gacagataca gaatcatcaa tcaaagagtg agaaaggact  55020
catccgctct aaaaaataca tataagatca tgggtgcgac ctggttcgca tctttactct  55080
gtgcgggagc cgcacctatg ttcactacgc tgataaatca cgataacgtt gatccggaaa  55140
atcccgatta tcagacctgt gtcacctact tcagattcga tcaaatacac acgttgttat  55200
ctggctttac ggcgttggtg accattgtct ggggtatcat tccggtgatg gtcatgagtt  55260
ggttctatac gttcttctat cgcacgctca aacgcgcttc gtgtaaaaaa cgtaatagaa  55320
caatagcttt tatctgtata cttttatgtt ctttcttgtg cttacaagtg ccttttacat  55380
tgcttatgat gtatgaaacc tacgtaacca tcatttggaa aagcgattgc gccgacataa  55440
```

```
acgccttaaa ggtattacat tacgtctccc ggctcatacc gaacatgcac tgcttgttaa  55500
accccatatt gtacgctttt atagggaacg atttcataac gcgtcttaaa gaatgtttcc  55560
gcggggaact gttcaaccgc aggcaataca tccagtccca ctccaaatgc gacaacagca  55620
aaatctctac cttacccagg ccgacgagac agagtaagat aaaacgtagt aagtcaatag  55680
agacactgaa aaacgctcgg atgtcgagat gcgagctaac cgtcccaaac gaacagaacg  55740
tattctccag cctgccgaac gccaaaaagc agaacaaacc gtcggcgcgc gacgcgcaga  55800
acgacacgga caatgcgaca tcgttaacga aaacggagtt tctctctatg agagtgctaa  55860
cgggttaacc gtcccgaata cgacgtattg taaatccaat actcatcacg cgatactaat  55920
gatacgtcgt acggttcatg tgatgtgcgt gttacacaat cttggaactc tgtccaataa  55980
attctgtact tgttttaact acctcagact cgtcgtattc ttccttcccg ccccaccgcg  56040
aaaggatcgg ttttctcgac gaacaaagac agaactcttt acgcattggg aaatcacacg  56100
ctacgcaaag tagcacgaga ccgatacgac gccccgagcg tgtacgtaaa aaggagtcac  56160
aggaaacgcc ggggtcattc gagcctccgg acgccgacac tctcacctcg gacgtccaac  56220
atgatggaaa acaaagattt ccccggcgat tcgagctttc agcccgaaaa acaagaggac  56280
ttcgacaacg tcgacgcgtt ggtccgtgcc gtgtcacagg agtacaagtc tatacgtcgg  56340
gccgagtgca ggaagcgact cctggaccac catctcccgg acttcataac gtctaaaacg  56400
gcaacgtcca ctttcatctt ctgcaccaag gtcgactggc aagacgccga gcacggcctg  56460
atccaactca agagaaccgg atacgatccg gactccgacg gcacgagcgc catagaacag  56520
atgatgcaac agatccgttg taggatcaga aagaaccaaa gcaaattaaa cgatccggcg  56580
aaacaacgga tgatcctgac catacgggcg ttctgcgtta cgttcaacag actggccttc  56640
ctggccagga cacgtcacta ccacacggcg gatagcagag cgcaagattt cctgagaaaa  56700
gagatcaccg aaagatgtag cgaagactcc aggttgaccg aacacgcgaa ctcgctgatt  56760
cacatggtgg acccaaagaa gtacgagtct ctgatacgga tcctgaccgg aatgttgtgc  56820
cagacgcccc acatgtggtc tagagccata cgcctcttca gtcgaatgaa aatgttttac  56880
cagatctgtt tcctccagat aatgcaagat atggacatcc acataccggg agtgttcgaa  56940
cctcaattca aatcaccgtt gaaaagactg atcgcttaca tacaagacct gaatccgtcc  57000
gacatgatga tcaagaatac tccgctaccg gaatcggcga gaaaacggcg caagagagaa  57060
ttggaagcca tgagggcggc catgggagag gaacccgata cggcagacca cgtcgaagac  57120
gaggaagatg acgatgaaac ggtaccggcc tccctggcac caccgcccgt caaagtagct  57180
aaaatgaaga ccaaaaaagc cggtaagggt cccaaagacg gcgcttccaa cgcaaccgac  57240
aagccaaaac gacaaccgtc tacagtaacg tcggccaaaa agacaaaaaa agcacagaac  57300
aaagcgagtg cgtccagagc ggcgaatgac gaactggtcg cggccagttc gtttctagaa  57360
caggataaca agatggcgtg tgagatgcac tgcgacttcg agtcggtgcc gctggacctg  57420
accacttcga cgcgacacat ggcgatggag tcggacgacg aaaacgaaga agtcccgagc  57480
atcaggttcg ccaccgaatc cgacgccgaa tctctgatag acgccatcaa cgaaaatcgt  57540
ctatcaccga cgtcgtccga cttcgacccg tacacgtacc agctaccgtc cgaatctcct  57600
aaaaatgaat cgagcttcca cctccacggc agctcttcgt cacagatcgg acccaggaac  57660
ccggcgaaat ccgcccgtcc gtcagaatct ccgtcggaca gctcaccacg ttccttcgtg  57720
ccggaggaca acgtcaacgg cgcgagagag gatcgggaga cgacggaccc accgagcccg  57780
agcggatcca tgatatttgg atgagacgcc atcggacgat atgtactgtg tataatatat  57840
```

```
aaacatttgt ctgtcgattt acgtttcatc accggtatac gtctagtatt taatgttttg  57900
tatatacaat aaaaatatta ttaacctaaa ctgtatcact gtgagtgtgt gtgtcgtgtg  57960
tgcattaacg taaacatata tcgcgcgtca cttcgaactg ccacgcgatg tccgaggga  58020
ctagtgctca ggaacccgag ccggaaatac cgctggacga aaactataat ttttcaccga  58080
gcgttttaac ggaagaagat atcagatacg tcacgcacag actagtagag gaaccgtgtc  58140
tgcgaaagct ggcatttttt aactccggaa taccggtgcc cgcttttgaa ttagaggcca  58200
acatacgcgt cgacgtcaag cggcaatgtc tccggatcag tcaggtagcg gagcaggccg  58260
taaagatcgc ggtctgtgcg agccatctag tcaacagtaa attgttatta gtcaaataca  58320
cggacgcgat caccatcttt atgaactctc cgcatcggga acgtttagaa acgggctatc  58380
gcagattatg ccaggcgcta aacgacgact caaatccggc cgatatgata cagagcctag  58440
acgatacgta tcttccgaca agcatataca aacacagact gcaacaccta tatgatctcg  58500
ctgacagtat aaacatcgac gtcgaggacg aagcgagacg acattatcac aaactcggag  58560
tattcaataa tttctacaaa tctcctctgt tcttcaccac ggaagccgtc ctggcgtacg  58620
cgacaaatat cgaacagata actaggggaa atacattgga ttttgattta atgacaatca  58680
aaaaattatc caaagatccg atcgacgtcc tgaacgatat gatgttcata ctatccttca  58740
atcatatggt cttcgtgcag acggaagact gctttaccct gcgtaaatgg atcataacgt  58800
cgttaaacaa ctttacccta gatatgcaca cggcctacac gcaggtaccg gaaacacgga  58860
taacgttttt aaatctggtg gacatggtgg cttccatgat aaacactaac accgacatag  58920
aagatgacga cgaggattcg caatttaaac cggcgctgag ggtcgtgttc aacatgctgc  58980
gtgagctgga gaaagcttcc gtgtatgtgc ttccggagtt tatgagattt gcgtcattcg  59040
tcgttttgtt gaaacttttg aacagacgaa cggaaaccca ttgcgcgggt ctggacctgg  59100
cattcagagg tcaggaaagc actgccgatt tagacccgtc taccccgtac agcgtggtag  59160
aatacaacct aaagaatcca tacggtaaca aacagctgtt tcgctgtccc agaaacgttc  59220
cgaagtatct cggagaagat ctcgtggaaa tgaatatgac acaaccgata atatccaccg  59280
cggaagacgg ttccccgact gtagactact acgaattgca gaaacaggca tgcttgatga  59340
tggaaggggc cgctcaacag ctaagaatga caccagagca gatcaaagcg tacgcataca  59400
acaaggaact ggtagccccg gccgaagcgg aaaccacggt caccgaagac gtcctggaac  59460
cagaagatcc tctgttcgcc aacgtgtcca gacgacacgt ccgacagtcg tcgaaacatc  59520
atcacggaaa gatgcagggg aaatcacacc gcacgcagat accgaatcta cgtccgtatc  59580
aaacaaccaa acctaagaga cacagaccag atgtaacggc taagctcagc aaacaactgc  59640
agcaagcgtc tatttcggac tcgtgacgtt ttaattgacg aacgcatcat cgatcccttt  59700
tactatgtga aataaacaat atatcaaacg tatttgtgtt ttatgttttt attaaggtcg  59760
gtgggggagg cgggcgacga tcgtcggtca cacgtaatgc ataaagctgc ctctgctgga  59820
tttcatgtcc cgcgagaagt gatggcggca tttgacgacg aatacggtga tcataaaaag  59880
aaacatggcc acgccgctgg agagcaccac gactcccgta gtcctctggt ccgccttggc  59940
cgtcacatcc gattcgtcca catctatgat atagctaggc ttttccgtac cggcgcctat  60000
ttcatcgtac ttgttccaat cgttccaaag atttttccac tcgctcaaca atttctgttt  60060
cttgcatgtt ccaggatagt ccttctttat catgactgta tttacaacat cataattcag  60120
tacccttata cataaaaacg tcatgaaagc tgcgtcgtag cttgttctga cattcatctt  60180
```

```
ctgcaacaac gagtcttgcc gattcgatcc catccacggc gagtcggtat gatttttttgt  60240
attgtgagtc gcgttccaag aaaacgaata ttttccaaaa acgtcttccc cttcaacact  60300
tagctgtcct gtcacgagaa cgtcgttact cctccgacat tccagcgttc cgtggatttc  60360
atgtctatcg atggtcgatt ccttttcatg cattgccagc aatggtttta cgatgtaccc  60420
agaaacataa tacttaacgg ctactcgcag gacagaactc acttgcgacg tgatgccttc  60480
catattatat aaaccatcga acatgacgtc ggcgttatca catatcccgt gatataccgt  60540
tgtcccatcc tttttacaca tggcagtaca accgtacaag ctgcctccgg tgtatctgtc  60600
gttgaaacac gcggtgtacg aacacacgaa ctcattagcc gtcctcgtac tccgcgctag  60660
cgacatgcgt gtcagcacca tgcacaacaa catcgatccg gtccaccccca tatcgcggcc  60720
catactcgcc gccacgtatt tggcccatga agatcagccc gtgtcgcaga ccgaaacaca  60780
taccagaccc gaaacattta ttatctttta gaacaaaaac aggaaaccag aggtgtgtct  60840
aaatgagtaa gcacgttttt atttaaatca tacacccaaa aaccgtatac aatcaataat  60900
tgcagggggt aacgttttca aagctttttt ctctgcttgc gagtcccgga ctggttcctt  60960
ggcttttcga aattaggcgc ggcacggctt cctgcgaacg caaggcaaca gagaggatta  61020
acgagagaac agcgaccacc gttacacgtc cacacttctc acacacgcta tccgtctaca  61080
tatttctgta catcgtcccc tctcgtcgaa taagaagcgt ccctacttcc cacggagatc  61140
ttaaacggat cgtagaagaa ttcactggga tacgggagcg gacgagattt aagagcgatc  61200
atccgtcgga cgacgttcgt ctcgggcgcc acgcttccgc tgcaattacg ctttctgatc  61260
cacggcgcga tgaaatgttc gtagaacggg acgtcgcagt tcagtctgat cgcgtcgtcg  61320
tctatgaaca ccggcgtcag gttcccgtcc ctggcggctc tggtcgccgc gatcagtatc  61380
tgctgttctc gcgaccgagg ccccttctcg aacaccggca cgctcccatt ctgtatggac  61440
ttatcggtcc tgccctccat caccgccatc tccagtctaa aacgacgata cacccggatc  61500
atgtcttcga cggttacggc gttcaatctg actctatcgc agatcgagac gggcatcgcg  61560
acgttatcgt actccatcat aacgggactt ccccagaaat cgcgcatcga cggcgcctga  61620
taaaatatca gatccgaatc gtaggcgaag acgtcccaat cggaggtcat gaaaaacact  61680
atctgccggt acgggagccg agatctcatc ttccatctgg tacacatccc gaatatggcg  61740
atatctcccg tgatgggacg atagtttcct tttatccaca atttcttcat cgaattgatc  61800
gccgcgtacc gataccgctc atcgcatata cggatccata gcccgaaacg gtgagccacg  61860
acgactcctt cctccgccat ggtggccacg cactccgaca acgccgagca tcccaacatc  61920
gaggactgga tcagcttgcc gacgtaaccg ccgaagcacg gaccctcgcg ttcctcgtcg  61980
ccatccatat ctgacaacca agacccctgc cagagacctg tccgaatgat ctataccgcg  62040
ggacacccta tactgatcaa acacagggca cacagccaag caaatgacta ccctacctac  62100
ccgcgcttca ataataaaca ccctcatcat atgatttacc ccttctgctt gccaaactcc  62160
cgaatacgct cgctcatcgt aatgacgtca ggatcgttcc gcagcatatc ccacatgttg  62220
gtgtgaccga gtcgttccgc gaagtcgtac tgcagccgtc tgtaccacca gattctccgc  62280
tcgaggggca acgagtcgta ctcctcctta gtccagacga cggctcttct cacgctcctc  62340
atcagtctat cctcggtgcg gtagatgatg atctttcgcc acatcatcat ggcgaaaaac  62400
gatccggcaa gccctccgac cactctagcg acgtggaacc aattcatctt cgctatctta  62460
cagatccccc gcgacgattc cgagccctct cgagcggctc agctcgcagc tcaccgagat  62520
agtgaagatg catcaacccg atatgcacca ttcttatata acttgtaggg cggaagtcat  62580
```

```
attaacatac aacagatata ctgtcactca tccgatttcg ttacgcgcac acataagaca  62640
tttccagtac gggtaaaacg ttcacgacac acgtcacgcg tacactgtac ctgactcctg  62700
acttttaaac actcgtctgc ctcggtcgtc tctgctcaaa tctcacgtcc tcatccgttt  62760
cctcctcgtc gaggccattc agttcgcttc tgtcgggtcg aacgaactgc tcgccgtcgt  62820
agcctcggat gcataacagg gccaatctga tatcatcgac ctccgccttc gcggccctac  62880
cgtccgggtg atcgaatatg tcatccataa aacgcctggc cgtatccaac ttgccgtctg  62940
gcatcgggag aatcccgtca tggaccgcca agaggacaca ccgatcctcg atcagaaagt  63000
tccacaggtt cttattctct atgcgcttat tcacgtccgt cgccagcatc cgatacagcc  63060
tcttcctgtc gctctcgctc agggcacagt acatcagata cgtccaattg gcactggccg  63120
tgtaccgata gaacgtgtag tccctccaac gtcgcacccc gtacatgatc acctcgcagg  63180
tgacataaaa ccccagagaa ccgaaaaccc atctacagac cgacggagac ggtctcggga  63240
tgaacttcac caaccgatcc atgatcgcag accgtcgcag ctctatcgaa cacagagttc  63300
gctctgtcca gatagctgtc tcctggacta tcctccccag aaatggacct cttttataat  63360
agcagtctga agaaattatg caaaatgcca gactttttcc ctttccgccc tcatcgtcac  63420
gcccccgtcc acacaaactg tgtgacgttg tgtcataacg tgtcacctcc cgataccggt  63480
tatctcccca cgcgatacgc gaccgaccgg tcgcagcttc gcgacgtatc gaattgaaaa  63540
aatcacataa acgtatctca ttcaaataaa taatactttt attcacattt gacacacagg  63600
acttccccac cgccacccct cacactatct ttctggcaaa ctcgtgctcc gcgatcttct  63660
cctcggcaag ttccagctta acagccgtag tgctaaacat gtacattgct acaagatatg  63720
caataactgc aattattaac atcactacca gaccaatgac agaataccat gccggatcgg  63780
caaccagttt ctcggtaaac tttctaaacc aagtccgaat gtcagttcga ggcacgacgg  63840
gagtgtaggc gtcagtttct ttcccgttct gcatgcacac acacctagca ctatcgtatc  63900
tatccaatgg cgtaattgcc cacaaataac cttctctgga ataatgccga ttgactgctc  63960
catacgcatc tggaaaaaca tctctgttcc catgaacaat cttgatagac gaagtgcggt  64020
ccaccgcatc tcctctcata acacataaga gtctatcatc ttcgttgtca tgaacaaccc  64080
gttgagccac acactcaaaa gctccactca ttggagcgaa atcatgtaca acgttgactt  64140
gtagaacttt ttcgtgagcc agctctacgt cgacatgccc agcggtgtgc atcgcaaggc  64200
gttgtctcgc gattgtggca tctcgacgta tcttatcaga gatgtaatct ttgaagtaca  64260
aagccaccga ctcacataaa tcgctagcaa atctcgttgc aacaacccat tttgagggat  64320
ccgttttgta tgtcaccgat acttgtccat cgctgtcgat acggcacaat aagtccacca  64380
ttcgatcctt cggaggtcgg tcgtgcacgt ggggcctgaa aaggttcgtg tcctcggata  64440
acttgacata agcaaagcta tcatggccat cactcacaag cgaagctgca accaccgaaa  64500
tgtgatcagg aaatttcaac agcttagtgt tctcttcggt ggcgtgtctt tccacgacgg  64560
agaataaacg ttcaagtgtc ataccggtgt tagcaatgaa gccgacacaa ccgcccgcta  64620
atgcgccggt cgtggcagca tcaacgccag atccaaatat tttgacaccg gatactgaga  64680
cgtctccatc tacgttcaca cctccgttta accagaacgt gcttcgaatg acgaactgag  64740
tcgatgaaac atgcggagat tcttcatcca tcggatcgtg acaatctccg tatagtccat  64800
gatctttcaa agcatcacga ctcataccca tacacagggt aaagagaccg aagaaaaagt  64860
acgcaggaca catcttcgat gattgaagcg tcctcaacgc acaggctatt atgcgataat  64920
```

```
agctcctcgg catagatctg tctccgaagt agcttcttat actcctctgg caagatgacc  64980
acgcctatcg gggacggac atttcccgtg tgtgacgtta cgtattcacc cgtatcaggt  65040
acacaggtgc acatttgagg tacacggacg acgtattgct atatacgtat tacagaccgt  65100
atcgccagaa tggtacggaa tcgtcaccga aaccggtgca ggagatatgc cccgacaacg  65160
gtatatcacg atacggtctg aaaaccgtat cgtggaatat tgtaccgaat cggcgtcccc  65220
gatacggttc caaaaccgtt gcattcctgg cggcgcgata ccgtgttatt aatacggttt  65280
ccggaccgta atacgatagt ttcgtcaatg tcgtttgccg atacggcgac gccgtcacat  65340
tacgacgata cggtcccacg accgtttccg ccatacgtat accaaaacgt atcacaattt  65400
tccgtaatat catactcaac atcgaccgcg tatttcatca tccgggtaat aaaccgtaac  65460
gtgtgcgtga ttgtgacgta tccgatcaca tgtgctcgta cttcaatcac gatacgtatc  65520
ggcgcaacgg atccataatc gccgttgcga cacgtcaacc ccgtacgtta cacgaatatg  65580
ataccgtaac gttctttata tagtatcgtc caaatgacaa acatcaattg acggagctgc  65640
tgtattcgaa aagatcttct tcggatccgt gcagggcaag cctgaccatc cttctttccg  65700
tacttttgac ggtcgccaaa aagtacacga cgaggaataa cgataccgtt ataatcacta  65760
tcatgaagcc agatatcacg acgaccgcac ccacgctctt catcaatatg ttcaccgcac  65820
cttccagatc cgcagaagtc gcgtttctct tcgcgccggc gtccctatcc ccgccactac  65880
gtacgacggc gctcgcaccg ttgcggttcc tcgccttcac cgccgggagc gtagacgtga  65940
cggcatcacg atcgtcattt ctagtcgtaa cgtccgattc tatcggtgaa agatctatga  66000
tcggaaaatc cgtgccgtgc gtggtagtct tggacatcga agaaaccgta cccgaagtga  66060
tcgcaccacc gggcgtcgtt tcgtaactcg aggatccgta aagcggtgaa gtagaaacgt  66120
catcggaagt agggacagaa ctcgccgtag acacgtcggt cgtcggtatg ccgactgtgc  66180
ttgatgcggt ctcgttaccg ggactagtga tcacattagt cgcagaaccc gtcgaggata  66240
cgacggacgt agtatcggta accgtcccgg acgtaaaact agccgtagtg acggcactac  66300
tggacgaagt ggagcgccca gtcgtattat cggaactaac gatatcgctc gagttcccgg  66360
tcgtaaacgt tgatctctga gtagtggtgc tcgactcacc acgcacgaat gcgatgatga  66420
tcacaaacgt gaatagagat acacagagca ccatgtcgac gaccgaaatc gcgcgcatgt  66480
cgcgtcgaac gcagaaaaag tccacgcgtg acacaatacc atcgatcaca cgataatagt  66540
ctcacgggat aactttttat taacggaata ttaacaggat gagaaacacc ataccgagta  66600
aagtcgctag gaaaataaca tactttcggt caagatccgg aatcaaacgc aaagccacac  66660
aacacccaga tgaacccctg gcgtccgcgg cagcactcgt cgcctcgtcg tctatgatca  66720
actccaccgt gtcatccggg atgagggtcg tagaatcgat gaccgcgtcg tcggatacgt  66780
cctcgtgaac ggtcatcata gcagcgtgtc tccgcgaatc ggcatcacgg actccgttca  66840
cgtgctcgaa tccaaacgac cgggtcccat ctccgaaatc acccgaaaac cgcacactcc  66900
ggaatctgta atttcaagga tacgaaacat ccgtcaaaga ccgatgaagc gttccgggcg  66960
atcgaccaga tcatctccac acacacccga tttaccttaa ttttccccgc gaacgatact  67020
taagctcgat ttcataagcg taccaaaagc gactaacagt aagattaaca tgaagacgga  67080
gatggcgcag cagacacagt gctttacgcc gttcctcacg ctcctatcct cgtcgtcatc  67140
gcatacgctc tgccgcagaa tcacacgact gtcgtatcgg tagagcgaga ccgcgtccga  67200
cgcgtcgtga cacacttcga aataatcggg aggggggtcc aaatgtgact ctaggaccgt  67260
ctcgaaatag gaaggaggct cggcgtacag ctgtcgacct tcaggatcgc cgctcacgta  67320
```

```
gcccagtaca tctaattcgt aactctcaat cgcaccgtcc atatctagta ataactctca  67380
tgaggtatct tatcgttttg accagagtaa acatcctagg cagagcgacc gagcgcgacc  67440
tctgtcctca gaggatcgag acgactactt tcgtccgcag atatacccgg tcaggagaag  67500
catgtttttg taatcctcca cgagcacata tccgatcaga cagatgccta gcgcgagaac  67560
tatagtccta atgatctccc gctcgtccgc gcccaggacg acgtcattta ctatctcctc  67620
ctcaccaatc atcttcgatc gccgatcgac ggcaccccgt tcccccgact tttcaaaaac  67680
agacgcgtcg ccgccacgca gcgatcagac cgcgtccatg tcgcatagac gcgatacgtc  67740
acgagcaaac ccttctccgc tcgcccctac cacgccgtat tactaaacga gatcgtgact  67800
ttaaatacac agaccgtcca cgccgtccga cccgtgtcga taggaacaca ccagaccggg  67860
gacacacgat acgagcgatt atagttactt tattaattaa acacgaacat acatgaggtt  67920
acatacgcgt cggacaggta ccgaggacac tcagatacat accatcaaca acaacatcga  67980
cacaaaacac gccgtattac ccaaaaacac gtccctccac ctaaatttgt acagtacgta  68040
gttcctaacc gcacatccga acaatccgat ggcaacgtcc ccgaccacga cgaggatcgc  68100
gaggtaatac cggatggcga cgatcagact gatcaacacg caaccgcacg ccgcgacgga  68160
aaaaagcgtc ccgcaatccg cgtaatcgaa acgaatatgc gacagaaagt agacgatgat  68220
gagcgactcg ggcacgatga gggattctcg catcgccacg ctggccacgg acacggcgga  68280
cgtgcagacg ataacgtgag cgatggacgt caagacgcga gaccgggatt cgaatttata  68340
cccgaatctg ctgcgccggt agatcttccg ataccaagac ctgccctcgg acacacattc  68400
gcccctggcg accgcgcgac ggaaggccag gaagacgatc gaagcgcaca cgctcagtat  68460
cacggaggcc ggattcctac cggccagcac gcggatcagc acgccgatcg tgagcgccgc  68520
gttgtacatc agatcgtcca gcatggcgac ggccgacagc tggttgacgg tcacgtacac  68580
caccacctcg gacacgacgt gtatgcagca gaagatgagc ctgtcgacgt atctgtggct  68640
caggttcagc aggcccccga acaccgtgag catgatgata gcgtccgccg tcaccttgca  68700
tccaaagaga agcctcacga ccatcgtcag gatcacgcaa gacagaccgg cgcacgcggc  68760
gcacgccgcg gcgatgaccg gcggaccgac ggcgccggtc gccgttcccg gagaagcggt  68820
agcattgccg ctccggagac gagacgttcc gaaatcacac aagtcctctt ccgaccaggt  68880
cttcaacaac atcaccacgg tatgtcccgg taccacgatc ccgacgaaga agcccaggaa  68940
cgcggatccc gtcaggcgga acatttctgc ttcttgacgt tagacacgaa atcgaacgtc  69000
agggactcat cgctgtcgct ctcctctttg gcgtcgccga aatagccgct accgccgccg  69060
cgctcgctac cgccgccgct tatgcccttc tgcgtcatgt aattcgttat cttatgctga  69120
tcgtacttat cacgctgcga agatccgtgt tgttgatcgt gatcctgtcc ggacggtgcc  69180
tttttagaac cgtgactctt ctttccgacc gacgacgtct ggtcggacag accatcttcg  69240
gccacgccgt ctacggcgtt ggcgcccgaa ccgatactgt tggcctgaga cggccgatga  69300
ccggcggagg cggtggagac cggcaggggc cgttcgatgt cgcgagagta cggttcttcc  69360
gttacgaaac tctccacggt gaaagagttg ttcttgctct gcaggtggac gatgttatcg  69420
tggtccgaca gcacgcggat ggcgcacgac agcttggtca ccgcgcactg cgtgagcgcg  69480
ttgtggaaat tcttagtatt cagcatgagg tggacgggct tcacgtcgtg gaagctgacg  69540
tgttcgttgg cgacgaactc caactcgttg ttggccccgc tgccgcaaat gatcagcttc  69600
aacgtcgggg ggttggcgtg cacgagcatc tgaaccgtgt tggcgggggc gctctgcttc  69660
```

```
ttgttggtcc tcttggcgcg cgtgtatggc gcgacccacc gtatcaactc ggtcacgacg  69720
gaatggctca ggtccgcccg cacgaaggac tctccgttct cgcggacgac gtcctgattg  69780
tgcacgcacg ccgagctgaa ctccatgttg aagtccgtgg ccaccatgct gatgtgcgcg  69840
tacatcggcg acaggtcctg gatgtacagc ttggtgaggt ccttgttcga actgagatgc  69900
atgaagctcc cgaccaacgg tacctggtta ttgatggtct tccgctggaa ctcgttacgg  69960
tcgctgatgt acagacacga gctgttgaac gtaatcttcg atacatgatt cgcgcgcgcc  70020
gtctgaacca ccatggccgg cgtttccaaa aaggtgatgg tcgtgttctc cttcagaccg  70080
cggatgatcg accgcaattg ctgcgtcgcg gccttgtacg gcctgaggcg cagagctagc  70140
gtgacgggct cccgttgaga cgtcttacgt tccatttccg tgcgtttcgt cccgataccc  70200
tccggcgtcg cagatcacca gaaactcgac ggggcgtgct gccggcagga gagcgatcta  70260
caaaaagccc gatagaccca aatggaagga gtcaaatact ttaaaaagtc tctctgaggg  70320
ccgtatgggc ggttcctaac gacatcatca tttaaaccgt gccacgatta cgtatacaac  70380
gcaccagaat cttcgaccgt acacccacca ataaaataaa ttccaacgcc tcccacgcgg  70440
agcgaggcga cgtattggat cgcacccgcg tcgcggtcgt tccctccctc gggaccgcac  70500
tcgcgcgctc gtcttccccg tcaccgtacc gttcaacagc cgcgagaaga acgcgagagg  70560
acccgattcc tatctcccta tcgagagacg agcgcgttga gaccgctaac ccaccgagat  70620
cggctcgtgt acaacccgga cagcacactc gctctgtcca aataaatatt aataaatgaa  70680
acttcatcgg gaacggcgtt ttaaacagaa aacacgcggt gacgtacggg caaaacatgc  70740
atacatactt catcatgaca cataaaaaac tttattgacc atgacaaatc tacagggcgg  70800
agcgatatca gaggaaaaac cacaagcgcg acacacgaga ccgtttccgg gccggagtcc  70860
gttcagaacc aacgcccacg atacgttcat ctgttcctaa aacttttagc ggcgtaacaa  70920
cgcacgacgc cgactttcag tctcaagtcg tacgctctct tcagagcttc gagaatggcc  70980
cccacaccgt ctccgtcctg cacgcaaaac gagggcgcca ccacttgatc gacgaaaggg  71040
ctcgccgcgg cgcacatagc caacacgcga tccataccga tgtcaaaagc gtccctgaaa  71100
atgcaagtcc tatcgctcac accccacttt ctgtccgaca cggccatctg cactctgggt  71160
tcctctctga tcaagaggtt gttgacgacg ggaatgccga cgaacggaac gtcctcgccg  71220
gcacgccggt cgatgtggca gaagccttcc tctctgaagc cctcgacgcg aggaattaga  71280
gcgtgagata tgtaatggtt cttcaatata ggcagaatcg acacgctgcc ctcggtcatg  71340
agacacacgc catcttctgg gtcttgacac gacgtaatga aagcgtttct caaaccgtgc  71400
ctcatgatgt tctgcctcaa cactatccag tgcttcgtgg ggaccgacgt gggcgtcacg  71460
ctgtatcgat cgaacatcat tatcccccgc gcgtacatgg tgcggccgaa ccacgtacac  71520
gccgacgctc cggcccggca cagactcatg ctggtcttca gggcctcgta gtagacgtgt  71580
tcgtgaatct tacggcagag ctcgacggcc tcgttgctgt cgtattcgac gtccaacttc  71640
atcagggctt tgtgaaatcc ggtaacgttg acggccagag cggcgaaacg gcgaaaccgc  71700
tctgcgagct tgctgctctc ccctccgcaa tttttgatca tggaatccag catggcgttg  71760
ccacacacaa ccgcgtgttc caccagcatc ctgagatgag cgctgtctat cgcccaatcg  71820
gacgacgcgt agatgtacat catctcgtta tcgtgcatgc agtccggaac gacgtcggcc  71880
acgcactcct cgaggttgac actgaccgac acgaccggca gggtttcgcg agaaaacgga  71940
ttttcgaagt tgaccccggg accgagacac tggatcggct ggtaaaggtc gttcaggacg  72000
gaatgattgt gcacgttctc cggatagacg acggcgagac gcccggtgag aacgcattgc  72060
```

```
gcgatcttct cgcaaaacca cctcgcgctc accacgatac accgttcgtt gtccgcggcc  72120
ggcctcgccc gcttgagacg gctaatgaac tgatccatgt tctctttaga gaaagacgaa  72180
caccagtcaa agttccacag ggcccacgtc ccggaaccgt taggggagat ggcgtcgaaa  72240
agagggctca ccacgttgat gccaaaactc agccccgaaa agacctcctc gtccagaccc  72300
aagatgtatt ccagaatccc ggtggcgtgc cagctccaac tatcgaaata gattctcagc  72360
ctagaccgca cccgctgcgt cgttctgatg atctgcaact gactggccat gtgcgctatc  72420
ttgagaaggg gatcccccgc gccccgcgtc acgttgatcg acacggccgt tccctttcgc  72480
atgaaaagta acatctcctg aacgttctta tccaggtagg agctgacggt ctgctccgcg  72540
caccggcaag aaaacccgcc gacgaaaaac tgatcgcgga gccccagacc gaaaaggcta  72600
taattcggca agcacaaccg tctcaaacac aatctctcca aaaacaaata catgatgtcc  72660
ctgacgtgct gcgtgtccat acagctcgtg tagacatcca tgtgctgcga ggccatcatg  72720
gcacaagtgg ccctgatgaa cggacctatg cagtcctcac gaaacccaaa cagacaccga  72780
cacactccgt ccaacatgta caccgcggca cacaatccat acgacgcctt cctatcgcag  72840
tggagacgta tgtacccgct gatcgatctc aaccggtcgg cggccccggc cacgaacgca  72900
gaggtctccg ccgtcatata cctaggattc gaatacgtga cgaccgggca cgccggatcg  72960
ttgctcgtcc ggagaaacaa ccgtccgagg ttgccgtagt tctgcagatc gcgcatcacc  73020
atggccgcgc ctcccatgac gatacagtag tacatgaact ttttgtcgtc gattatggcg  73080
agactctcca ccagcgcggc caactcctcc acgctgttca tggtgggctt caccatgccg  73140
ctcaagcaaa agcgtatcat gctcttccgt ctctttacgt cgtagcagca ctgacactga  73200
tccatcagga tgtcgaattc gtctctggat ccgggaccgt acgcatccga cacgtctctg  73260
cccgccatat ccatgtgttc tatcgcgctg agaacccgct gcaccgcgtc gcgtccaccg  73320
ccacgacgcg ttcccaagtc tccgtccgcc gcaccgtcac ccgtctgatc caacgacgga  73380
ccggacgttc cgacgacctc gaaggattcc gacgggaccg cgtccgactg ttcctggaca  73440
tacacattcg tgtttctatt gaaattacac gtaacgtcct ggcgcacgat ggcgacgttt  73500
tcgtggccga actgaacatt ggaagagttg actattatgg ccgaggacag ggaggatcca  73560
gaggtctgaa aaccgagagc gtcgctggtc ccggccgcgt cctcatcgga gttcatggcg  73620
gtccaatacg ccttccggac gaagtcttcg tcttccccgt cccacgaagc catatccccc  73680
gctattcgcg actcagttca tgaaaaaaaa aataaacgat cacctaatcc acccactgta  73740
cactccacgt acacgccgac gaaggtagat tagaaacttc acacaaattc aaacatggtg  73800
ccaacgtcag tgtagaactt ctcaagtttc acgacaggta tctgcgcact cttgtaaccg  73860
agcaccccag tttttatatc tcccgactcg tcacaccaac cgagtcgctg gaccacgccc  73920
acacatgcac tagcatcgtt cggtcgcacg atctttctat ctaaatatag aaatctttcc  73980
gttacgaacc gttgccgtaa caggttcagc agcacggatc tattacgcac gctgctgacc  74040
acgatgtata tgttcggttt gggttctgga ccggcgtgat tatagacgat caccaggtag  74100
gcgtacagag ggccctccgg gctgccgtga acgtccaact tcacgtacat atccttgggg  74160
aacacaaacg gatagatctc cgtcttcagc atgttatacg cgtgccccg catcacgcag  74220
gtgataaggc tggtgatacc cggagacacc gagttcatgc agcccacggc gctgacgacc  74280
ttgtgtatgg tcgctatgga aggctccagc cagctggata ccgcgccgca aggagcagat  74340
gtatataacg ccgataatgc ggtacgtacc gccgaacata cgttggccgc ccgtatagcg  74400
```

-continued

```
agaaaaaaca gactgatcat cacgtatctc gggctctcgg ccgaagtgtc caatctgagc  74460
atgagacagc cgtagtgcac cgtctctatc tccaacaggc cctcttgtac gaagaaccgt  74520
atggcgatgg cctcgtggtc cgccccgtag atgtatttgg cgaacgcccg ctccatcttg  74580
cggagtttcg cctcccgttc cgcgtctgtc ctcccggtga tctggccata gctgcgcttg  74640
gtcattatcg atcccaggct ctccgaggaa gccatggcga cccgcgtatt ggattttaac  74700
gaattgctgg ccgaattgac cagagccaac aggagacgtc gatccgcgct gccgatcata  74760
gccaagctgg atgtgagatc gataaatata acacagatca cggccatctc gatcgaacgt  74820
tttctggtgt acgttcgcga cgaccgacac gatctcccgt tcatcatcag ccactacgcg  74880
tactatctca tcagccacgc gtcgttcgga gcagagacga cggactggtt cgacagattc  74940
ggcgaggcgt tgcgcgagat cgaatcctac tacaccgcga cccggacgcc cctggacgat  75000
tccgaccaga gcctcgtgtc caacaaacag gtcatcaaca tatcgagacg tttcctggat  75060
cgcgtgtccg acgtccgagc cgtgttctcg atacgcgctc ccgtcgacgg atctccgccg  75120
tccgccaaga acaagccgat caaacgatcg cccaccaaga cgcaggccga acgcgccgct  75180
atggccgtcg tcgacaacac ggacgtcaag acgaaaaccc tccgggacgt cgacgcggcc  75240
atagcggcag tacgtccgtt gatcaactgt cgggccgtcg ccgaactact cgacaggctg  75300
taccgcatca ccctggcgtg gatcgcccag agagaaccgg tcatgcaagt cggcacgaac  75360
gcgagacgcg cgacgagcga ccgtctcgac cgactgctac gatcgtatta cttctatcac  75420
catcacggag cgtcgaaccc gaacgccgcg cgcgtcttcg cggaagcctc gaaggacaaa  75480
gaggcgatat ccaaatttac gaccggcgac accggacaga taaacttcgc tacggtacag  75540
ataatgaaac ccatcagcta cgcggtcttc tcgcaagacc ccgccgcggg aaactacgcc  75600
agatacgtct ttcccctaat cgtgagcgac ctacgtatca tcgggcagca actgtccgta  75660
gaaaacgcgt tcttccaccc gggactcatc cacagcatcc tgatcatgcc ggacgaggga  75720
gagcttcccc cagaaacgat agacgggctc caggacctag cggaatactg cgagagaata  75780
accgaacagc tcttcagaaa cgtttcgtcg aggcccgcac acgcggtaga aaaactagag  75840
acgctagtct cgtacgccgt acggctctcc gaaatgggtc tcaacggcaa aacgtcttcc  75900
atgtattccg acatgatcgt aaaatcgtac gcgtcgccgc aacaggcgtt ttccaacgcg  75960
gacggctcca gagtcgcgtc cgtactctct tcgcagacct acaccgacgt gaccgagctc  76020
aaacaccgca tcatagtact cgtgtacaac gctcacatgt ttcacctgtg tctcgaacgt  76080
tacagcccta cgtttctgtt tcacaacaga agacggctac tgctagagca gcgatactcc  76140
gtactgatag gagaacgcga agagctacag ttcgtgtggg acaacgtcgt aaacaacatc  76200
aaccgtctct tctacgcgtg gttcagcgag acggaattcg acgatctagt cggaaactcg  76260
tccgaaaagg atgtcgaata catctacagg gatcttctgg tcaaatgggg agacattcta  76320
ttcaacaaac agaaaacgat agaggtggac atggaggaca agagcgacac gaagagcaag  76380
ccggaagcga aagaggatgc catatccccg acggagatac gagagatctg ccggtcactc  76440
cgagaaaaac ccatcgacga cgtgctggac gtggtgatgg cgatcaccaa agaacccggg  76500
ttcctcccca tattcttgga ggcgtacgtc ataccggagt acgaagacgc gttagacatg  76560
gattacacaa agtattccct ggaaggaacc ccgaaactac tacagctcat ctacctgacc  76620
aagctcctga tacccgacca gctgcagctg agccagggcc tcgtacaggt gtacaacctg  76680
acacagttcg tgtcgcgcct agacgtgggc ctcttcaaac tgcttcacga cgcctcgcag  76740
acgcttctgt cgatcttcca aaacctctca ccgcaagccg agatacgtcg caccttctct  76800
```

```
ctactaggag agctgctgat cacggctatc gtgaacgagt acaaggaagc gctggaacct  76860
ctgttaggag acgtgatccc ctccggctcg gaggttctgc aacagtacgc cgaacacacg  76920
aaacgctgca ccgcgatatc catgtccacc gccaagacgg aacacatgcc gcagcgcata  76980
ggtctctact tcgaaaacgt gcacatcatg acggttcaac tgtcggaagt acggaacacg  77040
tgcgaaacgc tcgttcgaaa gaacaaaaat ctgttctcgg cggccacgtc cgtcgaacaa  77100
cggatagagc acacgaacgc ggtgctgaac gcgctgtcta aaaggatcga accgtataag  77160
caagcgctcg cgggcgaact ctttctgcgc gaccacgtca aatccgtaaa aaccatcgaa  77220
tcctcattaa agacgacgca cgagaaatta aagaccgtct tggaagagtc cgaaaaatcc  77280
aaccggctgg taacagacgc cgtaatacgg atattaaagc tcgtatcgat catatcgacg  77340
gaaaacttgc aacgtttcgg tgtcgccgat tgcatcgccg aagccaacgg attgatacaa  77400
gcttccagcc gcatcacggc gccaccaaag ccgaccaagg agcaagagga ggccatatcg  77460
cgacacatca taagcgaact gctgcacgac acctttcagg cgtcgaccga ggccccgaag  77520
gatgccgcca aggaacagac gcaggacaac gggcggtcca tgacggagca ggtcgatgat  77580
atgagctcag agaccgcatc gtacggaaac gtcgtatcgg acaagtatat ggtgcccaaa  77640
gattatcaca aagctctgct gggctggtac atcgagacgt cgcaacaggc caaagacgac  77700
ctcctatccc ctatcctctc caaactcacc gccgagctga acacgagctc ccccatccgt  77760
tcccaagagg aaccgatgac aacatgaaaa tttacaaggc cagttacaat cagaacaacc  77820
cgcggttcgg agaccgagcc ggttcccaat gcatgtccaa ctgcttcacc taccttcacg  77880
cggccttcct cgataaaatc ggctatcccc ccaaccaaga gacgctcaac gccatcctag  77940
acgagggcac cgcgctagat cgacgggtca ccaacgacct ggtcgccaag aacccgggaa  78000
ccgcgcccca cgtcttcaga ctgaacacgg agataagacg tctgatcaac acccagttcg  78060
gtagcacgta ccacgtcctc tccaaaccca taaatggtac atacgtatcc cgaacgttag  78120
acaacatcac gtaccccgga gtgaccgatc tagtgaaact cgtcctccag aaagcaccat  78180
gttacctaat catcacggta gacgctttca cgcgagccat atccagcacg cgaacgcgcg  78240
aactgtactt gttcgaccca cacccgacgc gtctcgagag catggcggcg atctatcact  78300
gcgaacgccc ggacgagctg gtgtcattga tagcccccaa cgaatccgat cgcagcgact  78360
tttattacga cgcggcgacc gtatatttcg tgtcggccgg atccgtcacg gacgagaaca  78420
cgttactgca acgcatcatg acgacgtatc cgaacgatcc ggacatagac ctcccgatag  78480
ccaggcccca gaagcgaccg ttgaggcgaa acgcgccaga agtgcaaacg gtcgcgacga  78540
tcgcgaaacg acagcgaaag aacctaaaga taaagagcga agtcaacgac aaggtgctgg  78600
cgatgctgga ctatgccatc aagctagagg gcatgatcga cgacctgctg gaatcggtcg  78660
gaccctacgt gattcgcgcg ccaccgaccg cagggtggat catctacggc gagaacgggc  78720
taccgttcga acgggacttc ctccaagaca gaatctatca catactcggg tgtcacctgg  78780
ataagttcct gaggttggaa ccccgcagga ccgatgagat ggaaatcgat cgaaacagac  78840
cggccgaaca atactaccgc cgaatcatgc taaaatactt ccaaagcttc gtgggattcg  78900
acaagcagct agacgaattt atagacattc tacagaaaca cagcctggac atcctaacgc  78960
tttacaaatc ttatctgata aacaaacgcg atcagagcga gtactctcag ctcgacaaac  79020
tcttagccgc gaagacgcta gccgtcttta gacgactgag caagcaacac ggggccgaag  79080
tggttcgctg gataaagcgc gtcctcaagg cgatagataa actgccgccc aaggagacca  79140
```

```
aggaggccct ggactcgttc ctgatcaata accggtttcc catcgacgac gattctttcg  79200
tctgtctaga cgaacagagc aaatcggacg tatcgttcga gatacaactt aaagagacgg  79260
aactcatcag gaagatcgaa acccaaaccc aggaattctt caagctcaaa aacactatct  79320
tcagtcatct catctcgttg ctggaagtcg acggcgcggg cgaaacgaag agaaagagac  79380
ccctctccac caccgtggaa caggtcctgc gtaagctaga ctccaaggcc gcggacgcct  79440
tgcgctactt cacggtcgag acgatacgag atatacaaga gagcctcgac gggcagttgg  79500
aggacatcat atctgaacac tacaacagaa tcataacggg ccatctcccg aaaaaagagc  79560
tcaccgagta catgtcgaaa gtggacgcga tgatcgcggc gaccgcggag ctagaagcat  79620
tggggttgtg tgacacggaa gaagagctgg ttcccctgca gaggttatac gatacggcct  79680
ccgtgcttca ctcgggtcga catcgttacg actcatcgta ctgctcgcag agtacccgcg  79740
atctcaggaa gctgtacgac gaattcgtcc agagactgga acgcgacgat gcgcgtatcg  79800
aagatatgct ctccgaggtg gagttcgcta tccgggatct acaggccaac ggacccacga  79860
cgaccttgga gctcatcaac gatcagctga gagacctgaa cgaggcggac gtatccagga  79920
tccgtaaggc agacgagcgt ctcaggcgta tcaacgacac cgtcaagaaa ctacgaatag  79980
aagatacggc catacgacaa ttcgtaaacg ggatctcgta cctcaccctg ccgaccgtga  80040
cccagataaa taagcacgtt cacttgaaag actcgttacg cgaagacgcg caactgcgat  80100
ctcaattcga cgatatcatg aaaacaattc tcgtcacgat gactaagaaa ctggcggctc  80160
gagaattccc gaagaacgac gtcttcgcgt ctatcaaaca tctgctgaac cagagacacc  80220
cgccgggtcc ggacgtgatc attctagaaa acgcatcgga gctactagag aagctgacca  80280
aagaactaaa aaacaccgca tcagccacga aacaggataa gatccaaacg ttgacatccg  80340
cgatccagtt cttcgccgac aacaaagacg gtttcaccac catgatgaac cacggcgtgg  80400
gcaaggacga actgacgggg atctatcaga atctcaaaaa agacctagga gtcgccgtca  80460
tggaattacg agaactcgaa tgggagaaaa gcgtcaagga gttcaagccg agctcggcgc  80520
aagaactaca cgattgtctc gcaacggcac cgagcgatcg cgtacgggac aaattaaaac  80580
cggaattaga aaagcgttta agaaactcgc tggaatcgca atatcgcgag cagatggcca  80640
tcaaggacaa aaacgtccgc gacgttcgag ataaggccga aaacgaattg aagaggatcg  80700
cggacgcatt ttcggctatg accccgtcga ccgtctccat gatagacatg gagatcaccc  80760
agggaatgat agtcaacata gaagaagata cgaatagcat cctggaacca ttcaatagaa  80820
acatgagatc ggcgttgacg aagctcaacg gcctactctc ctcaacacga accgccctgt  80880
tgacgatcat gttgagaggg gagcagccga gactgaccga aacggatccg ttgacggaaa  80940
aacgactcgg tcacctgcac gatctggcgt acaacgtggc ggacaagata ccggacctcc  81000
ttaacgagga gacgaaagac gtcctgcaga ccgcgatcac tcgtatagat tttatcaaca  81060
agatattgag atcatggcaa actccggacg agatcttctc tggatcggaa ttcgcgagcg  81120
attactctaa gtacaaagac gcgcgacacc aattagatct cgcgcacgct aaaacgagag  81180
acgatatcgc ccgcgatacc gcgagatacg tgcaggagat aacctcggcc gacaaacccg  81240
tcaccaaaat accgaaagtc gccgtcgcgg acgtcccaca gaaaagcctc aaagatgaga  81300
tagacgcgat gaaacctccg ttctctacgg atctcaagga ccggttacgg aatgtctcgt  81360
cttcgctgcg cgacaccacg acgctagcga ataacgagat acagacgcag gcggagttta  81420
agaatcagac gctgaaatca tcccaagcca gatggctaga tctcgtacaa cgccatcgcc  81480
taggcgcgcc cgatatggat atccccatag ataagctcat cgcgtctccg acggagacgc  81540
```

```
tatattctct cttgaaacag acggaaggca cgacgtactc cgccgcggcg aaacagatac  81600
gatggatctg cgacttctgc tcggacgtca tggccaacgc gctggacgta ctcactccgg  81660
aaaccggatc gtacatgtcg gacatctccg tccgggcgca acagcttttg agcgcaacgg  81720
aacagaaact aaagatatac gctacctgcg aaaccacggc gaatctctta gagacagaat  81780
cttacggaca gcgcgtggga gaactcgtcg atactctgga atcatcattg aacgaattag  81840
atccgaaacg gatctccgga ggagagaagc gatatcagca gctgaagagc ctgatatccg  81900
agagacgaat ggaattaaac gttctagagg attgtgagac actgatcgga aaatatttcg  81960
aactgatcga agacgtgaag agatttcggt acggattcca cttcactcag atagataata  82020
tcatacagaa cctcagacag gagttcgtcg ccattctacc gaccaaatcg ctaaccagac  82080
atccggcgat cgtaaggttc cccaaaccct ccgatgatac cgtccccata gacgaaggcc  82140
ccgacgccat gaaagcctac atatctacat ttatcagcgg cctcgcggcc atccaaaaga  82200
gggttcacga acaatcggcc tatcttaaca atatgtccac ccagcaatcc cttcttcaga  82260
tctccgcgtc cgacgtgacg ttaccgtccg acgaactgac gacggccatt cccgtgcccg  82320
ttacgctcac cagactcaaa ctgtcaacca gaacggcgac gatgtacgaa gtggaagacg  82380
tgttcggcgt ccgaacgacc accaacacga ccggaacacc gatagaactc gccgtaccct  82440
atcacaatag catcaccaag ctattttcta tacggaccgc agaggatatc aagaatatca  82500
tggacgccac cgccctggtc cctccggaca cggtgaccac acgttacagg gcaatcaaaa  82560
cggctcacgc tataatgcaa tcagtaaaga cattctggga acagatacga gactacgatc  82620
tcggggattc gttgcacaac aagctggaat ccaccgccag agagacgaac atacttcaca  82680
atctaaagct attcctctac ctgttggtga tagcgtggac gagcgcatac gaggaaccca  82740
agaaaccgcg tatgccgcta cgagactcgg gccgacacga gacatcgatg gccatatcgg  82800
aagaagatct gctgctcacg cacgtagccc tgttccccaa cagactcctg ggcacctgtt  82860
ccactcccac accggtggcg ctggggatgt tgatacagac cctggacaaa gatacgttca  82920
cggaggccat aaacgtacac gccgtgccac cgacgggtgc cgccgaagac ttaccggctt  82980
tctgcgtgga tccgaaggaa tggaaagaat tcgatctgtc ttccgaactg tggaaccata  83040
acttactcgt gcaactgtgt ggcaaaaaac agggcggagg gacggttata ccaccgaagc  83100
tgttacagta cgagatcgcc ctggtcacct tcccgccgaa catcattcac catctgtggc  83160
tgcaattcaa gccggctttc gcggaagact tcaagaccat gtacgacatg gtactcgaat  83220
tacaccgcga tctcctagac agaaatgacg tcgtcgtacg accgcgcgaa gacggagacc  83280
ccgagacctt gcccgcaggc gacaaggtca cggcgaagat ctcggtcacc tcctcaccgg  83340
gacagaaacg gctgctcgac caatttctgt cacaaaacag cgtcttagac tacatcgtgg  83400
gctcctacct attcggggtc cagatggtct gcgcggccga cggcggctac gtcctatcta  83460
agaacagaag actgctacta aaacaactga gcaacacgca catcgacgac gattttaaca  83520
ccatactcaa ttccagattg ttcgacagcg acatcatcct acgcgagacg tggacgggag  83580
aggtgttgga acacgcgtgg ttccgggccc aggtactgat cctccaggag cacgtcatgc  83640
tccacaaatc cgcggagagc atccccctgg tgatctacga cctccacacc aacggcaacg  83700
cgtccgcgct taaacgcacg cccgtcgaga tatcccacga cataatcgta tcggtcgata  83760
acagattctc cgtaccggtc tcacacgaga tcatagagac gaccgaggag gactcgacgt  83820
tattctcaga aaccccgctc gacgtagaat tcttatacat ttcaccaccc aaagaaaaac  83880
```

-continued cgcaggagcc acagaccgac acggtcccca cgtcatccct gtccgtaccg gtcttccacc 83940
agaagacgat aaccgacatc acgccgaagg atcaggtgac gacgctagag gccgaaatcg 84000
ccgtcccgaa ctttacggaa gaaccgtacg tctccctgca caagaggcta tccttcgcca 84060
ttgacgcgct taaagacatc agacaggaca taaacgacct catacaagaa atacacgaag 84120
gcgtaaaacg gttgagaata atgtatgttt attaataatg taaataaatg tctaaagtga 84180
tatgtatgta tacagccggc tacgagtgct ttcttatccg aaaaaactca atccgtatca 84240
ttgcgattgt tgtatgacgg gtctgttcct ggtcacggag agcatcctca gcaggtctaa 84300
tttgtaccct tccaagtcct cgggccgcat attcctggca tatctgggaa taaccgcggc 84360
aatagtcgga tgagcggcgt agtccccaat ttccagcatc ttgataacgg cattgtgtct 84420
cttttcctcc tccttttcgc gatccttttt gctacttggg ttactcatcg tgcgtctgtt 84480
agacacgttc ccctccctgc gcgtatcggc aataggtgtc ccgcacgatc tcgcacccta 84540
cgcagatccc gtcgcttcgc ccctctccgt ccagacaggt ctcacgatag ttgttctgac 84600
agagctgaca agagaagtcg ctcccgtgcg tgatcagcct caacagccta tctgtagtga 84660
tcttgcgcag caccacggtg gagaagcacg tcctggaaga acacgggaca atgatatcaa 84720
caccgacgtt gttattatac acggcacacg acgagttaga accggtcacg gcccgccaca 84780
gcacattggc gatcctgaat ccacatacgt catatcgcag cacagagtag ataggttctt 84840
tgctcagata ctggctgccg caaagagagc agtgcgcgag atcgttatgc gtgctaaata 84900
tgacgctctt ttcctgctta tccctataat acaacataga gttcagcgga aacgtatatc 84960
cgcaatacag ccgctcttta cccaggttta ggcagtggcc gcagttgtta cagacaacgg 85020
cgtagaggct tccgggcgta cggtaccgct cgcatttagt tttgcagaaa caggacatcg 85080
gcaggtttaa caaactgtga ctgatgccgt gccgcaaagc caccgacagg ccgaacataa 85140
tgatcttatc cggttcggaa aacgcattcc ccgtaccggt cctacacacg ccgaccgagc 85200
cgcgtccgtg cacgctcccg cggtgcttgt gtctagagtg gtgtatgacc gtgtgcttta 85260
cacgtaaaat gtcggggaaa gtcgacttcc cgagcggtat gagatagcgg ctcctgttcc 85320
gacagtagtt ctccaccagc gccttggcca tcacgtatag ggggtttcca cagggagcgg 85380
acacggcggc ccgtctcagg ccctccacga gcgatttaga agccgcgaac gagtccccgc 85440
acgatccgcg cccggaccaa ttgacgccgt tgtacaacac gatatccggc acgcactcgt 85500
agtccttcag tctcaacagg gacatacacg gcgtgctcat ctgattagaa aacggtatcc 85560
tgaaatcgac accgaacacg tggcgatgca ggtcgctaaa gtgttgcatg ctcatacact 85620
ccaacaaggt ctccaatcta tcgacgggat acgaccttag tttttctcc acgtccgacc 85680
acctcaccgt acccacgaaa ggtatggaca tgatatcggt gatctgacag atacagtgga 85740
gcaggtacat gtagtttatg aacatgaaaa acgactttgt gatcaacacg cgcttgaaca 85800
tgacactgat acattctctc ttttccgagc ccagttcgag ccaggccttg gagaacttgg 85860
aatagaacct gtccaccaag tctttgctca ggaagcggcg atccgtgacg aacagatcca 85920
acgtgcaaaa aaacgcgtcc cgagaatgtt ccctgtccgc gctcgccgac gacgattgag 85980
cgtgtcgagc gttgacacag cgaacacctc gatcgaccag ggtgctcccg gtcagcaaca 86040
gtccgaaatg atgatcgccg tcgtgacggc acagcgggaa caacagttca cacactatct 86100
gccgcaagcg aaacgccatc ccggaaccac ttcacggcgt agacgagcgc gcacagaacg 86160
acaatggcgc cgacgatcaa gaccttagcg tgcctctcta gcacgccaaa gacgaacggc 86220
gttcccacag cgccacaccg ccgacgcctc tcgcgctgac cggcgtcctt gccccgcgga 86280

```
gaaagacggc cggtgccgtt ccgctcgtca ccgccgaacg ccctgtcgta tcgctcctca  86340
tcgtcactat actcgtctcc gcagacgttc gcaaaactga acggttccgc gccggcgtcc  86400
ttatctatac ctccgcacgc gtcatagcgc acgccgcgag actcgtgacc ggcgatcaat  86460
ccgaatcgac gatgacacgt ttctctgtat ccggcatcta cgtgacccac cctgacgacc  86520
gcgtccctct cgtcgtggtt tccgacgtag cagaaaccgc tcctggaagc gccctcgatc  86580
gccgggattc cgtcatccac cacccgcccg tccgaacagt gactgcggcc gcagaaagtc  86640
gacggtaaaa aagtcttcgt gtgtaattcc ctgaggaggt tgaaatattc tgtttcgttt  86700
tccgggccaa acgccaccag ttccaggctg aacgccccgg atccgaacgt cgatcgccgc  86760
accacgaact tcgtcaggat accgttctgc gtcggcttta tcatgtctat gtcgtgggag  86820
tccacgatga gcacgtcatt catgcgcagg agattatatt ccctcacgtg tcgcatggac  86880
gtgaacttat cgggcatatg tacgtaacaa cacaacgata tcacagaacc cgtattctta  86940
aacgcgaaac agggcaattg acacgtaagg gattcccagg agctcaacag gtattcgata  87000
gaatataacg tctccggacg taacactata tcgcagacgg agtagttggg gttcttttcc  87060
accagcgcgt actcggtgac gcgcatctcg tgcggcgaca atcgcatgat acgctgcgtc  87120
gtagcgatca ggtccgtgta gaccgcacgc tccaacatac cgatcgcgaa atcccgacga  87180
tcgtccgcga cccggtaaac accgcggata ccggcgagcc cgcactttcg agtccgtgcc  87240
aagaaaagac cctcactccc cgaccgatgt atgacctcgg tcagtcgtcc ttgcggtcta  87300
atattccgtt gacatctaaa agcttagtga gaatggcggt aagcagcctg gtcttatcta  87360
acagtatgtc tttgtgcgcg cacgcgtcac atcctccctt ctttccgtga cgaacgaacg  87420
ctgtatattt ctgtccgacg ttgatgaaat tcaacctcgc gtcgatggaa ggcagcatga  87480
tatcatacac ccgcggcagc atgggtttga atatcagatc ggtgacatcc tccacatcca  87540
cgacattcgc ctcgtccgaa gaaccgttca cggccgccat cgccccgcgg cacgcagggg  87600
acacgccgta ccgtcgcgta ccgtatcgca agatgagcgc gcccgcggac gcgacgagac  87660
gcgcgacgac taagagctcc gacggagaac gcgtcgtacg ggacgtcgta cgttacatac  87720
cgctgctcat ctacctcgcc caccgagaac ggcacagcat tgtttacgaa gcgcggggtg  87780
actcattatc atacaaaccg ctctcacgcg cgcgatattt atagtctaca aaacgcgctc  87840
cgcccgagat cgtcgcgacc cgtacgagat cggttcctaa aaacagaata aagccaacaa  87900
tggatttcac atacaaaggc tggtgtcatc atttctcaaa catggacgct cctcacgtca  87960
acgagatcct ggcctacgcg caccccaggg tctccgtatc cgcggaggag gcgcaggaac  88020
acgtatcctt agacgatccg gagaccttgg cgaacgtgac ggacgaacag gcgtcacgtt  88080
ccgaaaacgg tacgcccgta cctccgagag acgtggaggc cgaactggcc atccagcaga  88140
actccacgga gttatcggaa tgcataaaag acctgtgcac gacgttagag atagataaca  88200
ggtgcaacct atgcgccatc gtatccatct gcgtacggct ggactccaac agcgcctggt  88260
tcctagacta cggcctactg tgctacaaat cgaccgtggc cccgaggacc gccatgtcga  88320
cgctgatagt gaccatggag ttcatgtatc tgctcaacag gcactttaag aacatcaagt  88380
tcgacaacct gttttcccaa aaaattctca ctacgttcga cttccagact cacttttttta  88440
tcaatcgttg tttcgccgga gacgaccgga acccggtgct cagggaaaac ctcacgctga  88500
actacgtcaa cgtcaccaaa gccatcctga ctcgagacaa ttacataccg tacaacaagc  88560
accgccgacc gatcgggcct cgaaaaaccc ccgcgctgaa acagatccaa ctggtggtag  88620
```

```
aagaaaacga agacgaagcc gcaaatatcc tgaaacaaca cgccaagacc tccaagagca  88680
actttacgaa cctgctgttc tacatctggt ccggaaccaa cgtcttcttc aacgtatcgc  88740
tcacgaacct ggcgatccgc aagaaccaca acatctcgat cgcgtacctc ggggacgaac  88800
gcatcgaaca ccacatcgga cccatctacc tatctcccgt accggtcttc gcgataaaaa  88860
acaacacgac caccgtctgc ctgctctgtg agctgatggc ctgctcgcac cagcacaacg  88920
tgctgctgcg gcacatccgc tccaagatca cgaactactg ccgaaataac atcaagctca  88980
tcgacaagat ccagctcacc ctggcggaca tcttgcgcgc gtcgggcttt cagacgcaac  89040
tcggaagagg gaacaaggac ctcagcgagc aagtgtttat gccggaatcc gtcaaattgg  89100
ccgacgacgt gtatctagac cgtcacgctt tcatcatact caaacaggtg ggcatcacag  89160
gattatataa acacttcttc tgcgatccgc aatgcgccat caatatcagg gcgacgaatc  89220
cggacgtctt attcgccgat atcgacgtgc ggtacctccg cgaactaaaa ttggctatct  89280
gctactccag tacgtacacg atacccgtgg aaccgcgcat ctcgctgttc gctcagacgt  89340
tcaaggcgtt ccagacgtgc aataggaact tcaaagcaaa aacgcacctg gcggactttc  89400
taagagaatt caatcacgtt ctcgaggaga gcgagatcca tctgatagaa ccgtcatacg  89460
tcgtggataa atatgtctga gccgaaacag cccgacagac atcactcgac gaccagagac  89520
acctcggtac caaggacacc ccagaaatgt cgagagcgcg tggcttctct gtcccggcac  89580
cgcctgacac ccagggagtt cgcgttctca ccttaccgca attaccacgt cccgggcccg  89640
agcccgagaa cgaggtctcg gctctcgacg ccgtacagag accgccgaga atccataccg  89700
agacccgtat gcgacggcgg ctgcgaagac atccaacacc tatcgctcaa acagctccac  89760
gccgtcttca gagagttccc ggaactcgaa aagaagtatc tggacatcat gaagatgccc  89820
ataaccggaa aagagcccat atccctgccg ttcgacttcc actctcaccg tcagtacacg  89880
tgcctggacc tctcgccgta cggcaacgat cagatctcca agagcgcgtg cgtctcgtgc  89940
cgagataaca acacgtcgct ggccaccgcg tccgacgcga tggtggaatt tctgaaccaa  90000
cccatgaaca cgatgaagca tcgaaaattc tactacgcct tcagaaagga cacggagacc  90060
atgaagctgt ccggaagcca cccccaactg tttcagctgt actacctcgt aaacaccacc  90120
atcccagaga tgaccccgct gatattgaac aaggagaaca tgttgcacat gtatttaatt  90180
tttgaccgaa cagaattaca cattccgtgt gactgcatca ttcaaatgct catagcggcg  90240
aaagacaatt actccgtcag cctggacatc atacacgatc acgtagtcat agtagttaca  90300
tgcattcgcg aaacgcaacc cacgatcaaa atcgatacat tgaccctcca gaggaagata  90360
gacgaactcg aagtcccacc cgagatcacg gccaagttcg aacagtacgc aaagatcatc  90420
aacagcgaag accgccatta cataagttct tatccgtaaa cacggcagcg tacacaccga  90480
tccaggccgt cccgtgtacc cacagaaacc aataaagtta tcacgcaatg ttctcatcga  90540
tcctttttat ttaattcgtt acagacaccc cacacattac aggtttgatc ccatacacac  90600
ccatcatcac gccgccatcg tcacacgcga caaccaattc gttcgcggca caggcgtagg  90660
gcataaacgg tctcgacacg tacacgcgct gcggtaagac gtacgatagg aatttttcct  90720
tcctaacgca gtctttgggt atgatggggc ccaacacgtt ggtcaccgtc ttcacgacgt  90780
gttcgaaata cttttcaccg ttcacgggca acttgtgctc gatgacatat ccgggatcct  90840
cggatatctc atagttgggc acgtttttgc tagagcccgg aggtggcgcg atcaacacgt  90900
agggcaccct gtcgcccaca gagggcaact cctcccgtct ggcggccaat ctctggatga  90960
ctctgaggtg aggcaggttc tgctgcttgt acgcggacac ctcctgcgat agactcgcgg  91020
```

```
agaggaccag tttcttcaca tctacccgat tcaggtagag ttcgtccctg gcattgctca  91080
atgcctcgac gatcctatag aatcccgacg gcacaccgtg gcgcttcaca tcgtccatag  91140
tcattctaga cagctccaca gcaccagccg acacgtcgtc ctcgaagaat atcatgttga  91200
ggacgttccg caccgtagac ttaacgtact cgcacgccgt ctttctgacc agttctatcc  91260
ccttcatgct aagcttagtc tgcccgtata tgcgccccac ataccgcttc ttacatatca  91320
tcatgagatt cataaacacc ttttcgaact ccaacttaat gggttcccga aataaagccc  91380
gagtgatgtg gcccgctatc gattcaccgt gctcgagtac ggacccgcac ttcacaccgc  91440
cgcatatgac aaagacactg tccgtgtccc cgtatatcac cttaacgttc agggcatccc  91500
cggtaagatc ctcctcgccg aggtatcgta accagaattc agcgtgaccc atgtacgtat  91560
tgacataatc gaccaccgac atgagcatgt ctcttcctat gcgggttatc gcggccgcta  91620
tgggcaagca gggcatcatg ccgctgctga ccccggtgaa accgtaaaac gcgttgcacg  91680
tcactttgag ggccaactga tatttgtcca atatcagctt ctcgacctcg tcctgacact  91740
ccgccaatac tttcctgacc gctttccgtt ttgccaacca acgggccagc aattccccca  91800
gtatagattt ccgtacgtgt tcgcggacga atccgtatcg cgtaccgtca tcgaattcca  91860
gaaggaacac atcgttgtcg gacagaccgt cgtctcgacc gagcggaaga tacgtcgagt  91920
aacacaggtt gtgtcgcata atgatagacg gatacagact ggcgaaatcg aagacggcca  91980
cgggggtgtc gtagaagccg acgtcgggct ccaagaccgt agccccctgg tagcccactc  92040
caccgtcgct gctgccctgg ctggacactt cgcccaagga gctgtccgaa gtttgctcac  92100
tatcttcctc gaacgacgcg acgggagacg attccgtcgc gagttctccg ggcctcttag  92160
cggtcaggaa gctaggcaag atcatgttcc gctccccggc ctcctcgagg atacaagaat  92220
agatacggat ctgttgtccc tcgaagatga cgctcctcag cggtatcctc gccaacctgg  92280
caacggatgc ggcttcgtaa tgatagttca atttttcgaa caaccgtttg acgagcagag  92340
cgtccttgat acaataccgc ccgacgacgg cgcgaccgtt atcattggcg agaaaagtcg  92400
gcgggatctc cttgtaggag agatcgtcct tgtgttcgtt cagatacatc tcggccatgg  92460
tctcgagctt gtaattaggc gccgaagtct tggccacgca cacgggatac atgtccagga  92520
cgacggtacc ggtacaatgc acctttatgg aagcggacga cgcgttacgg ggcttgttcc  92580
cgacgggaac gtatatgcta aaacgaccgc cgaaacgaag tttagtgaac tcggagacgt  92640
tggcgtggta gatcttctcc atgcgctgca gcaagtactt gatgtcgaag aggttgatgt  92700
tgtatcccgt caggatatct ggcgaatagg ctttgaagaa aatgaagaat cccagcaaca  92760
gttcatattc cgaggggaac tcatacacgt gagtcccggg tatcggcgca cagggcccca  92820
gggtaaacag atgttgatgc tctcgaacgg cggcctccgc acccgaaacg ccaccggact  92880
ccgcgctcga ccttcccacc gcgtagcata tgacggatat ctggatcact atatcatcta  92940
ccatagagga gtctggaaac ctatccccgc cactcataca ttcgatatca aaggacgcac  93000
accggtactc cggccacgac atgtccgaat cgtcggcttc cacatccccg atctcacaat  93060
ctatctcgat gtcgcagaac gacgcgagcc cggaactcct ggcgtagaat cgctttatca  93120
cacaccaacc gaacgacggt atcttcctat cgacgcagaa cctagccacc ggatccaccc  93180
cggcctcgta gaccctcagg cccctcgatt gcaaactctg cgccaatcgt ttacacacgg  93240
gccagttatt caacgtgacg cgatacaggt tttcgatgta tttcgtgtta tacccaaaca  93300
aggagtattt atggacgcgc tgcgcgtcta acgtgaaaac tatcttagta acatcctccg  93360
```

```
tctccttaag cacggtcgag agatagttgt ccagataacc ctccgagtca tcgtactcgc  93420
aataaaaata agacggctgc ccgaacacgt tgacacacac actacttcca tcgcacgttc  93480
tcccgaacat acgtatcacg ttcccgcaag ggactacgtg acgccgatat cccagaaaaa  93540
tctgctcgac ggaatcggcg tataccgtac tatctatctg gtcgaacgta tgaaaacgga  93600
gcggttgttc ccgaccgcac ccgaccctgc aggtttcccg atacggcagg gtcggccagc  93660
tcatttgcgg ttccaacaga tactgtacat tgttgtaaaa catcctcggg ggatgttggg  93720
tcactttctt gatcagtccc ttctcgccgt cgtatatcac gccgcggggt acgacctgaa  93780
ggaacgactt ctttcctttt ttagtaggtc cgttaccccg tcgagaatcg acggtcgagc  93840
atccgttacg tcttctagca gcaccgctgc acagataggg attaaaaaac acaggagccg  93900
acatggcgcg attaggtacc gtactctccc cccctcttcc tcacaattaa acatgcacgt  93960
cgtcttccgt gttcaatttt tgataacctc ctctccttct tagtctgtcc attatacccg  94020
gtctccgtcg ggtttcacta tttttatttg acgcgctatc cttagaagat ttttctatct  94080
cctgacgctt tttgtcatcc aaccgcttaa tagcacgtag catccgcacg gcgtcctctt  94140
cgttgaagtc cgccccggcg ccggcagacg aggacgacac tcgagtgtcc gcatccacgg  94200
acagatcctt atatccatag ggcgcctcgc cgggataggg aggtggagcg tcaccggacg  94260
ttccctcggg acctggatag gccactgcta tggagctgtc ggccacggag ctggtgatgg  94320
tctgggaggc gtacggaaag aagtagtcga aaggacgttg catggctctc ctctggcgac  94380
gatacacggt gatcaccaac gtgatacaac cgacgcagaa caggaacacc acgaaggctc  94440
cgaacggatt ggtaacgaag gtcaccaggg ccccgatgaa cgagcctatg gcgcctccga  94500
cggcacccac ggcctcgcct atgcctttac caatagcgcc cataccgttc atcatctcgt  94560
ccagaccctt caacgccggc ggtatgggat tgatgacccg ttcaaccacg aagtcgagcc  94620
tcttcttttg ataattgtat tcccgcatga tggactccag atcgaagaca ttggcctgcg  94680
ccagctcgtc cctcgaatat agctccagca ccttgaaatc tatattctcc aacggttcgg  94740
tcttcaatgc gatcatagta tcgataatat ctatttcgct gaggttgatc ttcttggtga  94800
aaacgtactg ttgaaattcg tatcctatat cgccggcgac aaagatccgg taatcctgcg  94860
tctgacacgt ctccatcctg tgcgttccga gtaatatctc gttgtcctca ccgagctgac  94920
cgagtcgcac ctccgtacta ttcttcatgg agaaccaaac cacgggtcta gaataacaac  94980
cctcaagctt accgtcgtcc gaaaattttc tcatatcacc ttttatgagc acagtagact  95040
gattgacctc gatgcattta gctaacgata tcacatcacc aaccactcta gcagccacag  95100
gcactccgaa tatcgccgat aagatattag aaggattaat cttactaagt tcgtgcagta  95160
cttccgcggt acgcttctga tccaaacacc acgcctctgc aatatgaccc aaggcctgat  95220
tgatgtatgt ccgcaaagta tcatacgcaa actgaagttg tgcataactt atgtcaccag  95280
tggattcatc aggcaacgat cttttcctac ggctattaga accagtagcg ctgaccgcag  95340
attcattcgc ggcaatctcc aacgccttta acgatttttg cttcaaaccc tgccacacga  95400
tgaccaagcc gccggtcgta acatgatacg tcgcatttcc atccatgtca tacgtctcat  95460
tataatcacg aagaaaaacc tcttctatct tcttttgcgc atcgtccttg aaacatttga  95520
tatcatcttc agttaaatta ttatctggac tgtatttgtt ctccacaaac gttgaggtca  95580
atgtgcgcgc cacataatga aacgcatttt cgtattcggt ccgaatggct ctatctacag  95640
tctcccataa aatcatctcg cacgtcacgt tagattgatc attaacttcc catccgatta  95700
ctacatcttc tctctcgtaa aaagccatct tcggtacgat tcgcgcttct aaagctctgg  95760
```

```
atccaaaatc ctttaaaatg ctataattac tccaaatgtg aaatttttct ctctgttcac  95820
ggaacgtctt cccattagag ccgttgtaaa atggagatat gttgactata acaccggacg  95880
gcaagacgaa catatcatac ggaaatttag atttgccttt agtcttagta actatacaat  95940
tcatgctaca tgtttcctta tacaaccaga cagatcccgg agtgcgagcg tgttctttta  96000
ccgttatgta ccgatatgtg tcatcgtttc ccatatcgtc cctcataagc cacatggtct  96060
cattaacttc attatcgtta tgatacgcta tatatctatc agcgccaata acgcgttggt  96120
gagaagtgta gcattgtcct ctgctgttta ccaaaaaaat ctcccacatc ggtaaagcaa  96180
caaactctcg gctgtaaccc aacaggtagt catacgttac atatttataa ctcctttgaa  96240
acaacaactc tttctgataa gtatacgccg taaagacgta tggcaaaata tttctcttgt  96300
aaatcaacat aatcccttcc tccgaattca ccctcggatt gaagggtacg cactgaatag  96360
tcctggcaaa tctgaccaga tcggttccca ttgacatgga acatatccga tacggatata  96420
attttcgttg actaaaatcc accgaggcgg tcaaatttct tatcacagta ttgttactcg  96480
atgcgtccga atgattgcca ttagacacgg tggtgtcctc gaccgtagta ggggtgaccg  96540
tcgtactctc acagtagaca ccgaggtaca agatcgtcaa agctgatgtc cacgtccctc  96600
gccaactgca ggagagaatt ctcgatctcg cgataccgcg tacgggtcgc attgtcgaaa  96660
gaagtcctcg tcttgacggg cgcaacttcc tcgtcctccg cacgcaccgt cacggtcttt  96720
ctagaccctt tgagatgttg ataaagaaga gaatacagat cgtctcctcg gcatattccc  96780
tcctcgtgca ccaaaaagag aggcgaccca acgttatacg ttaaaacaat ccccttgact  96840
tcagtcagag acacctcatc tatacgataa atttgtacct gtttaccaaa cttctcatta  96900
tatagtgcga ccgaagatac cagctcacga atatataacc acatcctgtt ctgtaacgtg  96960
ttcaaatcgg tcacatcgct aaaatcgaaa aactttctgt attcgctgac catccactcg  97020
ttggggttcg gcgtcccctc cacacaccgc accagatcgt ccttcatgtg tggcagcatg  97080
ccagcgttat cgcacgcata cgccatattg acattaaacg gcagtccgta aaaatcgcgg  97140
tgatgcgtaa acacgggacc gtttaaaaac cggtagatct cttgtcccag agccggcaga  97200
gactctaagg gcaacgtgcg atgtagtagg ttatttttaa cgtacaggtg atcgtcgtac  97260
gacaccatgt ccgatacgtg catgacgctt tcgtccacct cgatcctcct gatgaaaccg  97320
ttcatgagct tagatagggc ttccaaaacg accgtcccca tcacgttcac attcaccagc  97380
ttactgatac agttttcttg tttctttata caccgcatga ctttctcata accggcctcc  97440
gataccttc ggagataagc cctctttctc acaaccacct ccttgtctat gtcgtgctgc  97500
ttggcataag gatttccccc gtacagggga tcgcccgcct gaccggacac cgcggtatca  97560
tctaagatct cgctctcttt agaatcggcc ggcctacgta tctcctctat caggtatttt  97620
atcttcatat aaacttcatt attctcgtgc aaccgattaa agatggggtt gtcctcgaac  97680
atcttaatgc tcatggaagt gatcaggtca atgatctttc cgggagcggc gtacacggag  97740
cccacgaaca atctctcatc ttccgtgagg tccacgttca tgcaagtgaa catgtccact  97800
ataggttccc cgtaaaagat cttgctcaat tcgttctgca acaacgtaca caggtgatga  97860
tacatattca cctgcttgat ggtcacgttg acgtgtttca cgatagtctc tgacgtctta  97920
gaccagtacg tgaaatcgga gagagagtag atctgctgcg gtatctcgct gaatatgtta  97980
tactctttca gagcacgctc ggcctccccg atataagcgt gctgcccctc cgtcacggtc  98040
gcgatgttct ttatcgccga tattatccct atcaaccgat catgacggcc cacggtctcg  98100
```

```
atcacatcct gctcgatggt ctgcatatcg gtctccagct gcaccagggg cttgcacacg  98160
gctacgtgat cgcacaacag cccgctcaac ctcttcccga tcgacctccc ttgattaggt  98220
accacggtga gctcctcata acacttgtaa caggtggccg cctcgtgata cgtctccgtg  98280
gccacgaccg gggagacgcc gtgcgacctg gacagataat cgtgcaggtc acgacacagg  98340
gcgaagccct ccgagggaca catgagtccg tacacgcaat tgagcttaca tatcacccgt  98400
tccacgtcgt tcaaggtatc gaccttaacg tcgaaactca cgtgatcgtt cagactgacg  98460
atcttacggt aatgcctgtc acaaacatct aacctcaaca cgcgccgata gtaagcgacg  98520
cgatcaccgt cgtcgatgaa ccgcctcagc gcggcgtcca tacgcgtaaa gtcctcatgc  98580
atacaccgta tcagcatctc cagatataac gttaacacgg tagtggcctg ctcgttctgt  98640
tcccgcagtg acgggtacag cgtggcgtgt aacttcgcca cgatacgcgc gttcctcttg  98700
aacggaccgc cgtcggccaa tatggctacc ggatcgcagt acttcaagca ctgcaactcc  98760
agggcgcact cgttacattt agaacacaca acgcccagct tctgcaacga attcattatc  98820
gtcgataaaa acgtgtacgg agacgctcca ccttcgacac gcaataaaga cacacacgta  98880
agattctggt atcacactaa cgatttaata ataaccatga acgagagacc cagcccgaga  98940
cacacaaata ccacacaaac catgccttac aacctgaacc gcttatgcaa cggcatgtcg  99000
tcttcacagt cttcggcgac gtttaccaca tccccaccgt cgccctgtct agagtcctcg  99060
tcctctacaa agagagaaga aaggtcatat ttctcccgac tccccctctc tcgcgcctcg  99120
gcgacgccgt cggcgtcacc ttcaccggcg cccgaaaaat gcacgttcaa cgccctcctg  99180
atcccgtcga ccgaataatc atccgcaccg ctctcgataa caagcactat cttatcatac  99240
agagaccgcg ccagcgactc ctgcccgtcc acgaagaacg tgatctcgtc caacgtggga  99300
cacaaaccgt tctccccgga gacgctattc atgatctcgg acacggccac cagttcggga  99360
tcctcactag agtccagggc caacatgacc ctgttcttta tgacatcgct ctcgaatatc  99420
acgttatccc gctgcgtcct cctgatcagg acatccagca gcttagtggc caagatgcac  99480
ctctggcgca tgaacctata atcctgactg ttgaaactcc ccatcgcgtt cagactacgc  99540
tccaccccgg aacccacaaa ataccctatc tgtccgaact gaaagatgtc gtgactgtta  99600
ctgcccaccg cggcgtactt ctctataccg aacgccaccg tcactagaga ccgctgctca  99660
aagacggtcc tgaacaagga ttctcgagaa acagtggaaa ccaaaggggc cttcatgcca  99720
gcgatcttct tctccttcat ggccaagacg tactcggcca ccgacgcgta gctgggagac  99780
ttatccagca ggtaggggaa gttcaggtga tgattctcca tcaaccgagt ggtgaacccg  99840
tgaagggaag atatatagtc cttgaaacca aaaaaactca ggaacttgtt gtgaaatcgg  99900
tactccacgt agctcaggat actgtccggc gtcacgtcca ataaatcgtg ctcgttataa  99960
ttggacgtga cgccgatcag aaaccggacg aaattattga actcatcgag atcccccagg 100020
tgcacgctct tgggcaacgc gttgcagcac accttctgcc aaaagtcgaa acagctcagc 100080
ccgcagctgg gaaacaacgc gtcgtgaaac ctgtacagca gaaaggacat gcaccccttg 100140
atgggactcc gccgctggac cgaatcccgt ctgaagaaca cgtttccctg cgacgacttc 100200
gacgcgcgcg agatgggacg attcttgatg cgacacgtgc gaaaggagct cgtcgataac 100260
ttggagacct tggtctccat agatacccga gaatatctgc ccgtctcggc gtagacacga 100320
aagtcgatca accgttcgta ttccaccgcc ttagaacact tgacgtcgcg catgaacaga 100380
aagcccttgc gagccgagat attggcgaaa gctccaccga tggcctgcag atgttgaccc 100440
agccacctgg agatggaggc gcccgtcaga gggttgtccg cgatgtacac ggctatactg 100500
```

accaaggcta tgttctgcac gatcatcgaa acggccttgt gatactggaa agacaggacc 100560
ggcgaaaagc cgacggcgta agggttcata tccaaattaa acacctgcgt ggcaccgatc 100620
aggtcgtcct tactggattt cctcctgacc tcagacacga agctcaccgc catatcgtcc 100680
acgaacctat tcaaagccgt gatgcagttc atgaactcgg ttttattctt cacggcgatg 100740
gcatcctcac cgctgatggg gtcgatcagg ccgttcttct tgcaataatc catcatctga 100800
ttgagatact tgacgcgatc cacggaccct gcaccgacgc cgccgccacc gccaccgccg 100860
ggtccgatga ttcccggatt ccccatcgcg agaccatcag atccccgtcc gtcgttcagc 100920
aatccgccgc ctcctccgat cccactcatg ggcgaatccc gttggtccaa tacgtaacgt 100980
tttccatacg atcccagcac gtctccatcg ttcacgaatc tggagaagaa gcacaccacg 101040
atgggttcct tcctcaggcg gcgactgacg ttcggaaacc ggctcttggt acgcacgtac 101100
gccgtcgcgt aacacgtatg acagcagttc ccaccgcaag cctcacagct cctgctcccg 101160
cagccaacta tgtgattgat cagacagttt ccaccttccc cacctgtatt gtacatggcc 101220
accctgttga ggtaccacac cagatccgac accagctgcg ggctcgtcgc acaagcccaa 101280
gcgagatgcg ccatggaaaa gccttcgtct cgcgcggaca tgccgttacc gacgcgcacc 101340
agcttcttct gatccgtgta tacgtcttca tcgagacacc cgagtccgtt ggcgaactga 101400
acagaccgca acagcatgtc gtgagagccc gccgaactcg aggacaggga accgccgccg 101460
gttccgctac cgccaccgcc ggccgcaccg gacccccttgc cgttgccgcc gagaaagatc 101520
acccggttgc agtataacac cgaattctcg ctaaagatca gcgccgctat gtgcgtagac 101580
aggtgcaact tgaactcgtc gatcctgcgc agcagatcga cgtgatcgct agcgctcttc 101640
accatcggcc actcggagaa gacgagagta gggggacatt cgtacgcgga gtccaagaac 101700
gtgggtacga aatgaaacgc caattccgcc atggccgcat cgctcaacat gagctggtcc 101760
cgctccgcgt tgttcaactt ctggctcaga tatccgctat atcgtttctg cggagcgaga 101820
cgtacgccca acgctctgtc gtcgtcgaac tgttgcagac cgcatcgtat cagatgccgc 101880
gtatcgtcta cgcggagcga ctgaccgatg gcagtaaaaa tgaaataaaa caacgtttca 101940
cttaaactgt cacagtaaaa acatttagcg ctcacgggac ctccgcgggt caacctacta 102000
tccgaggcgt ccgcgtcccc ggccgcgacg tccgcgtgac cgtcctttcg atcgttatcg 102060
ttacacatct cccccccaaa gagagtgaca gggtacaacg gcactttagt gccggaggac 102120
tgtcctatct gtatctgaac ggcttcctcc aagcacatta ccatgcgccc ggcatacacc 102180
agttctttca cagcattagt gaatacgatg taaccgacaa ccttagacgg atccgcacca 102240
acggccccac acagggcgcc gacgtccgtg tcacgtttat tagcgtccgg ttcgtattct 102300
tgcatatgga acctaacgcg cgtttccgag cacagcttgg tcacgttgcc atgacgctcc 102360
acgaggtccg ataaaagaga cgcattgtga aacgcgaacg cgtactgata gaaagacgag 102420
atcttgcaga gtacgcctcc gtcgtacgaa ctgacgggcg ttttcacgga aacggaaaac 102480
tctctgtcta cgaccaaatc tatcagaagc ggcatcactg cgacactcac atccgagtcg 102540
cacagggaga gtctagcgat cacctccctg cgctcgtcgt cgaattccac gaagtagagc 102600
cacgcggaag gaccgacaga cgcgagattc gccagattat cttcctgcat tttcgcttac 102660
gttacgagca accgtatcgg aacgccgaga cccacgcgat tatttttttc ttaacacagg 102720
atagattcga ttttttagaa aaacggtgtc cggcattcat gtgtgctaac agataaaaaa 102780
acagacacgc cgttcacgta cggcacagca ccgtatcaaa tataaaaacc taagaccgac 102840

```
gtcaccacgc aaaacacacc cagcactgct tccccgagtt gtatggcatc ctttacaatt 102900
cgagacactt tatattgcct cccgtcgaag cgtcatcatt atagattaat cacatctgtc 102960
cgtcaataaa tcattgccaa gaaccccata taagcgttgc aggcacatat ctctgtccga 103020
gcattccccc gcacagacac aagcttttca tgtcaccggg gaatacatat gcgtccccga 103080
tgccaagtca atcccccgag acgtgaccca gttccgagca cacgatcatc atcataatat 103140
tctcgaaagg caaaaccgtg aaaccacaat caggaccata ccgatccctt acagttgaca 103200
tagttataaa acgcacccca ccagactgcg acataccgat tacgctaacg aaccgcactc 103260
ataccataca gcgtcacacc gatcctgtac cgggaactcg gccaacatca ctcagcatca 103320
cacaacgtgg cgtcgatcct tctgatctcg cggttacaaa accgttacta tacgaacact 103380
tacgtgtatg ctcccaaacc gagcaccgtc atcacaatgt tattacggaa tttcaggaaa 103440
gaattttgtt tttttttac aacaccccgt cggtcaggac ttagtctctg aagcaaaaca 103500
gcccattgta aattcccata gcgttgatac gtctttttgg acttagtctc tatagctcaa 103560
agcatgcatt accaaatccc attgacccga tatgtccgtt cgcacttagt ccctgagacc 103620
tccctcggag gggggggct cggacttagt ctctggtcgc gatgtctacg tggtctgctc 103680
ccataacgcc gatacgtcag atcggactta gtctcagggg cactcgcgat caagtccgca 103740
cttagtctct ggtcccgatg tctgcgtggt ctgatcccat agcaccgata cgtcgaatcg 103800
gacagtctcg gggcactcgc gatcgagtcc gcacttagtc tctgtgcacg atgcctgcgt 103860
ggtctgatcc catagcgcag atacgtcaga tcggacttag tctcaggggc actcgcgatc 103920
aagtccgcac ttagtctctg gccgcgatgt ctgcgtggtt caatcccata gcgccgatac 103980
ggcggccgga cttagtatct ggagcgaaat acccattgta aattcccata gcaccgatac 104040
gtgtttttgg acttagtctc tgacagcgag gtccccgcgg tccgattcca ttgaaccgat 104100
acgtcgggat tggacttagt ctacagccgg agcctccgcg ctgtcaataa tttgcataaa 104160
taaaatgatt gacgtgcata tccaatgaga atgcaaatag tttgctcatt acatatgcgt 104220
gacgcacttt gattgacagc cgttcggtcg cagagtcggc ccgctctcgg acagagggcg 104280
catcgtgtcg gtcgctttcc catagcgccg atacgtgacg catcggttgc attggtccgg 104340
tattgacggc gtgaccgcaa cgtatcagag tgctgggccg cgacccgttc cgagcccggc 104400
gtcgggtagc tcatcgggtc gtgcgccata ggaacgaaac gtcacatatc aaatgcattg 104460
ctccgacacg gcacacccga atatacagta tccaaatgca tagcgccgat gcggccgtgt 104520
cgccagacat aggaccaata cggcacgcat caaaacaatg ggccagatat gggaccgatg 104580
cccgtaacgt gtcaaaacac ataggcgcga tacggtcggg tctggcaccg ttgcgcggat 104640
acggccgtat ccgttgcacg gcgcgtggat ggggcgcgtg gtgaaaccgt atcgccagaa 104700
tgggaatagc actcgcgggg tcgtgcgcca tagggccgat acggccatat cgattgcacg 104760
gcgcgggaat gggcgccacg accgagacgt atcgaatggc ctgcatgcgc accggccaat 104820
ttattcccca tgccggcgat gcgggcgacg gcgcgcgacc cgcggccccg ctgggggcac 104880
cggcggccgg ccgccgccag gggcgcctc ggtcccgccc attcatcaac aagggcgtgt 104940
cctatcctgc cctgccatct ccatgaccac gcctgcatgc aaatgacacg taaataatat 105000
gcataagaga tgctaatgtt cacgcgcgcg cgtgcgtgtg cgcgcgcatg cgcgcgcgcg 105060
gtaattttat acgtgcgggt acgtatacgc cccctgtacg gtatgcaaat taccggtaga 105120
aacgataccg ttcaaaatac gtatactacc aatggtacgt aacggtaaca ttccggaaga 105180
aaatacacgt aaccacaccc tatatgcaaa tgataataaa caacgccgaa tcaggttacc 105240
```

```
ctaacgtatc cgttttatcc gaatgcaagt taatacggga cgtttctatt taaccaacgc 105300
tttcctgtaa cacccccaat aaacaaacag gtccttgtat ttgcatatgc aaacgaaccg 105360
ttttcacggc acgttacttt ccacgggtta cgaatattca ttggtgggcg taacctaatt 105420
tgcatacgta tccggtgcaa ttccgtatcc atccaatggg acgtactccc ccctacgtat 105480
aggttccaaa cctataaata caaaacctat aaatacaaaa cctataaata cactaggtac 105540
gtatatatgc tccctaacga atatacaccc cctaacggat atacacaccc cctacgtaac 105600
cacacccacc tacgtacaca cccacctacg tatacccacc ccctacgaat atacaaggtt 105660
tacggggggc gtaattcggg tctacgtata ggacctacca accctatcct tacttccccc 105720
ttactacccc ccccctaac ccccccccct tcatcccccc tcatccctcc ccttcctccc 105780
tagcccgaaa attcggcggc cggccgccga tgacgtcgaa gctggcgggc tgccaggcca 105840
cgtggctggg tgtgggagtg gctttgggac cacgtgacgg tgggtataag aggccgcgca 105900
cagcagtccc cgcccgcatt cggcgcggcg gacggaccag agcggacggg taggtgctgc 105960
gcggcggagc cccgggatcg ggtggcgggg ggatgggcgg ccgggtgggg ggggggatgg 106020
gacggctata ccccccgttt ccacaggctc ggagccgccg cgagcagcgc aggatcccgg 106080
acccggaccc ggacccggac ccggacccgg acccggccgc cgccgctgga acccgcgcca 106140
cccccacccg gctggatcgg caccccaccc ccaccccegg taagcgacct gcacccccac 106200
ccggctcggc ctgcaccccc acccggctcg gcctgcaccc ccacccggct cggcctgcac 106260
ccccacccgg ctcggcctgc acccccaccc ggctcggcct gcacccccac ccggctcggc 106320
ctgcaccccc acccggctcg gcctgcaccc ccacccggct cggcctgcac ccccacccgg 106380
ctcggcctgc acccccaccc ggctcggcct gcacccccac ccggctcggc ctgcaccccc 106440
acgcgcagct cctgcatccc tcaccggtaa gcgtcccctc ccccaccacc caggatccgc 106500
atcgccgacc gtcggaaccg caccgcagca agccgcatcc gcatcgtgag ccgttggatc 106560
tgcacccccg tcggtgagca cccccteccc tcagctaccg tacccccacc cggctcggcc 106620
tgcacccccct cccctcagct actgtacccc cacccggctc ggcctgcacc cccacccggc 106680
tcggcctgca cccccacccg gctcggcctg cacccccacc cggctcggcc tgcaccccca 106740
cccggctcgg cctgcacccc cacccggctc ggcctgcacc cccacccggc tcggcctgca 106800
cccccacccg gctcggcctg cacccccacc cggctcggcc tgcaccccca cccggctcgg 106860
cctgcacccc cacccggctc ggcctgcacc cccacccggc tcggcctgca cccccacccg 106920
gctcggcctg cacccccacc cggctcggcc tgcaccccca cccggctcgg cctgcacccc 106980
cacccggctc ggcctgcacc cccacccggc tcggcctgca cccccacccg gctcggcctg 107040
cacccccacc cggctcggcc tgcaccccca ccacccctcc cccaacacgc atccagaccg 107100
acctcggccc tgcagtggcc gggcccggaa cacgttacgt attgaaaagc cgtatcgcga 107160
ccgaaacccg tggcccatcc cccaccgcgg gcgaggccaa gccgggttgc ggcccacggc 107220
tcccactgtg ggcgaggctg tcaccgtgcc gcgacaggcc cctcccacat ctaggtgtgg 107280
ctgtcgcgtc accgtcatca gccacaccca caagcctcgt cacgataggg ccagacgtta 107340
cgcacaagca catcccccga gaagccacgc ccaccgccaa acacgcccgg gcggctctca 107400
cagacccaga agcagcagcc gctgtcggca gtagcttctt cgtctgccct cgaacgctag 107460
gagccttttt cgtacccagg cgtctttttc acacaaaaaa ggcaaaattt taccctttct 107520
tgttttcctc ccaataaaaa agctcgtccg agagcactcg gcaacgtttc catatggtga 107580
```

```
ggtttcgcgt acgcggcgtg accgtatcga aacgcttagg aaacgtacgt ccgcgaccca 107640
cgtttctcag ccgaggcctt ttctgtccgt tttgaaaggc ccggacgcgg catcagtgcc 107700
atcgagctcg cgctcggcag tcgacgcatc gcgtgtctcc cccttcggtg agagaaaaag 107760
cacgggtgcg gccggccggt ctgacaccgt attgcgcgga cgaggttcgt tcgccggttt 107820
tttatgagct aacatcgtcc gatttaggct cgtagcaggt tgccaggtct gcccacaaaa 107880
agctacgctc agcatgggcc tcgccgagct ggtaacattc atcgaaagcc tcttcatcac 107940
ggtcgacgcc gctgagccgg agggtccgta gtccggcggg aacgctcgac gcaaacccct 108000
tcgagaagaa aaaacccgca gtcgtaatat aagcatgcat aaaaacttaa aaaaaccatg 108060
gacgatgagc catgggtaga tcgcgagtca tgccccgtac acgaaggagc cccgtcacag 108120
tcacacaagc agcacacgaa cacggcccac tttgttatct gttgagaaac cgttagcgat 108180
acaatgcgag taacgataga aaatgagtaa accgtttgaa gagtcagtat cttttatttg 108240
ttacgcgttc tcgctgccct caatcccgct catcatcgtc ttcgatgatg tccacatcta 108300
aatcctcatc gtcttcctca tcaaagtccc tctcgtcctc actgtaacac aagtcgtcgc 108360
agtccatcag ttgatgcgac tgaaagtcca agtcctcggc gtcgtgcttc acgactccgt 108420
tttccatacc gtcgttctcg tcctcgctca ccgggtcgcc gtcggcgacc ccgggggtca 108480
gtaccacgtc catggtgccg gcgcgcaggg cgtcgggcgc gaaggacgat agcgcgtttt 108540
ggggtacgag accgaaaggg aaaacgggag aggaaccgca ctcgcgctcg gcctccgtgt 108600
gcggagacga tacggccttc gtcacggagg ccgtctgctg ggaaggctgt tgatacctag 108660
agatactgcc cggcccggga gtcgcggctt ggatgatagg ccacgcggtc gatatcgacg 108720
tcgggacgga cgtcggcagg gacaacggcg gcggggatag gggcgtggga gacgtcggct 108780
cgacggatgc ggcggtctgg gcctggatcg gaaagacgac ggcggcgacg ccggcgccag 108840
aagacgactg tcgctggggc ttctgttggt gctgctgctg gtgctgctgc tggtattgcg 108900
gctgttgctg acgacggacg gtctcgtgat acgtctggcg ccgatccgac gatctgttca 108960
acggactgcg gtgcttcgtg ggcgacgcgg tgtcgacgtc gcgacgcgcc gtctctctgc 109020
cgacgtctcc ggcggtccgt tgcggctcgc gctcgccgcg tctcggcctc ttgggtatca 109080
cgtagccgtc cagcgtcgag gtaacacacg cggaggccct cttcgcggcc gtcctggggt 109140
ctctggacga tatcttgccg gtgccgtcat ctcctctcag agaacgacga tgacgataag 109200
cgtcggactc gaggggagaa ccacacgtcg cggcctgggc tcccgatccg gtctgcggat 109260
gcagccgccg tttcttctcg aggcgcgtgt ccgagggagg ttccgacgcc gtcgctgaga 109320
cgcgcttctc ttcgcgtgca gggacgacgt cgtcccgtcg cggagaaaac tgtagggtgg 109380
acacggaagc gaggtcggag aggaaatctc cgtcgtccgc gccctcgccg acgcgatccg 109440
tcttcgcgag cgccaagtcg ggacgggcgt gggcgccgtc cagataggga tagtacatca 109500
gggtgaggcc gtagggactc aagaggcgcg taatgcggaa ctggcacacc tcgtcgtcac 109560
actcatgcgt cttgagggcc cgcaggacga cgtcggccag cataccgcat cggtagtgtc 109620
gcaaagcccc gttggcgtcg tagtcggaca gcacgtgcag gcgctggggt tgctgtctca 109680
tccggcgacg cagggatccg atgctgcggt tgaagtaggt gagcatagcc agggcgcgat 109740
gtaacggctg gtcgaaacgc gcgatatgct tgcactgcgc cgcgggttgg aagcccttgc 109800
cgccgacgac gccttcgacc gcgccgttgc cggccatctg tcccaggggc agtttattgg 109860
ccagctgccg gaagatctgg tagtcgttct gcgacctgtt gggaccgcag gcgccacgca 109920
tgatgcacat caggttcgcc atgttcaact tattgaacag agcgtatctc agcgggctca 109980
```

```
gagtggtgag gtacgggtcg cccaggttga cgggcagccg atgcacgtag tgatatttga 110040
tataggacag gtgctcgtcg gccagggcgc agatgatgct caggctgggc gcgttgttga 110100
tcatgaacag ccgctcgagc tgaaacctgt gcagcgacat cgggtccatg tcgtccaacg 110160
tcttgcgcaa ctccaacagg tagtcggtct tcatgagctc gtcgtcggcg acgagcatgc 110220
gagggttctt gggcccggcg atctcgccgt acgcgtcgac ggttctgagg tcgctcgagt 110280
gtttccgcaa acccaaggac tctctcgtga aagatgataa atcgaacggg agctctggct 110340
tgcgcgtccg cgttccgtcg gagcttcgga cgcgaaccac gacggcggtc gtactggtgg 110400
aggcgacgga atcggcggca tcgtcgatct tcgcgtcatc gacgcgtcgg gacggttttt 110460
cttggccggt ccctctgtcg tcttgttccg tgggctcgaa cctgacgctg cggacccgtt 110520
cgcaccatcg attgcgacgt cctataaccc cgtcctcgtc ctcgtcttcg tcttcgtctt 110580
cgtcttcgtc ttcgtcttcg tcttcgtctt cgtcttcgtc ctcgtcctcg ccgtcgttcc 110640
catcttcgtc ttcctcctcg aaaccgtctt cgtccgaaac gccgcgcaca aagacggtgc 110700
gcaccggccc gtcgtccgcc acggtcgact catcggccgc gtcgtccgcg aacgtgacgg 110760
tccgcaattc ggtcgcctcg ccggactccg atccgtccgc gagcgtcctg gaggacgaag 110820
aggaggacgg cgcgacgtag tccgcgtcgc gacggcggtg ccgatcgcgg tccccgccaa 110880
acgtcgattc tccgggacga gactcgccgc gcgagagggt ttccgcgcga cgtcgcgagg 110940
ctctcgccga tcgcagcttc tcggataggt ctctgagtcc cgaatcggag cgcggcgcgg 111000
cgtcgcgggc gccacaccgc tgcgccgaga cgtggctttc gcggcggtgc gccctgcgct 111060
cgtcgcgcgt ctcgcgggac gcatctctgc ggcgacgata ctgcgttccg tcgtgacggt 111120
cgtcgcgtcg acaggatcgg cgataatgat gatgatgata attcttgccg cgctcgtcgt 111180
agacgctctc tcgtctcccg tcgtacgccc tcaccgtgtt ccttctgaat ccgaacgttc 111240
gcccgcccga tctctcccgg atggtgtctg ggtcgcgaac atagtagccg tcgtccacgt 111300
cgttcatggt gacggtggta gtggtagtgg tggtggcggc cgtggccgtg gctagaccga 111360
cagaaaacgc agtgttgaga tcttgctgcg ttttggtcac cgtgcgttgg atcgtgcgta 111420
ggggagccat ggagcggccg cgcgtcggtc gggcgcgaga cgggcgaggt gtcggggata 111480
ggtgaagaga aaaggagggg agaggagaaa aggagaaggc aaaacgagga gatgcgggga 111540
cgatgtcgca ccgcggtgcg gtcgtacgta cggaggacag cgagatcgtg ccacagacgg 111600
cgaatcccgc gcgcaccgcc ggtcggtcag tctgaaaaag ctcgacgagc gggggacgcc 111660
ggcgtcgggc gacaccgctc ctcgagggga ccgcgcgcgc gcctctcttt ttaacgagca 111720
gcacgatcgg gccgcgaggc cgatgatgtt ggtgatgatc ctattttcca cgccccccacg 111780
ccgcctacgg gggcgcgcgt gtgtgcgtcc cgaggcccgc gggcccctta cctgggctgt 111840
atctgcgccc cgccgtccag aaattcgtcc gccgcgtgtg cgagaccatg tcgttcgccc 111900
tgtcttcgtc gggatcggag acgttcgcgc cggacgcaaa cgcgaagcgg gtaagtacga 111960
acgcgttacg gcgagaccgc cgggcgcgcg gccgtgcggc tcgcgcgagc cgtctccgtg 112020
cctcccgatc gccggtatgc gccgttttac aacacggacg gtacggcgta taataatatg 112080
agacctttcg gtgacggtcc gtcaccgaaa agactttccg atgggcgtcg acgcgtcaga 112140
ttcgataatc ggcggaataa tgtcgatcta tcttgatcga gatatgcgtc tgcttgctgt 112200
tggatttgca ccgcgtggtg aagcagcggc tccacagtat ggcccagatg acgccgccgg 112260
aggccgtgcg gaggtcgatg aagaactgaa cggtctgttg tctgttgcgg tgctgtctgg 112320
```

agatgcagta gaagtcgtgc gcgaaaccca gaaccagtct cttcagctgc acgcaggtcg 112380
ggttggagac gttgaatact atcgggtgct cggcaaactg ctccgaggcc caggattcgt 112440
aatgctgcag cagacgttcg cgaatagggg gccaggcgac ggtcctcacg aaacgtctga 112500
gggtatcctt ggtggccgcg gagaagtgga tccgcgcgtc gccgcggcct gccggggcct 112560
gatcgtcgtc tccgcgtgtc tggtctgcgt tctggtctgc gcccgtaacg agatcttgag 112620
ctggatctcc gcctggcgag cgcgcgcttc ttcccacgcc gaagcggtcg ttgtcgtcgg 112680
gaggcggcgg ggacgaagac gacgacgagc aggaggagga ggaagaggag gaagagacgc 112740
cagcgtcgta gttgccgtcc gggacgggag acgcggctga gcgaagatcg cgcgcgttgt 112800
tcagatgggc catgtgttcc gccacgaggg acaagagctc ggggttcctg ggcccccggt 112860
gcatctgcat ggctttggat tccatgaaag tcaagcccga gtctcgacat gcggtgtcat 112920
acaggcgtac gaccatgacg gtcacgggcg gcgggagcgt gcacgcgtcg cggtcgcgcg 112980
ccgcggcggc cgtcatcgag gcgcgggact gggagtgatg caggaggttc ctcacgtcgg 113040
tctggtcgcg gacgaacccc agacagtccg actgtctcct ggccggaggt accacgatca 113100
gagggttcag acggccgtgc atgatgtagc ccgactccct gtccagtttg tacatgaacg 113160
ggagtcgcac ggtgcgtccg gtgtggtaga tgccggtgtc gaaggcgtcg gccaggtgca 113220
cgacgtcgtt ggccagacgg accagctccg cgtccaggcc catcaggtgg ttgaggaacg 113280
tggcgagggt gcgcaccgcg tccgccgaga gcgcgtaccc gggcgggaaa ggagctatca 113340
cgcgtatccc gatcttctcc cggcagcgac agaaggcgtt gcgctcccag acgttcgggc 113400
ccgcgtcgtc gacgggcgac gggtgaagat ccgcgtatcg gagcgccgcg cgccgttcct 113460
cgaaacagcg gagctcgtcc tcgtcgaggt tgtccgcgat gtccgccaga gacgcgtacg 113520
tcgacatctc gccgaaacgg cggtggtggc cttcgtccgc gacgtcgcct ccgccgtcgg 113580
cgtcgtcatc gtcgtcccga caggccgtct tgaagaagaa caccgggtga tagtcctgtt 113640
cgacgacttc ggttccgaac aatctcgccc aggacctgac gatgacccgt ctgagcgccc 113700
tgcagaggtc aaagacaaag ggcttgtcaa cgcatctcct ggcgctcgcg ccgctgtccc 113760
tcagtttgag gtctagatcc ccgacgaagt tgaagaccgg gagtctggcg ttgaagaact 113820
cgtgtctcgt gcgaaagagc tgcgtctggt agctgggcga ggcgaccgcg tcgtcgttcg 113880
tccagacggc gtcggtgagg gcctcgtcgg agagggcctc gtcgggtagc atggagaaga 113940
aatccttggg gaacatgcgt ctggcccagt tttccttcgc cagacagcaa aaaacatgtc 114000
tggattcggc gatctccacg cgaaagacgg gcagcggccc gctccgcggg gggagcaggt 114060
cgggaaacag gtggtggcgt ctgtcggtca gggtctcgct cccgcccggc gggccctccg 114120
cagagcggac gacgcggccc gacgaggcga tctcgaggag accggagacg gagcgttcga 114180
tcgggtcgaa cagagtgccg acgttgcggt tgatcttggt cagcatcctg tccagggcgt 114240
gactcgatcc gaagtagccg gcggtgctgt cggcatacgc gtcgtagcgg tagccggtgt 114300
agtcgaggtc ccgtacgtcc gcgacgacgc ggtcgacgta gtgatcgaag aatccctccg 114360
gagaaaaata cctctccatg gtggagagga ggtcctggtc caggtatctt ccgagacaca 114420
gctcgtctcg cgtgcactgg tcctcgtccg gcacgtccgg gtcgtaggcc gccgcgtcgc 114480
agtaggtgag gattctctcc cggtgcagcg cggtgcgata cgccagatag atgtagtgca 114540
cgcaggtggc gtccgggagc ttggcctcct gtcggaatcg atcgatctgt cggtccacga 114600
aagcgagctc gcggcgatcg cgggcgttgc gcctcttggc gtactcggcg aatcgcgcga 114660
tcttgccgcg gaaacgcgag gcgagcagcg tgcgggacag gtccgccatg gagatgtagg 114720

```
tgagtatggg cgcgccggtg tccgcgacga aacacctgac gtagtctcgg gtggtctgca 114780
cggtgctgca ctggcgttcg aacagatagt aggacatggc gagcagtaac atgccctcgg 114840
tcgggccgaa ggtgctcatg aaccaggccg gggaattggg cgtgagaaag gtggtgttga 114900
ggtaccggat gatgcgcgtg cgactaaagt agacgaggtg tttaaactcg ggacgcgctc 114960
ggcccccggc gccgtctcca ccaccgtcgt ccgcgagcgc ggcgttgttg gccaggacgc 115020
gctcggcctc ttccgtgagg tgactatata gcggtttggt tcgctcctcg tcgaggaccg 115080
cggacaggac gtgcgcgggg atgggggagc cctcgcagac gtatcgggac agatcgagcc 115140
cgtcgccgtc gcagacgaac acggttccga tcctggaaga gtcggaacat ttctgcgtct 115200
gcagacagaa caaaacatgc gtggagggcc tgtatttgac gatcagcgga aacagaagat 115260
gatccgtagg cgttttcgat agtatattga cgattatatt agcggcatcg tactccgtgg 115320
cgaagaaaac ctccgtcatg tctgctcgcg ccgggtcttg ggcgtcccgc ctatgcgatc 115380
tcgtcctgtg cagatcgcgc gcgcgggagc ccagctatat cctgctgacg ggctctgacg 115440
aagacgcgga cctggcggat atggaggcca tcttggaaga gcgattcgag gccttcggcc 115500
tgaccagaca cgacatcgac gagctgaggc gggataacag cgtgacggct cacatgctgc 115560
agctgctccc catctataaa caatgtatgc agaactacag cgtgctgagc aaggtcctga 115620
aggacaagtg ccatccgcat atgcgctccg cggcggagac ggaatgctac aagtccctgc 115680
ggatcctgga ggtgttggac gtcatcatcc tgaaactgct cgtgggagag ttttccgtgc 115740
ccgagcagga cagcctgaac agactcctgg aaaagttctc cgcggatcag aatacgctat 115800
gtgaggtgca acgtatcaga cagctcgtga gcatggacgg gctggacacg caacgactga 115860
tgtcgtcggt ggcgggcatg gacgagagag aagtggacca gatcaccgac cagctgatac 115920
gtgacatttc cagactaccc ccgatccccg aggagcctcc ccaggacgag agcgagggga 115980
cggagacgga acgcgcgccg ccggcgtcgc cggacggcga gaagacgacg cgaacgaaac 116040
gggaggccgg cggcgcgaca tcgacaacgg acaccggtgg cgacagaaaa gagaggattt 116100
tattgggggc gtgacaacgg tgagggaaca cgtttctggg gacctcggga cggatcgggg 116160
gaattggaac gggccgccgt cacgggaagc gggaaacgcg ctacggcggc gggggaaacg 116220
tgccgcttat atagcgcgat gaggaaaggg atccgtcggg tagggcggga cggggatcag 116280
gtcgccgact gaggcacgga cctcccctgc agcatggtgg aggccatgca gacattctcg 116340
tccgacgtga aaaccacccg ggctatgggc gagtgggcct gcagtctgac cgtgtacgcc 116400
gtcacgttat gtatggtgac gacgggcatg gtgccggcgt gccagatggt ggggcacacg 116460
acgacgccgc tgcggttgag gtgtctcgtt ccgatgatga tggcgctgtg ttgcggagcg 116520
cacacgtgcg tcgcctcggg gacgacggtg agaatccggt agggcttgat cctgagggtc 116580
tctcgcgtgc gtataaagtg atggaagccc tcgtgcggag gcgtcatatt gatcacctcc 116640
cacggttccg ggacgaagta gcggaagatc aggatggtgc cctcgatgga gccgggcgcc 116700
agcgcctggc tgaggataga cgagatgtta gagatctgaa cctcgaaggc tcgctgaccg 116760
ggctccacga gttccgtggg ggagaagaag gagggacacg agtttctgta catgattatg 116820
ccgaaacagc ccttggggat ctccagcatg ccgttcaccc gtatgacgtg cgtggcgccg 116880
gcgctcaacc agatgatggc ccggttggtg aagatggcca tcgatttatc cagttggctc 116940
atgcgaaagt tagtgcccgt cgtcttgagg gagatacggg gtatgggctg cgacagctcc 117000
agggaccggc tcggcttctc cgtggcgtcg ggtggccgtg ttattaaaga cggcgtttcc 117060
```

```
ggaccgtccc gacgcgagtc ggtcgtctcg tcgtcgggac gcggaggggc gaggccggat 117120
ctcctggcgt cgcgcgcatc ggagacgtcc tccggaaaca tacggtttag ggacctcgat 117180
cgcgggaggc atctcagggg aggaccgtag ctgtcgataa actgctccgg caaaagtacg 117240
ccgagcaccg cgtccatctc gcttttgcgg gacgtcgcgg cgcagtccgg acggccggtc 117300
gcgtttctgg acccggcgtc tatccgttgc ttttttgagt gtcgcggcat cggccttcgc 117360
gcggacggtc gagaagcacg cggtggatac ggaactgtca gatcgcggcg cagggcaggg 117420
agaacatcgc gatgaagagt tatcttatag ggcccctatc ggctgtgtca tcgccgtcga 117480
cctcgtcatg tggtcgacga caccgtgtga ccatcgcggg gctcgcgttg tgctacctga 117540
tcgtggtatc gatggtgtcg gggg cgagtt ccaatagcac gagcgtgact acgccgtcac 117600
cggcttcgca ggcctcatcg gtgatgtctt caacaacggt cgcgagcaca actaagacgg 117660
ccttagggtt ttacgacgta ggctgcgtat cccatgccta caacgtttcg atacggtctt 117720
tcgcctccct gtggattttg gcaaacgttt ttatcctgct gtgctctttt ggaatattcc 117780
taaggcactg ttgttaccgg tcgtttgcca gcgagaccgc cagaggttac taaaggatgc 117840
tcgtttgtcg tcggacgcga tggatatggt gagtgtcgga aatcgtccgt tcctaattcg 117900
cgactgactc ggacgaagcg cgtgttgtac aacggatgtg tattgttcgt gatgttgcgc 117960
tccaacacta atgattgcac atatccatgt accagtgtcg tgttgattaa agtctcgtta 118020
aggctgtcat ccgcccatga gacgttttgg agtagcgata gtctcatatc gttaagtgtg 118080
gcgttcgtag atatgtaaga attggatcgc cccgtgtgac ataacgaact tttataaagc 118140
atcccgtaaa gataaaaatt gaaaccgagg aatgcgtttg cggatacggg aggtatccaa 118200
gtttcgtttt tcactgcgcc ggtatcattt ttccggtttc tagacttctt tggttcttct 118260
tcgatcgtac ggtttgcctg ctgcagacgt ttcagttttc gaaaaaacga tttggtcagg 118320
gtccagttgg atcgtaactg gggtgacagc tgaaacaaat tttttgatag ggcggttagg 118380
taagaaccgc ctccggcaca tacgtcaaac tcacgcctgg acgcaaccga gacggataag 118440
gccatataaa tcaggtcgtc gctgttgagg tgataaaagc ctccgcttgg tagacgcaac 118500
ttaaccgtcc acctaggaat attatacagc tgagcgttgt acgtcgtcag attgcatgtc 118560
gacgtgcctc tgtggtctgc cgatacggca agcatcgtat caagacatga aggagaaggt 118620
acggtcgtgc aatggggtcc ggcaagctgt atggtctggg ttgcgttgtc gtagtatgct 118680
aaaaaatgat gtctgatgtt agtgacggac tttggatacc aaatcggtat gacacttccg 118740
ttcataggcg ccgcttgtat ccacttcgaa ttatacgtaa cggtgatatt tttcataaat 118800
ccattaaatc tcgatataaa ttgttcaatt acgtttgtgg attttgggga tgtatagaca 118860
gctgccagca atgggcataa gaataacacc aggatccacg tcatgttttt tttttttgcg 118920
aacacggcat gcgtgttgat aaacgaatgt acgttttaaa tatatcccgt tttgttaata 118980
atgattcttt ctcgtttcgt taggagcgct gtgcatgtgg tgacacgtgc cgaacattgt 119040
gggctacgtt cgtcaacctc gtggcggtcg tggcgatgat cctgctcata ctgcgatgca 119100
tcgtgggttt cgacggcttt ctggtgacgc gattccaaca gatgataaac tcgacgtgtc 119160
atccggtgac ctgtaacgtg actggttcaa gctcatagtc tatcggatcg cagcctcggc 119220
gctcatcgtc ggtgtacgac gtacaagatc cgcataataa atgtttatcg cacatacggt 119280
ctcggtcgct tgtctttgtc gtgttggtag gtatgtcccg tgacgcgata tacttgtctt 119340
gaccgttctt aaatcatatg taagaggcgg tatagaccgt ataacagcaa tacgccaagc 119400
gagcagtaca gcattatcat gaaaatcgac gtctggcgga tgtctatgat gaccgacgtt 119460
```

atctctatga gggtgccgtt ggccgtcatc atgatgtagc gggttctcgg agagctggcc 119520
aggatgcgat tatccaggtt ggtcaccaaa actaggtccg ccgtatccgc cagatacact 119580
atgttactga gtccgtttac ttcgtcgtac tccattatag ccgacttaca gtattcgcag 119640
tcgttgccga tggtgatgtt ttttactatc gggatgcttc tcgtggcgtg cgccacctcg 119700
gtctgttcgc agggctgttg cgccgggctg accgtgacga tcatggtctt atccaccgct 119760
aggttggtta cggggtacga cgttcctttg agaatcacgt tactggaaac cacgtaagtg 119820
acatctttga gcgtgacggc gacgtatccg ctgagatgcg agatgcagga caacgctgga 119880
aagttagtaa ggttggatct gtcgaagtgg gctagtattc gatacaggtc cgccggtgtc 119940
ttcgtcgtca gcggattcag ttgtacgatc tccgcgatgc gggcctcgct gtagtctcta 120000
cgaccgctcc cggaacacgg ggtgaacatc tcttgcatcg tgagccccgc gctcgatacg 120060
tgaggagccc aattgtagag ctcttgcggc gaacagaggc tcgtctgcat ggcgagcatt 120120
tcccgacgaa tatcgggaaa cgccgctgtg tggtgcatga cgtaggccat catgtacagc 120180
aggtttcgct gtcgcgggga cagcggagac accagcccgg cccggtgtat gctcttcatc 120240
tcgtataacg cgttctcgat gtctcgttcc tccgttaggt tagtgttatt gccgaatatc 120300
aacgcaaacg tcagggacaa ttttatagct cggtctacgt ctcgggaatt tctgatcagc 120360
ttgaggaata ctgagacagc tccatcgatc atcggaaatc tcatataacg gggctcaata 120420
ttgaagcact gttgtagaaa cgttctggcg agcgtcagtt tgacatacct gagggttacg 120480
tcttccagtc gcgccgtcat gttggccgtg tgatacaggg ctctgatcag gatggcgtac 120540
gagaacacca ttgaaaccgt acggttgtcg ggaggtgcgt cgcacagacc gttcatcata 120600
ttgtgtgtca cgagacgact gaattcggtg tatacgcgat cgaaatccaa atagttgttg 120660
cttaaaattt cttttaagaa accttgcgtc tgtataaacg ggtatatggt ggttacggta 120720
gacgtcttgg cgacgatcag cagatcgtcc cgagagctct gtctcaacgt cagtacgggt 120780
ttcgaatagg gcgctttgac atctatttcc tgtatgtctc cgaaaatcag aagggtgtct 120840
tcgtcgtcct ctgtagtgtg ggaacggcgg gtagtttgta tgttaagcac aaaaaaattc 120900
ggcgtaaacg tcagtgcgat cgtgaatcga tgtgcaccta attggtgaag gtacagttct 120960
cgcgaacacg gaatcttcat atcgaatacc acggtgtggt tagaaaataa attgcagtct 121020
tcaaactccg gtgtgacgac gtctagcaga ggtatcacgt acgatcccga ccgtgtgcgc 121080
catacggtga tgttagggag cgtgtcgtcc gcacgtacgt tgagttcttc cgtcgaaggt 121140
acgaggtccg tacgcagttc atgaatgaat atctggaacg cagcgtgtac tggaacgatt 121200
atatatgagt aatatcgtaa cttgtaagat tctagacttt cgaacagatc cacgctctgc 121260
ataatggatt tcgatatcgt ggtcatgaaa atgcattttg gtacttggta ggtcctgacg 121320
gttttcggcg cttcgtaaaa attaaacgat atgagtcctt ccgtcgtcag ggaccgttgg 121380
ccggtgtggt tgtttaagca agtcatgttt agactgctct tggtccaatt gacatccggg 121440
taagtccatg acgagaaaga agtctcagac ggcgtgatca gagaaacgac gaggcacgag 121500
atcacggtaa accgcgccgc gggtgacata tttgctacat cgaaggcttt ccgatgcgga 121560
attaaatagc gtgcgatgct ctattttata aaacgtgagc ttctgacgcc tgtggcgtca 121620
aatgagtccc ggcggacgtc cggctgggga gaagtggacg cgctaaacgg tgcgtctgac 121680
ccggctgacg atcatggacg tcctgcgcat gttgccccccg tctagaaaaa ggatcgggaa 121740
ctactatcac cggcggatat atcgcgtcat gcagaacacg tttcacgatt acgcggcctt 121800

```
caacgcgttc gtcggaaacg tcctacccgc gtcttgggcg ggaaagaaca ggaggctgta 121860
tttcgaggtg aatctcgggt gcaggatccc cgacgccatc gtcacgctgg agacctccac 121920
ttcggaggcc tcgtcttccg cggtccacgt tagatgttac atatttgaat ttaagacgac 121980
ctgtgcctgg tcctcgaggc cgcgggaggc cgtcctgagt aacaaggtgc acaggtccca 122040
atacgtgcag gggctgaagc agctcgtcga ctccgtgacg ctgttcaggg atctctccac 122100
cggcgtcggc agggtctggg agatcgtccc ggtcatcgtg ttcttccggc agcggcccct 122160
ggccgccgtg gctcgccgcg tcttccgcgg gcggcgttac gttctgtcgg acgcggccgt 122220
cgcggactat ctggcttcac accaggatga gtctactcag gcatttttat caaaatccgg 122280
tctacgaacc gcacgtccaa aacacgctgc tatgtcccga agagtacctc caccggctgc 122340
gagacgaatc ggccattcag ctgcgtcggt accgcgaaga agcgctgcgc gaccgaatac 122400
tgcgatacca catgggcgaa gacgtgagcg aactcgcgtc tcgactgacg gaccgttgca 122460
cagagctaag ggccagggtg ggtctggtaa gcgaaacgct gtcgggacac gcgtccggag 122520
gcgagttcgg tgatctcgtc gtctcggcct accgagacga cgacggcggt gcggctaggg 122580
cgtcggaggc gccgacctcc cggccgacgg cggacgacag accatccggc cagggcgccg 122640
ggccgtcgag cgaaacgcga gccgacagga acggacgttt cggcatcgcg cagtgcgatc 122700
cggagatacg tttccagtcg gatttccgcg gagaactgat agccaccctg tattccgaat 122760
cgcaacattg gacgttctct ctgggcgtct ggtattacag gctgaagcga acgttgtacg 122820
gctatccgag ctggaggagg atctacaaga tcagtaacgt cgacggcttc aacgtatctc 122880
aggagctctt gatgggggtg atcaacgcgg tcgagaacgt gacggtctgt cccacgtacg 122940
actgtctcgt ctccgatctg gaagcggccg cctgtctgct ggcggcgtac tacgccgtgc 123000
gcgtcgtccg cagatcggac tccagcacgc cggacgcggc gctggagtcc gtgtccgcgg 123060
tgctcagaaa cagcggcagg gtcttgaagg tcctgttgga agacatgacc gccgaggccg 123120
aggaccgcgg cggcggcgga cgcctcgcgg cgaaccgtta cggttatcgg gatccgtccg 123180
gcatgcggta ctacatcccc ctgaagggcg gcaaacggta cgcgacgggc acgttcgacc 123240
agcacgccgt ggtgcgcgtg atgctgaaac acggcgtgtt gacgcgtctg ccggggagcc 123300
gggacgccga catggactac gtggtgtcgg agatggcctt cgggaagacg ccgcacgatc 123360
cgttgttcac ctggtcgtcg cggctcctgc gcgacctgct agggacggaa cgggttcccg 123420
ttctgacggg cgagcagcag tatctgaggt cggggctcac gtgcatcatg ggcatgctct 123480
tgatgttcca gacgtctaac ctgcagagcg tgttcggcgg cagagaaggt cactttaact 123540
tcaccgacgt gctcaggtcc gattttcccg cgtcgtccgc ctcgacctcc ggctccgttg 123600
gcgagcccgg gtacgttccc aacgtcgtca ggaactacga gtatctcatg gaggcgtacg 123660
tagtacggtg gtatcggcgg gacaggaacg tcacgttctc gcaactcttc ccgggcctgg 123720
tattggcctg cgcggcggac agcgtgcggt ccggatgggt gcacggatcc ggggacgacg 123780
acgagctctc ctccgcctcg tccggggaca acgtgacgac gctgctcagg aacgccagat 123840
ccaaccccgt cgtcgagttc atgttcgccc agcacgaggg gaagcacagg ttgggcgacg 123900
atccgaagag gctggaggcg cacgacgctc tcctgttcca ctacgagaac ggcttggggc 123960
gcgtcctgtc caacccgctt cccggacagt tcgtgctggg cctgatgtcc tcgctcttcg 124020
gagtcggtaa cgtgtacgat tatctgtatt tcaccgcatt ggggttcttg cccgtcgtgc 124080
aggtctcctg acgggcggcc gagacgggat gatgacgagg gactcgagag cggtcgagga 124140
ggagggcggc gtcgcgagcg gccggacaaa gcgtatttga cacggcgtac gcgcggccgc 124200
```

```
ggcggagtcg gccgtcggaa aggaggaaat gaaatgatcg gtggtcgcct cagtcacgtg 124260
tgcggtccgc catcatccga aaggcatata tatcgtccgg tcacgggata aggctacggt 124320
gtattatttg gcacgcgtcg cgcgttcctg ggcccgtcgg gtccggactt gatctatgct 124380
tcgagtcccg acggcgagcc ggccgcgcgg cgaggtcgcg ggatagcgat cgtcatccgg 124440
gcgaaaggat atagagagaa gacgggtcga tcatggcgac gacggcggcg acgacgacgg 124500
tgttgaccgt cgtccatcgg ctcagcctgg ccgagaccct ggccaggaac tacagttact 124560
tctacattcc catagtgccc cagtcgtttc agatctgggt ggtgccctcg gccgtcttct 124620
tctccgtgtt gtacgttatc accctgtaca agaggaggtt cagcgacgcc ggcagcgtcg 124680
tcagcatcgg catcatggcc ggctggttca cgtccttgct ggccaacgcg gttctgcagg 124740
tacccgtgta cagggatttc gggttcagcg acaagacgtg caagacgctg ctcttcatgg 124800
acgacatcgg cagctacgcg tgcgtgttgc agttcatcta catgatcgtg gacatgatct 124860
acgcgacgat ccatccgcgc ttcgacagga agaccttcac cgccgttacc accatgcagg 124920
cgtgcgccct gtgctgggtg accgccgcgt tcctggccgc cccgtccggg atcgtgtccg 124980
tctcgacgcg ccagctcggc agtcgcgccg cgtgcacggt cccccctgacg cacagcacgc 125040
tggtcatgac catcaagatc tccttcgccg gctgcgtccc cctgctactg accataccgt 125100
tgtgcgccga ggtcgcgtac gccgagaggc gctccgacag gtacccgcag ctcggcgtgg 125160
cggtgctgca ccacatcctc atgttcctgt ttcacgcgcc gtaccccata gtcagggccg 125220
tgcgagccgt gtacggcgat ttcagggatc cccccgggat tctggactat gccgagaccg 125280
tgtcggaagg tctgcagctc gccagactcg ccgtgattcc catgatcgtg accctgttcg 125340
ccgagcccgg ctccctgggg aaggcgatgc gagacggctc gtccttcgtt ctggggctgt 125400
tgagatggtt ggtttctctc gtccgcgaaa agcgcgcgga cgtcgtcgca aaagtggtgc 125460
acgccgtcaa ggccctcctg ttgaaacagc tcctcggatg cgaatcgagg aaatggccga 125520
cggggcatga taagtgtttc gtgcattacg aagtacccag taactcgccc tcgatcgtcg 125580
acgaagaaga aggagaagaa gagggttctc ggtgcgattc cgtcgtgacc gcggagtgcg 125640
ggatctctga ccagaccgaa acggcgccca gcccagacgt atcggtagcg ttcgagcccg 125700
attgcgttaa gccgtgacgg cgccgtcggg cggccgggag acgcgcaacc gatacggccg 125760
gtgacgtgcg tgcgagcgtg caataaagac gcgatcggta cagaacaaaa aaaaaaacac 125820
gagacgacgt gtgtgtgcgc gtggttattt cgatacgtgt cagtttttat tcaaacaccc 125880
cgtgcggtcc agatgtctcc ctcccgtccg ccctcaacac aacgtgggta tccggctcgc 125940
gttggtcagg tcgttcacct cggggtacgt caccggaggt agcggtgggg ggtttcggta 126000
cagggtccca gtgaacgtcc tgcagtcctg tatcagaaag ttatagagtc cgagctcgtg 126060
atcgaaacgc tgatcccgga acgcccgacg ggagacgcgc agtttcccgt ccgacagcag 126120
ggacagcatc cacatcttct gacacaggag ccgcatcgcg ggctcgtact gatcttcccc 126180
ccagtgtttc gtgaagaacc tggccatcct gaaaaagcgg tggcagtaga ccgtccccag 126240
tgagaacaga aagttcccgt cctgcgtcat gtcccgcggc agccggatgg cgatgccgca 126300
ctggtccctg acgaagtcgc acaacagtcc gtgcgccgtg ggcatgctcg ccagcgaggc 126360
ggacagctgc gccgcgcgcg tctcgttgaa aatgccctcg atctgggcgt cgcgcaagac 126420
gcgggtgatg tagcggtaca gctgctgcca gtactgaaag gagatcttgc ggttcaagat 126480
cccgttgtcc cccacgccgg agttgtgcag cgtctccctg agcagtaggg tctccacccc 126540
```

```
cctgtgaaac agcaacacgc atcgcagtcg gaggaccttg agctcttcca gcctcatgct 126600
ggacaggggt ctcccggata gcatcttttc ggtgatttgt attattagat cgttctgggg 126660
atctatgtgc acgaacctcc ctatctgaaa tccgggccgg tcctcgtcct cccgcgggtc 126720
catggagacc gacagggttt tcgtgagcgg tttcctggcg ctgtacgggg agcagccgca 126780
ggaggactgt ctccggctat cccgagacgt ggtcgctgcg aatctacccg gcgtggatcc 126840
gtcctcgata gcgatcaaca tcaatcacga cgacaacgcc gtggtcggtc gcctgcacgg 126900
cctgttcgat ctaccgaacg ggctgttctg tttcggggag atcagctccc cgtctttcct 126960
ggatatcgtg cggcgcagcg ccgagaagtc gcagctggtg tctcggggtc cggggaacgg 127020
gctgaagccc gacgccgtcg tggagtacct cagcacgggg taccccggcc tctccctgtc 127080
cagccgttcc accgacgagc gccgctgtga cgcgccgtcc gggcccgcgc gcgctcatat 127140
agacggcgag acgacggacg agggtacgtt tttcaggcac gtcgccatat gcggcgtcgg 127200
tcggaggcga ggcacgctgg cgatctacgg tcgggacccc gggtggatgc tggacaggtt 127260
tcccggcatc tcgaacgagg acaaactccg gatggtcacc cgggtcgtct ccgccgtctt 127320
cgctccgggc gcgaggacgg gcgcggacgc gcgggatccg ttccgttccg atccgtacgg 127380
cctgctggcc aattccgtgg atacatcgta cattcgcgag aggttcccga aactggatta 127440
cgataagagg gtcctgcgga tacctcccga cacgtacgtg aaggccagcg agagtccgac 127500
ggcgtctcgg gccgaaggcg actgtattat taaaaggagt gagccttttc tcgtctggga 127560
acgtcgcgcc gaggagagcg gcccgtcgtg cggcgcggcc gagaccgaca tgtccgctca 127620
gccgcaggtc gtccccacag tcgtcccggc cgcctccgcg cccgccgtgc ccgccgccgc 127680
cgtcgtctcg gcctcgcccg cgccgctcgc cctgtctaac gattgcgtct atcttcccaa 127740
ggatacgttc ctgtcgctgg tgaacgcgtc caggcgagag gcgacgtttc ccgacgtcgg 127800
caggccgaaa gacgcggacg gcgcggccac cctgacttcg ctgccctcgt tcgtggctca 127860
gaccgcaccc gtccaacgct tcgtcctgcc cgagtcggtc acgtcgacga cgcgtctgca 127920
gccggcgccg tacgggtacg cgggcatgga gggcggtctc ggtcgtccgt ctcagatcgc 127980
ctcgtttcag actccgtacg atacgtctca gtacggcggg cccgcggggt ccggctactt 128040
cggacccctg ccgggaccgt cgccgcaggt cctcgcgccc atttcccagg cgtcgcccgc 128100
gtcccaggtc catccggccg tcgtgccgca tcacgtaccg tcggccgctc cgccgtatca 128160
gttcccgagc gcggtgcccg ccgcggcgcc gggcactctt catcctggcg gtacgtatcc 128220
gcagttctat ccgcagccga cgtattacgg tcatcggggg tactacggag cgtcgccgcc 128280
gccaccgccg ccgttggccg gagagcgtta cgggccctac gatcctcgct ggcccgcgga 128340
cgcgacggat ccttattcca gatatcctcg ggatcccgtc gcgagtaggg agcgggagca 128400
cgtcgggcga aagagacgcg cggaggcgga cgacggggac gaccagcaag tcgccagaga 128460
ggatctcagt ctgcccggtg acgccgacta tccccgctcc aagaggcccg ccgtcgaggc 128520
tcgagacgtg cggcagtccg gacgcgcgcg cgaggacccg gagtacgcgg aactcaggaa 128580
cgtgatacac gacctcagga gggacatcgc ggtcatacgc agcctgagcg gctcgcgttc 128640
cgacgccaac ggttctcccg ccccggtgca gtcgtcgtct tctccgtcct cggcgccccc 128700
gacggtcggg gacgaggaag acgcctcggt cccgagcgcc gcgacgaccg gcgtcccggc 128760
ggtcatcccc accgcacacg gtctgcccgt cacgacggcc ccgtcggcgc ccgcgcagcc 128820
gacggacgtc gcgcggaagg cgggcaaggc cggactcccc gtctccggcg gtcagcacca 128880
cgctcatcag cccgtcaggg cgaaacctcc cctggtggtg aacgcctcgt gcgtccccga 128940
```

ggcgcagccc ggcacgtccc gagacgccca gatgtccatt ctggacatta accgacaacg 129000
tttcgtggac gctctgcgga agatggaatg acgactccac ggtcgcgggg tcggaaaacg 129060
ggtagagaga gagaggaccg gggtgggatg ggaaaagtgg gaccgaaccc cgggcggcca 129120
gaaagaaccg tgcgtgtatc gattaaagat aacgtgacga cgtgtacgtg tggtctggtg 129180
cgttttatta atacgccggg ttgtatgcgt tcaacggata cgtgtggcgg gtacgttgaa 129240
cgggaacggg gccgcgatac gggttagaca cattaagcgg atacggcgtc catccgatac 129300
tcagatgcat acgggcgata cggtcaacgt cccgtatccg gccgcgccgt ggaccgcctc 129360
gtcgcgctcc gacgaggcgc gcctccgcag atcagaccgg tgtggtacat ggctccgtcc 129420
acgtcgaact cggtccgtct cactccgccg tcttccgggg atccggtcgt gtatctcatc 129480
agggagagcg cgcagcacgg catcgcgatg ccaaggtcgt acaacacgag ttcgggcagg 129540
atgcgcgcgg gacacgagcg gagttctagg ggcgcgtccg cggacggacg gtgtttttc 129600
ggtccggagg cagcgttctc gccgtcgctg tcgtcctcct ccccgctgtc gccgtcgctg 129660
ctgtccccgc tgctgtcgct gtcgtcgtcc gtgtccggag ggggggcgtc cagcccgtac 129720
ctcgcggacc tctgcatgcg gacgacctcg tccagccggg gcttcatggt gtaggacacg 129780
gtcatcgtcg ccggcgagca cctgacgggc gactccgcgg gctccggagg cctgtccgcg 129840
cttttaaata ggtccctgtg gaaaaagtgc gccgaaccca acagcatgcc cctcctcagg 129900
tcgacgcgcg cgatcgaagg gttgcgaatc ttgaccgtca gcatcacgcc ggggccccag 129960
cagccgacgt cgacgtcgac gtctttgtac ggcagggga aaaacagcgc gatgtggtcg 130020
gggctctcgt acgttgcctc tacggtcagc aggacgtgtt tcccgggcgg caggacggta 130080
tcgtgcggca ggacgatgtt gaggccgttc gcggagtgga acctcaggga tcttccggaa 130140
taccgcacaa gactcacggg ggactggcgt ttctccaatc tgagcctcag agacagcgtg 130200
gtgggagcct tctgggacca gcaggccacg tgtagggtca gcgtcccggg cttcttggtg 130260
cggtccggcg tctccgcgcc gacgatctcc acgtcgtcca gacgctgcag gtcatcctgg 130320
acgacgtgag tgaaaccgta cagtcccggg tgctcgatgg gtatgtgcaa cgcggcccgc 130380
agggatcccc tgcgatcgga gtgcttgtcg cacttgtagg tctcccaacg gatgctggtg 130440
accacggtgc agagcatcca gcggtcgtcg cagagacgtt ccacgtcgac gagaggttct 130500
ccgtgcgcgc gtagcaggcg atggccgcgg gcgggcctga cgccgtggac gagccggagg 130560
ccttcgatcg atatcctggg aaccggtatg gcgaagacga tgaggttcac caggtcttct 130620
ttcgagagcg agacgcgcct ggacgtcacg ttctgtatcg tgacgtgggg ttgctccagg 130680
gcgtccgtgt cgtagagcac ttcgaacctg actctgacgg cgcattgcct gtcgatggta 130740
tcttgcgcca cgcatacgac ggacggcgcg gtcagctgtt tcagggacag cgactggaga 130800
cgtaccctgc gtctctctcc gggcgacagc ggttccccga cgactacgca accgaggtgg 130860
atgcgggtcg ccagccccac gtacgccatg ttctacgatc cggagtcgcg gggacggacg 130920
gaggagaggg gggttcgcgt cgtcgggacg gatctgagaa cccgttgcga cctatccgca 130980
tatgaatata ccgtaattcg tgacggaatc aaaacaggga cgtgtacgcg cgtgtgtttt 131040
tacgggaacc gttttttat ttcgggaagt acagggggac gagacgcacg cggcggtgcc 131100
ggcggagcct actgtgcccc gcgatggctc ctacgggagg tgccggcgcc gccgtcgtcg 131160
tcacgccgcg tcctcgaaca cgcgtgcgac gcgggcctgg tgggtacgcc gtcgaaccac 131220
accgaaccgt cctgcacctc gccggacgag tgttcgctgc tgcatgccac cacgttgtag 131280

```
tgtatgtacg cgcagaaccc ggtcggtatg ctgagggccc acgggtagaa gagcacgctg 131340
gggaagatct cttcggagac cctcctcggt ctcaacgaag ggtcttccga ctcgtcgaga 131400
gtttcgcgct ccgcgcttcc ggacgcgccg tcttcccgag cgagcggccg ctcgcattcg 131460
aacacgtcgt cgtccccgtc gttgtcctcg ccgctgccta actcggattc cgagctagat 131520
tccgatccgt cgtctttggc gtccccgacg tcttcctcgc cgtcttcttc gccttcttcc 131580
ccgtcttcgt tttcgtcatc gtcgtcgtcg tcgccgccgt ctctgtctct ccggtgtcga 131640
gccgcgttgc cggtccgacg tccgccgctc ttcacgaaca cctgctcctg acaggactcc 131700
gagcaacgtc tgactctggt ctcgaactgt tttcccatca tgcaggtgtc tatgacgccg 131760
gccacgcggt ggaaggtgaa caggtcgttg tcgaagaagt ggacggttcc gaggacttcg 131820
tccttgcgca cggtcgtctc gccgtgcgag cggatgacga tgtccatgtt gtgacgcgct 131880
ttccactgcc cgcccgagac gtcggcgttg gggaagtcgg cggggaagaa cagggcggcg 131940
tgagaggtac tgtcgaaacc gtttctgagg gtcagacggt acgtctgccc agactgtaat 132000
cgaatgtcgc cagggcagtg gatcgtgaaa ccgttagagg gatgactctg cagcgccggg 132060
tacggattgt gcctcatgac gacctgagcg tgactggcca ggagctggaa gaacaacgtc 132120
agtttcttag gcgggggttt ggcggtcgtc tgtaacgtca ggccgagaac gttgggtctg 132180
cccttctgga agacctccgc cttgaacacc tgaacgtctt cgtgagaaca gttgatctcc 132240
gtgagggagt cgacgtgagt catgcaggcg ggtttgaccg acaggaggac ggtcacggtc 132300
agggctcggt cgacgtgcgc cctgtttccg acgccttccg tccacgctat gttgctgagc 132360
gcggtcctca cgccccagat ggccccgcag gcgcgacgca cgacggtctt gctgcaggtg 132420
gggaacgtct ccctgctggg tttcagggcg ctgttgaaga atatgtgtag aggagccgcg 132480
tggaccctgg gcagcggcag ggcgaagacc acgacgttga gatcgtagaa gctcttcgcc 132540
ggcaggggct ggtccgacgc gttgcgtacc tccaggttga gcagatccag ttcttcttgg 132600
ctgtggatcg ccctgaactt catccgcagg ggactggaag gcggcaggtg agagcctacc 132660
tgctcctcgg ccacgatcac cacggacggc gtcctgggaa ccgtgaaggt ggcgtcgaag 132720
tgtacgaatc tggtctcgtg gggcccgaac ggaccctcga cctggagggc caggtgcaag 132780
gtggtaccga gacccacgta ccgctccatg attccggccc ctctctctcc gcgccgcccg 132840
agtgccaacg tacggggacg atcgggggac gggacacgcg cgagcgaata aatacaatgt 132900
gatgggggcg cgttttgttt gctgtgggga cggatagagg caggggcggg cgatcggggc 132960
gcgcgagcga gaaaaatttt attaaacgaa cacgagacac ggataccgtt cacgatcgtt 133020
tttattagaa ccgccgttac gatttatatc ttacacggat ttgggcgcgg gatcgcttcc 133080
gtaaaagcgg gccgtcacga tataagggat tccctgcttc aggttttcgt accacgggta 133140
gtctacgccc atagcgtcgt agtcgtcgat ctgggcgcgg gtcttcttgc cgggcagcag 133200
gagactgggt aggttacgcg tcggtatctt gaggccggcc agtctgaggt tctcgtcgtc 133260
gaacccggtc aggatcgacc tgatggtgct gccgtactgg ggctccctgt agacgcggtc 133320
ccgcgtgacc gccgtgggga cgaagtagac ctttccgagc ccgtccccgc gctgcagccg 133380
aacgccgcac ctggacgcgt agagccgcac ggtgagccac tctctgggat gccacgtgcc 133440
caccgtcacc tgcaggccgt ccggtctgtg ccacgggacg aagagcccca ggtggcgacc 133500
gtagtgcttg cgctggacgt tgagctcgta cgcggtgtcg aaggggatct ctatgtcgac 133560
gggcgccgtc acgatcaagt ggccggtcat cgcgtcctgg atgaagtacg gcgtcatgga 133620
accggacaga tacggcaggt tagtcggcgc gtggtagagg ctcacggtga gctccagctc 133680
```

```
ccgggggacg tatttctgca cggccgtcga ggagacgtac acgcacaacg tatcggagct 133740
caggaaagcc ttggagatgc ggcacgagtc gtgcgacctg ttgaccatct tgatgaagcc 133800
gtggtgcccg ttgcggtccc gcgacatgag cgcgtttttc gtggcgggat ccagggtggc 133860
ggtgatgacc gtcgtggtga atctcggccc cctggccgtg gcctccggtt gacccggatg 133920
ccagatcggc tgggactttc tgaaggtcac ctcgatgctg tgtcgctcgt cgccgttctt 133980
ggccggggcg acgcagaccg aatcggcgtg acttgggggt aagagggtgc gggcggcctt 134040
atccgggtcc atggcgcgca gcgggatcct gtggatgtcg ggcacgatgg cgggaaaggc 134100
gaagaggttc agggtgacgt gcggcgtctc cgtcgtgcgg accgacgccg actttctgag 134160
gtatacgttg atgtggctcg tgtggagcga cgccacggtc atgctgcaga acgcgtcgct 134220
ggactcgtcg gcggacacgc acaggaggta ctcgacgtcg tcctgatcgt acatgtgtct 134280
gaggacgtcg ctctgaccgt ccgtggcgct cacctggatc tcgtctcgga gaacgtcgat 134340
cttcaggttc gaacgatcct cctgtctgaa acggtgacgc atctgaatca ctttacagat 134400
atgagtcgaa gaccgttcca gcccgaccgt gtctttgagc accagggtgg tggcgtacgg 134460
aaagggttcg gccgtctctt cgatcatctc cgtaatcgaa cccgtcggtt ctctcgcggc 134520
gagtgggtag acggcaagcc gatcgtcgat taaacgcggg ggtgagacgg cgggtgagga 134580
agcggtaata aaagagagtc cgcaacgcga agtcctcacg gtcggtttcg gaatctatcc 134640
gacgagtcgg gagattccct catccgccgg gaagcgggtg tacgcgagag gtggcgcgcg 134700
gcgtggcatt tataaaggat gaaatttttt tatttttttt cagatgtgtc gtcgatctct 134760
accgcgtcgg gagcctcgtc atcgtcagcc tttgaagata caagtagctg atttgttgtc 134820
tggggtcaca tcgcacacga taaaggcggg ttcctccatg accagctcta aaacctgtct 134880
caccatgacg agaaaagtag acatcttcgc ggcttcgtcc tccggagcca ggagctggcc 134940
gcgacgcccc ggattgttct cgccggggcg gtggtggtcg ccgacccggc ggacgagcag 135000
ctcctggcac ttggtcagga gcatggagcg atcctccagg gccagtttcc tgacgtatcc 135060
caacgtcagg tcggtggcga ggttggctat catggacatg gatatgcaga tgtttttcat 135120
gtcccacagc gtgttgtcgt cgttgacgac gtcgggtaag gtgaacgtgg ttcccctgaa 135180
ctgtatctgt cgcagccgag ctatcgccgc cctggcgtct tcgtagtttc tgtccaacga 135240
gagcagaccc atgacggtga gtttctgatt gatctccgcg gccagggagg acgggatgat 135300
ccaaggcacc accagctccc actccgggag actcatgata gagttctgct ggagggtcgt 135360
ggtcacggga ggatacacca ccagcgtgtc tcccttctcc cactgcacgg gtcccgtgtt 135420
acgtatcgtg tacagccggc cgtgcaccgg cacgcccagg agtatctgtc cgccctccac 135480
ctgccgcaag acggtgaggg tcatgttacg gagggtggtt ctgatcttat aaaagtcccg 135540
atgcgacttg atggtcttgt acaatcctat gtgcgagtgc gatatgaggt gttccctctg 135600
cgggatgggt atgacggccc cgatgaccct ggccagcttc cccatatcgg agggggacag 135660
cttctgttcg aaggtgcaga acgtcgtggt ctccatgtcc gcgtgcgcgc gagacccggc 135720
gtgcggacgc ggcgttcgcc tcccgccgtc gcgagacgac ggtccgaggg ctcagtggga 135780
atccgtgagg cgtcgacgtt cggcggcgcg gtcgggcgag tcgcgggcga ccgccacgcg 135840
taccatctaa tagttatttg ttactttttg ttcgccgttt cgcgcgcgct cgcccgcggg 135900
gcaccggtcg tcggggagcg atccgcggga tctcgacgag ggatggcggg tgtgccccca 135960
tccatccgcg tggagatcag agcgagttaa ataaaatact gtcctggagc ggtataactt 136020
```

-continued

```
cgccgatgat ataatttccg aaaagggtct cgttgccgtc cggcgggata cccttgaaat 136080
ggttctccag cagggcctgc gtcgtgctca cctgtagcgg gtaggcctcc tgcagcagtt 136140
tgcagggctt ctgcaccagt tcgtccgtgc cctccacgca cacgtattgc gtgtcggtgt 136200
ctccgcgtat gcagtcgcgg gctcgcgcga tgtactcgtc tatggtctta aagagcgtct 136260
tgttcgccgt tatgatagtg ttgacgtcga agaactgccg gcacgggctg tagaacatgg 136320
agttgtagcc cagtcggtcc ctgttctccg ggttgtacag gatgtccccg atggagcccg 136380
cctgggacgc ccaggggttg ttggtggtca ggaacgtctg ggcgtccggt tcgtggtggt 136440
tatagagcat gcggcgcgcg gcctcgtcgt cgtagggatc cacgccgagc atgcaggagg 136500
accggccccg ggggttgttc gtggtcttga aatagttgat gtccgccgtg accggggtca 136560
ggatgagctc gcacacggcc ctctggccgt gcatgagggc cgatcccggt ttctcggtca 136620
tgccgccgaa cgtcaggatg gagatggcgt cggcggtgag caggctctgc ctctccgccc 136680
cggtgtgctc gcggatccag ttgtccacgt ccttgttgcg gaacacgtgc atggggaaca 136740
cctgaaacag gtcctggacc ttggcgccca tgtcggtgcg cacccgccgc agcagcgcgg 136800
tgcaggtcgc cgagctgtag cccatgccca tgtcgacgct gcagatgttc tgcgtcacgt 136860
gaaaagtcgt attgatgtcc ctttcctcct tcgtgacggt cggggtgttg aggatgacgg 136920
ccgtgctgga cttgctgctg tatagcagcg agtccgtctc gaagacgtcc gtgcgcacgg 136980
cggtcagcgc gaatccggga tgcagccgga gccggctgtg cagggcggtg gagaccgcgg 137040
agaacttgtg gtgcatcgtc agcacggtca cgatggacag gagcgtgttc tggcagctgc 137100
cggtgtagcg ggagaagggg gaccggtgcc acgagaggta ttccctggcc agctcggggg 137160
tgagcgggaa cccgccgtcg ttgcgattat agttggggaa gacctccagg tagcgacgta 137220
tgtgttcgtt gtccatggcg cagatgttgg ggtccgagta gaacctgtgg aagggcacgc 137280
tctgcgcgaa cctggccagg atccgggggg cggtagtagt gcagcagccg ttgtacatga 137340
cgatctgcag cggctcgtag cccgggacgc cctgtctctg cgcggggtcg aggtccgtgc 137400
ggatgcctat gatcttggcg tgctccccga cgaacgccac gagcgcgaac agttccctgg 137460
cgacgtcgtg gtgcgcgcgg tctatcccgg cggcgttgaa cagttccacc gcgacggcgg 137520
ataactcgtg cgcgtcggcg ccgtactcgg cttccgcgtt caccagaaac ggcggtcgat 137580
agaacatctc cagcaggagg ctccgcaggc ggatggctag gccgcacgcc ctgttgttgc 137640
acatcgccgg tatgacgcag tagtagtaga tcttgtgcag gacgaagtcc tcgtcggaga 137700
tgtgctcgcc ctcgacgaac agccgtctgt cgtcgtccat ggccgccatc cgctgtgcgt 137760
cggacgttcc gtgagagcgc tgcgcgatgt cggcgtcggc tatcggttcc gtgtcgagga 137820
tgacctggta cctgggttcg tcctcgcgcg ggaaacggtc gaggaacggg gggaagagcc 137880
gcctgtcgtg cagcgcctgc acgtagctga tcatgggctc gtcggcgagt cgggtgttga 137940
gggtgctgag gcaggacacg cggtacagga accgcacgag ggacaggatg ttgcgataga 138000
tcgaatagat cccgggcagg agcacgccgc cgccgaggtt gttgacgatc aggatgatca 138060
tgtccaggct gtgcacgaag ggcaggatcc cgcgctgctg atagctcacc gtgatcacgc 138120
gcacgatcag cgcgcgggcg gtgttgaacg cggtctcgtt cccgtgcacc atgacggtga 138180
tcaggtggaa cagctccggg tactgggaat cgttcagcgc cgcgtgtatg accctcagca 138240
cgccgtcgac gtcgttgccg ggcttgatct tgacgtgctc caggacctgc tgggcccgca 138300
gttcctggaa ctccggcggc gccagggcca ggggcaggtt tccgatcatg atccgcgggg 138360
ccaccatggc cacgatctcc ctgttgagct cgtgatgcgt aaagtcgaac atggggtgca 138420
```

gctccgtgta gacggtgggg ttggagggct tgtagaactc caggtacgga aagtcctgtt 138480
tgatctcgtt gaccgtgcgc tgcgcctcgt gctggcgttc gtaaaagtgc acgaagcgac 138540
gcacgatgcc gccgaggcgg ccgccgtcga accggcaccg gcacagacgg gcctgcagga 138600
gttcgtcctt gggcggtcct ttggcctcga acgccctgaa ggaggcctcg gcatcgttga 138660
tgatggggtg gcacagcgtc aggagcgcgt cggagtagtc cagacgctgc atgatcctgt 138720
ctttgttgta aaagaacacg ctcagcggga gaatgttctg catggtctcc gtgagccgca 138780
cccgcaggtc cacggtggcg tagccctggt cgctggggag gaagaggccg acggggaaga 138840
agaacgtgag ctctagcgtg cgctccagcg ggtcgctggt gtcggtgttc ttgtagaccc 138900
gccgcagctg ctctatggcc acgatcttct cgccgaagcg tatcaggtcc atggccaggc 138960
tagtgtactt ggtggatccg tcgaagaact cggtggagtt caggttgtcc tgctgtcctc 139020
ccccggacgc catgcggtcg gcctgctgtc cgaaatccgc catgatcgaa tgatgcgcta 139080
tggccgtcac ggcgttctcc ttgctcatga cgaacgcgcc gtacgacgac ggcgcccgga 139140
cggattcgtg cacgatgtcc ttctcgaaca gcgagcggat ggcctggatg acggaggtgg 139200
tgctcaccac gacgccggct atcttggtcc ccgacggcgt cacgtagatg tcggggttgt 139260
ccaggatgct ctcggtgacg gcctcgatca tctgcgacag aaacttgtac acgacgtccc 139320
ggtccctggt ccggttgagc atgaacaccg tgccggacat cttggccttg aagctctgca 139380
gtatgttcgc cctctgcacg cggttgatcg tctgcctgtt gatgttggcg ttctccagga 139440
gggtccgcac cacgaaatac ggcggcgcct tccgcaacag cgtcagcaga aagttatgca 139500
ccaggccccg ctcgacggcg tcggccgtgt tctggacgac ccgcagcacg gtgttgatgg 139560
cgtccacgtt gaggagcttg tccagcagcg tgttgtcgaa ggtctccgcc aggtgggtca 139620
ggcaggcggc gctcagctcg aaggggatcg tgatgggatg cttctcactg tatttagtca 139680
ccatgatggt ggtctgtcgg gaggcggcga ctcccgtgcc ggtcgccacg cggggcacct 139740
ggatgtagaa gagcatcttg ccggtcgtca tcctgttcag atcgtcgaaa cggatggtgt 139800
gggccgccag cgccagcgtc gtgccgagga acgtaaccca ctccatcttg ttgcagtagg 139860
tggcgaagat ggcctcgaag ctgaggttgt aacgttccgg gtcgtctccg tagtacaggc 139920
ggaaactgtc gaacatctcc tctcccacca tcgtcttgat gtgcatcaac aggtccggag 139980
agatctccgc cttgggcagg agctccaccg ccgtccagtt ctccatgatc tcggtgtatt 140040
tgtaaccgcg gagccttcga tgcggacctc ctctccctca cgcggccgga cggatccttc 140100
ccgctggccc gttccgcgcg acggtcgagc ccgtcgggcg gcgccgctcg ctgatcccgc 140160
tcgcgacgtt ctaataaccg ttcggttcgt gtcgcggatc gcctccccgc tgcggtttag 140220
aacagggagg gtcggtcgac gccgcggggt cggttcggcc gcgaacgggg gagagggaac 140280
acgaaacgcg ttccgtcggg ggagaagagg gcgcggggcg tcgggagacg cgaagacggc 140340
gctccgggat cgacccgtcc gttgctcctc gtcctctggc gtcgaattcc acgaagaaag 140400
aaaacgatgt ctctgtgcaa acgactctct ccgtctttaa tagtaacatc cgatagattt 140460
attggcgtac ggagcgttcc ggtgtcggtg gattcgcata atctcaccag ggagctttcg 140520
tccgaggagg acgggcgcgt cgcgacgccc gtgcaggtgg accacgatca cgtcgacgag 140580
atcttcgacg tcctgctcga cgcgtctccc gtgccgaacg tcccggcgtc gaacggcgac 140640
gccgcctcgg gtctcgatac gcgcgaccgg gaccgcgcgc gcgtcgtgct gtgccgcctg 140700
ctgctgggac cgacggcggt cccttgctac tgcgacgagt gggacgccga cgagtacctc 140760
accgagtgcg tctttcgctg cgagggtccc ctgctgtacg cgtatcggaa aggctgtcag 140820
tgctacgagg cgagcgcgtt gcagtttacg gtgatctgta atcatccggt caatcgcgcc 140880
ttccgggggc tgctgtcgct gatggagtgg aacgctcacc tccgtaacgt gttttgcggc 140940
tgctgtcggt acaggacgga cagatacgtc ctcgccgcgc tgccggccag gtatcccatc 141000
ttcctggtct actatccgta tttcttgcgt tgtctctgcc gttatctgtc cgtggcggag 141060
atagacgact gcacgaacgc catgatgatc cacctcggaa gccagctgtc ggcccgcatc 141120
accatccatt acaaactgct cttcggcatg agcatccgtc ccgggttgac cccgtgcgcc 141180
gtcgcggcga acgagagctt tttcgtcctg gagttgcaga agctctggct cagcgtcaat 141240
tacatcaacg ccgtcaccac cgactttttc gaaaacgtgt tcgcggcctt ccatcgcgac 141300
aagagccagg ccatgctcgt gttgcgggtt ccctcccgca cggaaccgac cctgtcccgg 141360
ttctccatgt cccggttcaa gagccaggtg ctgtacttca ggttgccggt gagatacgtg 141420
cggaaccgac acgacgtgcc gcgcaacagc tttcaggtca agcgtctgtc catagtcttt 141480
cgggactcgg acgctatctg gcggaacctg ttcgtgcttt attacgcgta ctgctacgac 141540
ggtaacgagt gcgcggggtc cggcctcggc tccggagacg gcgacaacgc ctgcaggtcc 141600
gctacgtcgc ccccggccgc ggcgccgacc tgcgatacca gaggacggtc ccagcgcggc 141660
cgcgagtcct cgccgtcacg ctccgcgggt ccctgcgtcc gcagatccgg cgacggtccg 141720
tcgtcgctgc cgtcggatac ctgcgcgccg ccgccgtcgg cggcgacgac ggcgtcctcg 141780
cccgctctcg gcgccaagat accgagggcg ctgaggagcg ccatagacgg atcggccacg 141840
tcggtcaaga aatacgttcg catcgtgagt cgtctgacgt tcgcgaacta cagggaacgt 141900
ctggccagac gcgccgcggc cgcgggatcg gacgcggacc tcggagactc gttcgatttt 141960
tcctgcagac gggtccggtc gcgagacgga ttcgggtccg acgccgaggg cgaccgcgtc 142020
ccctctcccc gatgcgatcg tcgcctggtg atagggggcc gcgagttttc ggagatgacg 142080
tcggtaggtc tggacagaat gaccgtgaac gcgttcaaca cgaaccgcgt gatcaacctg 142140
aaggccgccc tggccaagtg taaatcggcc cgtctcagcc gacaccccaa gaacatgact 142200
cacagcttcg tgatgtacaa acacacgttc aaggagccgg cctgcaccat cagcacgttc 142260
gtgtcgaacg atgtggcgtg cacgaactct ctgaacgtca acatccgggg ttcctatctg 142320
gagttcatat acgccctcgg ggtctaccgt ctgtacgtgg acataaaaaa cttctttctg 142380
ccggccaccg tgtgcaacag caactcctcg ctggacgtcc acgggctgga ggaccagtcc 142440
gtcgtccgct cggagcgcca caaggtgtac tggaccacga acttcccctg catgatctcg 142500
acgaccgaca ggatcaacgt ggggtggttc aaggcggcca cggccatcat ccccaaggtc 142560
tcgggtcgct ccctggagac catcatgctg aaggagcttt ctcacatctg caggatgaag 142620
gacgttagca tagattacgg gatacaccgc attttcacgg aattagagac caggaactcg 142680
taccaggtgc cctttctggg caaacagttt attttatttc tcagggcgag cctgctgagg 142740
atacacggac acgaacataa aacaaagata gacaacatac tctttcgtgt tattaaagac 142800
ggattgtttg actaccacaa ggatatggtg gcgcacacca agataaagca cacgtgcgcg 142860
ctgataggca cgcgcctggc caacaacata ccgaaggtct tggttcgcaa caaaaagatc 142920
aagttggatt acttgggcag aaacgcgaac gtcctgactc tgtgccggta cctcgacctc 142980
agtcggatcg cgccctccag ggtgtccgtt ctcctggacg tgcttacgtg tctggcggag 143040
gcgagcgaca cgcctagaat caaagcggag atcctccgcg tgtgcggccg actgagggga 143100
gagacgacga cggcggcggc ggtcgcctcg acgggcagaa cgccgacgag gtcgagggag 143160

```
acgcctccgt cgcaggacgg tctcgtcgcg cgtcgccgtg gaatccccgc taccgcatcc 143220
gtcgagacgg atggcgtcgt ccgcctggac gacggcgatg acgggcatcg cggatctgac 143280
gttcgacgcg gggatctggc gagacggagc gctcctgctg ccagatgaca ccgtcgttca 143340
gcatacgttt cggcacgcgg aactggcgaa gatcgtggga cggggcgacg ttcaggggga 143400
tgttctgtcg gacgtcgtcg tcgtgtccga cggcggcggc gacgacgacg acggctgttt 143460
cgagacgaga ggacgcggcg acgctgtgag cgcctccgag atcgcggcgt acaccagcgg 143520
gcgccgaggg cgaaacgtgt cgggtttttc catctattgg cagagtcacg gagaactcat 143580
atacgccctg agcggcgtga cgcattgctt caagatgtac gtcgagtgcg gcaagcggac 143640
cgacaagggt aacgtcgtgt tcgcgactcc ggccctatat ctgatacggt cgtttcgggg 143700
cgtctcgctg ggcgccgcgg atatcgtgtg gccggagcgc cagaaggccg tgtggtcgag 143760
gctggtccgt atcggcgtgt gcgtggacag gaacaggtct gaggatacgt acggtccgtt 143820
ccagggctac cgagacggcg gccagaggtc cgtcgcgccg tccttcgcct ccgcgtcggc 143880
gatgcgcgag atgacggtag ccggcgtcga tgcgtccggg tttctgaagg cgacggggac 143940
gcccgcgttc gtgcacaggg tatccgtgac gtacaacgtc ttgaacctgg atctgccggg 144000
gacgccgggc ctcgtcctgg accgttgccg ggagttggcg gggacgaagc gcgtgaggct 144060
gtcgcaggac ggcggggtac agaacatgtt cctgtgccac gtgtgtctgt acaccatggg 144120
cgagaggagc gtggccgaag acatgatcgg ctcgctgtat cgccgcgacg tgccgggcga 144180
tccgacgttc gaccggcacg tcgccgtgtg gatgaacgct catctgctgg ccatgtcgct 144240
caatacggtg tacgacatgc ggcgttcgct gacgtgtccg gaggagcgtt tcgacctccg 144300
ttcgaacaac gcgtccatcg ccaggtatta cttcgaacgt tacgcgggcg tcaccatggc 144360
cgtcatatat tacgggatga gggtcctcga cgtgttctac gagacgtggt ccgccgcgga 144420
cgccctgaga cggctgggtt tcgtccagct cgtacaccgg gtctccaggg aagacctcgt 144480
cgcgctgctc aggctctgag cgggcgccgg cgcccgcgcg ctcggtcggc gtcggtcgtt 144540
gtcgtcagat cgccttgaac ctgtggtgat tgatggtctc gctgcagatg tacgtcgcca 144600
tgatgatggc gatcaccaga tcgtcggtct gaccgtgctt ctttccgctg tacgtgacgt 144660
actcgttgat cacgacgcgg tgtatgttct tgagctgctc gaggaggtac tccacggggt 144720
cgtgtgacag cttgatggtg tgggagacga gttcttggga ggccttgacg tatcccgaat 144780
taaactttcc tatgaacgct tccacggcca gcctcttctc tttccccatg aggtagaacg 144840
gttgctcgat ctcgttctga tcgggcgtgt gaaagaaggt gatcctgacg gccttggcgc 144900
attcgatgga ttgcttgatg atgcaggcga tcctcaccgc cgcggcctgg ttggagttac 144960
cttccaccgc caccctcacc tccgctatga aggggtgcag gtggagcacg gacagcagca 145020
tgtgcgccgc gcactccgcg atcgccatct ccgagctgtc cagcaggtct cgcaggaagt 145080
agtgttccag tccgtagatc accagctgat ttttgtacgt ccccaccgcc gctatgccgg 145140
tgccggacgc cctgcggttg gaggtgaacg cggggtccag gtagacgtac agcgtgtcgc 145200
ccagactctg tcttatcttt ctgttgatcg tgctgtaacg gaacatctcg aactcctcgc 145260
ggccgtcgtc cgtgatcagc acggtctcct ccgagatctt gttggtgccc cccatgatct 145320
cgtccatgaa ggaacccgcc aggaacatgt tggcggtcct ccgcacctcc gagctgatgg 145380
tgatgaacgt gggcttgtgc agccggtagc acgggcaggc cgtggcgtcc cccttctccg 145440
agaaggcccg catgtgctcc tcgcacacgt acgatatcac gttgagcatg tcgaacgggg 145500
```

agttgctcag tctggtcaga aagcaggtgg cgctcgtcgc cgtgttggtg gacgatatga 145560
atacgatctt ggtggtgtgt tgcgccagga acccgaggat ggtgttgaag gcgtccttct 145620
tgatgaagtg cgcctcgtcc acgaggagca ggtggaaatt ttggccccgt atgctctgag 145680
ggaaagaaaa aaataaaaaa ggtcgatgtg agtgacgggt gagaatagac gcgcgttttt 145740
ttcgagaaac gcggccatcg ccgacgggac cttacactct ttaaggaggg gacccgttgg 145800
acgttacgcc gcgaggcttc cgggagatcc gcgggagctc gtgtgggata aatagcggtc 145860
gacgcgagga gagcgagcga gtgggggaga ggagaggaag ggacgggaac gcgacgccac 145920
gcgacgcgga aaacagacgg acggtttacg tttcggagcg ccgtccgtgt gggagaagcg 145980
agggcgagag cgggggagcc ggagacgcgg ggagacggag aagacggcga cggggtaagg 146040
aacgaaggaa aacccgtctc ttctgccggg atccggagcc tcgtcctctc tccggcccgt 146100
catgaacgag gcgctgaagg acatcacgga ttccgccaaa gctcacgccg ccgtcgagga 146160
gctctttcgt tacgtggatt ccgtacatcg tcactttggc tttctctttc agactgacga 146220
gtccgggctg cggagggtgg agtgcgtggc gtccctcttc gatcacgtcg cggtggagag 146280
cgtccacgac gtcgcgtccc tgacgggcaa cgtgaacggg atagacggag actacggtct 146340
ggacggcggc gcgtcggaag gatgatcgtc gcgagggatc ccccggggca ccccggcgcg 146400
cacgtctgcg agatgcgcaa cctgcacaat ccggtcaccc aggagttgga tctcaacaac 146460
gtcttcgtgt gcacggagtg ctttcggact cacctgtgcg atctcaatca cggttgtcag 146520
ttgatcgcca ccccggaagg gtccgtgtgc gcgataaccg gtttatcgta cgagtcgatc 146580
tacgccacca cccgcatcga cgttttggaa cccacgacgg agtccaacat cgacgaggtg 146640
aacgtggtga ctatcatatt atcgtacgtc tacgcctatc tgatacggaa ctcggaacgt 146700
tacagagacg tgttggacga agtcgccgaa gacggcaagc tgacgccgca ggtggaaagc 146760
gccgtctact ttacgttcaa caaagttttc aagcaatcga acaacctgca caagatcccg 146820
ctgtccacga tcgggcagct gttcacccag ctgatcatcg gggtgcacgc gaaggtgacc 146880
aagtacgacg ccaccgtcat caaggtcagt cgtcgaaagc gagaggacgg attgctgaaa 146940
cagatgcgat tcgaatatgg aaacgcacct acgtgcagag ttagatcttg accgctacgg 147000
atcgctgcgg gagtgcgcgt cggggacggt cgggggggcgc gagggcgccc cgtcggagga 147060
ggacgaggag ggagagcggg gcagtacggt gttgccgcta cacatggtgc tgaccgagga 147120
agcgataagc ttcgacgatt tccgtcgcct ggagagcgcg tgttacaggt tcgtcggcgg 147180
cgacggctgc ggcgagtacg gatggaagag gtctcccttc tgcaaggtcg atcacgaact 147240
gcgcgtctta gagtacatcc gggactcccc gcatcgcctg ctggctctgg gagaaccggt 147300
ggggcggctc gccggggaca tccgcgccaa gttcgccgtc ttcctgtccg tgggcatctg 147360
ctgcgaccgg gacggggccg tctcaccttc gggcgtcgtg cgcctgaggc tcatccttaa 147420
agcgacgggc ggcaggctgg cgttcgggag ggagtcccgc gaggtcctgg acatcgattt 147480
cgccgcgaaa gacgtcgtgg cgagtcgcaa gcagttcgcc gacagatttc cggacggtcc 147540
cccgaggcgc gccgcgtcct cgtcgggacg ggcgcatccc gggccgccgt cgtccctgac 147600
ggagatcacc cgcagctccc gcgacgtcga gtcgttgacg gacgacgccg gggaagccga 147660
ttccgagatg gaagcgatcg gatgcggccc gcggttcttc gatatagtgc cggatcgtaa 147720
gatgtccaag cagctgtcct cgtatctgtc caaattcata cccgacctgg aggacggcgg 147780
cgacggctcc ggtcccttgg aaccgccgtc cgtggtgcgc ggcagaaccc tggtggctcg 147840
gatgggcgta tctcgcggag acgtcataga ggccgccgtc gcggagcgcg aagatctggc 147900

```
ggaggccgcc gcggccgaag ccgcctccgc cgtcgagccg tcgctcaccg gccgttggtt 147960
cgacgtccag agctacgtct ccgtgaggcg gctgcgcgac ctgtgccgca cccgcacggc 148020
cgtggccgtc tggtacgaac actcgctctg ggcggacgtg cgtctgaggg agcgcgcctc 148080
ggcggtgtcg gaccgcaacg cgggacgcgg agggatcctg tccagcatgc gcgacgtgtc 148140
gctcgccgtc tccgggctgt gcgccgccgt ggcgcgcgga ctgagcgagt cgctggccag 148200
cctcggctct ctgtcgcagc atttctcctg cgcggtgccg gagaacgtgg acttcggcgc 148260
tatcctcgat ctgctgtgca tctcgaagga cgtgtggatc aacaccatgg gcgaaaacag 148320
ctgcattatt aaggcaatag tatacaatat ccaaagagag cacgcggact cgcgggattc 148380
gtgcgattcc gaatcgggaa gggtgacggg ccgatggtgg gccgacgtga tagattgcgt 148440
gcggggcaag ctctacggcg gcctgccggt ctcccttagg gcctgcgagc ggaccgggct 148500
gttcatctcg caccacgaag acggaagaga aaccgagtgg gtccgggacc cggggttatg 148560
cgtcgtgtac gccaactgcg ttgacctgca gatctactgg gtggtgcccg gcggtttcgc 148620
ggtgccgttc aacgtgaaca ccgatggcgt gcgcctcgag tgcctccgcg atcgacttga 148680
ggtccctgaa gctgtttctc gaaagggagt gcgtatggcg caccgtcgtt aacgcccagt 148740
actacaagca gctgtgcgcc gtggccacca agtcggcctt cttcgaggcg ggcgtcggcg 148800
accggaatct ctgctacacc gtggtcaacg tcataatcct caagagggac ggcgagaacg 148860
ttctatgcat cagcgtgaac gggaaaccgt acgcgcagct ggcgggccgg gtcagacgcg 148920
tgaagaagcg catcgtcgac atggatccct tttacctgct tcgcctgata caggtgaggc 148980
ccgcggatct cgacttctct ccgatgttcg ccaccccgtc gagcgcggcg ggcgcgggcg 149040
cgatgtcgcc catgttcctc tacgaacact gcagcctcgt cggccccgag gaggcctccg 149100
ggttcgtcac gcgaggcggc gacgagcacg gcgacgtcag gctgcggaga ctcggggtcg 149160
gctcgtgggt tctggtgcag ggagacacct acacgatcta ctgcttcgtg ctctcctgcg 149220
atctgtacgt ggcctgctgc gaccgtcgct ttttcccgtc ggcggccagg atggtcgcca 149280
aaacgacggc gtgcgacagc gagacctgtt ccttctgtcg tgatcatggc aaacacgtgg 149340
acgtgaccgg gaaattcatc ggttgcgttc ccgagagggg ctgttgcctg tgttacacct 149400
cgtgcgggat caggatcacg ccaggacaga gcgagaccat cctgcccttc ctatgcgacg 149460
acgacgaatc cgtcgaggcc gtacaggcga ccgtgcgcca ggacaccaga ctcagcacca 149520
agctcagcga ttatgtgtgt ctcaagaacg tgaacggcga gaacgtcccc gtgaaagacg 149580
aggcgtggaa cctcatgaag atcgatcccg accttagcct acttatcatc ctgtcgtgtc 149640
cggtcctgaa gaggttgacc ctgagccaca gcaccctgtg aatcggatcg tgcgagtgcg 149700
ggagaaacag atacacggaa agcgggacga gggggtggat ggagaaaaac cggagggatg 149760
cagggaggag agggatagag ggatcaggga tcgggtaaga ggaccgcgat atttcccaga 149820
ttcgttacag ggtcgtgcta accgtacatt cgattataat gattgtacgg gtgtaaaaat 149880
gtgtagagat tacactacat ggtcgaataa agatcgaaaa gtcagataat cggttttggg 149940
aacgttgttg tgttgttatg cgtcccgccg ttctacctac cggggcgtgc gggaggggga 150000
gggagaggaa ggaggcgcca ggattactca cattggtgtt gtagcagctg gcgaagagcg 150060
cggtgctctt ggcgacgtgg tgatctatgc tgatcacgtt gtccttgttc tcgatggtgt 150120
gggtggacga gaacatccgt cggcatctga attccacctc cttgaggacg aactgcgaga 150180
cgtgtttctg atgcgcgacg tatcctatgc tgatccctat gatgttcttc agcaagaagc 150240
```

```
atatgatggg gatcatgaac cacgtcttac cgtgtctcct cgggacgagg aacaccgtgg 150300
ctttctgttt gaacaggttg accgagttcc tggagatgaa ctcgatgtcg aagacgtgca 150360
gcaggtattc cagcacgcgg ttcgccagca cgggcatctt ggtgacggcc acgaagaaga 150420
tcacgtgaat taatagattt ttctgaaacg gttccaggta aacgcgtcta tttatctgcc 150480
ggtccccgtc gtagccgcct tcagtccatc gtcggaaatc ggctatgaaa ttgcttatct 150540
gcacgaactc cggttcctgg tagaggccgg tcagcgccgc ggccttgtcc tgcgccgacc 150600
ggtcccgcac gagggcctcc tccaaacgta tccgcccgag cgcggactcc agcgcgtccg 150660
acaggaagag tttctgcgtg atgcattccg aattgtagtc tctgtacttg gtgcaaaact 150720
gcatgagcgg caggatagac tcgttgcacg cgtgtatcac tccgagttcg ggtgtacgg 150780
tttggaaacg tttcttgcag agcgtaccta cgctcgggaa ctcggaggag atcaccccgg 150840
tgcgccgttt tttagtacgt cgaagctcga tatattccga ccgcagcgac tgctgcgcca 150900
cgtcggacag catcgcgacg cgggtcgacg ccgggcgggg aagagagacg cggcggcgaa 150960
ggagatatgg acgggagatc gtcccaggcg ctctccgtgt ccacggccct ctgtgagatc 151020
gtcaagacga tgtccgcatc cgcggaaaac gggacggacg cgacggcggt ccggagcgag 151080
tccggcgagc cgccgtcctc gtcctcgtcc tcggcgggcc cggcggtcgc tccggatgga 151140
cccgcggccg gacgcgcgga gtcgtccgac gacgcgttac ggttcgacga ggcgatccgg 151200
atggccctca cggtttgcga ggcgacggcg cctcacgaca aattcagatt gatcgagacc 151260
ccgaatcaga attttctgtt ggttactaac gttctgccca aggaagagtg tttcggggag 151320
aactggcgcg ccggagacgg cggcggtaaa gggaggcccg gaacggcggc gacgacgtcg 151380
tcgtccgtat cgacgggcaa caacgttctc agggagctat ccgatacggt ccctggcgac 151440
aggggccgtc cgagtagaca caatagggat tacgctctgc gagacgtggc gactatcacg 151500
tacacggggc atctgatgag tagtacctac gtcgtgtaca ccaaggcgca cctggagaga 151560
gcgctgtcgc tcgacaaacg cgcttttata caacgcatcc tgaaacatgt ggataccccg 151620
ggcctgttgg accacaacaa cgtctgcgac gcggaggccc tgctgtggat gttgtactgc 151680
ggtcccatga gtttctgtca gtcggacccc tgtctgggca gggacaagac ggaatacggc 151740
ggggcctttc cggcgctgtt accgcctatc ttttacgagc ccgtgaccga ctacttggcc 151800
tacatgaacc tggcggagct gtacgtgcac gtgtggtaca gatcctacga gttcaaggtg 151860
gaggccgacg cgacgtgcgt cgagggaggc ctgggacagg tcacgctggg ccgcgcgcgc 151920
gacaccctgc gcatggtgag ggaccggttt cacgaccgag aggtcccccct gtggccggtg 151980
gcctcgagaa cctgcctctt ctgtgcgtta tataatcaga acagactgtg tctggacttc 152040
gccaagacca acgcgtcttg cacgtcatac agtcccatcg tgctgaagga ctgcccgggc 152100
atcgtgacca acgtcacgct gagccacgct ctgccgggca ccggcggcgc gaccctcttt 152160
cccgtataca acatcggcgt gctgctcaag gcgctgagac ggtcggagtc gggcgagctc 152220
gaacttcggc tctgaacgcg caatacggcg cctcgcgacg tcgcgaaacc gcggccgcgg 152280
gtcggacgac tccgggccgt tctgttcgac cgtccgttcg tttccgagcc gcatcgaaat 152340
cgagcctttc gccgcgggag ggatctccgc cgcgacgcga gcgtatgagc gggtcgagcg 152400
cgggcgctgc acgtgacggc gcccgcgttc ttggctccga tcggagattt cttcgtattg 152460
ctcagacatg acgtcaaaaa aagaactgtt aaaagagact atgcgccaca gactggagca 152520
gaaacactgt aagttcttgt ctgacgcact cggggagact cacccgagcg tggagcagca 152580
gaggatcaga gcggcctgcg tggcgttcga tctggagagg ctcgctacgc tgagcaccgc 152640
```

```
gagagccctg ttagacgtct ccgcccgtcg ggcctccgac gcgcagaaac ggaccgcgct 152700
cacgaagggc ctgttggacg gggatacgtt ctacgagagc aacgacgtgc tgatcgagat 152760
aaacgacagg gtcgccgaac tcaaagacaa cgtcctagac gccgcgcggt cggtctccga 152820
agacccttga ccggtgaccc cgcgtcgaga gagcgcggta aagggccgtc gttcggacgt 152880
acggacgggt cctccaccgt caaaacgcta tgtcgacgtc caatgtttta aagcggcgtc 152940
gcgacgtccc gggcgacgac cgtgccttgg agccggacgg gtctcggtct cccaagaggg 153000
gctttctaga cgtcttgcta gatctcccgg gggtgatacg taggtctctg gaaggggact 153060
tcgagggtga cgacagaggt tccgagccgt cgaagcgaaa gattggccac gatccaccga 153120
gatctctgtc tcggctcgag catccggggc ccctggcgca gacgtccggc agagcggtcg 153180
ccgcgacgcg cgcctcgagg agttcttgca cgtgcacccc tcgcgaacga tcgctctcct 153240
gctccgagga gatgatcatt tccagggccg ggcgcttacg gtactgcccc atctgtaaca 153300
gggaacggcg agtcatggag cagcggcctt ccgcgtcggc cgcggaaggc tctccgtacg 153360
acaacctgga tccggcgtgg accgacgatc gcttctgtca acacgcgtcc ctgtctaccg 153420
ataccatgct catctcgcac atccccgggc tggagtgcga cctcaggata ttcgatcagt 153480
tgcgggagcc gtgcctgaag cactacatgg gctccgaagg gtacctgacc gtgtacgtcc 153540
ccaagcggga ggatttctgc gacgcggtat gccgccgcgt cgaccggagc gtcgcggacg 153600
ccaggctcgg gatcggggcg ttcggtgagg tctggcccgt gcccggcacg gacaacgtcg 153660
tgaagatatc gaaacgggtg accgagtcga tcatcggcgt gtgggtgtcc ggcgtcatca 153720
gggcgaagtc cagacagaag gacgcgacga cgacgatggg gggtcggctc atccacgggt 153780
tcctggcggc tatggggtgc tgcatgtacc acaagacgac gctgtacgcg cgtatggacg 153840
tcgatatgta ccgctacgac ggctggaagc tagccggtat ggagagctac cgccacgcgt 153900
tcagcgggtt ggcggacgcg ctgcgttttc tgaacgggac ctgccacatc tgccacttcg 153960
acgtgtctcc catgaactgc ctgatcaagg tggacccgtc cgccccgtat cggatcgcgc 154020
gcgccgcgct gtgcgactac agcctgaccg agccccaccc gatgtacaat cgcaggtgcg 154080
ccgtggtcct ccaggagacc aagagcgtgc gcatgttgcc ggacagtcaa tataagctgt 154140
gcgagtgcta ccatcccgcg ttcagaccca tcatcctgca gcgcaccgtg tgcgccgagc 154200
cggacggcta ttttccgttc gaggactggg gccagttctg cgtcgccgag atctgcgcgc 154260
tgggcatggt ggtgtgtttc tgtctcatga ggaccttgga ctggcgcggg gtgccgaccg 154320
tcaggcgcgt gagcgagtcc ctactgttcc aggccacgcc gctggcctgc gacgccatgg 154380
agaagcagga tctggccggg tactccagcg cctgtctggc catcatggcc aggcagctgg 154440
cctacgtcgg ggcgatactc gggtcccgcg tctcggatac gttcgagcgc accaaacgtt 154500
tcgtgaaggt tcagtgcggt gacgtacggt atcaggaatt cacgaatgta tatgaggacg 154560
ccgtacgcat catctcgccc ttccacgtca gggacaggtt ggctttggcc agtaggcagt 154620
cggcggggag atacctgctg ggcgaactgg taaaagtctt cagcgtctcc gagacggagc 154680
acttgctctg cgacccgagg acgctgtttc aagcggacta ccgatagggt cgcacggcgc 154740
gcggcgatga ccgacgaagc cgccggaccg tcgcgcgacg gcggcggcaa cggcagcggt 154800
ggcgacagca gggacggcga cgacggccgc ggcggaggcg ccgcgtctcg caaacgcggt 154860
ctctcggaag gggacgaccg ccgagacgac ccgggagacg gactcggtct ggagcgcatg 154920
tgggcgctgt tctcggacga gcccatgacg ctctttctga gcgacaagtt catcctcaga 154980
```

```
agggccgaag ccgagaaggt gccctattac gcgttacggc taacgtatct atactacatg 155040
ttcaagaaga ccaacgtcct gtaccccgac ataggagcct gcgcctcctt cgtggcggtc 155100
gtcgacgagg agacgctccg ttttcgaaac gccgccgatc tccgcgggga cgtcttacgg 155160
ttcagcgacg accagttcat gacgttcgcg agagatctct tcgtggcgtg cggcggcggc 155220
cgccggctcg acaggctact gtgtcacctg gagaggggga cgcgcgggca gaccgaaaac 155280
tcggtctggc acgtgctgcg cggcgagacc atcaccgcca ccaggttcta ccagacgctg 155340
gtgtccgacc gcgcggcggt gaggttcgag aacccggggt ctcagagata cgccgagagc 155400
gtcgcgttcg ggcgcgcgcg cgagcccacc gtaaagcgcc tgatagaggt cttcgtggag 155460
aaacgcacgg aacccgtcgt cggcgggtta ggtctgctgc tggaccctgg ttccgcggtc 155520
ctgggcgcct cgctggacct ctgtttcggc gtctccgagt cgcgcgagga gggcctgctg 155580
cgcgtccacg aacgcgcgcg catcttcgag atcaagtgcc gatacaagta cctccgggcc 155640
tgcgaggacc cgtacgttct ccgcgtgctg cgcgagtcca ccgcggagtc ggtcgtcgcc 155700
tttctcctgt cgcacaagat cccggcggtg gattacaggc gcgagggcga gataccgggg 155760
acgcacgagt tcctcatgtc ccacgacggc gcgttcgaga cccgcaagcg gacccgtccg 155820
gggcgggtgg cgaccaacct gaagccgcac atccccgatc tcgtgtccct gaacagggcg 155880
ctgagctccg aggtgatcgt gttccacacg acgaccgcga gcggtgaaac tattaacggc 155940
tctccggacg tacccgtccg cgacgaagag cgagtcgtcg gcgacgagat cgacgatctc 156000
ggcggcgaaa acgacgacgg caacgaagac gattcgattt ccggcaggga gaccccggag 156060
ctgtcggacg ccgtgttcct tcgagagagg gcccgtttcc gacttcccgt gttcgtcaac 156120
ccgagacatc cgaacttctt tcaggtactg ttgcaacact acgtcctgtc ccagtactac 156180
tgctgtcagc acgaggaccc ggagagcata gaccccgaac agctgccctc cgctaaccta 156240
gtctccgcta tatttaggaa acgttcagag agagaagctg gaaaagatgt ctacctggac 156300
ggtcgtaggc tagattgcga cgacatcccc ctgttcatcg tgatcacccc gctggccttc 156360
gatcaccggg tgaccgggaa tgtcgtcgcc agagtgctga gcgcctggga gatcgccgtc 156420
cgaaagtgca gcggcgtgtc gatatgggtt ccggattctg taaggcgttt tgttgcgacc 156480
gctcggggaa gggttccaag cccttgtacg attactgcgg aaacgaaata gatctctcga 156540
gacgggactt ctcgcccctg tccgacacgt ccgacgatga cgacgacgaa aacgaaaacg 156600
agaacgagaa cgacatgacc ttcatcgaca acgacgacga cggcgacgat ctcggaatcg 156660
cgtccgacga acgggcgacg ttcgtcggcg agaacgtcgc aggggccggt tcgggttcat 156720
ccggcacggg taggaaaaag aaaaagagcg gcaggggcgg cctggacacc gtgccggtca 156780
tcgacatgcg tccccgctcg gacgccatgc cgaagaccat acccgtcccc gtgcagatgt 156840
cggcgtccaa cgggaccggc gcccgcagga agaccggcgt ctccgggggc gcgtccccga 156900
aaccctcttc gacgaaccgt tccaggaggc cgtcgagcgg acaggccaga ctgataaccc 156960
tgtgagagac agacagacag acagacaggg aatcgcgatc tctctccccg ctccaccctg 157020
cgaacgcaca tcgtcctctc cctcacgaac gtcccgacgt cgtacgatca ctgacatgta 157080
gtagtaaatc gtgacaaaaa cactcgttgt tattgtatta ttattttatt cattaaaaga 157140
atgcaacacg aattatgtgt cacggctggt ttctggcgtc tgcggtgcgg cgtccgccgg 157200
ctcgcctctc cccctcccca tcccgtcggg ttcctcgagc gaggaaaagc ctcgctggcg 157260
gcgtcatcgg tccctcctca ctcgtctatg tccaacttgg acgagagcgg cttgacctcc 157320
gatgggtccg gaaggggttt gtagctgggt ctgtgccgca ggatgaagaa acggatgatg 157380
```

```
cgacacaggg tcagcgtcag ccagctcagg aacatgaggc cgacgagcac gtacacggtc 157440
gtctcgtgct cgtggtgggt gatggcctcg tacttgatga tggggtacag ggctccgcac 157500
atcccgcaga aggcgccgaa gtggtagccg aattggatct tcatgtatct gatgagaacg 157560
gtctccagga ctatcaggta gatgcaggcc aggagggtaa agacgatgat ggtggagaac 157620
accatgtggc tggtcctgac caggaagctg ttgccgaatc ccaggcagag cgtcatggac 157680
aggaccatgg tggagaaccc catggccatc tgaaggaggt tcacgacggc cgtcttgaac 157740
ttgaccgtgc cccgcagctt ggggtgtagt ttattgagca tgaaggtgga gcggtcgaaa 157800
gactgatact gcgtgatcag ggtcaccacg aaggcggtga gcgcgatgaa gtgcatggcg 157860
aacgtgaacg agatgatggc gggcagacgg aaggacatgg ccaggatgaa cagctggaag 157920
gagtccaggg tcaggatgaa gagaaagcac gtgaggccgt ctcccatgta ctgtatgtct 157980
atggtggcct gattgacggc cgagccgtcc tttctaaaat tgatcttgat ccagcagacg 158040
acgtagtaga tggtgacgag gatgaagacg aactgcataa aggcgacgta ggccacgatc 158100
tgcccggagt cgagaaagag ctgcggggtg atctggtgca gcacgttgaa cgccgtcatg 158160
ttgaactgcc cgtagtccac gatgtggtag tagacgcacg ggaaccccag gccggggaag 158220
ttggcggtga tcaggaacac cgtgacgttt aggacgctca ggaaggcgca ggcgatggag 158280
aaggcccagg ttttggtgct caccccgtcc acgtgagaga gccccatggt cgccgcgacc 158340
gtcgtatcgt cgtccgcgga cccgtttctc tacggcgtgc gtcccgcgcg tgattattat 158400
ttactcccgg attcgtcata cgcgtctctc gataccgcgc gggcgacgcc ttcggccgcc 158460
cgcacgcata aaatagtcgc ggtcgatacg caggtatgcg ctcgtcagtc ggggtttagt 158520
agtgcgtgta cgatacgaga gttccccggc cgcgttcgtc gtcgtccccg cacgatcgcg 158580
taacgtaaca cggagggtcg gacggacggg tggccagagt ccgagggaga gggggaggcc 158640
ggccgcgtaa acggcgatgg cgtccgtcct gagacactac accggcgtgg tgtgccacct 158700
tgggctctac gggatcaagg acgacaggcc gatcctgcag tgcctgttca tggacatggt 158760
cggcggcgac gggccgcatc tcccgatcct gaagagcttc gtggtgctgg gcgatcccat 158820
cgccgacgcg gacgcggtgc gcgtgctgag gcggcccttc gattcgtacg tgcgcgacgt 158880
ccagagacac gtcgagttcg tcgcggctaa gagcagcctg ctgtcgaacg tcctcctgcg 158940
caggggcggg ctggtcggca cgctgtcccg gccgttcctg cccgtcacgg tggggatcgt 159000
gcagcccgac gactgcatca tcgcgagcgc cgagcgcgcg cggcccgtcc ggggtttcga 159060
ggacttcgtc tccgcgttca ggacggccag gctggccgtc gtgggcgagt actcgttcgc 159120
gggcgccgac tgcgaccgtc aggagcgcga gccgcagccc ccgtcgaaga cgacgagatc 159180
ctggggcggc accggcggcg gcggtcgagc cgacgtcgag gccgacgccg ggcagggaaa 159240
gcgtagagcc gaaacgtcgc gcgacgtctc ggaccgtcag acccagaccg tgaagaagat 159300
acggcgcggg tatagcgccg acagcgtgac gttttcgata cgcgtgggcg acaagagata 159360
cctgttcgat acgtccaacc ggggccgctg gccggtgtcc gcgctgttct ccgtggagga 159420
ccactcgctg gacgtgcgcg actccgcgcg gaagctccgg atccgtctgg tgacgccgag 159480
gggattcatc gcactggcgt tctccgacga acagtgcatc ctgctcctca ggacggccct 159540
gaaacagctg ttcgaacaca tctacgccga cttctccgga gtgcggcccc tgttcgacta 159600
cctggggccg gatctcttcc aggacggctt ccacagcaag tccgtcttct acaccggttt 159660
tcccaacgtg tgcatgtacg cggtgcccgg ggccgacgcc ctgggcaggg agacgtccct 159720
```

```
ggacgccatg aaagagatag tcagctgctg cggattgccg gacgtgctcg gggaagacgg 159780
caagctgacc agcggcctca acccggactc tgggctctcg ccggccgtat cggccgcgtt 159840
ccccgacgcc ggggacgtca ggatcaacgg ttccaggttc gtgacgtgcg acttcgcgtt 159900
tcccgccgac gtctcgccgg cggacgacgc ctgtcaacct acgaacgtgc agctgtacct 159960
ctcgcggggc tgcatcagga ggttgacgat cccggatttt cggtggaaga tcatgaagaa 160020
gtgtctcgtc gacaacgagt ttcccttccc gctgggtctg ggccccgacg gccggcgaga 160080
tcgccgcgag ttgtgtcacc gcttcgtgtc gcggctccgg ggcgccgcct ctcgagagat 160140
actggcggtg gagtcgttca tatcgcatca cgtcacggcc gcctgcacct ccagcaacct 160200
ggcgtggctg ctggtcagga acggctgcga gttcttcgtc gaggaggacc gttcggactt 160260
catgcgctcc gagacgtgcc tcaacacggt gatgtcctgc tactggaaga agtgtttcgg 160320
cggctcggcc tccgacgacc ccgtctgtaa cgtcacggga cggtacgagg gagcggtgat 160380
actggcggac gggctcttgc tcgtgtcggg ggaggcccac ccgctggcgc cggacggctc 160440
ggggacgcca ggctggcgca ccgtcatggc cgacgtgtcc acgtcgatcg tggacgagac 160500
gaaggcgaac gcgatcgagc ggctcttcgg ctcggactac ctaaagaacg tcctgcgttc 160560
catgatgctg cggctggccg ccaggagaaa cgacacggcg ttctggatag aacgcttcca 160620
gccgggggtc ctcgtgaggg agcacccggg cctgttggac tgcgcgccgt tctgcggcgt 160680
ctggggttcg tcgcggatgg ccgtggtgca gccgcgggac gcggcgctgt cggacaccat 160740
agactacagc gtgtacgtcc gcaggatcgt gcggtgcgtg cgcgcctgcg tgacggtcct 160800
ggtcctgcgc gaccgcgggg aacgcggctg ctccgtcgcc ggaggggccg cggacccccct 160860
ggtcggcaag gtggacagac tgtttcgcga cgtggagagg gagctgctgc gggactatct 160920
gtgcgtgttc aggatcaatt gaacggatac gggttactcg tgtgcgtgta cgggatacgg 160980
gtggcggtcg tgattgtggc gcgacgtgcg gacagaggct agcggggcga tacgtgtctc 161040
gaataaagac gtttattatg gatcgcaaac gttacggtac cgagagtgtc ttatttccat 161100
acgggcgata cgggcgccgg cacgtatcac ttgaccagag acggcccgac tgtggcgacg 161160
gtctccgaca ccacctcgtg catgacgtgt ctcacgccgt acccgtccct cgtttgtcgg 161220
gtggcgaacg agagcgagaa gaaagcgtcg ccgggggcga cgacggagcc caggaggccc 161280
gagatggcgg cgctcgccgc gtcgaggcgg gagcgccgta cctgctggtg caggatgtag 161340
gtcttgggaa cgtgggtcag gatgacgtcg gacgagacgt cgaagaacag atacaggcag 161400
gagcacgtca tgaccatgca gctgcgccgc acgagaccga agaacgaact cgttccccgg 161460
gccgtcgtct gcaggtagtt gaggacggcg agcagggtga cgcggctcac gggcaggcac 161520
tcggtcacgt agagcaggag gcagagcgcg aagtcgtcgt cggtggtcgg gcgggtgacg 161580
gccacgcggt gcttgagccg cgacttgacg agtttcgtct ccttgagcgt atcctcgttt 161640
tccaagacga aaacgaacgc gaagccgtag tacgcgtggt tgcacgcgcg ttcggcgcga 161700
tactcgtgcg ccgacatctc ccgcccggat tcggtgcgaa acagcagacg accggcgccc 161760
gagacggtca cgtccgtgac gtccgggttc accagcgacg tcccgcgctc cccgtcagta 161820
cgcacctcca gcatagccct ggggagcagc atagtgctgg atgttccgcg tccgcctgat 161880
gcggcgcacc ttgcgctgca ccggatcgag ctcgtcgctg aagggtccga cggggccgct 161940
tccgaagaga gcgacgtctt cggttaaaga gtgtttccga gaaccgtcgc cgaggctgac 162000
gaggggcccc gagtgacctt ccgtctgcgg ggaatcaccg acggtcccgc gcgatcgtac 162060
cttcagcacc tcgtgggcgc agacgaagcg cacgtaccga ttgagcttgc tgtctcggta 162120
```

```
ggagacgtgt atcagctctc cgtaggacag gcccacgtag tcctccggga tgggcgtgaa 162180
cgaggacagt cccataagtc gatgcacgag cgggaggagg acgcgctcga tcgtgtagtt 162240
ggagtactgg accgtctcct ccgtgccctg atacgtgacc aatttgcgta atttgaacgt 162300
cctggtgtac tccagctccc agagctcgtc caggtgacgg ccgatgggta ccgtgtccgg 162360
gatgtactgg gagaagaagc tgttggccac cagccggttg tcgtcgaccg ccaggggctc 162420
gaacggcagc gactgtgtct gctggacggc ctcgttgacg gagaggctgt tcaggtcgtc 162480
cagctgtcgg cgttcctgcc cgcactgcgc ctcgcgatgg ccgtagcggg ccagcgccag 162540
ggcgagctcc cgggcgcgac gctcccaatt ctgattgatc agtttgagat cctggatctg 162600
gtccatctga tcctggatct gatcctccag gcacttgatg acctgtttct tgaacagctc 162660
gcgtacgttc ctgtcggcgg cgccctggac gccggccgcc ccgccgggag cgtgagggtc 162720
ctggaacggc ggtctgctgg gcagcaggcg cgtctgatcc accatggacg gggtgacctc 162780
ctggatgaag gcctccacgc tgtcctccag gccgatctta gatttgctat ccgcgatgtt 162840
taataagaac ttcatgatgc tttttttggc gtcggcgccc ctgtcgtgct tctccatgag 162900
ctcgacgatc ttcttgctgt tgagctcgtg cctgctggtc gtgatggcct tcaccgggaa 162960
ggtgttgagg agctgacaca ctttctggtg ccggcagacc gcgtcgtatc ggctgagctc 163020
ccgatacagg tgcgcggccg gcgtcgtgta gatcacggcc tcgccgtcgc tcccgatccc 163080
gccgtacgcc agcggggtct gcgcgacgtg cagctccacc gacttgtccc cgaggtgagc 163140
cgcgagcttg ccgctgtgcc tgaagcgccg tatcgacagg tcgaccgagt tgtgtacgtc 163200
cagcgacctg agttcggtga tcgtcctggc caggtaggac ctgttcttct ccaggagggt 163260
ctctagcagc gggctgccgt tccgggacgc ctcggacacg gaacgccgga tgaactcgtc 163320
tctgtttcgg cgaaactcca cggtctccga cggcctggac agggggacca gtccgatcgt 163380
gacgatccag tccacataga gctcgtacac gtggttcttg aggtatctgt cgatcaggct 163440
tataagaacg ctacagagcg tggactccac gctctgctcg agcgccccgg cccaggcgtt 163500
gaggtagtcc agcacggccg gctcctgccg aaacgggtag gggaagagtc ggttgtgcga 163560
tctccactcc tcggcgacct cccgcatggt cacgctgttg agtatctcgt tgcagaggcc 163620
gtagaagatc tgcttgcgca gcacgctggg gtccctcagc acctgatgta tggtctgccc 163680
gctgcggctc cccatctccc cgtggatcag ctgaaagaag gcgatcgtct tctgcgtggg 163740
aaacagtatg tccgccgagt ccgtcaaccg gggatccagg tacgacgcga ccttcgtcct 163800
caatatgtca tccgcggcca agatcgagcg gatcgtggac aaggtgcgcg ggttgagcgc 163860
ctgcacgttc tccgaggacg acctgccccc ggggtggttc cgccgcatac tgtcggccga 163920
cggcagcagc gacggcgacg gcgcggcatc ggacgctcag ccgagcggag acgcgtcgtc 163980
ggggcccggg acgcgtaacg tcgagatacc gttcttcccc ttcaagaccc tgctgatcac 164040
gggcacggcc ggcgccggca agacgtccag cgtgcaggtg ctggcggcca acctggactg 164100
cgttatcacg ggcacgaccg gcgtggccgc gcagaacctg agcacggtcc tgaataggac 164160
caaatctgcg caggtgaaga cgatatatcg cgcgttcgga tttaatagta agcacgtttc 164220
catgacggag accgttctga cggctccgg gacgcgcgtc gcggacgggc cgggcgcgcg 164280
gcggacgatc ctgagggccc gctcgcgcac ccccgtcgcc gagcagcagt gtcgggacct 164340
gggcctgtac tggcccgtgg tggaggacat cgcctccaag cacctcggcc tgaccgacaa 164400
gaaacggtcg tcggaacgca gcgaactctg cgagagcaac gtgatcgtga tagacgaatg 164460
```

cggcgtgctc atgcggtacc tgctacacgt ggtggtcttc ttctactatt tctataacgc 164520
gctgtacgac accccctgt acagacggag gctggtgccc tgcgtggtct gcgtcgggtc 164580
gccgacgcag accgaggccc tggagacggc gttcgataac aggacgcagg cgaagacggt 164640
ccgtcgaggc atcgacgcac tgaccgccct catcaccgac cgcgccctgc tggaatactg 164700
cgacacgctg aacaactggg tcatgttcat caacaacaag cgctgcacgg acctggactt 164760
cggagatttc ctccgacacc tggagttcgg cctgccgctc aagccggagc acgtcgagta 164820
cgtggacaag ttcgtgcagc cggcgcagcg catccgcgat ccgtcgtacg cgctggacat 164880
gaccagactc ttcctgtcgc acgccgaggt caaccgatac ttcaagtccc tgcacgacaa 164940
actccggacg gagaacagcg accgtctgtt cgacatgccg gtgtattgca ttgtcaacaa 165000
cgcgaatttc gacgagtatt gcgatctgtc ggaggccccc gaacagctac ggcgtccgga 165060
agcgtggttt cgcgccaacc tgaccaggat catcaactac tctcagttcg ttgaccacaa 165120
cctgtctgat aacataacga tagaacgtct cgcgcaccag gacccgtcgg gggccgaccg 165180
cgacgacggc gagcgagctc gttacgattg ggacgccctg ttcgacggcg acggggacga 165240
cgatctcgac ggcggcggcg acggcgacga ggacgcggcg gtggggaggc ccaaagagac 165300
gctgctgatg accaacataa cgtacatcag ggacagttcg gtcggcgtga ccaccaagac 165360
ccgcggatgc gtgataggct acaacgggac tttcggggac ttcatgaacg tcctgcagca 165420
agaactgttc atcgaccgta ctccctgcga acaggccatc cacgcctact ccctcctctc 165480
gggtctgctg tactcctcca tgtacagctt ctgcatgtcg cccttcgcca cccgcgaggt 165540
gctgcgcgag ttcgccgaca tccccatgcc gttcataccg gccctgtgca tgggttccga 165600
ggaagacctg gagatgtgcg ccgcggcgga cggtgcgtgc ggcgacggcg acgcatcggg 165660
ctttcacgac ctgtccgccg tatcctccga gccgtcggga tccgacgccc gcgagcgaac 165720
ggaaggagga ggagaaggag aaggagatga attcgacgag atggaagtat cggacgcgga 165780
tctgctcgcg tccagcgaac tgtactgcga caagttcttc tccaggtacg ccaagccccc 165840
ggcgacgagc tgcctgctgt tcgaagaggt cgtgtacatc tacacgacgt tccgggacat 165900
cttctcgaag cggttcaaga tcatgcagat ccacagcaag ggcaagttcg gcaacagcaa 165960
gctggtgatg tacaatcgga ggaacgtgta ccagaaacgg tcgtgcgagt tcgtgtctca 166020
gaccggatcc ttcgtcggca tgatctcctt cgtctccccc gtgcacagct acgtcctgga 166080
gggcttcacc tatagcgacg tgctcacgct cttctcggac acccggcgca tccacccgcg 166140
cgtgctggag cgcgggctgc cgcggctggt cgtcagggac gcgctgggct tcgtgtacgt 166200
gttggagtcg aacatctcca agttcgtgga ctccagctac aaaaagagcc tgcacatctg 166260
cacgaccata gaccacggca tcacgtcgcg cacggccatg accatcgcca ggagccaggg 166320
actgtcgctg ggcagggtgg ccatcgattt cggggacaac ccgacgaacc tgaaactgag 166380
ccacatctac gtggccatgt ccagggtggt caacccggac gacctcatca tgaacctgaa 166440
ccccatgagg ttcccgtacg aaaagaacac gcacatcaca ccgtatatct gtcgcgcgtt 166500
gaataaccgc aacacgattt taattttta acgataacgg ggagggggtg cggggaagcg 166560
cgttcgacgg cgtcgtcgtc ttcgtcctca tcctcctcgt ccacggcgac gacgacgatg 166620
gcctcgcgac gccgggaaag gggaaatctc tggagccggt cctcgggaaa ccgggctgta 166680
agataaaaat cgataataaa aagacaagag ggagcgagcc gtctgtctgt tcttttcttc 166740
cctaaatcat accttgttac agatatttgc tagaacggtc atatgctgag aaaaaacaat 166800
gaatacaacg ataattaaaa gattctagtt cgaggtaaca taatcatcag tctgttggtc 166860
acacacggac gcggtgagta ttcgagaaag cggacacaat cggggaaaat agatgatgat 166920
gataaaagag tataccgtag gataggacta cgttaggcat gtccctgata gtcttctcta 166980
cttttggatt ttttcttttt cttttttctt ttttcttttg tctgtctatc agcttggtga 167040
aggctcgctc cgagaaaaat aaaagcttca aacaagaaaa aaaaaatatg ggtccgcggt 167100
cgtatctcga tgtcgcgata cgacctcggg ggagagaaaa atcgatctgc cgaatcgtaa 167160
acgccatcca tctcgacagc gatgatatcg ttgtttgctt gtttgtttca tgtgtatatg 167220
tcggcatcat ctttttatac actttttttat tctaagaaaa ataacctcat atgttactac 167280
gcttcccaat gtaaaaaaaa aaggtggatt gcttttggac aacggatatt aataatagta 167340
acggtaatat gtaaaagatc aaatgcgatt aagcgtgcct caaaagggca acaatgcgat 167400
gaaacaaacg agtaaccatt aaaacattaa cagcacataa gtagtttcct gttttatgag 167460
cgcttctacg taatgtaaag ttattcggtg agatcattag gaaggagaga ggtcagcaaa 167520
aagacggttt gaaacgggta ccgtgcaaga tccacggcga cgatgatccc ggagacccgc 167580
gagaaagaat ggaaatgaaa accagcactt ccccatagcc tcggaccagc tcacagacta 167640
cggttctctc gatcgcgacc ccgttcgccg aagtaccgcc gataaacgat gtatacggta 167700
tgaatggaac aaatgatgga ttaagtaagt aaaaaagaaa gatttcgatg attaaaaaaa 167760
aattatagac tagtctctat agaccttcca tctcaaaaaa agttagtgct agttaactcg 167820
ttagttattt agttaatttg gttagtttag ttagtcactt agttaattgg tcagttagtt 167880
acatctcccc aaacccggcg taccgagata tcgctatgaa caaggggagg gggaaacgat 167940
gagtatcagt aatgatagaa aatggtatgt attattttct cttttcgtca taaacaaaaa 168000
caggtatctg cctcattgcg cgactacctc gggtagatcc ggcaatttgg tttttgtcca 168060
gtttcactta aaatataatt ggcattatta gtttctatct ttcgtagttt ggtgaaaacc 168120
gaaaaaaaaa gatcttgata ttgttctatc gtgttattgg gtgtaatatc tattttcata 168180
aaacaataat gatatataaa ataacgcttc tcccctcttc ttgggctagg actgcctacg 168240
tgaagcggga cgtatgatga aacagtgaca gaaaaggttt tacatgtata tagcttcaga 168300
aggtagatat gatgttgaac aatctggaga tagtaggaag atgatacaga tttaatgcat 168360
ttgtttgtct tccccggtca tcatatgtga gtgaatatgt acaatacact atgtcgtcta 168420
aaagagtcga tgtgcgtcgc agtatacccg tctcacgtct gcgggtacgg ggacgatgat 168480
cggaatggtg tgatgatata aaattcgatg cgatgagacc atgcgttttg atgtcacggt 168540
ggatacgact acgaaacctt tcggcgccag ttttgttgga agatcatggt atgtatcgaa 168600
tttgttccta ttgtctggat taaaggagaa aaaaaaagaa ttcatacctt ttgagaggag 168660
acattccgtc cttggctaga tgaggtcata atgtgatata gtagtcacgt tcttctagaa 168720
taggcttttc tgtgttatta attactcgtt atatgacagg gtcgttacac acgataccgt 168780
cgccactatt tcacgtaagt aagagggaat ctatgtgtaa atgaatacaa gggacgtggc 168840
gttccttata gtgaagggta tcctcgcaag gtgttcctag agagacggcg cgaccgcgag 168900
atcacggtcg cgcgtccgat gatgttctag atgaaaataa aatgcataac tatcatcaga 168960
tgttactctg caacggatgg tggagacata ttcattaata ggcaaaaaaa acttaacggg 169020
ataagaaaaa cggatggagt aatcgtaccg tcatatgcgg gaaagaagaa gaagaaacaa 169080
aatctattgg ttgattgaga gaatatgttt gcgataataa gggtaatcct tttagcgaag 169140
aagagagata tcgacgtaga tagatagata gacatatgtt atcatcacta tcattgattc 169200

-continued tgttttttga ggtttctttt ttaggaaaga actctattat tttttactcc gaagcgattc 169260
gctataataa aacattaagt ttgcatatct agctaatcgt gtttccgtga aacattatgt 169320
gaatggagat tgtttttatt tttacatatc ttcatagtaa cgataaaaat aaaattcgtt 169380
ttacataatc atctgtcatc gatgtaagca ggagtaattc tatgtagatc gagatggaca 169440
gatagctaaa cgggtgcgta ccgtccgtct caatcgcatc gtcccgttgc gacgtgaaaa 169500
gaaaagaata caattgtgtc acttttagat caaggatcgg tacaattctt ctgtctttat 169560
acctgttacg tttttgtgtc agcttctgca ctgtatcgct aagtacatat gtatcgcggg 169620
acggtgaaac aggcacagat ttgtaatata ctatgtaaat aacaggcaag agaaatgaaa 169680
agaagcctta ttctagaaaa tgagatgcag taagctatac gaaaaagaaa tatcgtcgta 169740
agatatatga tgttttcgtt gtgttctggg gaagaagata ttctgatgaa aatcaacgcg 169800
atgcgttaag gatagcgttt tgcgatgtaa aatggaagaa aggggggaat gtcgaatgct 169860
atctagatta cgatatgcaa ttgcttggat gagcgtataa gattatcatc aatcctggac 169920
ttcgcggtct tgtaacgagt ttcgtaaaaa gaaaaaacaa aacgagatca taggagacgt 169980
aggcagattt catgctaacg ggatacgtaa tgtaggaagt gttttttttt tttttttttt 170040
tttttttttt tttagcttac gataaaccgc ggggaatacg gatcggctac ctcgcctatc 170100
gtcgtaatca tctgtagaga atatatatat tttctaataa atccgtcaat aaaagtacta 170160
gacatttaga atttagttaa tttttcgtgt gaagagaata catcgtgcgt atgcaaaaaa 170220
aaaaggacgc gcgtgacatc cgtcacgggg cgactcataa gcgataggtg gtggcaatcg 170280
aagaagaaac gatatctaaa gcgatttctc gtaaatgaag aaataatata tcagagaatg 170340
cgtagaaaaa agcagagttt ggatttttccg ctgactaata tactaattat tttcgagaaa 170400
atctctcttt ctatgcgttt aagaaggaat acgacagtat ataaatggaa aatctgtgaa 170460
aaggatcatg ttattaaatt tatctctgat ttttgtgaaa caagaataag agatcgtgtc 170520
actgtaacgt gttatcatca catcggctag gaagatcggt ccaccgaccc ttcctacata 170580
cagatcggac aatatattgt atctacggtt agtgcgatgg acgagcgcaa atgcggagag 170640
cgcgaaagag taccgtgcaa atacatatag aacgttagta gagatgatag aaacaaaaga 170700
aagttccttt ttccttcttt tttctatcgg tttttagaaa tgagtttcat agggttatta 170760
ttttgtgtat ctgtttctat gcgtacgcgc gcagagagac cttgtcattt ttgccataga 170820
gtgttttgta aattctcaga tgactgtatg tatatcgttc tccaatacgt cgaaagaata 170880
aactgtgaaa atcatcatca ctcagcatca accgatacga catgggaaaa agagatcttt 170940
ctacgcgtat agtctattcg caggatggcg atataaattc cgaatagcgg tcgatctata 171000
cgttataagg aaggctaacg attaaagtaa aagaaatcgt aatttatcgt cttacttagc 171060
aagaacctaa ggtgagaata cgtgtttgtc tactatcaag aaagacaagg aactctatac 171120
tttgttgatg tactagtaat taagaacgat tattcgatga aatataacga atatcttgtt 171180
ttttagtagt gatgaaattt cagacatgta gtatgccaaa gcatcgttgc gaataaagac 171240
gggaaagaga gacgccacga gcgtcgccgc cgctccgatc gtatcgcgat cgacaccagc 171300
gattgtctaa ttcaatacgg gttattccgc ttgcgttgtc tatagagtaa aactgacctc 171360
ttacttctac gatgaatttt attcgcaata atgtctacga gaataacgat ataaactact 171420
gattgattgg caaatatatt gtatctggta tgctaacaat taatagaaag aattatagtg 171480
agtttgtctt aataaatttc tactattcaa aaaaagataa atcatttccc cgctacgtta 171540
ttaacgaact aaatacttat tcttaactac cttaggattg cgaactataa caaaaaatca 171600

```
tcacgtcttt atctactaag tgtgaatatt ctctaaacgg acttatatct ataacaatgg 171660
catatgtgat cgttaactat gtgtgagact atcgtcaatg ttaaattgtt ttgcgaatta 171720
tccgtccata tagaatgtag aatttctaac taagttttac ttaatcaact atttttccta 171780
catgtgatta tatcgagata tatataaaag atgtcaccct atagtaatga gtcttataac 171840
gtgttagata ttgttaaatc gtatcatcta tagtttttca tgtgcatcac gcggagttta 171900
atctggtttc atgaattggt gatagaggaa gattgtggta tgacttcgat atcgatggtg 171960
atgatgtaat aaagattcgt taacactagc ggctacgaca gtcgaaaagg tcataacttg 172020
ttgtatatct tatcgcagtg tgtcatcttt tccccgaggg gaggaagacg atcagccttt 172080
cgttgatatg agatgatgcg agttgatgtg cacgtagatc ggttcgatcg aaatgtaaca 172140
tgaaaataat aataacagta aaccgatagt aagatcggta atgatgatag ccgaaaaggt 172200
agccggacta cgtcgtatga agcgagaaat atactcgttg tctgtaggta gttttcgatt 172260
cgttttcttg cccgtttatg tccctcgtca tgacggcgta gggtgttcat ccgttcataa 172320
gaaggtaatt tttgtgtgcg aatattacga gaaaaagagt tcaagagatg ggtccggtgg 172380
ttagctgatc tcttctgtta taaaagtagt tttatcaata taattcagta tttgcattca 172440
tatattttct ttttaaacga cgaatgatcg tatcgacggt ttaaatcaca acaactatgc 172500
tatctcgata actcttaaat cggaggcgtg tatattctcc aggtctgtaa caatacaaat 172560
cacacatgta ataaaaaagt gcctcattga tctttacgga tgacagagat gcatttcgat 172620
aacgtatcat cgatagatga acgcactaag attgagatga gttcacgatt actatctacc 172680
tcattggtat agtgttgttt ttagtcgatt attaaagcgc tgctgggttt aatcgatcag 172740
tttcagggaa aacgtattct gatttatccc cagtttaggt gtttacagta aataaatagt 172800
tttaatacat gtcctttcta gataaaattc gcatagactt cactttttct caggtgaaga 172860
aaaataggca atcgccgact ttcataaatc gaacattgaa agatttaact gtgatatcaa 172920
ctcataaaca tatttaaggt tttatataac taatgtcttg caaatagatt ggatcaattt 172980
ccataatgaa aaaatatcat atatccgtat tcatttgaaa cgataggcaa atacaggctt 173040
gactcgatat cgtgttatcc aatgatgagt tctgcgtcaa gatcgtctca agctgtccgt 173100
cgtcgaacaa acacgctgac atcgttactt ttcttttttt ttaattactt cgctgtctac 173160
atgtgggcga ttcgggtttt tttttttttt ttttttttgg taattaatta tctagcgagt 173220
cgtaccccat cgacggggcc gtatgtttat tctttttttct tttgtaatcg gaagccgaat 173280
agaccgctcc tatcgttccg cgtggcggtc ggactgcctt atctttttct ttgttttttt 173340
ttttttggtg tattattagt gaatgtatat aaaagagact tgtacaacaa aacattttgg 173400
tttttttatat atggaattat actttggcta ttatatcgca ataacatagc atagaagcct 173460
taaaaatggt ctgtcccttc gtttggagat gctaatgtaa aattgcatcg cggtatcatg 173520
acgagtcccg ctatatcttt cgaaaataat gaggatccgt accgtatacg aacggaatta 173580
tacaaacaaa aacattttat atgtgcttat acgttccaca cggtcgtcta tgcaggcaga 173640
catttgattt ggaaatcgtg tcacataaaa agtatgagta tcgcggtttc gtgtatggac 173700
ttaaatacgc tcagattcat accatgctgt ttgtcgagaa aagaattaga aatgtctagg 173760
acgtcaggaa gatcagatga cgatcggttc gtttatgaca tccgaacgtt acgaggcgta 173820
gagacacacg atattgaatt cgtcttttct acatgtatca aatgttgtga ttcaaagatg 173880
tttcacggtg tatgataact tatgagtgca taggatttat gacaaatggc cacaacatgt 173940
```

-continued

```
acttttttatg tatctagtac tcagtgatat attcgtccct tgctcttact tcattatcaa 174000
tttaaaacga tctgcgtctt ttcagaaatt ttttattaaa agctcacgta cgtatgatcg 174060
tcattgacga gacggacacg atctagtgct cgtgtcggat atatcgattt caatcagcta 174120
tctttccaca ttccagtaat attaatatgc tttatttctt ttcttttgtt ttcgggattt 174180
gctgtatatc atataaatta tgtcgttcgt cgatctgtct ttttaagcaa tgaatgtttt 174240
tcataaacac agaaaggata tttgtatatg aatagaagac ctgtaaagag tattcaatta 174300
tctcttccaa taaaacctct ttatataatg atacgacgaa aatcgtcatt atgcctccga 174360
atttcacaat tacttttttg ttaaaaaaaa gcatgcgtta gtgaattcct tgctcgtcaa 174420
aaataatcga ttgagggctt acgctattgc cgtttgtacg aagatagcgg gaattttttta 174480
tgctgtttgt ttcataccgt gaacattttg aaatactatt agtctttttt attattcgct 174540
catgttaagt cgcatcataa aattagaggg acagatccgt aatagctcaa tagttttgaa 174600
atagtgattt agaaggatct ttgataataa aaaagcgtct tttttgtatt tgtgtcagta 174660
tcctattagt ttttatcttc tgtacctttt ttccataatt cgtagtagtt agtatagagc 174720
tcaaatttgt tttaatgttt ccgtacgata aagtatcatt atcatctatg cgagatgaaa 174780
ttgtgtaggc agataacgaa aaagtttttt gtttactcct attattttct caatgtcgac 174840
tttttaattc atcttctttt gttttgcaac tgctataata acatattgtg cctttttttag 174900
aatggtttta ggagaaattt cttttaaaag atgctctata attttttttag gtgacaaaga 174960
taataacgat gttcgatggt atcgcatatt acatgcatat actagttaat ctcctttgag 175020
atatttgtgg attctgtgat gtttgaaaat atcccttgtt ttttaaaata taaaacgaga 175080
tttaacgagt gaatgaatta cgggaatgat cattgaggat caaatgtcat tatactttaa 175140
tctttttctc tccgatacct taagaaaaat tgtaacattt ttagctaatg aaatgatttc 175200
accttgtcta tactatacga tctatatact gtgtcaattt atgttcaacg ttcgttcgtg 175260
cggtcacgtt tgtccaatgt gattgtgtga attgtgagat gatagagggt ctatcatctt 175320
cggtttgtaa caaaaaaata aaattcgttt ctggcaaaac taatctgtct gattcggttg 175380
caccttatgt tatggtaaaa aagattagtc ttctcatttt ttctgcttct attgtgacat 175440
aaggttgtaa aacgtcatga tcttatgtaa tcatattatc aaaattgtgt ttagatggat 175500
actatatgaa aaatcttacg agatggattt ttttctttac tttttaaaga atatagacac 175560
ttctaaatac cgatctcaac ctttcgctta ggataaaaat tttccataaa cttatgggag 175620
agggacagat cgtgaggtcg tgaaggtaag agagggaata tacgtataga tggtttgtga 175680
tgatagaagc atcagataag aggtgtcttt ctctgtctag aaaaacaaat atataactat 175740
ggctatgctt gaaagatttt ttgaaagatt acaagagttt ccttgtaaaa aagtaccctt 175800
ttctcgtaag tttgatcttt ttgtacctac ctatggaaga tttccgtcgt acgtgacgtt 175860
tgcgggggac accgtcctcg gcacgacgat gcgtcggact tacgcgccgc cggtgatgat 175920
acgtcgtcga gcgtctcgcg gccgcatcgt cggaaccggt cgaggcggat cgtactctga 175980
accgtttgtc gtcattatct tttaatatgt cgttacgata tcgagaccgg agtttatccg 176040
agcgagtcgt accgttcggt atatatatcg aaccgttcta atacgttatg gatttcataa 176100
cgtaaccgtt acatcgcgcg aaaacccgtg acacgtctgt ggatacggcc gtagcgcgca 176160
ttccgagagt agggttcgga tacggtttcg gagccgcatg tcggccgtca cgtatcgccc 176220
atacgatccc tgcgtatatc acgtccgtgt aaccgttacg ttttacggga cgtatccgtc 176280
gaacggtccc gtgaacgcgc cgtagacgac acgtattccc gtaacgtgtt cgatccgcgt 176340
```

cgggtctcgc atgattcatc agagtatcat cggggcggcc aatcagtgct tcgcggcggt 176400
tggccgcggc ctgggcggga atttcctgga cgaaataccg taggcgtgct tggaaaacac 176460
ggtcttatat atatcgagtc gcgagtcagc gggcattgcg tctccagagc tctacatgga 176520
cgcatcgatt ttcgcgtgag agacggcgat cgaagaccca caattatttt aacgacgatt 176580
ttcgtctaga cgggcctcgc gtccgggctc cccgaggacc ggatcggttc tcccgatccg 176640
gcgacacgcg aaaacgctcg ccgcgggtcc gctgacaacc gcgcaccatt taccttcgta 176700
tttaaacgcc ttaaagacgt tacggtttaa cgtccggagg tataatggtg gatgagaaaa 176760
tgacgttcag caggacttac atcacgttta gcggcgtggt ccgcacgctg caccagagca 176820
tgagcaaggt cttggaggta aaacagtact cgttcgacag cgcccggatc tttgactgta 176880
aggagggcaa cggacgtacc gagacctggg gaaaggggtg gatgtgcgtg acggtggttc 176940
agaacacaga ggcgcccacg gctccaagcg gcgggatgca gggcttcatg acgatagaca 177000
tcacggtgga cgacagtctg gtcgacagca tgttcttcaa gggcaccgtg gtgtccagca 177060
agaccgcgtc ttctgtggct ggcaccacga ttcagagcaa cggcgagcag aggtcgagtc 177120
tcgtcaccct cctgtccgac ggaggctcgt tgcaattcac cagagtcgtg cactgcttca 177180
ggggtcacgg acacgcggcg caccccggct cctcggcggg ccccgtgggg tccggcggat 177240
cggtggcgcc cggcgcctcg ccggccgcgg cgacgtcttc ttcgagctcg gatcagggcg 177300
aggatcgtcg tcgcgaccgt ccagaccgac agcaacagga cgacgaccgg cgcaagagac 177360
ccggttccgt cgacggttcg caatcgacga cgtcttccaa cgggccatcg tcgagcacgg 177420
gatcctcatc gtccagggtg gaccgagatc cccggatatc ggcaaaacag aaagagcgca 177480
ggagacaggc cgatgacggt aagttacgtt acgtgtcgag ttccaccgta gtgatagtat 177540
cgattaattc tcgcgacgcg atactgagcg ccgccgtctg atctgttgtg tccccggttc 177600
cgcaggctcg ccgcgatcca gcggggatcc gatcaaacgc ccgaaaatat ttcacgatgg 177660
cgggagaccg gacaaggaga ctgacatcgg ccgtatcctg gaaaacagcg gaaacagcag 177720
cgacgcggtg gccttcttga actataccaa cggcattccc gggttgtcgt ccagcgccga 177780
cggtgcgtgt tgtgtggagt gtgatgattg ttgtgatgag gctgatgatg atgataacgt 177840
taacggcggt cgttggcctc ctcggatgcg taagtccggg gacgacggcg atacacggga 177900
ccgctcgccg acggtcgggt atcggtcggt cagttgtaac gggactcggg agggacataa 177960
aaaggccaga cgtaagacta ataatatcgt aagcggagcc ggtgacaccg aggcgctcgc 178020
gacggccgtc gacgcgacat cggtgaaggg ttcagagacc gatacgatcg ctgcagggcg 178080
attatctaac atcgatgttc tcccgcattc acaggagaac gaaccagcta gacggtcact 178140
gcgcgacgac gacgtcttac attttttatc gaccttccta gatgggaccg gtaaatctat 178200
aagcgcgccc gcaacgaacg accgcggtcc tgggtccatc gagatcccgg cggcgaacgg 178260
cgtcgctccg caatccgacg agaggcgtca cgagtcggtt gacgtggcca cgtctccgtt 178320
gcggcccccg agaacgccga cgatctcacc taatccgtgt actcgggact ttttttttcaa 178380 gtgtgacgcg caagataata cgaaacccgt ctgtgagatc aaacctttca tcagtctaga 178440
ggcggtgaga cgagccaacc aggggtcgac gagacggggc cggggacgcg ggggaaggaa 178500
cgtcgccacg gtcagatcca gaagacgcgg agacgccgcc ggggagacca gcggtacggc 178560
gcgaaggacg acacggagcc gagggaacaa cgagacgctg gtggcggagg ccgtggcgtt 178620
cctgtcgcag gcgtctaacc gccgacgcga cgccgacgcc gacgacggtg cggaacggaa 178680
cagcgcggac gactcggacg gtcaggagcc gcacggcgtc cgggaccgac tctcttccca 178740
caccgaaccc gcgacgtcgt cggcgtcgtt ttcctcctcg tcgagcacca tatcgagaca 178800
accgtctctg gcggaggacg gtttggaaat agtgggggac gtggagcaga atgacttatt 178860
ggacgagatc gagaaccagg cgtctaggat gagcgacgaa gccgcgtccg cggccgcgtc 178920
tctgatggac cttgaccttt tttaactgac ctaaaccggt accaagtgta tgtatatatg 178980
aacatatatg tatgatactg atttttacgg aaccacttgt atgacggagg tgtgtgtgtg 179040
tgtggggcac tgtgaaataa aaaaataaaa gacgtcgatg cagtgagtgc caatgatagc 179100
gtctttattg atcgatagaa aacgtttaca cgccatcccc gtcgtcccgg ggctcctcta 179160
ccagtacgtt ccaatcgacg gccgttttcc cacgagagga aagatactgg ttcgctttga 179220
caaagtgacc gttcccgacg aaagcgtatc tcgtggccgt aacgcagggc gaagggtgat 179280
aggacttcag tatgagatgt tttccacctc cgaggaggta ttctttctcc tgagcgtggt 179340
tgccccataa catgaacacg aggtcgttct tgttcctggc cagagcggat agtatcttgt 179400
tagataatac gttccacccg acgtgctcgt gagacccggg tttcccggcg cggacggtga 179460
acaccgtatt gagcagcaac accccctgag cgcaccaagg atccaggcaa ccgtgatccg 179520
gcgtcttaaa gtcgggcatc gacctacgca gctctttaaa aacgtttaga agagacggag 179580
ggggcctccg accgcggacc gttccgaaag cgattccgca cgcggagtcg ttgggatacg 179640
gatcctgtcc caggatgacg accttgacgt cgtcgggtcc gcagagccga ctccagcgat 179700
gtacgttgtc gtggtcggga tggatcacgc actcgcaccg ctcgtgaaaa acggtcttag 179760
tcgtacgttt cagttgatcg tattcaaaag cgttcaggtc taagaaacgt aaccacctct 179820
cgtctatccc gagctgtctg gcctgctccg tcacatcgac gtccagagat cgagggatgt 179880
cgtctaagat gttagcgatc atccaagccc tcagagccat cccgagtcgc gctgaagacg 179940
gatcgacgtg cggtctgcgg agcaacggct ggagcggccg ctgtatcagc tcagatccct 180000
gtttaagtaa ttgtgtatgg gtgcgtcacg gtggggaccg ctcaatgaag cctgatatag 180060
aatcaatcgt cttacgacat cgacatttcg tgcaccgatg gatctgaaaa acgtcaagac 180120
ggtgttatac agcgcgtcga ataacgtaag actggtggag gtgattctga ggaccttggt 180180
tatcttgggc ttggtgttgc tcacggcgat caacacggac atgttatgcg ggggcgctcc 180240
tagatcgaac ccgacgacgt tctctaagaa tatatctttt ccatacggta attcttccag 180300
gttgtattgt tgacactttt cttctacaca cgtgtagatg ataggatgat ctaaacactg 180360
actataaccc cgcatgaatt ttacccacgg tggcgcagaa tcggatctga atatcgtaag 180420
gagcgttctc agttgatttt cgttgttatg taggagactc actatatcca aaaactcacg 180480
atctacgtgg atgagtttat cgtgtcgcag atcccaggtc ggtttctcgt atcgtatcaa 180540
ttccgagtac ttccacctgt cggatatata aaaaaacgtg tggttactaa cggtcgttct 180600
attataagtg tccgaattgg cgcacgatat cgccgctaca gtacacgcgg tcttttgtcg 180660
ctctccgagc gactccgaca aactcgatat agtcgtcaag acgataagcg gtatgtaaaa 180720
tccgatcgtt agacgatgcg aaaaaaacat acattcatac attgcccgtg attaatctag 180780
ttaatcctat ctgatatcga ttcagatcag tgatcatatc gtaccacgtc tcggataaat 180840
ctaatcgttt atatattgta gtcagtgcgg aagcaagtac accgggattt acccagatga 180900
tgagggaatc gctgagggtt agaaacgcac cgtgaccgta accgcatatc tgcggagtga 180960
acgatacgtt aatcgccagc agaaaggcgg tgtaatcatg taaagattta ttcgaatcac 181020
acgtcacatt tagcgtgtct acgctctgct tccattcgat gtatgagccg tacaccgtcg 181080
gtccctcatc gatcgtttcc tgtgataatg aaaagttctt accgtcagcg tcggtgtcgg 181140
tgacggtggg cgaatccgtg cgaggctcat cgtacccaga tccgtcggaa tttccagacg 181200
atacatctat atcgtccttt acaggcgtag taggttcgtg tacattaatc gtagtcgata 181260
ctcccgcgac atgtttggtc acgccgatag ttccgacaac tttcggtgtc gtcgattcgg 181320
tcgtgtatga tatctcttta gatacgttat cgggtacctc cggtgtcttt gatacttcca 181380
atactttagg tgcctccgac gcttccgatg cgttcggtac gttcgatgtc tccgatacgt 181440
tctgtgtccc cgataccccc ggcccttccg acgcttccag aacctccggt ttactggttt 181500
tgtcggtttc ggaggtctgg gtatcggaaa ccgtcacgta atacaattcc gctccactaa 181560
cgggttgtcc cgtgacgggt aacgtcatcg acgatactcg tgtcgtcgct aagaacgtta 181620
cgcatatcgc cacggtgacg atgagcgcgt tcatgatcga ttattcgacg gagatcgaca 181680
cccgatatgc cgaaggtttt gtgatccggg gcttcctagc caaatgtgtt atttttataa 181740
tctacatgag cggtcttacg ccagaacgga aagagcacgc gatgaccgct cgggaacggg 181800
ttaaacgggg cacgggaaaa taagtacaga tatacacact tcatttaaac atagcgtttt 181860
tattatttaa tagtattcac gcggacgtcg acggttgcgg ctttctcggt actttctgtg 181920
tctgcgatgc gtacgccgtg tatatcgggg cgtgaaacga cgttaatagc gggaacgata 181980
attttgctat attcaggtcg aatagatccg gacggtgttt cgtgatccct atgcacacgt 182040
gtaacgcgtc gaacagttct ttggttgtag cggccgacac gaatagcatg tgcatgccgg 182100
acggcgaggc gttctgcgag accggcaata gttgcacgcg actattcggg tcatagtctg 182160
gatggatatc ggtcgagttc agtagcgctt cgtgaaacct ggcactgaca tcggggtttg 182220
ggagcacgcg ttgtgtcatg gtttgcgaac tgccgacgat actgatgttt atgactttag 182280
agagggcttc tcgtagtgtt ctcatggatc gttcacacga acagctcact tgtatctgaa 182340
ttagtgtcga gtcgcactct ttggccagcc tggttagttc tctcaaaata gaggcacatc 182400
gctcatcgtg attcaccgta tgtaaccgta tcaacatatc atcgcctcgg tcggtcaccg 182460
tcgagacgtc cacaaatctg catctcgggg acgtcagtcc cttacccaat accaaagtat 182520
cgtctttatc ggacttgttc gctctatagg atttcgcgtt acggcgatac gggtgccgca 182580
ggataggtat acgtttcttc gacggggttt cgagtgtcgt gttctgttga tattcccggt 182640
gaggcatatg aatctctcgg tattcgggag gaaattttct agaattcgga aacctcggga 182700
agaacgacgc ttcggataca tcatcgtttt ctaacgactt cgcgtgacag tcgcctaggc 182760
tcgtcgcgtc ggcgccgtcg tcgtatacga cgggggccgt atcggctacg gcgcaaagat 182820
cgtccacgcc ggggtcgagc atgaacgagt cgtccgtcag cgtttcaaaa tcatcgcgta 182880
tcgacctctc ggtgtcatct aacaactttc gaaacgtatt caggtccacg gtttgtatat 182940
cgttatcgtt ccccgcggtc tcgtcgtccc tcgggatgat ggccccgacg gcgctcgccg 183000
tctcctgatc gatcggtacg aaggtggcgt gtcccagacc tttcatcgtg gagatgttta 183060
agcgcgccat gccgtaggac gcgaacaccc gattaatcgt acgggatacg acgacgttag 183120
ataatgccga tacgcaattg atataactag aaaccaccga accgcgatgc gggggatgta 183180
tttgttgcat cgcgaagagg gcggtgacgc cttcgtcatt gggggtccgg taagcgcgcg 183240
tcggacgcga gcgtccgtcc atcgaatcac gggtatctca ttttgatgta actgatattg 183300
acgggtctga accgacggat gatatatatc accgagccga ctaagaatac aacaaagata 183360
gctaccaaaa aagttctccg caagatttcc accaccgtta ttgggtcaat aatgcctaag 183420

```
aattggacaa atgtgagacc gtcgtagctt atattagcgt agaaggcaga cgcggagcta 183480
tctgagtaat agaagacgaa tgtagtgtca tttccccaga ggatcgtctc gctggcgttt 183540
aacaccgtat cgttggcatt ggcgagtacc gtgacgttgc cgccgggcgc gttgagtccg 183600
acgagcagta tggtctgcga ccacgcgggc ttcaccgtga gctccgcgag tagagtgacg 183660
aacgtccatt ctccgctata gttaccgtac agtcctctac acgtacacac gaaacgttgg 183720
gtggccgtca cggaaccgtc cctcacgata cgtatcgttt tgttttcata cgtaaagttc 183780
aggtgacctg aaagcagaat aaaaacggtt aggggaccgg tgtcaggcta gcggtccgaa 183840
cgtatgaaac acacgtaacg tcttaccggc atgggccgtg tgattgatgc cggtcgtctg 183900
tatcgcagcc acatgggtcc atgtcaccgg gttcgcgccg tcccgcagat aacagtgaat 183960
atctatgatt tccgagatat tggtggtctt aaccgcacag gtcgtagcga cctgagtgcc 184020
tctaacgtga tatgtatcgc gacacgacac gttagccgac tcgacgatcg tcgagcacag 184080
gtacacgcac actacaacac acgtcgcgaa tacgtttgcg gccatcgcgg tcaaagcgta 184140
ccgcggggtc cgatcctcat ccgtgtcaga atcgtaccct cataccggac cacccggccg 184200
cgcgcgtggc atgtcgtgca agtctaaagt gcgatcagga caaccggagg tctaatgtat 184260
gcgcgatgac cgcgtctgag gatgtcgtac ggacggtgat cggaattcca tgtgggaata 184320
ccgatacacc cgaacgacct atcgggaaga atccgacacg aagagcgacc gaagacagat 184380
acgacaggac acatataata ttagcgctga tgataattta tgtgtatatt atatgattgt 184440
catcgtgctc cgcgcgttgg tactgtacgc cacgtcgaaa gaggtctaga gcgcgctgcc 184500
tcgccatcct catggtcaat cttttacgaa tatatttgat aatatacagt atcgcgatga 184560
gcactaacat gatcattaag gtggaaaaca atatcgcggc cccgagagcg aggttcgact 184620
ttttgtggtc attgttatat cgatctctag tcaccgtgtc gttcgtcgat aacagatgga 184680
gggcctccgg gtagttcggc attccgggac aagagcctaa tatgggatta tgtggactct 184740
tatcgattga gatcaacgac ggagtgctag aatcacattt tcttatctcg gtcgcgttga 184800
cggttatctc gagagcacat ataagggtcg cggtggcgtt aatcttaaca acacactgta 184860
cgaattctcc ccaaaaggag ccacttaata cacgttctat aaatattacg tatataagtc 184920
cgtcgccgcg tgttatcggt ctgtcaggac gcccgtctcg taagatatct ctaaattcca 184980
aataagccga tttaggttta aaatcagcca cgactgtgca atttatcttt agtttgtagt 185040
cgtaatacca cacacccaat gatgcggtca gaaacgtata tgtccgcgga taaatgaaaa 185100
acaatatgag aaattgacgc atgatatcgc cgccagataa gacgatatca catgtaaaac 185160
taaacatacg gattgaacga aaccgctcgc tgtctcccca cgaggttata tacgcctcgc 185220
cttgacacgt aacaacacat ccaggggggt atcagccatt ggaatctcgc gctggtgtac 185280
aataatataa aaaacagcat gaaggataaa acaagcgcag agacgtacac gtccgcgtgc 185340
gttgttgtgt ttttgccgga tatggttatt gatgaaaggt taaaaaaatc cgtcggggat 185400
gtcgtgcccg cgacacatcg attggataaa ttacaattcg ggttcgaaac gacaaccgtg 185460
ctttgggaag attttccatt atatcctacg cataatattc tcgtatcatt ctgtacggta 185520
gtaatgttga tgacagagag tgtagacggt ccgtcgtcaa tattttcata tgaattgctc 185580
aaaacggtgt cacaataagc tagtgacacc gttaaaaagc caaattgact gctaaccgta 185640
caatttatcg ttacgttgca accgtggtat gacaacgtta atagcactac cggtggatac 185700
gtctgcgacg ctatcgcggc aacgaacaga tatgttgtca gaagtataac ggccagggaa 185760
cgaggcgaac tgaccatgat ctcgtcgtgt acagccgacc cagaaatgtg tgaggtagcg 185820
```

tcgacccgag tcatattaat acgaataggg ggcccataaa tacacacatg tgtgaattga 185880
ccacagaatg atagacagaa attaagtgtg tcgtaaaaat cgcagcagaa gaaatgaaaa 185940
acaacaccaa cgacatatat ttagatcata atttatatag cagcatcacg gtgtccatac 186000
acgtagaacc gatacggtca tcgaccaata caggcacaat ggacaggata cggccgacgt 186060
aatggtatat accggacacg ttcggacgcc agtccaggaa tacggtcacc tgtcagtagt 186120
cgtgtgcacc ggtcttctgt cagacgcgtc taccccatca cccagatatg cttttaatgt 186180
tgattcgaaa tcatagaggt cgatatgttg attaacggat gtaattatag cagctttcgt 186240
tggaacaatc acgtttatgg tgttattatg agattatcat catacgcagt atctacttct 186300
atgcggcacc ggccgtatat ccagagtact gttgtcttcg aacggcttct tttctgagac 186360
aatatactgt gcagcaaatg atacacgtca acagaatgca gcctgatact acgagagcca 186420
cgactagtat cgcgacatgc tccgtcccaa ccggcgtgac tctaaatgtt gtaagagacg 186480
tcggatatga aaccgttggt ggattttgta ccagaaaccc tttggctgga aatttgccta 186540
ttccatttgc atctagatag gtctgaatac attcaattat agtatcatac ggccaaatgc 186600
cgttcaagca accgttacac ccattaccta cgatcgtata gttggatatg ctattattag 186660
catacgtggt tttgtttcca gttgtccatc caaggtacgt agaattagcg taccattgta 186720
acgtcgcatt gccggcatat gtacagtttg aattgccgca acatacagtc gagtcgttga 186780
agaccgaaac ggtcatgttt ctgttgatac tgagaatctg tgtctcaccg ctgatattgc 186840
acatatacca accgtaaccc ccatatggcc caggcttgat gaccaatacg ccagtgacat 186900
gtggatcttg cttctgatta taattattag gatatcttac ggtaacatta atgttaatca 186960
cagattcatt tttcggggag agccagacgt agcttccatt gacatatttt gtccatgtga 187020
cgttcggggt attcgatgaa cccgatcctc cggatttttg ccatctacaa aagagagtac 187080
atatcgttcc attacattgt cgttcgtgat ttatcagccc tgtagcgtat tggtagatga 187140
taagaaatag tactgattgt ccgaggagta acatgtcttc ttgatggtta tcagtactgc 187200
gacgatgatt ataaagagca ggaaaaaaaa taaagtgatg tagaacggtc cgtcttcgtc 187260
tatgtgcgtt aatatctgtt ggtcagtact attgagcccg agatacttat gtagactgct 187320
atcgtggcca tgaggaggaa ccatgcagat tcgactatag acagatcgca cggatctatc 187380
ctcttgcggt ccttcggtcc gggtctattc gtgatcctca ctatcggctt ggagagttct 187440
ttacgatata cgatttcaca gcttatctgt gagtcgtctg cgatcactat ggtcgacttc 187500
atccttttat ctgttttgtg aaaggtactt gtcaagtttg aagcgtgcgc atcattaaga 187560
tgagtgacat tatatgatac gagaatgttc tcggacgcgt tgatccatcg catgtgctcc 187620
agcccctcgt agatctccga ctcgcaagta aatacgtatt tcatgtcagc ggacacgcat 187680
gaccgcaatg acatggccgt cgtctctcgg accaggagac tcaagagcgt cacggcgccg 187740
gtcacgagta tcgcgtgtat tttacgggca cccatgtcac cggagcggcg gggcatgtat 187800
ctcataagga ctttttccca cgctgtcagt tatatagtag ggcaagcatc aaacgtgacg 187860
cattttaaat ggtcatcata atactttttt attggtgtgc gtacaaaacc cggaactgaa 187920
agacacccaa cccgcccgtc gcccttcgga tgtttcaaca tcctacccgt cccataaaaa 187980
gataacaccc cctcacttcg aacagtccgt tccgcgactc gcgctcgtcg aagcgccggc 188040
ttctggggcc gcggccgtgt ccgccgcgtt ctcgataccg ggagcgttct tcgcggacgt 188100
cgcggaaccc acgcagccct cgtcgctgga gacgtcgaat tggcaagcct cgtactcttc 188160

```
ggacgcggtg tcgtagatcg ggagagggtt gcagcctccg tccacggtgc aggtacggac 188220
gcatacctgt ctgggatact tgttcgatac ggctaggcag atcttcaggg cggccatgaa 188280
gtcacacggg gtcgccgcgt agacgaccat ggtgcggtag tccgaggccc tcggggagaa 188340
actatgcgtg tgtctctcct tcagtttcca aacgtctctc gccgtgccgt tgcaggcttc 188400
tatcacgcgg ttgaccgtct ccttcttgtg cggcctggca taagtgtgct ccatggtgaa 188460
tggagcagag atagtcaggt tcacgatcga acccagatgc gtacgcatcc gatcgatctg 188520
agccttgata tcgctaccgc gggtgaagtt gatcatgatc atgcggttgg tcacccgcaa 188580
ctgtctgcag taatgcatgg cattctctaa gacggagacg gtggaaggac acttaaaagg 188640
caggttcttg tactctaagg cgcggtgtgt ctttctgaag atcctgtccg tgtgctctag 188700
cctgactcgc cccctcttgg tctgaaacgg gggctcgtgc accaacttct tacttatcat 188760
tagggtcctg atcttttcgg aggctatccc gggggccctg tgctttcgtc ccttgccgac 188820
gggagtagga cacggagcgc cggtagcgtt ctcgtcgtcg gataacgata gtgctccgct 188880
cgccggctcc cccggggact tagggcgaca ccgaccggca tcgctgtcgt cgctgtccga 188940
ggaggacccc gacgaaccgg agcacataga gcacgagcac tcgttatccg aagacgacga 189000
ggattccgcg tccacggcag actccaacct ttccctcttt atcttcctgg ctctggcagt 189060
cttttcttcc ttaactgacg ggtgacgaga tcccgctcca tgtctatcgc tatcgtcatt 189120
cccggcctgt cgggtcgcat caggtctgcc atgttccctt tctttcttaa tgttgcgtgc 189180
tctgaccggg gagttggact cgtcattact ccggggacgt ttagcgggac gtgcttttct 189240
gatagcctta tcatctctgc cccgtttagt tgaatctgat ctattcttag ccctactctt 189300
cctggggttg tctttacctt tgtctttact cggtctcttt tcctgcttat ccgaaacgtt 189360
tggagacaga cgtttcggag aggtatcaaa agtatcaaag gtgtcatact ctaacagtct 189420
cagcggctca ggcgggggcg gtgtcgcggt gtcgctatcg gacgtgtctg agttttctgc 189480
gtctatgttt ctgtgccaca actttgtctt gatcggttgc caatcagaca gaccggtgtc 189540
aaaatctgac tccgtgtctg aggaatcatc tatcactaca cactctgggg attttggaaa 189600
cttagatgtg cttggggcgt caatgggctc gggtttgatc tgtgagatgg aaggtgtcag 189660
ccatccctcg ggcgtgtcta cgaaagatta aaggaaaaga gaaaaaacaa ctcaagttag 189720
ggagtattgt gtatttattg aatattgaaa ttgatacaat acatagtata acacgtgtac 189780
atgcatagaa taaacatgtg tacatgcata gaataacatg tgttacatat aaatgatact 189840
catgaaacaa caggcataca taagatacat attgtgggta taaatgagca gtatatataa 189900
tcaagattac tctgtggtat aaatgtcttc atctagctga gtctcatcgc ccgagtcggc 189960
tatgttagaa gtgctcggct ccccagctaa ttcaacaact ttagcgcgtg tcagcatggt 190020
gctttccgcc tttctctttc ttggcctggg tctaagtcta ccagaagtac cctcaggttg 190080
cgacagagga cccgtaatgg gtgtattaag ggggggtaga agtcccgcgt acttgttgcg 190140
caggtacgaa ggaaggcact gtaagaaagc actgctggga ctcacgcagg tcagatcaca 190200
caaggccttc tctataacag gtaacataga ctgcactatg agcgacgcgt ctgtctggcc 190260
ccacgtaaac tgtctgataa cctcctctat gataaacgcg ttcagcgcgt ctaagtactg 190320
agtgtgacgc gtaactgtca tgaagagctt agtggtaaaa tctctctcca tggcgtcaaa 190380
tgatgaactg acagtctcga caatatccgt tctgagtcta gagaacacat cagaatagta 190440
ataatcacgc ctggctacat catccaccaa cagctcaatc aaagtcagtg ccgttttgac 190500
ctgtgtttca ttaaaccagc tatcaggctt tatgttgtta acgaaacacg cggcggttct 190560
```

```
caagctatga ttgtgatacg gcacgtcaca gaaactagta tagtgcagcc aacgccgcaa 190620
catcatctcc ctggtatcca ccacaaactc attgcggagg gaatccagac tattcttaag 190680
ggctttcaat atgagagtat caaaatgagt cgcgtgcgaa gcgatctctc tcaacgcgct 190740
ctgaactaca gcaaaagggg tcatggtctc gtagttcttt agcatacgtt tcatcccttg 190800
gaccatggaa catgtctgct tatttgcatt aaagatactt tcagtgacac gatcctgtct 190860
ctgaagttta acccacacca ggtcaatgca acgtttacat tctgcccatg ccagttccct 190920
gtgctgccta agactatctt gtaactcctg aatgtttcgt ttcatgacga gtaccagggc 190980
gcgaactgta agagataaac aaggggtgtg tgagggaagg aaatgaacag tgtggaaaat 191040
agatatcacg tgatagcagt cttataaatc tcactcacct gcaacagcgc tcagtctatc 191100
gtttgacata tcgcccctgg agacggatcc actggtaaaa ctttctatct ccgcattttc 191160
tgagggtgtt ggttgaaaat tgagatcgat gtctgggtta gttacgaact gatctaagtc 191220
gaacgtgttg ttgactctct ccaatacatc tttcatgaat gtggagacgc tctcgtattc 191280
gtctcggagg agggacggtg tggcatttga cctgtcgagt gcatacgttg catatgaatt 191340
aatgtgatat ataaaaaagt gtgacggatt gttcatgtat aaaagtttag tgtaataatt 191400
accgggtgtc attattctga gagcttgatg cggcatcact tgtggcggca gccccagtgg 191460
atgattctga tacgggggag tttctggacg gggaagtgga ctctctgttt gtttctatgc 191520
tgcaataagt aacatgagca tttttttgtg ttcaggtgac gacgacacgt acaaccacag 191580
acaatatgga tagccggctt tttcggatcg tgtggtgcta cgttatatgc atagcgattt 191640
taactggtgc aagtaatagc accactaatt ctacaagtgc cagtaacgtc actgtaacga 191700
cacctgtcac gagtaccaca aactcatctg tcacggaatt gtctacggtt atgaatgcaa 191760
ctggtacgtc acgtatgaat ggtaacacaa gttcaaaagt atcatcacac gtgtccgagg 191820
tggaagtgtc atctgttctc aagtacttta tatctctgat atatgtcaac tatctgcttt 191880
gctaatgcct catttattac aagaaccata taatcttctc aggtacgact aaacactcct 191940
catatgcaac agcaacttct tcgcgcgtga gagtcagttc acccaccttg gatcttaaat 192000
cactgatctc tgaagtctcc aactctgtta agaattcgac gcatggaaaa cggtcgaaca 192060
gaggcgggag cagcctgcat caccagaagt ggtttcaacc gctaactaca gtggccgcta 192120
tcattggggt attctctgta ttcatgtttg gtatgctatg tcatctatca tatatggggc 192180
gacgatcgct taaaaaatgc caaaaattgc acgacgagat cgtatatgaa gagtcggcgc 192240
ggttacaaga aaatgtacgg acatccgtcg aggtctctcc gcaagacata gctatgattg 192300
atagacttga acgggctttt atgctctgat tcaccttatg gtaatccatc atctataaga 192360
ataataatgg tggattacga tttcaaaacg gatcaaaaat agagagtgaa aaaatcagcg 192420
agtgtgaaaa cgtgtcggaa aagcacttag gataagagct ggtcaaaaat gacatggggg 192480
ggggggggag aagaaggccc ggtcaccaat acagacaccg acttggaagg gaaatagaca 192540
aaaatgcgac catcaccatc aaatcaacat gctgcctaac cagatcacct acagagaagc 192600
catcaccata tagcaccaac actataacct atatcatgca cgtctgtctt ctataaaatg 192660
tgtataaaat aaccggagtg gtttcttacc ttgaattgat gggggggggg ggcagaagaa 192720
ccgggcgtct ggcaaggttt actgtccagg cacgtagccg agaagtaaag ttgaaaaagc 192780
ggtcttaaac agtaaaagcc gagcgcccga cgggtttaaa accgaagctt caaccctaaa 192840
acaaaaaatt aagaaaaaat caaaaaattg gcaaaaatcc aacattggca ccatgccaac 192900
```

agctggcata ttgccaagag tcggggtctc cacttggcac ggtgccaaga gcgggggtct 192960
tcttggcacc gtgccaagtc tgaggtctcc acttggcacg gtgccaagaa tggggggtcc 193020
atgttggcaa ggtgccaagc tcacctggct ggtcctcccg agatggcggc gtccttggaa 193080
gatgtccact tggaagcgtg gccacctggt gaagaaaatg gcggcgctcc gaagcaggcg 193140
tggtccaagg tgcagtcctc tgggcagccg cggggtgtcg ctcctggacg atgtgctctc 193200
ttgcagagcc tcctcgctct gcccggcttc taaaccggag cccccttatat actcataaac 193260 cactccccca tagggtacgt ggaccaatag tggagtgggg cgtgctctcc aaaaatgcaa 193320
agtcaccatg atacagtact tgagcggttt ccagggactt tccagaggac ggtcaaatgt 193380
cagtgaatca cccagtatgt actgccaatt tggcagtaat tggataccgc atgactaagg 193440
aaaaagttat aattgacagg gaaaatcccc tttgtggctg atttgcataa aactaagtgt 193500
aatttactgg aatattggcc ctggaaagat gtacttaact ctgagtgacc ctttccctct 193560
gccaagtgac tataatgctg cccgggactt tccagatgct ctttgccaaa aagaacatga 193620
ctaaatatgg ctgtgctttg tccccgtatc agtttactgt aaatggcccg ggactttcca 193680
cgtttccttt gccaaaagaa cactgttaac tctggctgac cctatcccat gccaatcaaa 193740
cgtcccataa ccgtatccct ttgccaaaaa ggacacagct acctctggct gaccttcttt 193800
catattaatc agacgtccca cgtccaggga ctttccatag accctctgcc aagcaataca 193860
tgactaaata tggctgtgct ttgtccccgt atcagtttac tgtaaatggc ccgggacttt 193920
ccacgtttcc tttgccaaaa gaacactgtt aactctggct gaccctatcc catgccaatc 193980
aaacgtccca taaccgtatc cctttgccaa aaaggacatg actaattctg gctgaccttt 194040
ccccatatca ctcaaacgtc ccatgaccgt atccctttgc caaaaaggac atggctaact 194100
ctggctgacc tttccccata tcactcaaac gtcccatgac cgtatccctt tgccaaaaag 194160
gacatgacta actttggctg acctttcccc atatcactca aacgtcctat gaccgtatcc 194220
ctttgccaaa aaggacatga ctaactctgg ctgacctgtc tccatatcaa tcaaacgtcc 194280
cgtgaccgta tccaccgtgc caaaaaggac atgagtaatc atgaccgtac ttcgtccccg 194340
tattagttta ctgtaatttg gccagggact ttccacatca tccaaattaa tcaataatga 194400
ttacaagtgg acaggttgtt ggcatctact tattcagaaa aatccatatg cgtgctgcca 194460
gcatcaaaac aatgtaatat attcatgaga tcatgattaa tttaatggaa aacacctaaa 194520
aaatccagtc atcatctgga aagcacctaa cgttacgtaa aattttaata tgattcagag 194580
atgggccggg ttatacggaa tacgcctata aaagaggagg agttcgctgg tttagaatca 194640
gtattgtgcc agactccgaa gaggacacat ctcccgtgct cggaatgctg ccaatatatt 194700
aaaagaatag gtgcgtatgg ttatctttga tatagcacag gtagaatacg cgtatagagg 194760
tgacctttac ctgtgagagt aggttagtaa acaaagaatc gtgccagact gaaggtacag 194820
caagtcaatt tatatgtgat agttaataat atagattaca ttgatctgat attgtatagt 194880
ttgacgtgga atgtaggttt gcttactaga tgatcgatag cgcaggctta tagcgtaaga 194940
gatgtgatag atgcgatggt atgcatcggc agtttccgac agatgttcgt actgaattgt 195000
tctaataata aaaatgactt cacgtccata taagtctctc tagtttttct tattggatga 195060
ctgtcgagaa ggcggtaaca tgattgccgg gaaatcattt gcatgtaagc ctccgggtat 195120
cggcccgacg ggatgtggaa cacgcaggtc atctataata tagatatctc gcacaaaata 195180
gcgaccgggc tggctttgag atgtcatgag aagctcgcgt tgatatggta cgtacactta 195240
aaaaccggag accccggact cgtttctctg cccttagccc tacatatgag gctttacatc 195300

```
tggagacgtc cgcgtttcgc gatcgccgtt gaggtggccg ccgtgccgcg agtataaatc 195360
gtagaggggg gaaacccgtt gcgtcgtgcg gttccgatca tgagtcccgt cgtcaatcga 195420
ctgcccgcgg ccaggcttcg gaccaggggt ccgttacgat ccgttcaatg gtccgtcgga 195480
tacgcaaagt atctctcccg tctgccgggt tgcaagacgg acttgtcgtc gctacgtccg 195540
tacgtcggaa ataaaatcga cctacgttgt ttcatatcca cgtataacga cacgttcttc 195600
agactatcgt ggccgaccca gaaatcggta tacgtttcgg agctgtcgga gatcgtccgc 195660
gcgaagatag acaagataat atgcgcccgt tacgggatac acagtccgca ttggatcgta 195720
actctcggat cggtcgtaaa cgataagagc aggcccctca tcccgggcgc gtcgccttta 195780
ctcctgacgg acgacagggg acggtttctg ctgtacgacg gacccatact gagctgttat 195840
caagagacgt ccggcggagg cggcggtcgc ggcgcgtacg tcgactccct gtgcgtggtg 195900
gcggaaagcg tggaactgtt gatatctcaa ggtctgagca gatcggactg gtgctacagc 195960
gccataggag gagccccgta ctgcacggcg ccggatcaac cgttacggtt gctgacgaac 196020
tgggcgctag acacgaagca gttatgcgcc atggcgtaca cgatgggggg gtactgttgg 196080
gatatgcgcg gggtcccgac cgcggaacgc gacgcttttt ttgtattaag catgggcgac 196140
atcccccgct ccatgaggct gtactgcatg ctgcgcccgg agttcacttt cctggggtat 196200
atggtagaaa cccccgcgac tccgctagcc agatgtcaga ttctcatact gttatccgag 196260
aagaaagaag tgtacgctta catacggtcc gaacgaaggt cttataagat agcgaaaacc 196320
gtcgatagtt tctttagggt ctccacacag aggttatacg tgaacacgac gttccatcgg 196380
ggggaggaca cacgtaggta cccgcaggtt tgcctgccgc cgccccagga gttacttccc 196440
gttaccatcg actgaataaa actcgctacc gcagacgtcc actgtcgtgt tataaaacgt 196500
gtcgtttttt tctagaaaag tacataataa accgttgaaa tctctcggga agtgtggcgt 196560
cggtatcatt acggtatagt ctacacggta ggtcaccccc aagatactag gcttctccgg 196620
cttcgacggc accttcggca tcctcggata gcgtatgcat ttcacttgtt tgttaatgcc 196680
tacctccaca ctacgataca aaatcgacaa cgtgagatat atcgtgagta acgttattga 196740
cgtaaacgat ccggtacggt tacttacggt ccgaacttgc attccggtgc tagtgtgtgg 196800
agttcttgcc gcgacacgtt taaggctaac gaatcgaaaa ggttttcttc caaggagaac 196860
tcacaaaacg aatcggtata ccgtttggca accctgtatc ggcgaaagat atgcgaatgt 196920
aactctccta caggagaaag gatgcttcac cgcgcatcgc acgacatacg tacatcagat 196980
tatctttaca tcgtattaat ctccacgtat cgtttgacgt ggtgaagtct tgcacgaggc 197040
gatctctaga actatatata caacacgggt cgtcaaacat accgggacgg gtacagcaaa 197100
acattgccaa taaaacaata acacgcattt tatcacgtcc agttccagtt tattagcagg 197160
caagcgatag aatcggcggg gtgccgactg attataactc ccccctcaaa taataccgtc 197220
tgtaccgctc cataactatt caattcaaaa tggactctag acgttacata gacatcacag 197280
tccaacgttt tagcaccgtc cttcatccgt atcgtgtagt gccacaggaa ggacgagtcc 197340
ctgtcaccga aatacgttct cacactggtc aatgagggta acgtagacgc cgccgtcccg 197400
gtgcttcctc gatctattcg acgtttgata aaagtgaata tatcggatag agtcggagga 197460
acgacgtatc tgatgaatat aaagaacatt tagttaagtc gtggcatgaa taaaacctac 197520
taacgtatac gtgcgacacg attacttact gtaatgttgt tatatatccg tcgacccacg 197580
tgttgagcat gttaacgtag agcttagcgt cgtttgtcag ggtcaggaca gccaccgtgt 197640
```

```
cattttcgca ctcgggaagg gaccgcacag tatctacacg cttgacgaac ctcttgggta 197700
tcggtgtgga aggatagtaa caacgtcctg catgtccgaa cgacgtacag aacatcatcc 197760
aagataataa tatgagacgt cttttcatca caccgttcta tctatacgtg cggatatcca 197820
aacacctttc tgttgcgtcc tagtactttg ttgaatagaa atacgtattc cgtcagagct 197880
cactaaccct ttcttataac gtcccttcaa acgacgtatg gagtccgata acgtatgcac 197940
actatggata tcgagatcgt tggacagctg ttccgtacat tcgtctcccg ttcgtagcct 198000
acggtgatga gtcagaacta tcgtttttaa gatgtaatgg gccagttggt tttctttctt 198060
aattcttgta ttatcggtca ctcctcccaa ccaccacgta tcgatgccct cgtcatccgc 198120
gccgaccgaa agcaatagcg ataccagata gacatataca ggacgccaaa acataatgcg 198180
ttggtgacaa tcgtatgtac atctttattc ggccgcatat aatgaacaaa cgattacgta 198240
taaaaagctg gtatttacaa ggcgtttcta aggttcatca gtccacacat tttcatacac 198300
gacggcgttg ggcctcctcg tcggaaaagg agcccgacgc ggaccgttcc ccatgtagtt 198360
aatgtacggc gtttcgtcgt ccgtgatcaa cgttttgtca ctcgtatccg tagtgtctat 198420
ttcactccag ttgctgacgg cgacactagg acgttggcct ctagccgcca agagtccgct 198480
catgtccacg tactccgact tgtcgtggac cacggcagtg atgttctcct ccatcatctg 198540
tcgatgcgac ataatcctgt cgcgcggatt gtacggctct ttcgacgcca caatgtactc 198600
gagttccacg tcttctagag gcattctgat taccaccttc tgtctcggtc cgcatctcat 198660
cgcgacgatc aacgacagaa caagtatgag caaaaagaac aagaaagccg caacagatat 198720
gaccaagggc ttggcgtatt ggtgagacgt aagaatagct tgcagaagat ccttagactc 198780
tatcacggtg ctgttcatgc ttcccgtaga actcacagtc gctgccataa cgcatttcac 198840
attaatatca agcgtgtttc caatgacgaa caataatctg ttacgggata atgtaattgc 198900
aatgcttatg ataaagtctc taattgacca gtcaatcgta cccgtgttca ttcgtccgac 198960
tgctgtcacg gctccgttag ggaattttga agatcaacac cgtattacaa atcgatatgc 199020
acaacgttac gacggctttc gaaacagatc gttcataaca ttctacaaca atcacctcca 199080
gagctccgcg tatacatgac aggtaactca acccagtttc gacttttata aacacgcgtt 199140
tcgtacgaat gtggtaacgt gatgatgtac aggaagaaaa attgctaaat aactctaaac 199200
tgtatcaata taataacata tatcgtatta tattcaacaa tatcgatcta agtaatccag 199260
tatatataat tattgtatcc gtacatcgac gatttatcat aaatatttaa acggtaagtt 199320
gttaaaaacg agctaataca cttataagat gctgatttat atctatctac aatgaaacaa 199380
tacaagggag tctatggcgt acagtataca aatatataag tatgatgata atacatccta 199440
ccactatcac aatggttact ggaacggtcc aattcaccga tcccgatgtg tgtggtgtcg 199500
tcgacggatt atcttcagga ttatctttaa gattattttg tatgatacgt tccccaatta 199560
ataattcaca cacgacgtta tctgtgatac tcgtatttgt ataaaaagat gctatgatta 199620
tatatccaaa atactcagaa tactcaatct cggttgagtt tttgccacat ggaacatgtc 199680
tgatcaatac atcattgacg gcagtcgaca agcgcttaaa atacatgggt aactgaatgg 199740
gttcggcgac acatctaact tcgtcgtatt ctggatgttg tattatggtc ttaaaaactt 199800
gtggtaacat ctcaactgtg cttgtataac agttagtcat atcacatata ccgcaagtgt 199860
acacaccata ccgtctaaca tcagtcaaca ttcgcaaagt tatgttccat tctgatgtat 199920
cgcgattctc agattggccc gtcaatacat cttcaatagt atactcataa aaactataaa 199980
aaactttcaa agttttcctt tcaaaaatat ctgtatatat aaaattccta atgtgacata 200040
```

cttccggttc agtgtcgtcg atgtatcggc tgtatgagta tccgcatgtg ttatgaaagt 200100
aaaaagtatc ttctggatgc ataaacattg gatttgagta tgctatccga ccccaatatg 200160
caaatacggg gtgtcgacca tatattgatg ccgtacaagt aatggtagat ctcgctgttt 200220
ccacaccgac gtttggtcgt attttattcg aatccaaata tacagcagcg taacgtagga 200280
caacgtcgac gtcctgtaga ctatattgac atgtatattt tcttcccatc atcttcgtga 200340
tgttataaag attcgatctt gtactgctac aattaatagc gtcctgcgac acgtgtgtcc 200400
cattggataa ggacatggtt cccggaagcg ttggatcgag actcgtacaa ttaatcagta 200460
cagcgttctt gagtgttact gtgctcgccc ttataactcc aagtgggatt agtattgtaa 200520
ggttctttac tattccgttc tcgatgcagt aatattttcc tgtataatta agattaaaca 200580
taaaagttac caatatttca tgatgatcat gttgattatg tatagaatag ttccttggat 200640
ccgatctggt ggatggtgta aaaccgttcc cgtgtctgac atatacgttc atcggcggcc 200700
ctccgatttg catgctgctg atcgtaatca catcctgtag agtagaactc gtacatgaca 200760
acgaaatgat atcgtcagat gttacatata agttttgcgt gacagtatca aacctagata 200820
ctgacataca tgctgtttct aaacaaacag tgagtaggag tacacgggaa tccatgtcgt 200880
aaatgaaaag tgtaaggccg gggagtgtgg gtcctattta tctttacatt gtgaatcaca 200940
tgtcgataca gaaacaatta tgggtaatga tagttacgtg ttataaataa gcatttggtt 201000
ttacatatga aatatctgct aataacgaac agcatgattc gtgatacaat tcgacgtaca 201060
attttgtgca ctatatgctt ttattggaat taatgtcgcg atttaagccg aacataagta 201120
ttacgtagca taggcacaga aatacagaca ataacagtta tgcataaagt tactaacata 201180
ccaagtaaac ctattagcca tgcaggtgat gtggattgac tgggaccgtt atgaacagat 201240
gggatggtaa tggacataac gtttttaggt gtgttagtta ccaacggtcc cagcgaaaat 201300
ttgggtgccc tccgagttaa attacatgtg ccaattgtga caacacaaat aatgtcagtc 201360
gcgttcgttt tcgggtgcaa acgcgacgtg cttgtcaacg tgctatttgt atatgtttgg 201420
aaatcgtcac ctaatccagg tggtttctgt gtgatgtgca gttgatgatt cgattctgtc 201480
gtgaccatgt tcaacgtaac cggatagatt gaacagttaa ctcgtctatc atcgggcaac 201540
cgttcgactc gtaccgtgat cattggtaat agagtgatgt gacgcgtatg acacgtacct 201600
atataacata taccgcaaaa gtacgttccg tatgcaccga tattcatcgt atgttttagg 201660
gtagtactgg ataagatggt cggatggcct acgaactgag gtgaaatact ggtagatatg 201720
gaataacccg aaaccgtata caacatcgag ccgttttcgg gttttcctat gttatataac 201780
tgcctcgcat cgcatacgtc gcgtcgaccg gaacggaaaa gatcgtgtat acacggtttg 201840
agatcccaat atatcatact gggggcaccg ttattcgata attgactaca cgaaataata 201900
aattcgttcg ccgagtactg aatcgacgat tttatctcgc ttgattcgag gtatagatga 201960
gagtggtcca tagtcaatgg agcgcattgt gtcggatgga acacacaccc gagacgcttg 202020
cccggaaaag acgtcgaatt gtacatgtac gaaacggaat ctccttgcga acagaccgta 202080
acccgttgtc tggagagttg tataggaccg gtctcattgt gtaagaacat gtaacccgaa 202140
aatgccccac tggttatggt acaatttatc caaaccgtgt cgttatacac cacgcttgac 202200
gcttctacga tgtctatggg cgtaagccag ctactatttc gtagttggct cccgacgatg 202260
cattcgtaga ttccagtgag tgttgtttga aacgtaaatc gtatttctat tctataatta 202320
gtagaatata ttctctccat gaaagtcgca ttcaatctgg agagtaatgt acggttcgat 202380

```
atactaccac tatcttgcga tctagacacc gcgtactcat cgccaaatat acacagacgg 202440
gatcgaatcg tgatcgtaga tgacaggtta aaagacgcac acgataatgt tacgcggtct 202500
cccgattgca gatataattt atctacgtta ttattatcgg tcgccgcagt cgctgaagta 202560
catacgtaat aaatcaatag aacatgaata gacacgtaca ccagcattat tgaatgtaat 202620
gctttattac acgcaaacga tttcttaaac gtacaaacag gtaataaaat atgtgaccga 202680
tcagacgacc ggtcgtcaac cctattcacg tgatgttacg gcacgtcggg acgcgatcta 202740
ccttgactat ggctttcgcg gtcatcaccc tctccatcag gcgtctgcga cgagcttcaa 202800
ggtcgtcgta ggataccggc agcagccatt cgtcctcgta gttaggttcg tacaagatgt 202860
catatatcgc aaactccgat tcgctcggca ggcacgcgtc aggccgtatc gacaccgcag 202920
cggcggtttg gccgcacggc gccgtatccg cagccgcgtt gccggtcgtg gtgttaccgt 202980
ctttcgatgc acgatctcgt acgcatcctc cgttcgtgag aagcgggccg gccgcgaccc 203040
ccgtatccga atccgtctcc gacgacgtac tcgaatcgat gatctgaggt aaggacggca 203100
acgtcaccgt gccgtagtac atagattccg ggagaaagac ctcgtcgtcg ctgtcgtcct 203160
cgtcgtccga ctttcgtatg atcaccatgg gtctctcgtc gggtctcccc gacgttccga 203220
cgacgggtag gtcggcagat tcggaggaag gggtgagatc agacttcggt acggcaccgt 203280
ctttctcgtc cctgatacga ctaatcacgt ttacgttata cagttctctg atcaggtatc 203340
gcggcatcgt cgtgatgccc actcgcagtt ttctagaccc cagaggaact ctgtccggtt 203400
ccatggcgcc ggccgtgcgc cggtggggat attccttgat gtagacggtg tttctcggta 203460
tcgtttccgg gagatctcta acgggaggtt cgtgttccat cgcctccacg cagacgtccc 203520
cgagttctac gtaagggcac tttatgaaaa gctgtcgcat gtggtatctc atgtaaaatt 203580
ctttcttgct cggaaaggat tccctgattt ttacgtacct gaaatcttcc tcgtggggac 203640
atacgcccgc cggctccaga cggttcacgt tcctgttgtg gcggtcgaaa cgtatggcac 203700
agtactgttt gagcatgccg catctaaaaa acatcggcag atcgtcggcg agccgttcca 203760
cctccatagt gtggagcacg agcgcgaaca ccgccccgcc gccgtccatc acgatcaacg 203820
tgtgacactc caggcactct ggttcctcgt acgacatcat gcagcccacg acgtacgcgg 203880
ccgagcacag tcgggtggtc agataacgtt tcaaccagat acggtccttc acgctcatca 203940
acacgaaggg caactgctcc gtcatagttc tatcgagctg tccagatacg tacagcacgc 204000
atcgctccga tctgtatccc ggcgtgtcca tcacgatgat acccgggttg gactccgtgg 204060
tcctgcagaa cacgtctagc cccatctggt acgccctgag taacgtggcc acgagcctgt 204120
cgttgcaaca ccagggcgtc aggttgtggc gatacactgt ctcgcacttc gccagaccgg 204180
tggtggccaa ctgtctgacg ttggtggtaa cgagcgacag accatcggtc tcgcagtcgt 204240
aagtgtacac ccttccgaac gttcccaata acatgattgc gggggtcgta tcgtaagtaa 204300
cgtccccgct cctgaccacg agcctcccca cggccatcag aggctcttcg caacacagat 204360
actttctgaa gtcccgattc ttcacctccg gcatcttgtg tccgggagtg acgagcaagt 204420
accaccaatc cggttgtcga agacggatca gttcgccctc atgtgcctct aaccgttttt 204480
ctagctcgct cggggaatcc tgacgtaggt ataaccagtc tatggcttgc atgaatctcc 204540
tatacgcttc tatcttgtcc aaaatcggga gctcgctgag ctttcgttgg tactcggaaa 204600
cgtttaggaa cctaaaagcg gctatgtccg cctcgagttc cctcagggac ggaaggttcg 204660
tgtcttccat cagaacgtta tcgtgggtgg aattgtacgt tatcctgtca cattcgcaca 204720
gcaacgccag ggccgacagc tcactgtcgg ccaccggcag gcccgcctcg acgtcgagta 204780
```

tcctttccgt catcgcggat cctctattcc ccccaccgaa cgtgtgctcg tcggatagag 204840
cacggtcgtc gtttccgagg acagaggcga attacacctg tatatatagg ccgagaacga 204900
gcaggtgccc ggaaatacct gtgcgttgac aaatgagaaa agaggacgcg cggagcgtga 204960
ccgcaccggc acccgtcctg cgtggacgat tatgtgatac gtttttaata ttcgttcgac 205020
ggtacgccga gacggatacg tccgatcgta ccctatatca ggtagctaga aaagtcgtag 205080
ataggggcct ccgtgctttc cgtcagagag ttatagtgcg cgatgcgtct agaaccgacc 205140
tcgctcatcg taggttccga ttccgtgaaa tatccgtaga tcagctgcgc gtcggtctcc 205200
gcctgccagg gagtatatct ttcgttggta gaacccggag gtaggagtcg cctctggttg 205260
actacgtaca cgccgttggt gtcctcttcc tcggaatcgg aagacgataa ctcgatcgcg 205320
gagtctcggt ccgaatcctc tgaatcgtca ttcggaaaac cggcggcggc cgctccgtcg 205380
cgttcgtctc gtcgcgcgtc gccacctcca ccggccgcgg cggggccttc ttccggagga 205440
accgcgtcgc gaacgtcgtt ctcatctcgg atcgcgggaa cgttctcgat cactctggct 205500
ttccacagag ctagagaatc gacgtcgtcc cagacgcgag tctcgtcttc cctgaatcgt 205560
ccgtcgcggc acaaccactg atgttgcttc tcgtagtcgt gggcgacccc gacgtcgaag 205620
aacttgtggt gtcccacggt cgtgggtaga tggtggcgac agacggaagg ccgttctagt 205680
ctgcagatcg tgagagactt aaaatcgtaa caccgtcgcg agtagcactt gttcagtcca 205740
cccttgaata actcccaaac gttatccgct acgcgataga agcacccgtc tcgcgtgacc 205800
agggcgtaca ccgctccgaa tctatccacg accaggacgt gcgaggtgtg gaaaaacccg 205860
gtcgcgtggt aagcgccgac ggcgccgagg atgaaccaca gacaacgcag gcgaaacgtg 205920
atacgtttcg aacaaaactc catgtcggcc gggggcatgg cgcagaacgg ccaggtccgc 205980
cgcagatcgt caaaatgcga cagcagtttg agaggctgcg tgcagacgcc cggagtatgc 206040
agttcgacgt cgaccccact gatggtggag agaaacttca ccagctccgg cgtgcggaac 206100
gtacgctcca gtataccgta gacctccgcc gagtagtgcg tgatcacagg ggccgtaccg 206160
tcgtccagga cgaaacaccc ggagggaatc aacccgtacc tcgccaggtg atctatgtgt 206220
aacgcgatga gaagcagcct gcgtctcatc acgtggtaga agtataaccg attctccgct 206280
cccatgaaag ccacgaattt ggtgcgtctg tagcagccgt ggccttcgag agtttcgcgg 206340
accacgacgt gccccagagg agataggttt tccacgcagc acagcatgcg tgaacattcg 206400
tgcgcgtata cgtccacctg cggtatgtcc tcggcggccg tgagctctag gaaccagtcg 206460
tggggaatcc ccagggagag tttttcaccg gccctccgcc gagcgatctc caagatcttc 206520
tcgggatcgt cctgcgccac gaatagttct ttaaaatctg tcatgactcg taagaacgca 206580
tctctcgagg cgtgataata gtaccgggga tcaggatcca gcatcctctc ccatccgaga 206640
accctgttca gtcgccacat cgcgcgccgg ccgccgcgcg cgacggacgg gaaaggatcc 206700
ggcgctcgcg atacggcgcg tcggcgtagt gacgatatga gagtcgcaaa tatacggcgt 206760
gcggatagcc gctcgttaag aatcgacaac gagagatgta aaagtaaagt tcatttattg 206820
atggaatatc gtgtgtttta tactcgatct gttgcgcaac acgcgaaaca gctatgattc 206880
tccatatatg gagaaacgac gggccggtcg gtcccgtcgc tcggccgtca cgtagcgtcg 206940
tcccactctt cgttcccgga ccccgggtcc ctcgggaaga ccgaatacgg ccttaccatg 207000
catatggaag gcagatcgag acacatcccc gtatacccca gtaaccgttt gttttgaacg 207060
taacccctca tgtggctcac ggatgactgt tccggaacgg gcacgggaca cggaacttcc 207120
cgcaaccaga gggtttcgcg ttcgtctccc gcgtttctaa acgcggtacg tttccaggag 207180
aaaagttctt ccacccctcc gaggcccgcg gacagcggcg aggcggtggg cggcctggag 207240
ccctcgtcgg ggccccagga ctcagtccgg ggtatcaccc aggcggtcgc cgagtgcgtc 207300
gtcccgaaat cgtttctgta taggagaacg gcgtttttat ccgtgtggtc ccagggatcg 207360
acggcgcggc cgcgtctgtg ccgcagcatc catcgatagt gatcgtcgac ctcgtctcgc 207420
ccgtgcctcg gatccggcag accgctgagc ttcattatat tgttgatggc ctcgatggcc 207480
gcgtcgtttc cgtgcgggca tcgccccggg tactcgcatc gacagcgctg atccagcgtg 207540
gactcgaagc gtctaccggg aaacacgatt ttcaagactc ctatcctgaa gaactcacaa 207600
agggtgtccg cgacgcgaca caccatatga ctcccgtgca tggtgacggc gtagaccgcc 207660
gacagagaat cgacgacgat cagggcttcg gcctgaaact cggtgaaagg agtacacagg 207720
ctggtcgacg accgcttcgg cgtatcgtcc gaccccgcgc gagagggcct cggagtgcct 207780
tccgtcagtt tcggcatccc cgtcacgccc aacggatacc agggcgtaca cagcttggcg 207840
cccacggcgt ctttccagct ctgaaagtcc aaaccggtga ggatcgatag cggccacgcc 207900
cggcggagtt ccctcacgtc cgaaaccagc cttaggatcg ataacccgta cccgggcgta 207960
tacagcggaa cgtctccgtt cggcagtctg tgcaaagtca cccgctcttc tatcgcgccg 208020
ttcagtgatc tgaacgccac ggtgatctcg gaaccgggac gcggctttcc gtaatacggt 208080
tcgaccgccc tgagcctcgc ggggtcggcg cgcccgtggc ggtgcgagaa ctcgcaccgg 208140
acaacgccgt acgtcgccag ttcctcgacg ttcagggcaa cgaggtacag cacgacgtgg 208200
atacagtcgt agacgtagaa acggccgtgt tctcccagat acgcgacgta gcccgcgtcc 208260
aaccggtcgt gacccgggcc gcgacaacga ttccgcacgg aaaagtacgc gtcggggacg 208320
tcgcgcgtcg ccgctttctc ttcggggtcg tcgccgtccg ggcgttccgc gccccgatcg 208380
tcgaccgcgt acagactgcc gaggcgaacg aagcgctcgg cgcaacacag cagcatggcc 208440
ggattcgatc tctcgcgtcc gtctcccggg tcgtgttcca gtctcagata ccagttcccc 208500
ggctggccca agcacagaat gctcccgaca tttctgctca agtagttttt gagtttctga 208560
ggccttctgc ggaacgcgta gatctggtga aaatccgtca gcacacgatc gtacaggtcc 208620
atcgcgcgac cgattagaaa aggcggtacc gggcaccgcg gagcgaccgc gggcgattgc 208680
gattccaggc gccgcgcggc gggttttctt atatccccca cccgaccccc acaagaaaaa 208740
tgatgacacc cgagacgaac accgcgaccg atcccgggtc ggatcgcgaa tgagctttaa 208800
tcgattttta tatacatcgg aatcaaaaga ctggaaagat gggaaacggg agcacacggg 208860
ttcgcgcggc cggactaggg gaaatattcg ctcgggattt tgggttttac taacacgtag 208920
ccgttcgaga tgatcttctt ggcgaacgtc acccgtctgt gtatgagcgt ccgctcgtcc 208980
ggggggagct gatcatcctg atggtcgtgt tccacgctgc agtcgaagac cttaaggtct 209040
tcgacgcgga tggagcgtcc accgtcctct tctccgtcgg acgtcccgtc gcggtcggcc 209100
tccgaggccg taggccccgc cgacgtttcg gacgtacggg agacgggcga cgtatcgcct 209160
gaacgcgctt gcttcggcgc ggtcgtgctc ggatcgggcg cggccgacgc cgtcgaggag 209220
atgacgctga cggcgcgcgc ctttaccgcg ctcacgcctc ggagctccga gggacacagg 209280
aacggatatc taaagttctt cggtccgcgt ctcaataggg atctcttgcg ccgcgcttcc 209340
gtcacggcgg acggtcggtc gaactctcgt atgtagacgg acgacggcgg aaaggaagcc 209400
tgaatcacgg gcgtgttatc cggcacgtag ctcagcgacg acgggaaaac gtcggcggag 209460
agcatctccc acatgtgttc gaaccattgc tgtctgtccc agatatccgg tctcctgtcc 209520
gcccgttcgg ccaggttccg cagacgcgcg tctcgtttgt gcgggcaccg cggagcgcgt 209580
tccagtcgca gggcccctcc ggtgtcgcga tcgaagcggc tcacgtcgta gtggtagaac 209640
aggaggccgc aacgtaagaa catcgccagg tcctccgcta tccgcgacac gtcgctcgtg 209700
gtcgagtcgt acgcgtagat actcccgacg gcgtccatga ggatgcacgc tttggcgacc 209760
gggtacgcct ggtacctgta gtggctcacc gcggcgatga ggtggtatct gcactggagg 209820
agcgcgttga gatactcgtg catccgcagg agttcgtctt ggtgcatggc gcagaacggg 209880
aagaagtgct tgctgaaaac ggccatgtcg tccagaaacg tcacggcgtc cggcgtcgcg 209940
gtcgtcgaat aaggacagta catggacacc cggacccagc ggaggtccga gacgacgctc 210000
atgatgcgct ccacgcccac gaaggacgcc tcgacgagcc tgttcatcac gtcgcccggt 210060
agcgtgctgg gcgtcgtcgg gagcagaggg tggcgataga cgggcgggca gaacctgaga 210120
ccgatgtccg ccaggtgcac tacgtgatcc agcacgtaat acagtccgtc cgtatggccg 210180
tcgtacacgt acacccgtcc gaagtcgctc accgtcacga ccaggtcggt gttgtcgaac 210240
atcctctcgc cggtccggac gaccagcacg cccaccacgg tcagggtctc ctcgcagcac 210300
aggtagtcgg cgaagttctt gtgatgcgcg gggaacacgg tcgagtacga ccggatcaac 210360
aagtaccagt tgtccggaac cctgaccgag atcagcgttc cggcggagag cctgacgtac 210420
tccgcgaact tgttggatcc gtagaaggtg catagaccgt agaggtcggg tatgacccgt 210480
ctgaccgaaa gctttctgtc ttcggtcgca ggggaacgca gacgtctcgc gagctcctgc 210540
gggtgcatgc actgtaaacc gtttatatct ctcagaaaga tctccctagc ctgtatgtca 210600
gacggcatct ttccgttcgg gacgatcctg gagcaccccg tgtgcgccgc ggccgcggcg 210660
aggtcttcgc cgacgagggc cctgacgtcc gcgcgcacgg gaatgtgccc gacgggggat 210720
ctgcggatgc gcatatctag agggccctcg ccatcgccgt cgtcgccccg accgtagccg 210780
tcgcccgcct cgcgctcgcg tttcttagaa cacgagcaga cgcagcgaca tttcgcgtcg 210840
ggcgccgggc tcccctcccc gtccatcccc ggtctcgttc gcgtgggttc agacagaccc 210900
gtgcgtcccg gagacagccc tcgaaaataa agagagaccg agtcgctcgt aacgagtcac 210960
acacagcaag ctttattatg ttccccggac ccacaaaaga gctcagtcat ttccgagtgg 211020
gaggggaaac aaggcaacat tccacagaac acgactcgac ggcggcccgt cgggtcgtac 211080
ccgccgtatg aaaagcgtac ggcgcaaatc agttctgatg ttttctcggc ggtttatgcg 211140
gagcccggag gacggaatcg gggcaccacg tccgcatgtc cacctggacg gccgtatcga 211200
ccttaaccgg agcgcgaccg tttccgcgcg agtcttcttc ggtttttccg acgacaccgt 211260
ccacgtcgta tccagtcagc gggtcgggtc cgtcgccgtg gaccgcgtcc gcatcgcggg 211320
gcgctccgcg cgacggcgaa tcggtcggtc tcgtcttgga cgacgcgggg ctgtggtgct 211380
ccaccaggtg gatcaccgtg tccgtcgggc tggagtcgtc gccgtcgctg cacgtcgact 211440
ctccgtccgc ggtgcggccg ccgccagcct ccgtcaacag gttcccgttg gcgtctctgc 211500
gcctgagacg cctcatcatc accgctcgga cgggcgatct ctttccgccg tctgccccgt 211560
tgatacggat acgtcgggcg cgagcggaac cgtccgcgct ttcggcatcg ccgtcgtcgt 211620
tgagcagact gacgtacgcc gacgggttcc cgagcgaaga acccagagaa gcgtcgtccc 211680
cgtcgtcgtc gtcgaagttt agtctcctga cgacttcgtc gtggctcgcg tctccgttac 211740
gtctctgaga ttccggagaa gagtccgcga acgtcggaga cgagctcgcc cgagacgcgg 211800
ggtcaccgaa gatcctggcg gacggccgtc gacgtagcgg cggcggtggc ctgaacctcg 211860

-continued

```
cctgtgagag caggtgaggc aaccgcgagg catcgggcag cgcgtccgga gaccgtggag 211920
aagtaatggg cgcctcccgc cgtcctggag gggtacaacg agaagacccc gttccccggg 211980
agccgcgcgg tgtcggcacc ggccgcgggg gatcgtccgc ctcgtcgcac tcgtcctgcg 212040
atgccgtcgt cgtcgcgtcc gggatgtcaa acggtctcga cagcacccaa ccgtggcggc 212100
gggagaccgg tatgacgacg cgcgcttccc cgtcgcagcg cgaatcgccg aagccgcgac 212160
agggcgcgac gagcggcgta cgcggctctc tgatcaggga cgccgctctg cccgcgcgcg 212220
ggcagaaccc ggggtccgcc ggctccgacg ggacgccggt cgcgtcgagg cgacgttcgt 212280
aacctagaaa gctgtctctg aaacggttcg gtcgggacag ccagtcgaac gccgtctcgt 212340
actgcccgcc gtcgtgggcc ccgctcgtct ggcaacaacc ccatctccga tctccgacgt 212400
gcacgcacag gggcgggtgc tccaatctct gcagatcgcg cgccggcgtg tcgaacctgg 212460
tgcccgcggc gtaccacttc agcagtccgc acgcgaagaa catctgcagg ctgtcggcca 212520
gcctgaacac cgacatctct ttgtgatcga atccgtatat cgcgccgtcc tgtcccagga 212580
tgacggccac gtcgacgcgg aagagacccg tggcgagggc ctcgcccacc gtgcccagga 212640
gccaccaacg gcggtccaga cggtacgtga tggattccat caacagccag aacgtgtcgt 212700
gcgacatgtc tatgaaaggc agctgctgtc gtaacatgtc tgagaagccg cacaggcaga 212760
acgcgtgttc tccctctccc ggcgtgctga gcgcgacgca tcggagtctg tgcttacgca 212820
ccgtctcgat cagggccgga tggccgtctc tgggcacgga cgtcccctcc ggcggcgccg 212880
cgtcgagcag cgcgcgcacc acgtctctgg gatacgcggt gccgcgcggc gccagcctca 212940
gctgatagat gggctcgaag tgcaggagac cgcgtcgggc cagcgagtct atgtccggcg 213000
ccacgaggtg cagcacgccg tccgacaggt tcacggccca tatgttgcag caactgccca 213060
tgaacatgac aataggcatc ggatcgcact cgccggtctc ggtccagcgg acgcactggc 213120
ccaggggttc cagccggtcg gcgcagcaca gcaggtcgcc gaccccttcc acgcaccgtc 213180
tggcttccgc gtcccgataa gcggccgtgt gctggagcgg gttcaccagg agataccagt 213240
cggagggcac gctgagggac agcagggtcc ccctgagccg tacgacgcaa cttttgacct 213300
cggccaggtc tccctgagcg aggaataact ctctgaagtc cttcaacacg cgctgcacgc 213360
gcggagccgc cgcgtagcgg tatctggaga cgagcttggg catcttcgcg acgcgcgcgg 213420
agacggtgag aagaccggaa cgcggagacc gacggacgcc gacccgaggg cgtccgcgtc 213480
gcgagcgagc gagttaacag agcagatcgc gatggacgcg acgctccaca aaagaccgag 213540
actggcagtc ggagagtcca aaatctggct ttttattaga aaaatctaca agggaacacc 213600
cacccggata cagtccgcgt caccgcgcgc ggcccccccg cgccgactcc cgcctcccgg 213660
atcgcggccc cgacgttcag gaacactcct cgtcgctgga gatgttgatg ctgcgtatct 213720
tgccgcacag ttcgtcgggg tccgggatgg tgccgtccgg acgcacgtgg ccgcggtcgc 213780
ccagccagac ccactcgtcc gtgagataga cgtatcccag ggaggacggc aggcacaggt 213840
cccacatgcg ctggctctgc tcgtagagca cgttctcgtc gtagcgctcg tcggtgtcga 213900
cgagctgcac catgcgttcc ccgtccaggg cgtcgtggtt cgcggtgaac agctgctgga 213960
aacggtctcg gggacaggcc cagaacccgt aatcggtggg cggcaggcaa cgggccgcgc 214020
tcttactgga ctcctccttg agatacgtgt ttcccggcag gaggcagcgc agggtgccca 214080
tcctgaagaa ctgtagcatg tcgtccgcca gaccgcagat ctcgccgtcc gccgtgcggt 214140
agccgcggac gcggcccttg tggtcgcaga acacgaccgc catgcagcag aaggaaccgt 214200
ccttcccgcc gtaagcgccc acggcgccca agagcgtgac ggacgcctga cactgctcct 214260
```

ccacgatgcg ttgcacgtcc cgggtgatct gagggccgtg atgctcgtcg cagaacggga 214320
agaaggaccg caggccttcc caacggtcca tgatcttcag cacgacgggc tgatcccgat 214380
acggcaccgg gatcgtcacg tccacgcagc ggtactgggc gaccaagcgc tgcagatacg 214440
ggggattacg ttgcatgtcg gagagcagca gcgccgtctc gaagggttcc acgctggcgg 214500
gcagataggc gtccaggtac tcggcgctgt acaacgccga gaccatgccg agtccccgga 214560
gcgccagctc ctcggcgtct cgcgccgcga ggtacatctc ggaggtgcgg cggtcgtaca 214620
ccaggacgcg gagcctcggg cccagcatga acaggagctg ggactcggcc ggccccttgt 214680
gcaccctgcc cgtcgcgtcc tgcgtccaga cgacgccggc gatcacgagc cacggctccg 214740
tcgtgggaca ctgcctcttg acgtccagcg cgcccacgtc gctgaaatcg gtcctggccc 214800
cgatcgtgac gtgcgcccag ggcggcatgc ccacgggaaa cgtcaggccg gaatacgccc 214860
gcacgcgttt cttcatggcc ctggccgaac tctggccgaa ggcgagctgt cccatggcgg 214920
ccagcaccgc gtgatacgtg gcgcggtcgt tgatggacgg cgggccgccg aacgcgtccg 214980
aatacgaggc cgcgcctccg tagctttccc tggccatcat cttgaccatc ttcagctgca 215040
cctgacgggt ctcgtcctgc gatctggtgg acggcagggc cgacccgagc ggagacggcg 215100
aaggaggcga agaagaggat gcggcgatcg acgacagcgg cccgacggcg gcggcggcgc 215160
gcaccccggt ccccgccgcc gcctcctcgc cgtcatgtcc acctcccgca tcgatctgca 215220
ggctccgcgc cgcgcaacca ccgcacccgc cgccaccgaa catgctgggc ggaggcggcg 215280
gcgggtgcga cggcggcggt cctcgcacga acggcggtcc cctcggcgcg tatcgcggac 215340
cgtcggccgg gcgatacggc gagcgcacgc tgttgtgcgg ggcgaacggc gtccagcacg 215400
gatcgacgtt cctcgatccg ttctgcgccg gggcgaaccg cgatggggta gcgccgtatt 215460
gccagccgcc tcgggccgct cctctgtgaa aggatcccga gccgcgcatc gaccagcgac 215520
acgccagacg tccccgaccg ggacgcgtcg cgtcggacga aacgcctcgg tacatctttc 215580
cgtatctgtc tggaatcggt cgatgcgatc cgtgagatca ccgactatat cgttcgattc 215640
tggcgcggcg acgagcgagg cgagcgacct gtccgtcggg caatacaacg tgaccgctat 215700
cagccgctcc acggggagca gtcgagagcg aggctgttaa tatacccttc accgggtcac 215760
tcccttcggc gtgactcatg atcggagtgg gcagtcgccg aatggcgcgc gcgagggcgc 215820
gatcgtctcg tccgcggacg ttttcgagct ccgggggtcg cgggcgggaa ggcgagacgc 215880
ggcccgacga cgggcgatct aaatactttg cttacgggac gcgtcgcgcc cctacgcgag 215940
tcccgtcggg agggacaacg tccatcggcg cgtcgccccg gcgggaacgt ccgcgaggag 216000
ccgggagcaa cgtccgtggt ccgcccgaca cgggacggga gcggaagaca gttttctaaa 216060
acgtctcaca cggtgggcca tcatgtcgtg ataggtaacg tccccgccgt cgtcgctatc 216120
gtcgccgtcc gtcgcacgaa acgcgggatc ggaaacgtgt tccagaccgc gcgagccgcg 216180
cctaggtcga gacggccccg gcggtatcac cttcttcgat aggatgtggg ggatactccc 216240
agggaaacag catccgtcgt tcaacagaat ccgggccgaa cagcctagag ataatagacc 216300
gtaccagggc aacgacctct ctatagcgat gaagcgatcg taacatagtc tccgcgggcc 216360
gcgccacgtg tctgcgacgg gcgtctctgc cgaacctgag agaggtgcgt agcatggcgt 216420
ccggtcccca agggtccgcc gaccgtctcc tccgtcttct tccccgtcgc tcgtcgtccc 216480
ctcgctcccg cgtctcgccc gccgtatccc gccgacgaga cgcgagaccg cgtcgccgca 216540
acggcaggga acgccgtcgt cgcaggccga gtctcgtccg ccgtcgtgcc acatcgccgc 216600
gaggcgtcca gaggcgccgt ccgtcgagac tccggcgcgc gtctctgtcg tcggcgccga 216660
ggcccgcggg cgcgacgtcg cgccgagacc ccgtccgtcc cggctccggc agatccagcg 216720
gcacgcgtcc gcctccgccg tcagcctggt ggcccaggtg tccgcgtcct ggccgtggga 216780
ctccgcgccc gtcgtcaggc tgcggagcag acccacccgc agcaggtgcc gcaggtcctc 216840
cgacagcctg tacaggcgcc cgtcgacgct gcggtaagag tacacggcgc cgaactgatc 216900
tcccacgacg agctgagcgc agcgaaacgg atccccctcc gccgcgacgg cccgacggtc 216960
tcggatcgcg acgtcgcgga cggggacgct cggccgctgc cgccgcgacg gcagcagcgg 217020
acgggctcgg gaaccgtcga ggctgccggg gaggagacgg ctcgcggcgt cgacggcccg 217080
tctccgggac gtctcgagcc aggtcccgcg acggagacgg tcgggacgct cgccgatcag 217140
ccccacgacg cgcgcgcggc accccagccg gtctcgtatg aaacgaacga acgccgacca 217200
cgaagaatcc gatatctcgc agaacggcca tgcctccctg accccgttca gaccgtcgac 217260
caggaggagc acgcagggag cccggcccgg agtgtgcagg aggagccggt ctccccgcct 217320
cgcccgcagg aactcttccg cggcggcgac gccgtccgtc aagacgaccg cgtccaacgc 217380
ggcggcgacg ggttgtcgcg ccacgacagc gggcagcggg gcgaagtgag gctcgtacac 217440
gccgggcacc aacaacatgc cccgcacggc gaactcgtgc aggtctctgg ccaccagaaa 217500
gacttctctg gtcaagtggt cgtacgtcag cactctcatc gcgcgcccga tgagcacgaa 217560
cagggggtgt tcggcgcgcg gatcgcccgc gtccgagacg ggcgtcgaag aagagatcac 217620
cgtcccggcg aacaccgccc agggctcggc ggcgggacag atggtctgca cgtcgatccc 217680
ggtcaacgac gggaaatcgt atctgggcgc gacgcgaatc cgaatgttag gcggccgccc 217740
caccgggagc aggacgccgc gatactgaca gacccggcgg gagacggtga tctcgttctc 217800
gctggagaag cgcgcgaaca tctcgtacac ccgctcgaac cccagacggg tgttcatcgc 217860
gggcgcgccg ccggcgtcgg ggaagaagac gccgcgagat gcagaacgcg acatgccgtc 217920
gctcctaccc gcccggaggg gacgataccg tttggcgccc aacgccggag acgggagagg 217980
gagagaaagg ggaccgaggg ggcgggcggc acccgctaat aggcggcggg aaccccggga 218040
ggacacgggc gaccgcgggg aagatgggaa gatggaaaga cggaaaaaag acgaaaaaaa 218100
agaaacgaac gaggctaatc gtcagaacaa aattatccgt ttattattgc agaaaaaaaa 218160
aacatatata cataacgttt tgaaagagac atcttgcgta gtcagtgttg tgtttgctag 218220
tagctctctc atgcggttgc caagaaataa tataacataa ccgatgaaca agacagaaaa 218280
cacagatctg gcataaaaaa gatgcttgat tgcttgctcg cttgctgcgc gtctccggga 218340
gacgcgcggt ttgcacgtga agcgattcac accagcgtga tcgattcgct ccgtccaagt 218400
cacgatccaa aggatatttt tggtgttact atactcttgt ggtacggtgc aaagaaaaaa 218460
tatcattcaa tcaatcattc aatcgatcag tcactcaatc gcgtgtgaga cgtcaccgag 218520
tctgttgctc cattaccttg aaagatgatc atcgaatgaa aacgcgaaaa ctaatgttgt 218580
ccgtacacta cttcgtctcg ttaacggtaa tctacgaaaa cgttacttgt ttgacgtaca 218640
tgcaatttgt aaaacgatca aagtaaaaga tacatggcgc gttgcgttta acagatgtcg 218700
tttttatctt ttccagccca gcgtttggaa aaaacgaagc atataaatca ctccaatcct 218760
tctctcggta cacatttgta aaaaaattaa caacgagtac aaaaacacaa taccatatca 218820
tttcacatca tagtataata taatatataa tatacacacg agtaaccgtc acctatagaa 218880
attttacagc tcttgtctta gcctggaaac ggtaaatgtt catcattcat tttaccttat 218940
ttttaatctc actttatctt attttattct gtctttacca acactatcaa agttcagcgg 219000
ttcctaattt tgcttaatca atctatacat atcagctcga tttatctgtc tcgttaaagc 219060
tattattaca taacgtagtt ttgttttatc ctctacatgt tttatttctt acatagcttt 219120
ttggtaatat cgttaaattt tttatcattt ctttcagagt cgtcaagaaa acggtagacc 219180
ttcgaacgtt ccaacccctc gatacttttt ttgccttcta cattctcgtt tctccttcat 219240
cagtgtctgt ctatcaatca tcaatcaggt aggttgtctt tgcagtatga atttcttcct 219300
ctaggacagg gactacgtta tagaagacga tgaacaggaa aaaaaaagca ttactattac 219360
gaatatgagg acctgatgag cgttcccaaa aaaaaaaaga acaaagtgaa gtaatgataa 219420
tggatgatga cgatattgct attacaacca aataactcat tgataaataa taagattcat 219480
tttgttttag ttgtaaatta aaaaaaaaaa aaactcatca acgtgtcttc gttatgttca 219540
gctcaaattg tcgtcttacc cactcgtcgt gtaccgggat cgtctccccg atcggagatt 219600
ccctcccggg attctctctc tccctctctc tatatataca tacatgggtc caaaagggtt 219660
tgtgtggttt cctgtcatag ttaaaacaaa agaccgtaca gcagaaccga tatatgtgtt 219720
tgttttcttt tatacaatcg gtaagaacca agtttctagg aacatgaaac attaaataaa 219780
gcttactagt agtttttga ctcaagtcat cgtgtgtggg agatatctgt tataatcgtt 219840
cataaaaagt caattattat tgaaatcggg ccatcggata cacatttttt aaaatctttt 219900
taaatggatc tacggaacaa aaaataaaaa taaaatcaaa cgaaagaata agatgtatgt 219960
tattctattc ccttccgcag taccggagcg ccgtgtgcgc tccgggagaa acggtagatg 220020
atagatgtat ataaatatta caaaaaaaaa aagcataata atataggtaa gtctatggga 220080
ctctttcttt ggtaacttca tatgagaatg gaagaaaatt cgattctgtt attgttgtta 220140
cttcttataa ataaaaaaac aaaagccaca aggtatataa agatacaaaa ttctttccct 220200
ttttttgata agaaaatata ccacatagaa tatgctctaa tggataagta cgtagaaaca 220260
tcgttttgta tgtgtcgtgt gaaaattgca acattgaatt atatctttca gtattctaga 220320
agtaagaacg tctttctttg ttaattgatg gaataatttg tgatagaaat cataattccg 220380
atttgcgtat ggtatatgac tgaacatgaa caactatcgt atgtaaggac aaaaaaggac 220440
caaatataat atcaatagat cgcctgataa aagtaaaaaa gtctaactaa ctacctatct 220500
aaaaattgtt tttccacttt tgtatgtgct acacgtcacc atgtcgctgt cgcgaaaaac 220560
caggtatgca cgtaaacaaa caaagaaagc ttcatctata tcaccggcat tggttgtgtg 220620
cagaataaca taacagacgt gaaaaatcga taaattataa aaaagcaata aataaatagc 220680
cgagtataaa aaataaagag tcctgtaaac agttcttcgt aaaacgaaga tggcatttag 220740
acaaaaaagc ggctctcgct tcgatacgaa gcgtaataga cataataaca gtaataagtt 220800
aatcaactaa actagtacac agctacgttt gaacagacgc gataagctat cggatacgat 220860
acggagagac actctatata cgtgtgcatg tcgcagcgaa tcagtctgtc tgattgatct 220920
gttttcactt ctttcgcttt gtgtatattt gttccccata gcggtctcga ggagtttcgt 220980
acacgttctt ttattattac tatctttcta ctactcagtt accttgtatt ggattttttc 221040
atagttacct tcaaaaagtc gggcgataac atgtaaggtt taaaagaaaa gaacattcga 221100
cgttcggtag aacgtcggat attttgctag ctttttctgt ttttgttttg atcccatatc 221160
atcttttgcg ttgtaatata tatgtataaa agtatgaata cgtaccgcgg cctcgcgggg 221220
tacaaattca ataacgagta gagagttagt tacactatga ttttttacat tctatcccag 221280
cctgcaacct ttcgtttttt tttttcgtcg tcatttaaag catgcactta tcatatcccg 221340
tcccgacccg tcccacccgc atccgccccc gcccccgtcc ccgttcccgt ccccgtcccc 221400
gtcccaccct cccctatccc atgttccatt tccatacccg ttctcatcat acaaaatcgt 221460
acccatgcat atccctctag tctctgtcgt tttaaactct ggtttgtttt tttttttgt 221520 ctgttcccta cgtggacagg atccccaaat ttctgtcgtc ggcgaattgt agttatggct 221580
tgcttctgtc tgacccgaag accattcaag tagctttaga gtggagtcgt atctgaatcg 221640
aatgtatcgc gcgcatacac acaaacgtat aactttgatt attatggaca gcacgatgta 221700
tcgtagcctg cgatggaact ttaacggtct gatcggcact agacgaggta aacgcgatcg 221760
tcctctgtct ttccggcgaa ccgcacggtg ggcgttcctt tcgacgctcc gacgcgacgc 221820
tggcgtgcga cgaacgcgca taccatgagg agcaaggcaa gtagtagccc gcagaagaaa 221880
ccgacgttac ggtgtgtcgt tccgttctca cgctcctccg tatctcgtaa aggtggcgac 221940
atgaaacgag tcgtgttcaa tgaatggttc gctacggaca tcatagaaag agcgtatgat 222000
tcctcgacga agctcgcggt ataatgataa ctgcattgat aattcttcgg atcaaccgcg 222060
gtggtaacat taacacatcc cttgtccaag tatgttccgt tgtccgaggg cagccgttcc 222120
tgccgcgggc ccgggtgata ggcactatcg gagagagtat accaacctac gtgcggtctg 222180
attatagcgg tcccaacgac aatgcaacat agcgtgctga cgttgtcggc cgtgttcgtg 222240
tccttgatcg tacgcatgta gatcttagtt ctcatgtgaa aatcgatcag tttccaagat 222300
cgttcatcgt gcttttgtcc ctcggcaacg gtcctatagc actcgtgacg tataaatgag 222360
gttaccaggt cgctcttcag aatttctgta aaacgttcac tgtcggagtc gtttgaggcc 222420
gacagaacgg aatgtgaatc gttcccacac ggcgcggcga gagtcgcggg taaagtggca 222480
ttgcattctt ggcgtatgga atatctgtca ccgtacgacc aatgagcgct ccacctagaa 222540
tcgaaagccg acggcatagt gcacccgacc gagagttgaa aagtatccgg tccgcttgat 222600
tcggtgtcgt tacgatatga tgcgttacca cttgcgataa atcgcgtatc attaataaac 222660
gcagagacgt acgactgtat ggatgccgtg tagaatcgcg tcaagttaac gtggagccag 222720
tgagccacag gagtgcctac gacctggccg ctcgtcgaat cgacgtccac gcgtatcgcc 222780
ggctcgtcgg acagatgcag cacgatggct ggcgcggaca tccatgtgga gttataggtg 222840
acgtacattg ctagtctgaa gtcccttgag agcgagacgt aaaacgctgt atttcgttcg 222900
agagccagtg tgagcaacac cagccaaaac cacatcgcta gattgtcgcg tacggcactg 222960
aacacgacca cacgattttc aaaacggtgt gcgccgcgca gtcgctgacc gaccgcgccg 223020
tcgagtctgt cctgtagagt atgccctgca tcgcctcggg gtttttatgt tggcaggagc 223080
gatcggaagc acacacgcac atgacatcac atcacatcat cgatcaatcg acaagataga 223140
ccaagtcatc ctctctgtct cgaacgaacc acaccgtgag agaccttccc tgttccctga 223200
gacgccgttc ccagacggcc agaaagcaaa caaagatgaa taagacgaaa atcgatgtac 223260
acagcagacc gatgttgatg cgtgtcccgg tgtcgtatgt tcccgcgtgc ctcggtggtg 223320
gcgatataag acgggtcctg ctccacgatc cgtttgccac ggagagtagg tacgtgtccg 223380
atctgtcgtc gaaactcaca gtgtaatata gactgcactc gtagttacga gcactcgccg 223440
cgccgctgac attcatgcag cctcgctcca gatacgtccc gtttcccagc ggtaaccggt 223500
cttgcctcgc ggtgcggtga taagagttgc tggcgctatc gtaccacgcc acgtgcggtt 223560
taattatgga tgtgccggcg atggtgcagc acattttagt cacgttacgg ccgtcctcgg 223620
tctcgttggt gacgcgcgtg tgaagggtgg gcttcacaaa atcagagacc tggttccaga 223680
aatgcctatc gtagtgtctt cctccgacga cggttctata acagtcgtaa cggacgaaag 223740
cggccaccgc atcatcgtgt acgacggcac gaagatgaag tccgagaccg gaactgctgg 223800
aacccggtct gacgaggtca gtgtcgtttc cgcagggcac gagccagctc gaagacgtcg 223860
tggaattgca ctcttgccac gtcgaaccgt tatgaccgta cgaccagtac gctttccaac 223920
cgaagctcct gctcgccggt acgctacatc ctatcgccag ctgaaggacg tccgaatcgt 223980
ttccgagcag agatccattg ttcgcgatga attccgtatc gttcacgaat gctaagacat 224040
aaggcgcaag gcatttagta taaaagcgcg tcagattggt atcgatccaa tgggcgatag 224100
ggacccccgt gacgttgttc gtcgttctgt tcaccgtgag gcgtatcgcc ggttcatcgg 224160
agaggtgcag tgtgacggta ggatcggaca cccatgtaga gttgtacgta acgtacatcg 224220
ccagcctgag atcttttgag accgatacgt agggagacgc ccattgctgg cggaaacgta 224280
gcatgatcgc ggctatcatc agagaccacg tcgcgcggat ctggcatacc ggaacgtgca 224340
tggtctgggg ttctcaaaaa cgagttcagg cacggagatg tgtatatgcc tgcgagagct 224400
cacaaagcga gtagagtgtg gtttggctcg atcccgagca ttttatgtcc tccgggttga 224460
tggtcaatcc aaggacatga catcatatca acagtcggaa gagagccctg ataccatggt 224520
atgcggagaa tcgtgagacg tcgtggccgt gcgagatata cggatcgtaa aacgagagat 224580
ctcgccgcac tagaatgccg tggggtgaaa atatcccgga gacgccgtcc cgaaaacccc 224640
caaaacagga acgtccatgg gacgagttcg gttgagttgc cgtcagcacg agcgacatgg 224700
cgtgcgctgt caacggtgtg taacgtaagg gcaacgtgcc tcgttcgcta gatacgactt 224760
tgttccttgg ccgtcacacg gatcgtatat gcgtgtcaga gatacaagac gagatctcgg 224820
tcgtcttcgt gtacgaccag ggtatagatg cacggatcgt cgtccgtccc gtcgggaaga 224880
gacgtgggtc ccccgacgag acgcccgaga ctccgatcgt gcgaggtgaa gatggcgtct 224940
ttgtcccgca tgtcgggctc catctcctcg tatctccgtt tacccatgac gagtctcccc 225000
gatcggctca gcgcgcggag acgctcggcc gttgcggaaa acgcacggcc taaatagtgt 225060
gtaaacgtaa gtgactcgga acgagtgacg ttacggatgc atgccccgga aagccgccgt 225120
aacgacgaca cggcgcgcgg ccgccgtact gaacgccgct gtacggcaac ggcccggccg 225180
acgcaaccac acaacgcgat cggacagacg ttaccggaga acgtcggaag acaacgggga 225240
aggtctcggg ctaagacgga gacagacacg gaaacacaac gcgactgcca gaacgagatt 225300
tcaaacgatt ctttattgac tttcctaagt atctcattca aaaaaggtag atgaatcatc 225360
tacaataccg gcatgcagtc atttctggtt tgccaggatc tcgtaagggg cgtagcggtc 225420
gtcgatcacg catcgggaga gggctggcat ccacacgtcg cagcacgacg gctgcagcct 225480
ccgggacatc gcgacgatcc aggccgccac catcacgatg gcgagcgtcg cggggatggc 225540
ggtcatcacc acggcgagcg cgatccgccg cagccctcgt aaaccgtctc cccgggacac 225600
gtcgtccgga ccgtcgtccg gaaacggggc ctcttggtaa tgcgcccaat acgtccacca 225660
cggataggcg tctccctggt agttcgagac gcggggtcgc gccgattccg gggtattccg 225720
gagccccagc agatactgca cgtcgctcac acaagaacgc tctatgttgt ctctgaacca 225780
catggcgtag agatggccca tctgagtggc gcaccacctc ttggatgtac ggtcgtccgt 225840
tccgtcgatt ctcgtcggga gcagagcgcc gcacgcgacg ctctttctat gtctccgccg 225900
ttctcgggac ctttcgttcc gttcgaggaa gtcggaactc aaggagaaat aggtcctgtc 225960
atcgcgaacc atctgatgcg ccgtccggac cagcttaccg gtgtcgttca ccacgcatac 226020
agagaagacg tccagtctgt gcacgccggc ggtcgtcgcg ttctcgttcc tgacgtattt 226080

-continued

```
cggctcggtg agatcggcgg gcatggtcaa cagctttccc acggcgaggc catactcccg 226140
gttccaaaac cgcacgtctg ccggccgaac ccagtctacc gtgggtcgca acatgatgcc 226200
gagggcctcc ccgtctccgt ctacgaccgt atgaccgtcc agggaaatcc tgaccatatg 226260
tctgaagacc caggtgccgg gtctggcggt gatgatggta tagctccgcg ttaacctgtg 226320
ttcctccccg ctattcttcc agaccgtcgt gagcccccga cccggctccg cctgcgccgc 226380
ggccaaggtc gcgagcaaga cgagcaacgc cgccaacgtc gccggcattt gaggtgccat 226440
ggtctcgtcg tcgcccgagg aaccgtcgtg aggctctgga gaaacctcta cgcgcgcgat 226500
gtgcgtaccc gacccgcgag ggcatctcca cttatagagc tgggttcgta ctcctcccat 226560
tctccatcct ttccctccct tccttccctt tcttcctccg ttcctccctc cgcgtgtact 226620
ctgcgcgtct gccccttgcc tccccgtctc ccgtctccca tcccccgtct ccccagggca 226680
ccgcgtttta tataacgcgt aaggcagaaa taaaaagaaa gagacgtcga caaaacatca 226740
tcttggcttc atgtcttttt attagtaatt gctatcgatg gtcactgcac acaacacaat 226800
taatgacatc ggtttgttta gattgcgcgt atgatcggca tgtttgtggt atacggttag 226860
tcgatcggta tataaatcaa gcactgcggg ttagtcagtc aaaagcgtcg gcatttcctt 226920
atatcgctac tacgtgatta tatacggaga gattacaatc aatcaataaa acattcgtct 226980
acttaaaaac ctacgtaacc tatggaaaaa atgagagaaa taaaacaact actactataa 227040
ctaacttatc tactaaatat aactaccgta ctaagaaact tatccaaact acacatctta 227100
acactaaaaa agaatcaaac catcaatcaa atgaaatcaa ctaaatgctg ctactactat 227160
gattgcgatt acgattcgtt acttatcatt accgtgatta gcaaactaac tatcgtctac 227220
gcatctatga aaaaacaact aatacactta acgttatagg ctaaacaact tgctgaatac 227280
ctattgtttt ataggatgag acacacaaga aaatcatctt gactagaatg ttggtcgtct 227340
gcgattatat atgtggttgg tcgattgaca gttaaaaaaa aaacaattac aatactaacg 227400
ctaacactag tactatggag atataacgac aaaaaacacg agcgtaactc acttatctat 227460
cggctaggtt aataaagaag caaagactcg gatcaagatt cttgatgata tcgccactaa 227520
tcaacaatag taattatcac ggttacaagt tctcgtcgcc gtcatcgttg tcgttgatgt 227580
cgatcgcccg cgacgccggc acagatcggc ggcggtcacg acggtgttac tgtcgtcttt 227640
ttggctgcgc aacatttaaa aaatgcaaac taaagattga tagctaagct aaactaaact 227700
aaagaaaaaa agagtaataa tgatgatgct aatgatagaa cgatgcccct cacgtatgcg 227760
ccgctccccg cggacgggga gcggtctgcc gtcgttgtca ttgacgctaa aaaaagatac 227820
gcatatgatc gttaaggatt tctttcttct tttttctttt ctctttttc tgttgtttct 227880
atatctcgct cctatcacct attgttgaac tgcaaacaaa cagaaaacga ggctcggttc 227940
taacgcgact acacgataca tcgatcttca atcaatcata cataaaacac aacggatggt 228000
aaaaaagtag aaaaaacaaa aaacatcaag cttttttttt ttactcgtta tgcatctcta 228060
atcttatcag acatgtcatc taactccgtg tttacatcag gggtgtgcca tcatggggac 228120
gggcgacgat acgcgccgta tcgtctcctt ctctctgagg aggaaaactg ttgtgttcgt 228180
ttgggcccat gttgctctcg tcggagctcg gaatctagcg atcggttttc agtctttaga 228240
tttttatctc gttttcattc aacatatcta atctatcatc ttgcttgtct gcggtctcgt 228300
cgtcgtcgat caccttatcg tcattttttt cttcttcctt tcgggtagcg tcgttggtcg 228360
cggcgtcctc gggacaggcg gcggtcgccg ccaggaccac ggtgccggcg atggcgagcg 228420
cgtcggagac ggccgacccg cggcgcccgc cggcggagaa cgaccgggaa ggcgaggtcg 228480
```

ggcgtctagg agagcggcga gactcgtttc gtggcgcggc gcactcctcg acgagggtct 228540
cgctgtaggg aggcagcgat ctcagcgact cgtatctggg gagacgcacc cccacgggag 228600
gcgacagcga cagctcgctg ggaaactggg cgctggaggc gacgctcatc agcgtcgcct 228660
cgctcaggag cgtgtcgcac tcccggtcgt cgagggcgag cttcggcgac ggcttttcct 228720
gttgcttgca ctcgtcggcc gcttccagcc ggtgcgtgcg acggtcggtg caccttcgta 228780
agaaatcgta cagccgggtc gccgccacga tgacgcacag gaaggccagg acgaggagga 228840
cgacggcgca ggcggtcatg gagacttctc tcagcgagat cccccacgcg tcccaatagt 228900
agacggtctc ctctacgcaa aagccgttgg tgagctgttc caaaagggtg cagttctggc 228960
ggacgcggct gtcggccgcg gggtcgtaga cggaaccgtc ggagttgtga ggggtaacga 229020
tcgtcagcgg cttgtccttt acctcggggt tccgtccggc gtagggggcc atgatcttcc 229080
accactgcac gggagccgtc gttacgtttg tgaacgctcc ggaccgatag ccgagtagtt 229140
tccggccgtc ggagacgcag aggttcgtgg tgtacgaggc aaacattttc gcgaacgcgg 229200
tggacatgtc gtctctgcaa cgattgcgcg tctcctcgct ccagtacgac cctccgtcgc 229260
tcagtagata tcgacacatg ataaacgcgt tgtccacgtc cggtgaccaa tacgtatcgc 229320
tgccgttttc ccatctcagc gtgaagtacg gtcttccgtt gtacgagaag aagaggaacg 229380
gattctcgac ggagtcgtta ttcgcgtcgt agtcacatcc gatcgacaca ctcatgcgtc 229440
tcctatgcgg ttttcccgtg ttgttcaagt aatcgtcgat gtccctgatg taactgccca 229500
gctcgacgat ccacccgagc atctcgtctc gttctcgtcg ccaaaactct agtggtgcga 229560
gagccgccca gcgcgcacgc ggccagatgt tgacggacgg ccccttgtcg tacgccgaga 229620
acaccgagac gttgtcgaga tgcaggaggc cggcatgaga caggttccaa gtgccgggca 229680
gactcgtcca caccgcatat gttctctgaa tacgatgtcg ttggctcgcg ggccgcgtcg 229740
tcgctgctgc tgtcgggttt ggcgcggctg tgtgtggtga cgccgttata cttgggtcgg 229800
actgattgcg ggtcgaagtg acgggagccg tcgcgtcgcc ggcgctggtg gaaacatcga 229860
cgcgcggcgt gtcgctcgct gacggttccg agctggccgt cggagtggcc tccgtcggcg 229920
acgaggtggt gttgccggcg agcgccgagg tcgcggtgtc gttcgaatcg ccgccgcgcg 229980
tcgtcgcgtt ggtgcccgtt gcggtcgtgg cggccgatgg cactgcgctt ggggcggccg 230040
cgctcgtgtc cgcgccgttc gagcccgtcg cggacggact gcggtcgctt actgtggtgt 230100
ctacaggcga cgtctcaagc gtcgtggcga gcgtcgtgtt tgccacagct ctcgtcgaga 230160
gcatgaggat cgcgacgcct gtaaaaagca gcgacatgtc tcgatccatg tcccgtggga 230220
cgatctcggc tcaggaatgg gtcgtgcagc gtggtgggcc taacacgagc gtcgccgagt 230280
gggcgtcctt cggtggcggg atctcgcagg aagagtgttc gagctgtgct aatatactct 230340
cgtctcgaag gagtggtctc gcgtcgttga ggcggcgctt ccgcgagcgg gggcgattgt 230400
gggaccggcc ccgtcggttc acagggactc cggggccggc tggttccgag gcagggtgtc 230460
ggtgaggcgc gcgagcagac gtcggcggcg ggcacgacac gatgatgcgg cgttccgcgc 230520
gtcacggttc cgtgatggtg tgctggctgt gggcgcacca cggggtgacg aagtccaccg 230580
cgttagccgg atcgagtgta taactgggca ccctgatttc aacggaaggc gtcctccatg 230640
ttagcgcctg cgaacaatgt gacggcagca tcaacaatat cagcagcgat aacgggatag 230700
cgagtctccc gccgtagtat gcgttcatgc tcgtggcgtc ggcggcagct cgcgtgcggg 230760
gtctgtggcg tcgaggtggt ttcggcgaga cggggaccga acgagggagt ctcgggcgag 230820

```
tctcgggttg gttatacccg gccgggatcg ggcggccggg atcggagccg cggacggaga 230880

ctctcacgag gtgagggctg gtagttgtca tgacagcgat gtgaacgggg tgctgccata 230940

taaaggcggg cggccgctgc cctcctgacc cacgtggaga aaaagcaaca gaaaaaaaag 231000

caaaagcgga caccaaaacg gagcgcaatg gtcggcggac cggcgagcga cgcccgcggc 231060

ggcacgatgg aaacgtgccg gccgcaccgc cgcaacggga aacggccgga agcattgtcg 231120

ccaccgccgc cgcccacgca ccggcacgtc agatcgaccc gcgtcgacgg cgccccgagt 231180

gacagcggca gcgacagcga catccgtgtc cgtgaccgtg acggagcgac cacggcccgt 231240

cagggccgaa cagcgaaccg tagccccacg tcaaaaaagg gtcgaacagc aacagcaggg 231300

acgcgcacag cagcagcgcc agcatgcacg ccaacaggag cagcaccgcc ggcgccagcc 231360

tgacggacta cgcggacgca aaaacacaca cggacacaca cggcgcccaa gcgccacaca 231420

gacacacgtt acggaagcgc gcggaacacg cgcgtaaaca gctcgctaca gacacgtgcc 231480

tcctcaccca ccaacggcca cgccgtctcc gccacccgca gcagggtgcc ggagtccaac 231540

acgcacagaa cgaacacaca aacgaacgaa aagcttagcg ccgccgccag gcagcaacaa 231600

caacccatcc cccgacgcag acacatagcc accgacgggc acaaacacca cttttaagcc 231660

cgcacacgcc ctcccggcgt ctcacacgca cacatcagac acaacgcacc acacacaccg 231720

cctaccccgc gtcgcgcaaa acacgccagc acaaaagcgc atacccgaga cgcgcacaat 231780

gcgcccaaaa aaacagcacc ccgccaccca atgcgaccgc tccgcgctac gattttcccc 231840

tctccacatc tatccacacg tcacacacac agcgcgacca cacacacgct tccaaaccct 231900

cgatctcacc cgctccctaa accctgcgcg taaaagcctc ggagtcccgc cgtaccggtt 231960

ttgccacccc cggggggcct ttcgggcggg gggccttttg ttgcggtttg ggggcgcggc 232020

gccggcgctt cccgagcggt ttcgggggtg ggcgccggag ccttttgttg cggtttaggc 232080

ccgcggcgcc ggcgcttctc tggtggtcac ggcgaggttt cgatgagctt tcgatgcgac 232140

cgcaggcggg tttcgatgag ctttcgcggt cgcggtcgga ggtcggcgga cgggtcacag 232200

cggctgctcg gcgcgccgct tgcgcgcgcg ccggcgggac gccgacgacg gacgctggcg 232260

gtggtgctgc tgttgctgca ctcgatgcgg cggctgctgt tgctgctgct gcgtgcgctg 232320

cgccggcggc cagcgaggcc ggtctcgcgc ccggtcgcgg tccagctgca tgcggacgca 232380

cggccgctcg cccgtctcca gcgcgcgccg cacgcccgcc gcctccacct ccgtgcggct 232440

ccagcgccgc tcgtccgtct cgatctcgat ctcgacctcg gtcccggggc cggcctcggc 232500

catctcgccg ctccactcca ccacgcgctc gcctcctgct cttcccccgt tctcgtgccc 232560

ggaaccgccg acttctgcct cgtcctcctc tttctcctcc tcctccgccg acgagcccgt 232620

gctccagtcg gggctccagt cctcgtccca cgcgtcccag tccccgccaa agctcatctc 232680

gccgcctcgc ctcgcccgac tccggccttt agcgctcgcc cggcgccgcc gcgacgcccc 232740

tttttctcga acccaagcac gcgggtgcgc gaccagca                         232778
```

<210> SEQ ID NO 2
<211> LENGTH: 180
<212> TYPE: PRT
<213> ORGANISM: Caviid herpesvirus
<220> FEATURE:
<223> OTHER INFORMATION: CIDMTR Strain GP129

<400> SEQUENCE: 2

```
Met Arg Val Ile Val Leu Leu Ala Met Phe Cys Cys Thr Arg Pro Gly
1               5                   10                  15
```

```
Met Phe Asp Asp Pro Cys Cys Ile Tyr Ser Ser Arg Asp Arg Leu Val
            20                  25                  30

Gln Asp Phe Thr Thr Ser Asn Asp Thr Trp Arg Leu Ile Arg Cys Lys
        35                  40                  45

Asp Asn Leu Met Val Ala Lys Arg Tyr Thr Asp Ser Phe Cys Glu Phe
    50                  55                  60

Ser Leu Glu Glu Asn Leu Phe Asp Ser Leu Ala Leu Asn Val Ser Arg
65                  70                  75                  80

Gln Glu Leu His Thr Leu Ala Pro Glu Cys Lys Phe Gly Pro Ser Val
                85                  90                  95

Glu Val Gly Ile Asn Lys Gln Val Lys Cys Ile Arg Tyr Pro Arg Met
            100                 105                 110

Pro Lys Val Pro Ser Lys Pro Glu Lys Pro Ser Ile Leu Gly Val Thr
        115                 120                 125

Tyr Arg Val Asp Tyr Thr Val Met Ile Pro Thr Pro His Phe Pro Arg
    130                 135                 140

Asp Phe Asn Gly Leu Leu Cys Thr Phe Leu Glu Lys Asn Asp Thr Phe
145                 150                 155                 160

Tyr Asn Thr Thr Val Asp Val Cys Gly Ser Glu Phe Tyr Ser Val Asp
                165                 170                 175

Gly Asn Gly Lys
            180


<210> SEQ ID NO 3
<211> LENGTH: 191
<212> TYPE: PRT
<213> ORGANISM: Caviid herpesvirus
<220> FEATURE:
<223> OTHER INFORMATION: CIDMTR Strain GP131

<400> SEQUENCE: 3

Met Lys Arg Arg Leu Ile Leu Leu Ser Trp Met Met Phe Cys Thr Ser
1               5                   10                  15

Phe Gly His Ala Gly Arg Cys Tyr Tyr Pro Ser Thr Pro Ile Pro Lys
            20                  25                  30

Arg Phe Val Lys Arg Val Asp Thr Val Arg Ser Leu Pro Glu Cys Glu
        35                  40                  45

Asn Asp Thr Val Ala Val Leu Thr Leu Thr Asn Asp Ala Lys Leu Tyr
    50                  55                  60

Val Asn Met Leu Asn Thr Trp Val Asp Gly Tyr Ile Thr Thr Leu Gln
65                  70                  75                  80

Tyr Val Val Pro Pro Thr Leu Ser Asp Ile Phe Thr Phe Ile Lys Arg
                85                  90                  95

Arg Ile Asp Arg Gly Ser Thr Gly Thr Ala Ala Ser Thr Leu Pro Ser
            100                 105                 110

Leu Thr Ser Val Arg Thr Tyr Phe Gly Asp Arg Asp Ser Ser Phe Leu
        115                 120                 125

Trp His Tyr Thr Ile Arg Met Lys Asp Gly Ala Lys Thr Leu Asp Cys
    130                 135                 140

Asp Val Tyr Val Thr Ser Arg Val His Phe Glu Leu Asn Ser Tyr Gly
145                 150                 155                 160

Ala Val Gln Thr Val Leu Phe Glu Gly Gly Val Ile Ile Ser Arg His
                165                 170                 175

Pro Ala Asp Ser Ile Ala Cys Leu Leu Ile Asn Trp Asn Trp Thr
            180                 185                 190
```

<210> SEQ ID NO 4
<211> LENGTH: 374
<212> TYPE: PRT
<213> ORGANISM: Caviid herpesvirus
<220> FEATURE:
<223> OTHER INFORMATION: CIDMTR Strain gO (GP74)

<400> SEQUENCE: 4

```
Met Thr Trp Ile Leu Val Leu Phe Leu Cys Pro Leu Leu Ala Ala Val
1               5                   10                  15

Tyr Thr Ser Pro Lys Ser Thr Asn Val Ile Glu Gln Phe Ile Ser Arg
            20                  25                  30

Phe Asn Gly Phe Met Lys Asn Ile Thr Val Thr Tyr Asn Ser Lys Trp
        35                  40                  45

Ile Gln Ala Ala Pro Met Asn Gly Ser Val Ile Pro Ile Trp Tyr Pro
    50                  55                  60

Lys Ser Val Thr Asn Ile Arg His His Phe Leu Ala Tyr Tyr Asp Asn
65                  70                  75                  80

Ala Thr Gln Thr Ile Gln Leu Ala Gly Pro His Cys Thr Thr Val Pro
                85                  90                  95

Ser Pro Ser Cys Leu Asp Thr Met Leu Ala Val Ser Ala Asp His Arg
            100                 105                 110

Gly Thr Ser Thr Cys Asn Leu Thr Thr Tyr Asn Ala Gln Leu Tyr Asn
        115                 120                 125

Ile Pro Arg Trp Thr Val Lys Leu Arg Leu Pro Ser Gly Gly Phe Tyr
    130                 135                 140

His Leu Asn Ser Asp Asp Leu Ile Tyr Met Ala Leu Ser Val Ser Val
145                 150                 155                 160

Ala Ser Arg Arg Glu Phe Asp Val Cys Ala Gly Gly Gly Ser Tyr Leu
                165                 170                 175

Thr Ala Leu Ser Lys Asn Leu Phe Gln Leu Ser Pro Gln Leu Arg Ser
            180                 185                 190

Asn Trp Thr Leu Thr Lys Ser Phe Phe Arg Lys Leu Lys Arg Leu Gln
        195                 200                 205

Gln Ala Asn Arg Thr Ile Glu Glu Glu Pro Lys Lys Ser Arg Asn Arg
    210                 215                 220

Lys Asn Asp Thr Gly Ala Val Lys Asn Glu Thr Trp Ile Pro Pro Val
225                 230                 235                 240

Ser Ala Asn Ala Phe Leu Gly Phe Asn Phe Tyr Leu Tyr Gly Met Leu
                245                 250                 255

Tyr Lys Ser Ser Leu Cys His Thr Gly Arg Ser Asn Ser Tyr Ile Ser
            260                 265                 270

Thr Asn Ala Thr Leu Asn Asp Met Arg Leu Ser Leu Leu Gln Asn Val
        275                 280                 285

Ser Trp Ala Asp Asp Ser Leu Asn Glu Thr Leu Ile Asn Thr Thr Leu
    290                 295                 300

Val His Gly Tyr Val Gln Ser Leu Val Leu Glu Arg Asn Ile Thr Asn
305                 310                 315                 320

Asn Thr His Pro Leu Tyr Asn Thr Arg Phe Val Arg Val Ser Arg Glu
                325                 330                 335

Leu Gly Thr Asp Asp Phe Arg His Ser Pro Tyr Pro Ser Arg Pro Thr
            340                 345                 350

Thr Asn Glu His Pro Leu Val Thr Ser Gly Gly Leu Ala Gly Lys Arg
        355                 360                 365
```

```
Pro Val Thr Thr Val Pro
    370


<210> SEQ ID NO 5
<211> LENGTH: 726
<212> TYPE: PRT
<213> ORGANISM: Caviid herpesvirus
<220> FEATURE:
<223> OTHER INFORMATION: CIDMTR Strain gH (GP75)

<400> SEQUENCE: 5

Met Ser Pro Ala Ala Arg Phe Thr Val Ile Ser Cys Leu Val Val Ser
1               5                   10                  15

Leu Ile Thr Pro Ser Glu Thr Ser Phe Ser Ser Trp Thr Tyr Pro Asp
            20                  25                  30

Val Asn Trp Thr Lys Ser Ser Leu Asn Met Thr Cys Leu Asn Asn His
        35                  40                  45

Thr Gly Gln Arg Ser Leu Thr Thr Glu Gly Leu Ile Ser Phe Asn Phe
    50                  55                  60

Tyr Glu Ala Pro Lys Thr Val Arg Thr Tyr Gln Val Pro Lys Cys Ile
65                  70                  75                  80

Phe Met Thr Thr Ile Ser Lys Ser Ile Met Gln Ser Val Asp Leu Phe
                85                  90                  95

Glu Ser Leu Glu Ser Tyr Lys Leu Arg Tyr Tyr Ser Tyr Ile Ile Val
            100                 105                 110

Pro Val His Ala Ala Phe Gln Ile Phe Ile His Glu Leu Arg Thr Asp
        115                 120                 125

Leu Val Pro Ser Thr Glu Glu Leu Asn Val Arg Ala Asp Asp Thr Leu
    130                 135                 140

Pro Asn Ile Thr Val Trp Arg Thr Arg Ser Gly Ser Tyr Val Ile Pro
145                 150                 155                 160

Leu Leu Asp Val Val Thr Pro Glu Phe Glu Asp Cys Asn Leu Phe Ser
                165                 170                 175

Asn His Thr Val Val Phe Asp Met Lys Ile Pro Cys Ser Arg Glu Leu
            180                 185                 190

Tyr Leu His Gln Leu Gly Ala His Arg Phe Thr Ile Ala Leu Thr Phe
        195                 200                 205

Thr Pro Asn Phe Phe Val Leu Asn Ile Gln Thr Thr Arg Arg Ser His
    210                 215                 220

Thr Thr Glu Asp Asp Glu Asp Thr Leu Leu Ile Phe Gly Asp Ile Gln
225                 230                 235                 240

Glu Ile Asp Val Lys Ala Pro Tyr Ser Lys Pro Val Leu Thr Leu Arg
                245                 250                 255

Gln Ser Ser Arg Asp Asp Leu Leu Ile Val Ala Lys Thr Ser Thr Val
            260                 265                 270

Thr Thr Ile Tyr Pro Phe Ile Gln Thr Gln Gly Phe Leu Lys Glu Ile
        275                 280                 285

Leu Ser Asn Asn Tyr Leu Asp Phe Asp Arg Val Tyr Thr Glu Phe Ser
    290                 295                 300

Arg Leu Val Thr His Asn Met Met Asn Gly Leu Cys Asp Ala Pro Pro
305                 310                 315                 320

Asp Asn Arg Thr Val Ser Met Val Phe Ser Tyr Ala Ile Leu Ile Arg
                325                 330                 335

Ala Leu Tyr His Thr Ala Asn Met Thr Ala Arg Leu Glu Asp Val Thr
            340                 345                 350
```

```
Leu Arg Tyr Val Lys Leu Thr Leu Ala Arg Thr Phe Leu Gln Gln Cys
        355                 360                 365

Phe Asn Ile Glu Pro Arg Tyr Met Arg Phe Pro Met Ile Asp Gly Ala
    370                 375                 380

Val Ser Val Phe Leu Lys Leu Ile Arg Asn Ser Arg Asp Val Asp Arg
385                 390                 395                 400

Ala Ile Lys Leu Ser Leu Thr Phe Ala Leu Ile Phe Gly Asn Asn Thr
                405                 410                 415

Asn Leu Thr Glu Glu Arg Asp Ile Glu Asn Ala Leu Tyr Glu Met Lys
            420                 425                 430

Ser Ile His Arg Ala Gly Leu Val Ser Pro Leu Ser Pro Arg Gln Arg
        435                 440                 445

Asn Leu Leu Tyr Met Met Ala Tyr Val Met His His Thr Ala Ala Phe
    450                 455                 460

Pro Asp Ile Arg Arg Glu Met Leu Ala Met Gln Thr Ser Leu Cys Ser
465                 470                 475                 480

Pro Gln Glu Leu Tyr Asn Trp Ala Pro His Val Ser Ser Ala Gly Leu
                485                 490                 495

Thr Met Gln Glu Met Phe Thr Pro Cys Ser Gly Ser Gly Arg Arg Asp
            500                 505                 510

Tyr Ser Glu Ala Arg Ile Ala Glu Ile Val Gln Leu Asn Pro Leu Thr
        515                 520                 525

Thr Lys Thr Pro Ala Asp Leu Tyr Arg Ile Leu Ala His Phe Asp Arg
    530                 535                 540

Ser Asn Leu Thr Asn Phe Pro Ala Leu Ser Cys Ile Ser His Leu Ser
545                 550                 555                 560

Gly Tyr Val Ala Val Thr Leu Lys Asp Val Thr Tyr Val Val Ser Ser
                565                 570                 575

Asn Val Ile Leu Lys Gly Thr Ser Tyr Pro Val Thr Asn Leu Ala Val
            580                 585                 590

Asp Lys Thr Met Ile Val Thr Val Ser Pro Ala Gln Gln Pro Cys Glu
        595                 600                 605

Gln Thr Glu Val Ala His Ala Thr Arg Ser Ile Pro Ile Val Lys Asn
    610                 615                 620

Ile Thr Ile Gly Asn Asp Cys Glu Tyr Cys Lys Ser Ala Ile Met Glu
625                 630                 635                 640

Tyr Asp Glu Val Asn Gly Leu Ser Asn Ile Val Tyr Leu Ala Asp Thr
                645                 650                 655

Ala Asp Leu Val Leu Val Thr Asn Leu Asp Asn Arg Ile Leu Ala Ser
            660                 665                 670

Ser Pro Arg Thr Arg Tyr Ile Met Met Thr Ala Asn Gly Thr Leu Ile
        675                 680                 685

Glu Ile Thr Ser Val Ile Ile Asp Ile Arg Gln Thr Ser Ile Phe Met
    690                 695                 700

Ile Met Leu Tyr Cys Ser Leu Gly Val Leu Leu Leu Tyr Gly Leu Tyr
705                 710                 715                 720

Arg Leu Leu His Met Ile
                725
```

<210> SEQ ID NO 6
<211> LENGTH: 901
<212> TYPE: PRT
<213> ORGANISM: Caviid herpesvirus
<220> FEATURE:
<223> OTHER INFORMATION: CIDMTR Strain gB (GP55)

<400> SEQUENCE: 6

```
Met Arg Pro Val Arg Gly Ile Ala Arg Ser Arg Ile Leu Ser Cys Ser
1               5                   10                  15

Trp Arg Gly Thr Trp Thr Ser Ala Leu Thr Ile Leu Tyr Leu Gly Val
            20                  25                  30

Tyr Cys Glu Ser Thr Thr Val Thr Pro Thr Thr Val Glu Asp Thr Thr
        35                  40                  45

Val Ser Asn Gly Asn His Ser Asp Ala Ser Ser Asn Asn Thr Val Ile
    50                  55                  60

Arg Asn Leu Thr Ala Ser Val Asp Phe Ser Gln Arg Lys Leu Tyr Pro
65                  70                  75                  80

Tyr Arg Ile Cys Ser Met Ser Met Gly Thr Asp Leu Val Arg Phe Ala
                85                  90                  95

Arg Thr Ile Gln Cys Val Pro Phe Asn Pro Arg Val Asn Ser Glu Glu
            100                 105                 110

Gly Ile Met Leu Ile Tyr Lys Arg Asn Ile Leu Pro Tyr Val Phe Thr
        115                 120                 125

Ala Tyr Thr Tyr Gln Lys Glu Leu Leu Phe Gln Arg Ser Tyr Lys Tyr
    130                 135                 140

Val Thr Tyr Asp Tyr Leu Leu Gly Tyr Ser Arg Glu Phe Val Ala Leu
145                 150                 155                 160

Pro Met Trp Glu Ile Phe Leu Val Asn Ser Arg Gly Gln Cys Tyr Thr
                165                 170                 175

Ser His Gln Arg Val Ile Gly Ala Asp Arg Tyr Ile Ala Tyr His Asn
            180                 185                 190

Asp Asn Glu Val Asn Glu Thr Met Trp Leu Met Arg Asp Asp Met Gly
        195                 200                 205

Asn Asp Asp Thr Tyr Arg Tyr Ile Thr Val Lys Glu His Ala Arg Thr
    210                 215                 220

Pro Gly Ser Val Trp Leu Tyr Lys Glu Thr Cys Ser Met Asn Cys Ile
225                 230                 235                 240

Val Thr Lys Thr Lys Gly Lys Ser Lys Phe Pro Tyr Asp Met Phe Val
                245                 250                 255

Leu Pro Ser Gly Val Ile Val Asn Ile Ser Pro Phe Tyr Asn Gly Ser
            260                 265                 270

Asn Gly Lys Thr Phe Arg Glu Gln Arg Glu Lys Phe His Ile Trp Ser
        275                 280                 285

Asn Tyr Ser Ile Leu Lys Asp Phe Gly Ser Arg Ala Leu Glu Ala Arg
    290                 295                 300

Ile Val Pro Lys Met Ala Phe Tyr Glu Arg Glu Asp Val Val Ile Gly
305                 310                 315                 320

Trp Glu Val Asn Asp Gln Ser Asn Val Thr Cys Glu Met Ile Leu Trp
                325                 330                 335

Glu Thr Val Asp Arg Ala Ile Arg Thr Glu Tyr Glu Asn Ala Phe His
            340                 345                 350

Tyr Val Ala Arg Thr Leu Thr Ser Thr Phe Val Glu Asn Lys Tyr Ser
        355                 360                 365

Pro Asp Asn Asn Leu Thr Glu Asp Asp Ile Lys Cys Phe Lys Asp Asp
    370                 375                 380

Ala Gln Lys Lys Ile Glu Glu Val Phe Leu Arg Asp Tyr Asn Glu Thr
385                 390                 395                 400

Tyr Asp Met Asp Gly Asn Ala Thr Tyr His Val Thr Thr Gly Gly Leu
```

```
                405                 410                 415

Val Ile Val Trp Gln Gly Leu Lys Gln Lys Ser Leu Lys Ala Leu Glu
            420                 425                 430

Ile Ala Ala Asn Glu Ser Ala Val Ser Ala Thr Gly Ser Asn Ser Arg
        435                 440                 445

Arg Lys Arg Ser Leu Pro Asp Glu Ser Thr Gly Asp Ile Ser Tyr Ala
    450                 455                 460

Gln Leu Gln Phe Ala Tyr Asp Thr Leu Arg Thr Tyr Ile Asn Gln Ala
465                 470                 475                 480

Leu Gly His Ile Ala Glu Ala Trp Cys Leu Asp Gln Lys Arg Thr Ala
                485                 490                 495

Glu Val Leu His Glu Leu Ser Lys Ile Asn Pro Ser Asn Ile Leu Ser
            500                 505                 510

Ala Ile Phe Gly Val Pro Val Ala Ala Arg Val Val Gly Asp Val Ile
        515                 520                 525

Ser Leu Ala Lys Cys Ile Glu Val Asn Gln Ser Thr Val Leu Ile Lys
    530                 535                 540

Gly Asp Met Arg Lys Phe Ser Asp Asp Gly Lys Leu Glu Gly Cys Tyr
545                 550                 555                 560

Ser Arg Pro Val Val Trp Phe Ser Met Lys Asn Ser Thr Glu Val Arg
                565                 570                 575

Leu Gly Gln Leu Gly Glu Asp Asn Glu Ile Leu Leu Gly Thr His Arg
            580                 585                 590

Met Glu Thr Cys Gln Thr Gln Asp Tyr Arg Ile Phe Val Ala Gly Asp
        595                 600                 605

Ile Gly Tyr Glu Phe Gln Gln Tyr Val Phe Thr Lys Lys Ile Asn Leu
    610                 615                 620

Ser Glu Ile Asp Ile Ile Asp Thr Met Ile Ala Leu Lys Thr Glu Pro
625                 630                 635                 640

Leu Glu Asn Ile Asp Phe Lys Val Leu Glu Leu Tyr Ser Arg Asp Glu
                645                 650                 655

Leu Ala Gln Ala Asn Val Phe Asp Leu Glu Ser Ile Met Arg Glu Tyr
            660                 665                 670

Asn Tyr Gln Lys Lys Arg Leu Asp Phe Val Val Glu Arg Val Ile Asn
        675                 680                 685

Pro Ile Pro Pro Ala Leu Lys Gly Leu Asp Glu Met Met Asn Gly Met
    690                 695                 700

Gly Ala Ile Gly Lys Gly Ile Gly Glu Ala Val Gly Ala Val Gly Gly
705                 710                 715                 720

Ala Ile Gly Ser Phe Ile Gly Ala Leu Val Thr Phe Val Thr Asn Pro
                725                 730                 735

Phe Gly Ala Phe Val Val Phe Leu Phe Cys Val Gly Cys Ile Thr Leu
            740                 745                 750

Val Ile Thr Val Tyr Arg Arg Gln Arg Arg Ala Met Gln Arg Pro Phe
        755                 760                 765

Asp Tyr Phe Phe Pro Tyr Ala Ser Gln Thr Ile Thr Ser Ser Val Ala
    770                 775                 780

Asp Ser Ser Ile Ala Val Ala Tyr Pro Gly Pro Glu Gly Thr Ser Gly
785                 790                 795                 800

Asp Ala Pro Pro Pro Tyr Pro Gly Glu Ala Pro Tyr Gly Tyr Lys Asp
                805                 810                 815

Leu Ser Val Asp Ala Asp Thr Arg Val Ser Ser Ser Ser Ala Gly Ala
            820                 825                 830
```

```
Gly Ala Asp Phe Asn Glu Glu Asp Ala Val Arg Met Leu Arg Ala Ile
        835                 840                 845

Lys Arg Leu Asp Asp Lys Lys Arg Gln Glu Ile Glu Lys Ser Ser Lys
    850                 855                 860

Asp Ser Ala Ser Asn Lys Asn Ser Glu Thr Arg Arg Arg Pro Gly Ile
865                 870                 875                 880

Met Asp Arg Leu Arg Arg Arg Gly Gly Tyr Gln Lys Leu Asn Thr Glu
                885                 890                 895

Asp Asp Val His Val
            900
```

<210> SEQ ID NO 7
<211> LENGTH: 133
<212> TYPE: PRT
<213> ORGANISM: Caviid herpesvirus
<220> FEATURE:
<223> OTHER INFORMATION: CIDMTR Strain gN (GP73)

<400> SEQUENCE: 7

```
Met Lys Ser Tyr Leu Ile Gly Pro Leu Ser Ala Val Ser Ser Pro Ser
1               5                   10                  15

Thr Ser Ser Cys Gly Arg Arg His Arg Val Thr Ile Ala Gly Leu Ala
            20                  25                  30

Leu Cys Tyr Leu Ile Val Val Ser Met Val Ser Gly Ala Ser Ser Asn
        35                  40                  45

Ser Thr Ser Val Thr Thr Pro Ser Pro Ala Ser Gln Ala Ser Ser Val
    50                  55                  60

Met Ser Ser Thr Thr Val Ala Ser Thr Thr Lys Thr Ala Leu Gly Phe
65                  70                  75                  80

Tyr Asp Val Gly Cys Val Ser His Ala Tyr Asn Val Ser Ile Arg Ser
                85                  90                  95

Phe Ala Ser Leu Trp Ile Leu Ala Asn Val Phe Ile Leu Leu Cys Ser
            100                 105                 110

Phe Gly Ile Phe Leu Arg His Cys Cys Tyr Arg Ser Phe Ala Ser Glu
        115                 120                 125

Thr Ala Arg Gly Tyr
    130
```

<210> SEQ ID NO 8
<211> LENGTH: 253
<212> TYPE: PRT
<213> ORGANISM: Caviid herpesvirus
<220> FEATURE:
<223> OTHER INFORMATION: CIDMTR Strain gL (GP115)

<400> SEQUENCE: 8

```
Met Phe Phe Ser His Arg Leu Thr Ile Gly Phe Tyr Ile Pro Leu Ile
1               5                   10                  15

Val Leu Thr Thr Ile Ser Ser Leu Ser Glu Ser Leu Gly Glu Arg Gln
            20                  25                  30

Lys Thr Ala Cys Thr Val Ala Ala Ile Ser Cys Ala Asn Ser Asp Thr
        35                  40                  45

Tyr Asn Arg Thr Thr Val Ser Asn His Thr Phe Phe Tyr Ile Ser Asp
    50                  55                  60

Arg Trp Lys Tyr Ser Glu Leu Ile Arg Tyr Glu Lys Pro Thr Trp Asp
65                  70                  75                  80

Leu Arg His Asp Lys Leu Ile His Val Asp Arg Glu Phe Leu Asp Ile
```

```
                85                  90                  95

Val Ser Leu Leu His Asn Asn Glu Asn Gln Leu Arg Thr Leu Leu Thr
            100                 105                 110

Ile Phe Arg Ser Asp Ser Ala Pro Pro Trp Val Lys Phe Met Arg Gly
        115                 120                 125

Tyr Ser Gln Cys Leu Asp His Pro Ile Ile Tyr Thr Cys Val Glu Glu
    130                 135                 140

Lys Cys Gln Gln Tyr Asn Leu Glu Glu Leu Pro Tyr Gly Lys Asp Ile
145                 150                 155                 160

Phe Leu Glu Asn Val Val Gly Phe Asp Leu Gly Ala Pro Pro His Asn
                165                 170                 175

Met Ser Val Leu Ile Ala Val Ser Asn Thr Lys Pro Lys Ile Thr Lys
            180                 185                 190

Val Leu Arg Ile Thr Ser Thr Ser Leu Thr Leu Phe Asp Ala Leu Tyr
        195                 200                 205

Asn Thr Val Leu Thr Phe Phe Arg Ser Ile Gly Ala Arg Asn Val Asp
    210                 215                 220

Val Val Arg Arg Leu Ile Leu Tyr Gln Ala Ser Leu Ser Gly Pro His
225                 230                 235                 240

Arg Asp Ala Pro Ile His Asn Tyr Leu Asn Arg Asp Leu
                245                 250


<210> SEQ ID NO 9
<211> LENGTH: 566
<212> TYPE: PRT
<213> ORGANISM: Caviid herpesvirus
<220> FEATURE:
<223> OTHER INFORMATION: CIDMTR Strain GP83

<400> SEQUENCE: 9

Met Glu Arg Tyr Val Gly Leu Gly Thr Thr Leu His Leu Ala Leu Gln
1               5                   10                  15

Val Glu Gly Pro Phe Gly Pro His Glu Thr Arg Phe Val His Phe Asp
            20                  25                  30

Ala Thr Phe Thr Val Pro Arg Thr Pro Ser Val Val Ile Val Ala Glu
        35                  40                  45

Glu Gln Val Gly Ser His Leu Pro Pro Ser Ser Pro Leu Arg Met Lys
    50                  55                  60

Phe Arg Ala Ile His Ser Gln Glu Glu Leu Asp Leu Leu Asn Leu Glu
65                  70                  75                  80

Val Arg Asn Ala Ser Asp Gln Pro Leu Pro Ala Lys Ser Phe Tyr Asp
                85                  90                  95

Leu Asn Val Val Val Phe Ala Leu Pro Leu Pro Arg Val His Ala Ala
            100                 105                 110

Pro Leu His Ile Phe Phe Asn Ser Ala Leu Lys Pro Ser Arg Glu Thr
        115                 120                 125

Phe Pro Thr Cys Ser Lys Thr Val Val Arg Arg Ala Cys Gly Ala Ile
    130                 135                 140

Trp Gly Val Arg Thr Ala Leu Ser Asn Ile Ala Trp Thr Glu Gly Val
145                 150                 155                 160

Gly Asn Arg Ala His Val Asp Arg Ala Leu Thr Val Thr Val Leu Leu
                165                 170                 175

Ser Val Lys Pro Ala Cys Met Thr His Val Asp Ser Leu Thr Glu Ile
            180                 185                 190

Asn Cys Ser His Glu Asp Val Gln Val Phe Lys Ala Glu Val Phe Gln
```

```
        195                 200                 205

Lys Gly Arg Pro Asn Val Leu Gly Leu Thr Leu Gln Thr Thr Ala Lys
    210                 215                 220

Pro Pro Pro Lys Lys Leu Thr Leu Phe Phe Gln Leu Leu Ala Ser His
225                 230                 235                 240

Ala Gln Val Val Met Arg His Asn Pro Tyr Pro Ala Leu Gln Ser His
                245                 250                 255

Pro Ser Asn Gly Phe Thr Ile His Cys Pro Gly Asp Ile Arg Leu Gln
            260                 265                 270

Ser Gly Gln Thr Tyr Arg Leu Thr Leu Arg Asn Gly Phe Asp Ser Thr
        275                 280                 285

Ser His Ala Ala Leu Phe Phe Pro Ala Asp Phe Pro Asn Ala Asp Val
    290                 295                 300

Ser Gly Gly Gln Trp Lys Ala Arg His Asn Met Asp Ile Val Ile Arg
305                 310                 315                 320

Ser His Gly Glu Thr Thr Val Arg Lys Asp Glu Val Leu Gly Thr Val
                325                 330                 335

His Phe Phe Asp Asn Asp Leu Phe Thr Phe His Arg Val Ala Gly Val
            340                 345                 350

Ile Asp Thr Cys Met Met Gly Lys Gln Phe Glu Thr Arg Val Arg Arg
        355                 360                 365

Cys Ser Glu Ser Cys Gln Glu Gln Val Phe Val Lys Ser Gly Gly Arg
    370                 375                 380

Arg Thr Gly Asn Ala Ala Arg His Arg Arg Asp Arg Asp Gly Gly Asp
385                 390                 395                 400

Asp Asp Asp Asp Asp Glu Asn Glu Asp Gly Glu Glu Gly Glu Glu Asp
                405                 410                 415

Gly Glu Glu Asp Val Gly Asp Ala Lys Asp Asp Gly Ser Glu Ser Ser
            420                 425                 430

Ser Glu Ser Glu Leu Gly Ser Gly Glu Asp Asn Asp Gly Asp Asp Asp
        435                 440                 445

Val Phe Glu Cys Glu Arg Pro Leu Ala Arg Glu Asp Gly Ala Ser Gly
    450                 455                 460

Ser Ala Glu Arg Glu Thr Leu Asp Glu Ser Glu Asp Pro Ser Leu Arg
465                 470                 475                 480

Pro Arg Arg Val Ser Glu Glu Ile Phe Pro Ser Val Leu Phe Tyr Pro
                485                 490                 495

Trp Ala Leu Ser Ile Pro Thr Gly Phe Cys Ala Tyr Ile His Tyr Asn
            500                 505                 510

Val Val Ala Cys Ser Ser Glu His Ser Ser Gly Glu Val Gln Asp Gly
        515                 520                 525

Ser Val Trp Phe Asp Gly Val Pro Thr Arg Pro Ala Ser His Ala Cys
    530                 535                 540

Ser Arg Thr Arg Arg Asp Asp Asp Gly Gly Ala Gly Thr Ser Arg Arg
545                 550                 555                 560

Ser His Arg Gly Ala Gln
                565
```

<210> SEQ ID NO 10
<211> LENGTH: 1801
<212> TYPE: DNA
<213> ORGANISM: Caviid herpesvirus

<400> SEQUENCE: 10

```
cttgcagagc ctcctcgctc tgcccggctt ctaaaccgga gccccttata tactcataaa     60
ccactccccc atagggtacg tggaccaata gtggagtggg gcgtgctctc caaaaatgca    120
aagtcaccat gatacagtac ttgagcggtt tccagggact ttccagagga cggtcaaatg    180
tcagtgaatc acccagtatg tactgccaat ttggcagtaa ttggataccg catgactaag    240
gaaaaagtta taattgacag ggaaaatccc ctttgtggct gatttgcata aaactaagtg    300
taatttactg gaatattggc cctggaaaga tgtacttaac tctgagtgac cctttccctc    360
tgccaagtga ctataatgct gcccgggact ttccagatgc tctttgccaa aaagaacatg    420
actaaatatg gctgtgcttt gtccccgtat cagtttactg taaatggccc gggactttcc    480
acgtttcctt tgccaaaaga acactgttaa ctctggctga ccctatccca tgccaatcaa    540
acgtcccata accgtatccc tttgccaaaa aggacacagc tacctctggc tgaccttctt    600
tcatattaat cagacgtccc acgtccaggg actttccata gaccctctgc caagcaatac    660
atgactaaat atggctgtgc tttgtccccg tatcagttta ctgtaaatgg cccgggactt    720
tccacgtttc ctttgccaaa agaacactgt taactctggc tgaccctatc ccatgccaat    780
caaacgtccc ataaccgtat ccctttgcca aaaaggacat gactaattct ggctgacctt    840
tccccatatc actcaaacgt cccatgaccg tatccctttg ccaaaaagga catggctaac    900
tctggctgac ctttccccat atcactcaaa cgtcccatga ccgtatccct ttgccaaaaa    960
ggacatgact aactttggct gacctttccc catatcactc aaacgtccta tgaccgtatc   1020
cctttgccaa aaaggacatg actaactctg gctgacctgt ctccatatca atcaaacgtc   1080
ccgtgaccgt atccaccgtg ccaaaaagga catgagtaat catgaccgta cttcgtcccc   1140
gtattagttt actgtaattt ggccagggac tttccacatc atccaaatta atcaataatg   1200
attacaagtg gacaggttgt tggcatctac ttattcagaa aaatccatat gcgtgctgcc   1260
agcatcaaaa caatgtaata tattcatgag atcatgatta atttaatgga aaacacctaa   1320
aaaatccagt catcatctgg aaagcaccta acgttacgta aaattttaat atgattcaga   1380
gatgggccgg gttatacgga atacgcctat aaaagaggag gagttcgctg gtttagaatc   1440
agtattgtgc cagactccga agaggacaca tctcccgtgc tcggaatgct gccaatatat   1500
taaaagaata ggtgcgtatg gttatctttg atatagcaca ggtagaatac gcgtatagag   1560
gtgaccttta cctgtgagag taggttagta aacaaagaat cgtgccagac tgaaggtaca   1620
gcaagtcaat ttatatgtga tagttaataa tatagattac attgatctga tattgtatag   1680
tttgacgtgg aatgtaggtt tgcttactag atgatcgata gcgcaggctt atagcgtaag   1740
agatgtgata gatgcgatgg tatgcatcgg cagtttccga cagatgttcg tactgaattg   1800
t                                                                   1801
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11

```
gtgagacgta agaatagctt gc                                              22
```

<210> SEQ ID NO 12
<211> LENGTH: 21
<212> TYPE: DNA

<213> ORGANISM: Artificial Sequence
<220> FEATURE:
<223> OTHER INFORMATION: Description of Artificial Sequence: Synthetic
primer

<400> SEQUENCE: 12
gatccttaga ctctatcacg g 21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gtgttgtcac aattggcaca tg 22

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
acatggtcac gacagaatc 19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
gtggacagga tccccaaatt 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
ccaaatttct gtcgtcggcg 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
tgtttccgtg tctgtctccg t 21

<210> SEQ ID NO 18
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 18

gtcttagccc gagaccttc                                                  19


<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

tgcgaagcga tctctctcaa c                                               21


<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

gtggttgtac gtgtcgtcgt ca                                              22


<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

tgcgaagcga tctctctcaa c                                               21


<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

cttggaccat ggaacatgtc tg                                              22


<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

tcgctatgca tataacgtag c                                               21


<210> SEQ ID NO 24
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 24

atgcaacata gcgtgctgac                                                20


<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

gggacaaaag cacgatgaac                                                20


<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26

gtgttcgtgt ccttgatcgt acgca                                          25


<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

aatggttcgc tacggacatc                                                20


<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

cggacaacgg aacatacttg                                                20


<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29

ttcctcgacg aagctcgcgg tataat                                         26
```

GUINEA PIG CYTOMEGALOVIRUS (CIDMTR STRAIN)

CROSS REFERENCE TO RELATED APPLICATIONS

This application claims priority to U.S. Provisional Application No. 61/716,302 that was filed on Oct. 19, 2012. The entire content of this provisional application is hereby incorporated herein by reference.

FEDERAL GRANT SUPPORT

This invention was made with government support under HD38416 and HD044864 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 17, 2013, is named 09531.359US1_SL.txt and is 338,983 bytes in size.

BACKGROUND

Developing strategies to control and prevent congenital infection with cytomegalovirus (CMV) represents a major priority in perinatal medicine. CMV infection is the most common congenital infection in the developed world. The condition occurs in 0.5 to 2% of all births and is responsible for a wide range of neurodevelopmental disabilities in newborns. Of these disabilities, the most common is sensorineural hearing loss (SNHL), which occurs in up to 15% of all congenitally infected children. The outcome of SNHL is improved when antiviral therapy (ganciclovir) is administered to infants with neurological involvement who are congenitally infected with CMV. However, other forms of neurological injury associated with symptomatic congenital CMV may be irreversible.

Because pre-conceptual maternal immunity to CMV reduces the severity of injury caused by congenital CMV, the development of vaccines is considered to be of high priority. See, e.g., US Patent Publication No. 2010/0285059. A number of CMV vaccines are currently being evaluated in clinical trials, including live attenuated vaccines and subunit recombinant vaccines. Better elucidation of the determinants of the maternal immune response that result in protection of the fetus will help in prioritizing future vaccine studies for prevention of congenital infection.

Ideally, immunizations for CMV would first be evaluated in animal models prior to human clinical trials. Unfortunately, the strict species specificity of CMVs precludes any meaningful evaluation of candidate human CMV vaccines for protection in animal models. Although laboratory animals will engender immune responses to the candidate vaccines being evaluated in clinical trials, which allow study of safety and immunogenicity, laboratory animals cannot be infected with human CMV. As a result, the ability to analyze the protective effect of vaccines against experimental disease is restricted, and investigators have turned to species-specific animal CMVs to generate models of pathogenesis and immunity.

Among the small animal models of congenital CMV infection, the guinea pig cytomegalovirus (GPCMV) offers some unique advantages compared with rodent models. Chief among these advantages is the fact that GPCMV crosses the guinea pig placenta, causing infection in utero. For this reason, the guinea pig is well suited to the study of vaccines designed to interrupt vertical virus transmission. (Schleiss, *ILAR Journal* 47:65-72 (2006)). A limitation of the model, however, is that only one strain of the virus is available, the ATCC/22122 strain, discovered by Hartley in 1957 (Hartley J W, Rowe W P, Huebner R J. 1957. Serial propagation of the guinea pig salivary gland virus in tissue culture. Proc Soc Exp Biol Med 96:281-285). Thus, there is a current need for an alternative isolate of GPCMV.

SUMMARY

In certain embodiments, the present invention provides an isolated or purified guinea pig cytomegalovirus (GPCMV) Strain CIDMTR, which is ATCC® deposit number PTA-120714. The guinea pig cytomegalovirus (GPCMV) Strain CIDMTR has been deposited with the American Type Culture Collection Depository (ATCC® Depository, 10801 University Boulevard, Manassas, Va. 20110-2209 USA) and assigned ATCC® Patent Deposit Designation PTA-120714. The cell line was deposited on Nov. 19, 2013. Access to this deposit will be available during the pendency of the application to the Commissioner of Patents and Trademarks and persons determined by the Commissioner to be entitled thereto upon request. The deposits will be maintained in the ATCC® Depository, which is a public depository, for a period of 30 years, or 5 years after the most recent request, or for the enforceable life of the patent, whichever is longer, and will be replaced if it becomes nonviable during that period.

In certain embodiments, the present invention provides an isolated or purified guinea pig cytomegalovirus (GPCMV) Strain CIDMTR having at least 90% identity to SEQ ID NO:1.

In certain embodiments, the present invention provides an isolated or purified guinea pig cytomegalovirus (GPCMV) Strain CIDMTR comprising a glycoprotein (GP), wherein the GP has having at least 75% sequence identity to GPCMV glycoprotein 129 (GP129), GPCMV glycoprotein 131 (GP131), GP74 (gO), GP75 (gH), GPCMV glycoprotein 55 (gB), GPCMV glycoprotein 73 (gN), or GPCMV glycoprotein 115 (gL).

In certain embodiments, the present invention provides an isolated or purified guinea pig cytomegalovirus (GPCMV) Strain CIDMTR comprising a glycoprotein (GP), wherein the GP has having at least 84% sequence identity to GPCMV glycoprotein 129 (GP129, SEQ ID NO:2), at least 94% sequence identity to GPCMV glycoprotein 131 (GP131, SEQ ID NO:3), at least 78% sequence identity to gpUL74 (gO, SEQ ID NO:4), or at least 82% sequence identity to gpUL75 (gH, SEQ ID NO:5).

In certain embodiments, the present invention provides an isolated or purified guinea pig cytomegalovirus (GPCMV) Strain CIDMTR glycoprotein (GP), wherein the GP has having at least 75% sequence identity to GPCMV glycoprotein 129 (GP129), GPCMV glycoprotein 131 (GP131), GP74 (gO), GP75 (gH), GPCMV glycoprotein 55 (gB), GPCMV glycoprotein 73 (gN), or GPCMV glycoprotein 115 (gL).

In certain embodiments, the present invention provides an isolated or purified guinea pig cytomegalovirus (GPCMV) Strain CIDMTR glycoprotein (GP), wherein the GP has having at least 84% sequence identity to GPCMV glycoprotein 129 (GP129), at least 94% sequence identity to GPCMV glycoprotein 131 (GP131), at least 78% sequence identity to GP74 (gO), or at least 82% sequence identity to GP75 (gH).

In certain embodiments, the present invention provides a composition comprising a GP described above and a pharmaceutically-acceptable, non-toxic vehicle.

In certain embodiments, the present invention provides a purified antibody that binds specifically to GPCMV Strain CIDMTR, or the GP described above. In certain embodiments, the antibody is an antibody fragment.

In certain embodiments, the present invention provides a method of determining the effectiveness of a vaccine or therapeutic composition in preventing or ameliorating infection or re-infection with cytomegalovirus.

In certain embodiments, the present invention provides an isolated promoter sequence comprising (or consisting of) a nucleic acid of between 500 and 1801 nucleotides in length (or any integer there-between) having at least 90% identity to SEQ ID NO:10. In certain embodiments, the promoter has 90%, 91%, 92%, 93%, 94%, 95%, 96%, 97%, 98%, 99% or 100% identity to SEQ ID NO:10. In certain embodiments, the promoter is between 500 and 1700 nucleotides in length, such as between 1500 and 1700 nucleotides in length. In certain embodiments, the present invention provides an isolated polynucleotide comprising (a) an element comprising at least 200 contiguous nucleotides of SEQ ID NO:10; and (b) an element comprising an expressible polynucleotide sequence, wherein said element in (a) is directly operably linked to said expressible polynucleotide sequence in (b) and is not naturally operably linked to said expressible polynucleotide sequence. In certain embodiments, the polynucleotide comprises at least 500 contiguous nucleotides of SEQ ID NO: 10. In certain embodiments, the present invention provides an expression cassette comprising the promoter described above that is functional in a transformed cell operably linked to a preselected DNA segment encoding a protein or RNA transcript. In certain embodiments, the preselected DNA segment comprises a selectable marker gene or a reporter gene. In certain embodiments, the preselected DNA segment encodes a therapeutic composition.

In certain embodiments, the present invention provides a vector comprising the expression cassette described above.

In certain embodiments, the present invention provides a transformed cell comprising the expression cassette described above, or the vector described above. In certain embodiments, the host cell is a eukaryotic cell. In certain embodiments, the eukaryotic cell is an animal cell (e.g. a mammalian cell, such as a human cell).

In certain embodiments, the present invention provides a method for producing transformed cells comprising the steps of (i) introducing into cells a recombinant DNA which comprises a promoter described above operably linked to a DNA segment so as to yield transformed cells, and (ii) identifying or selecting a transformed cell line. In certain embodiments, the recombinant DNA is expressed so as to impart a phenotypic characteristic to the transformed cells. In certain embodiments, the transformed cells exhibit significantly increased expression of a reporter gene when introduced into the cells derived from Huntington's disease patients as compared to cells derived from control individuals.

In certain embodiments, the present invention provides transformed cell made by the method described above.

In certain embodiments, the present invention provides a transformed cell comprising the isolated promoter described above.

In certain embodiments, the present invention provides transformed cell comprising the expression cassette described above.

In certain embodiments, the present invention provides method of treating a neurodegenerative disease in a mammal comprising administering (a) the vector described above, or (b) the transformed cell described above.

BRIEF DESCRIPTION OF THE FIGURES

Figure 1C:
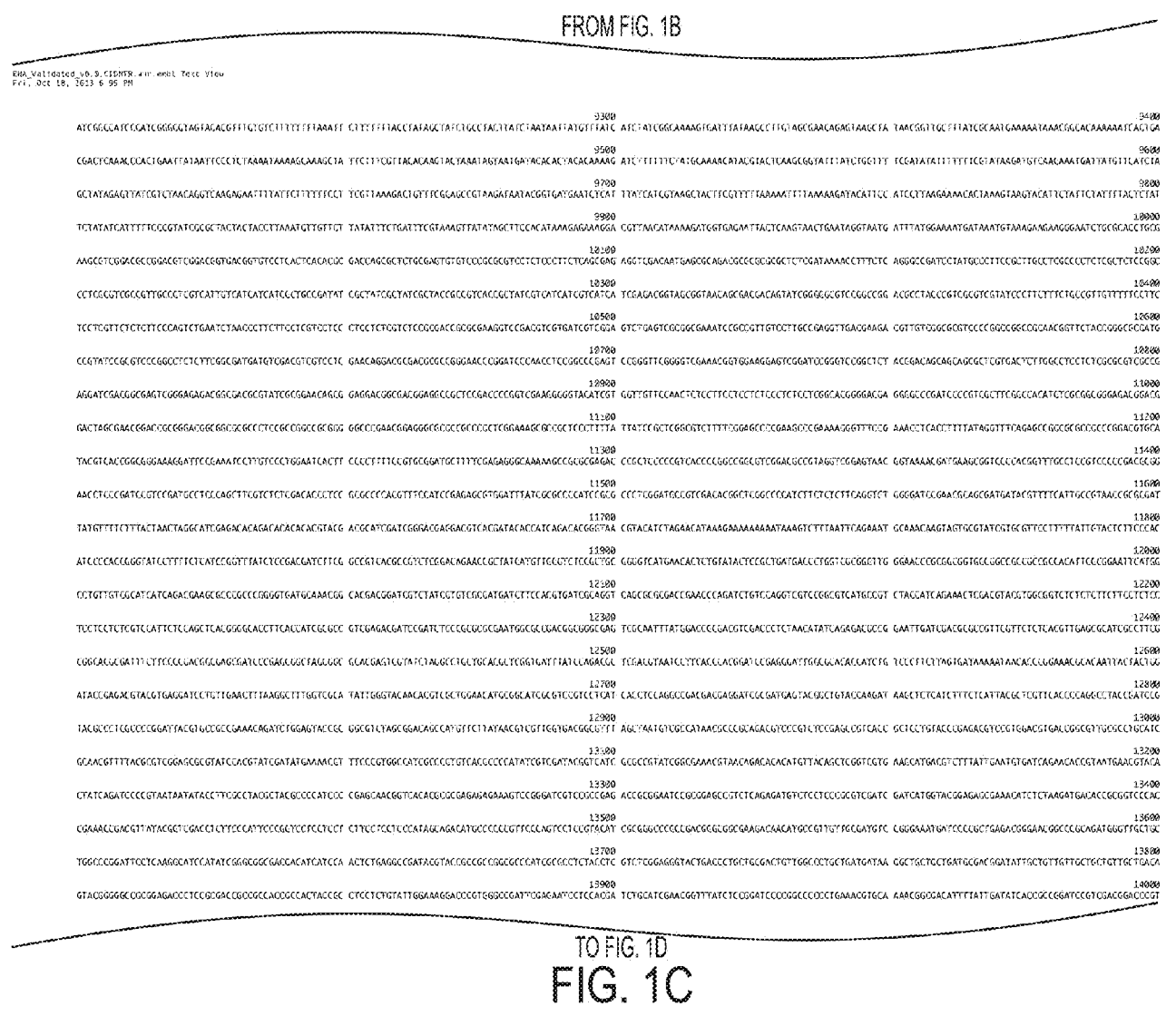
Figure 1D:
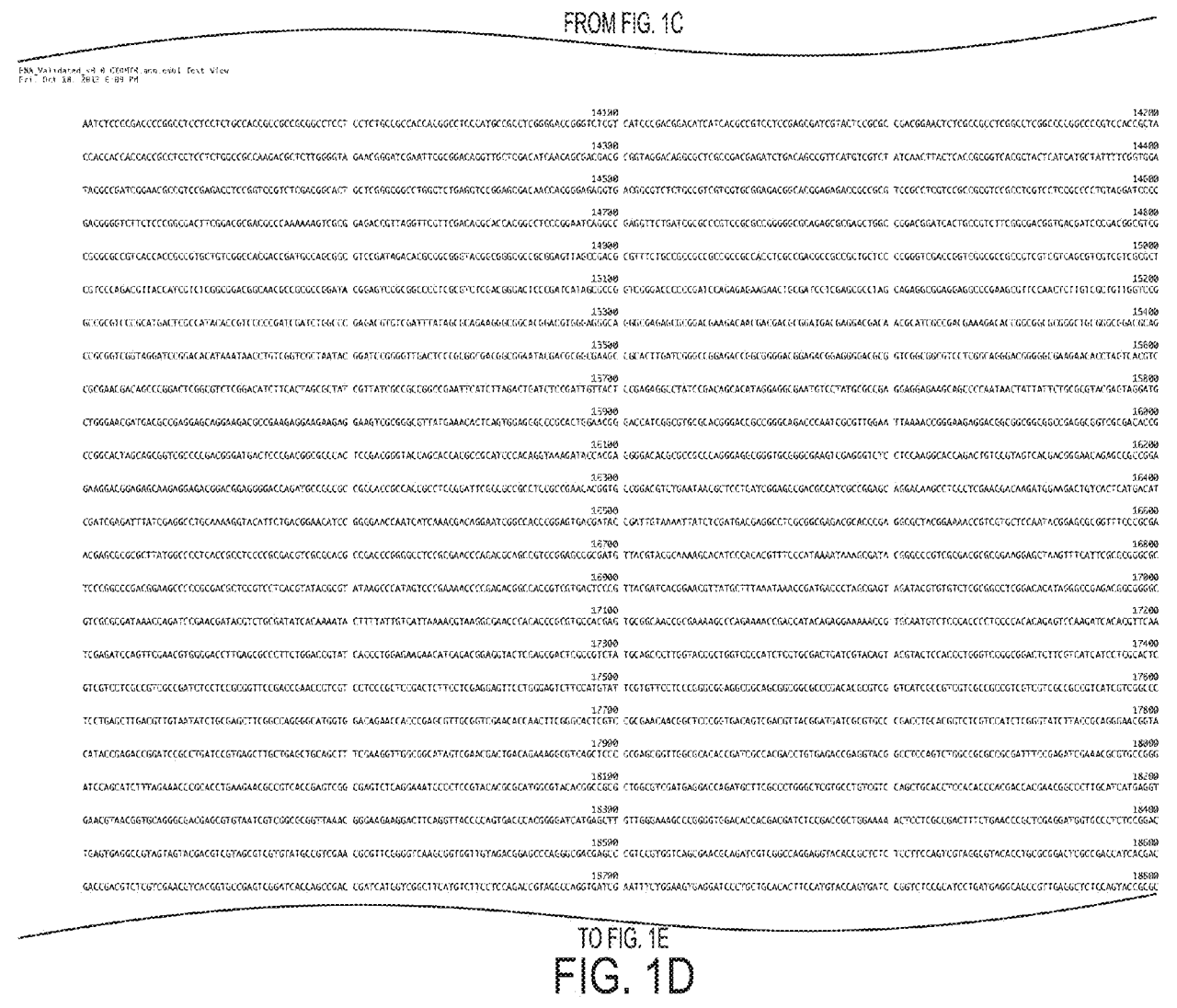
Figure 1I:
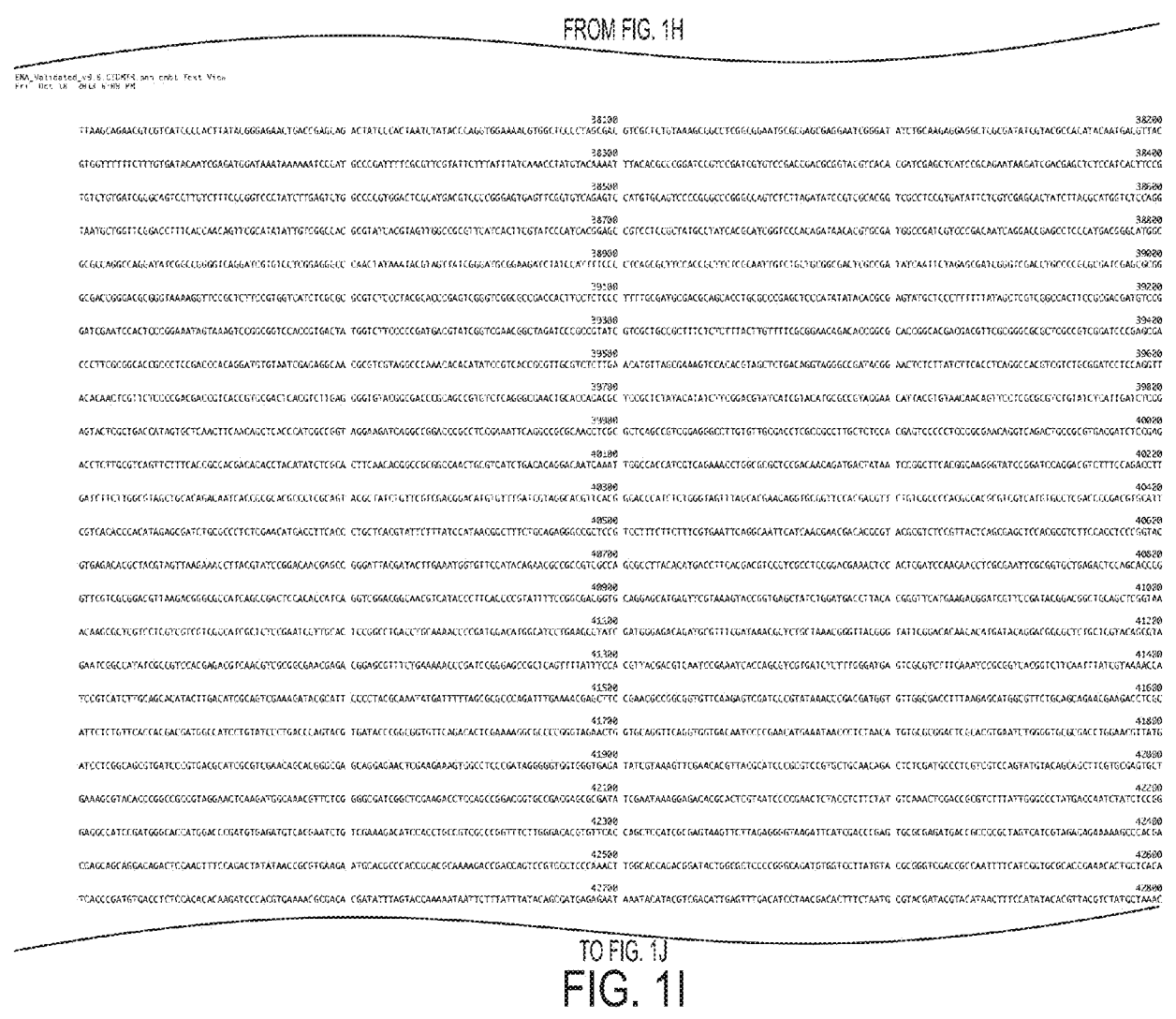
Figure 1J:
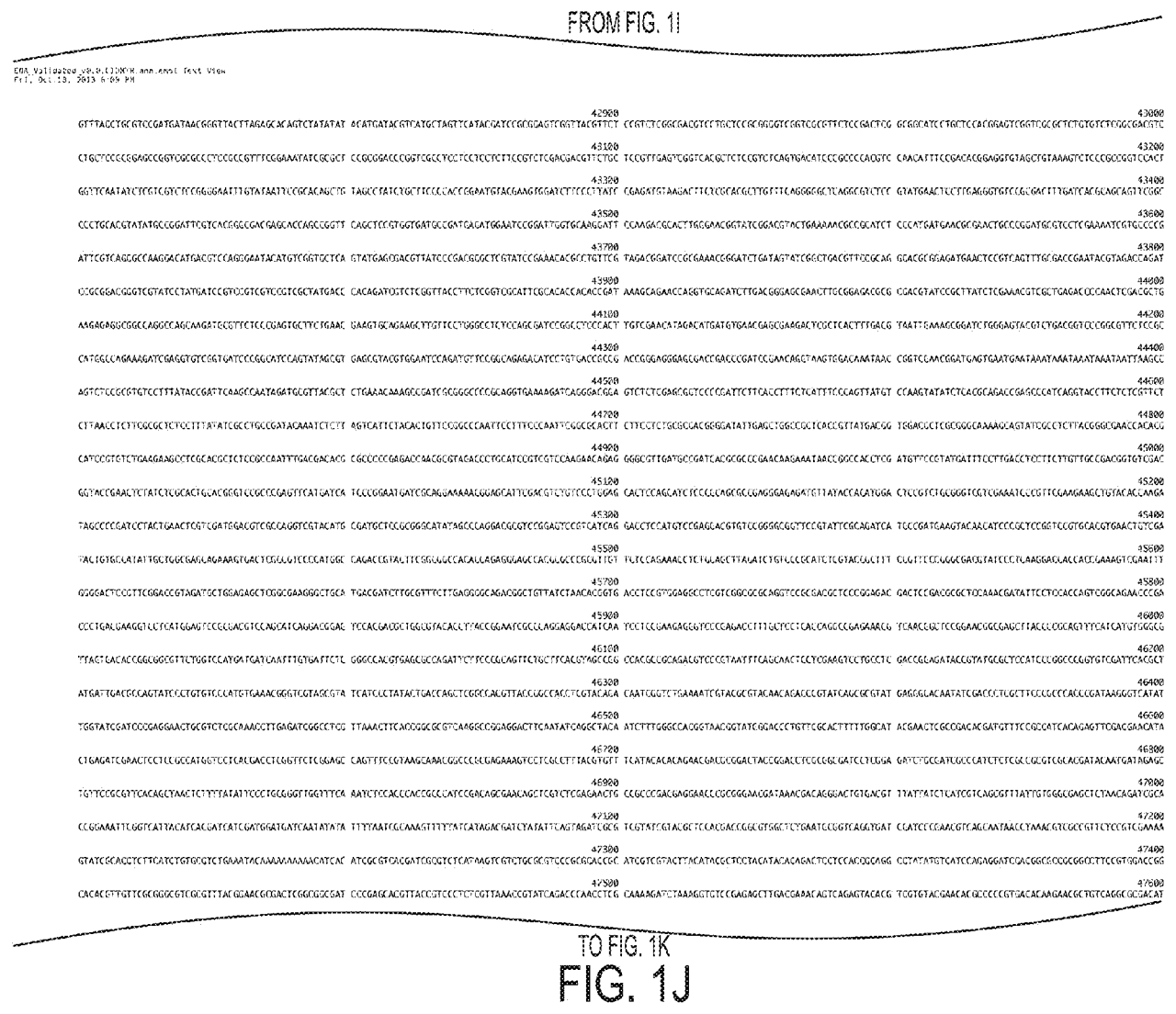
Figure 1M:
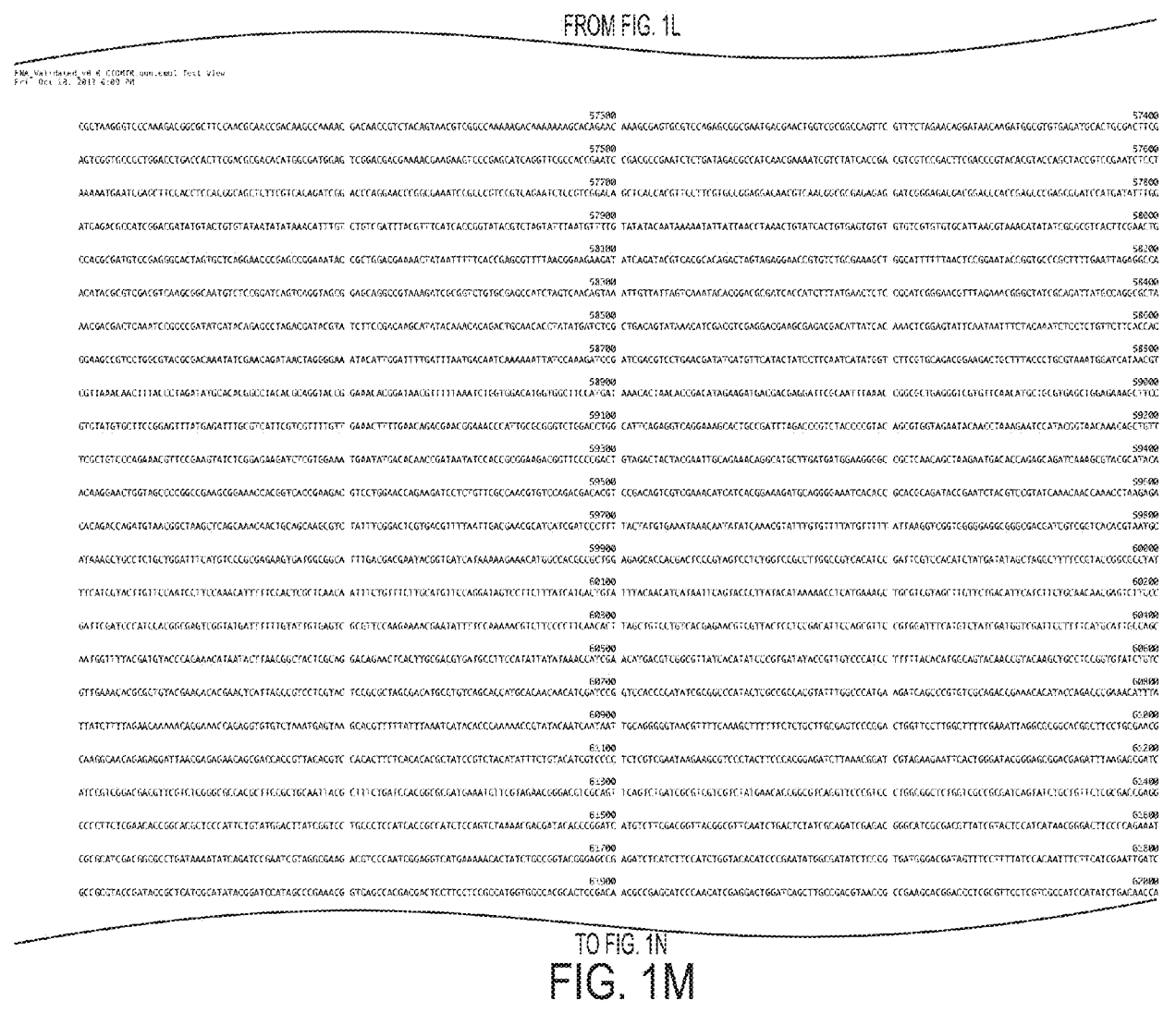
Figure 1N:
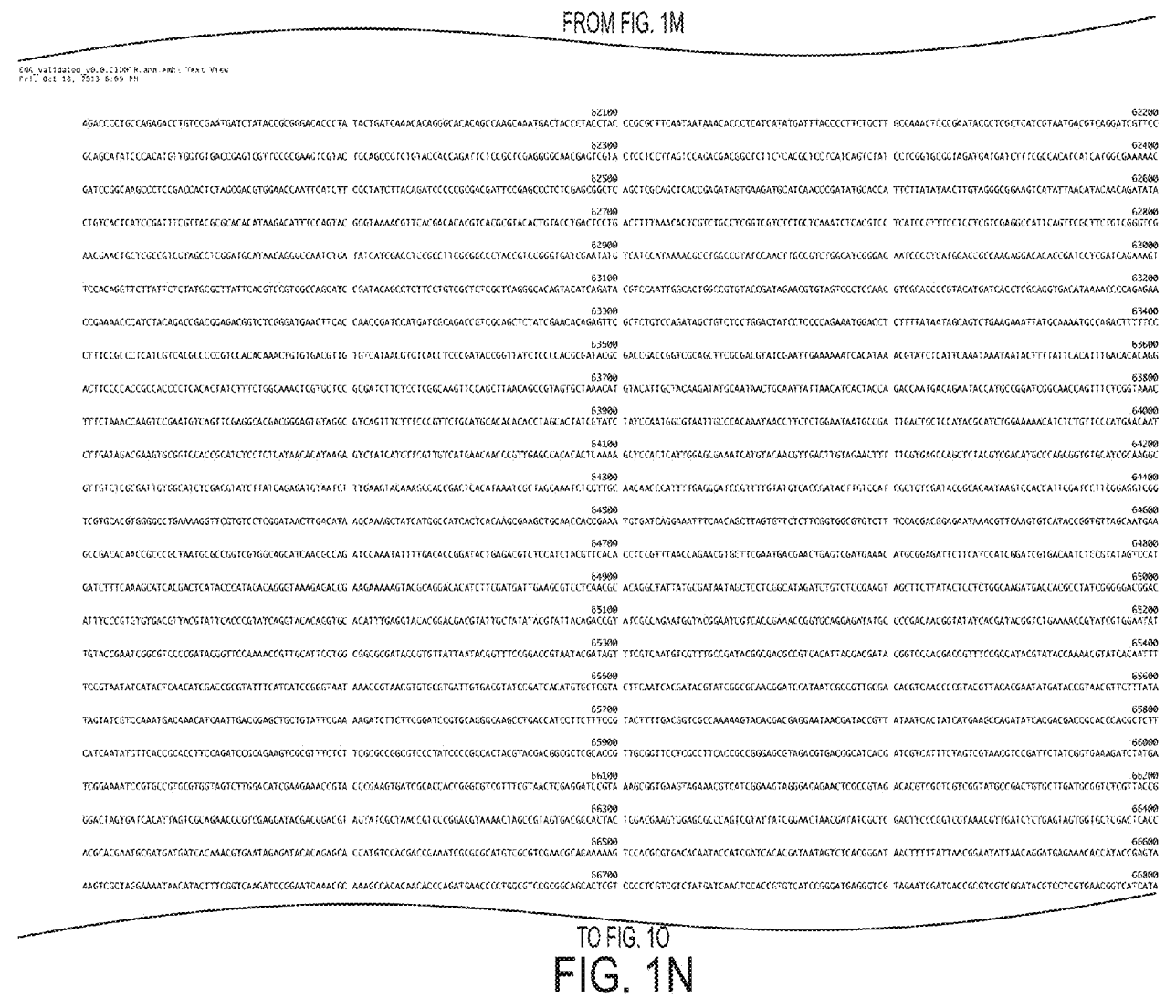
Figure 1O:
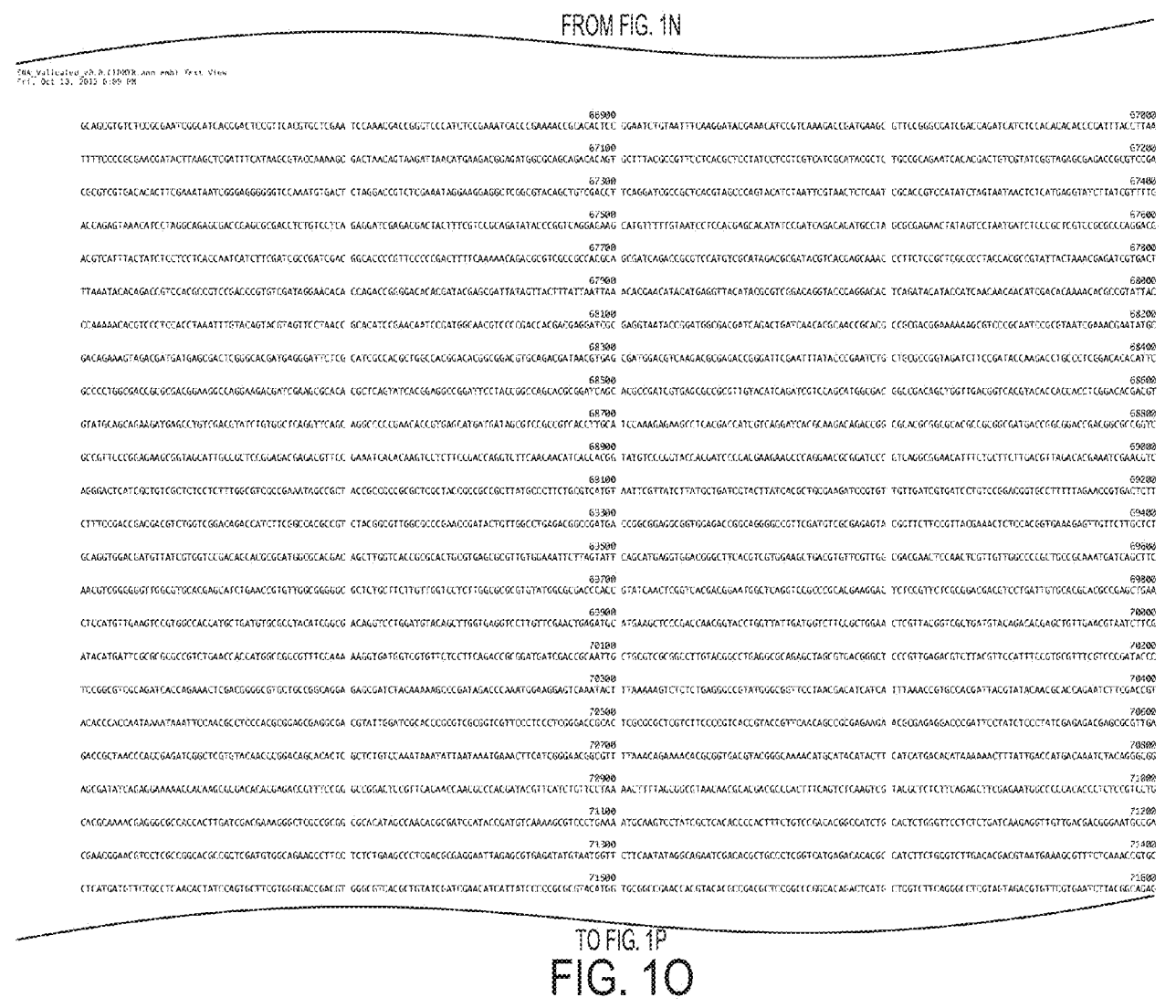
Figure 1P:
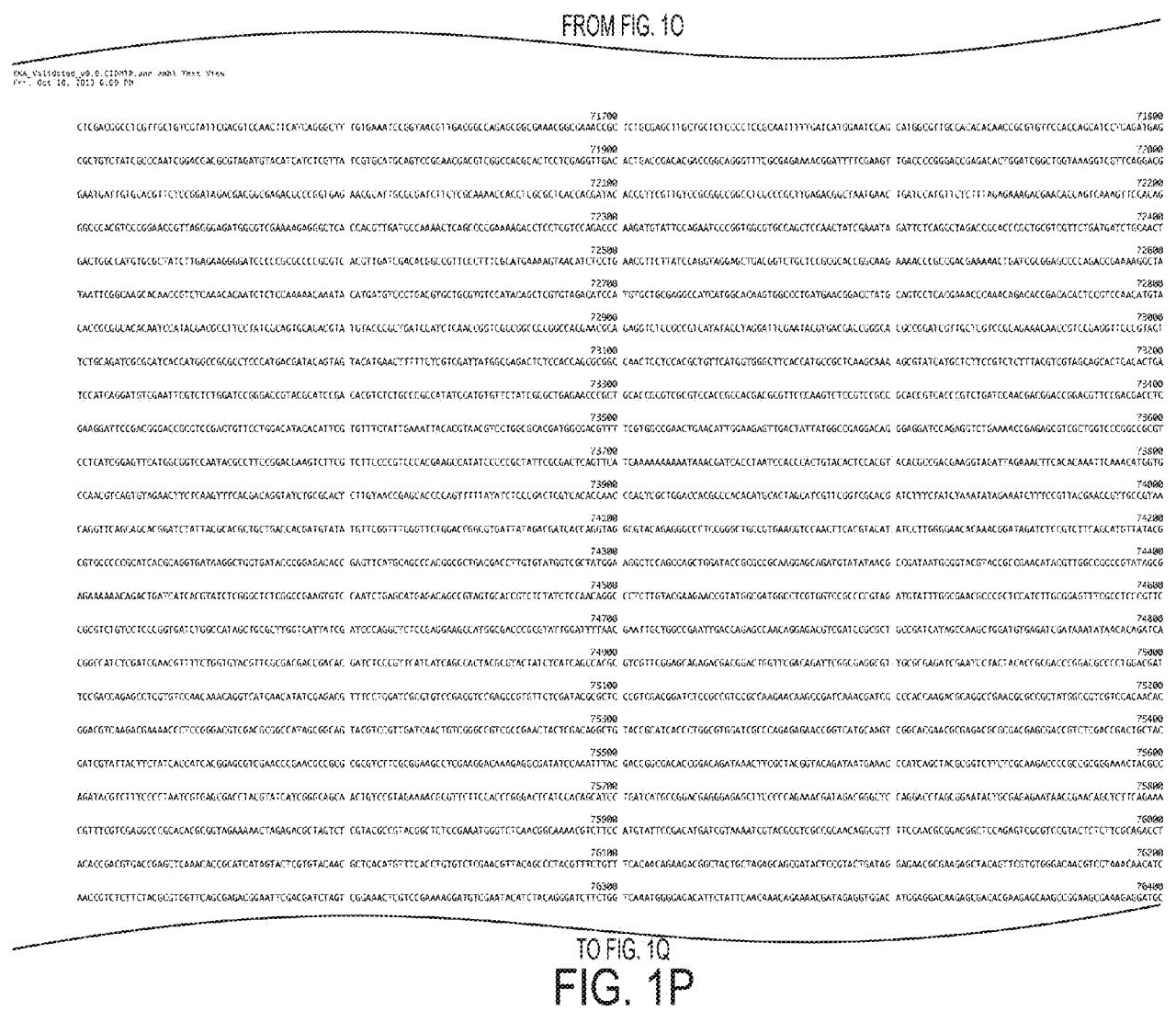
Figure 1Q:
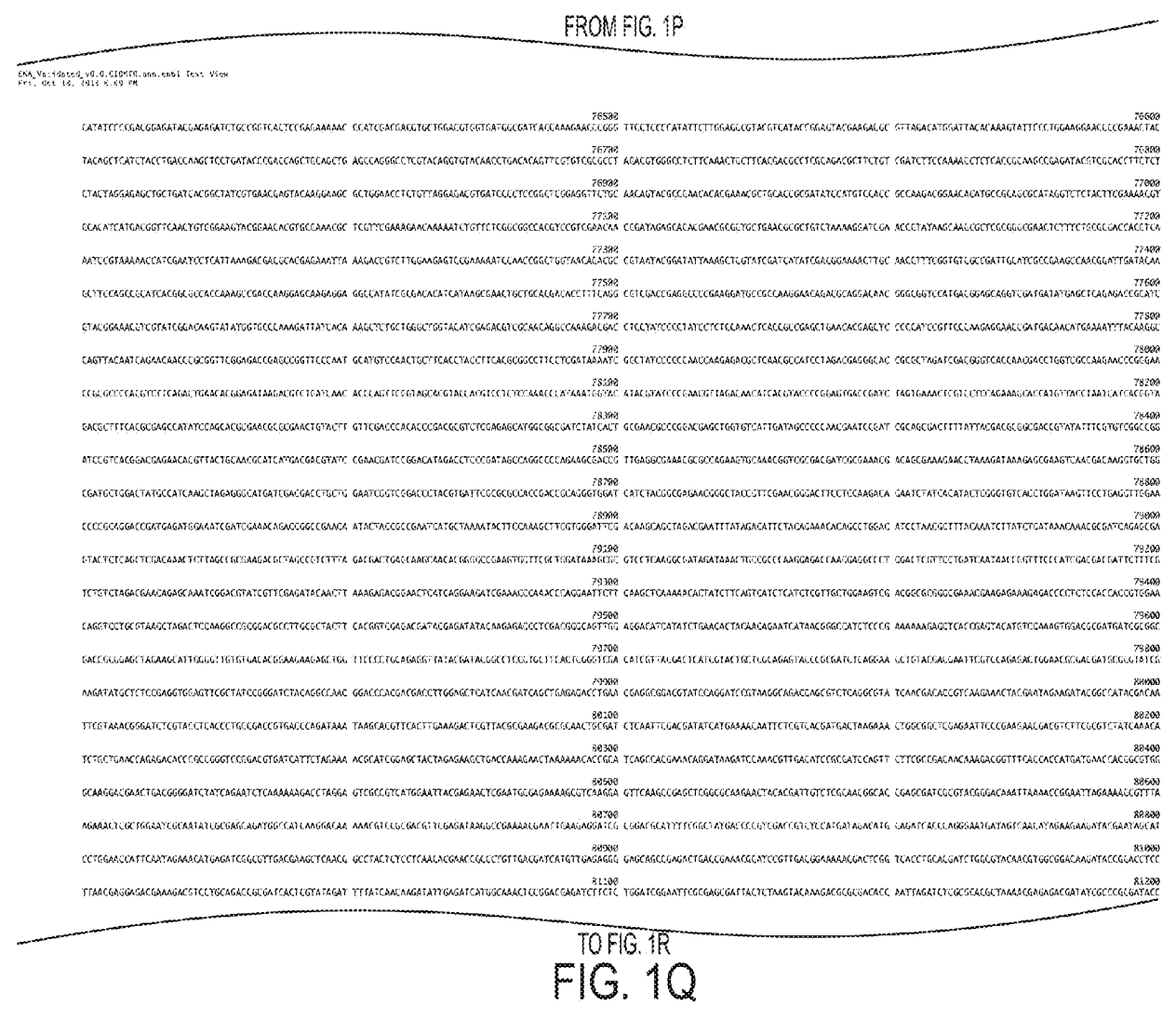
Figure 1R:
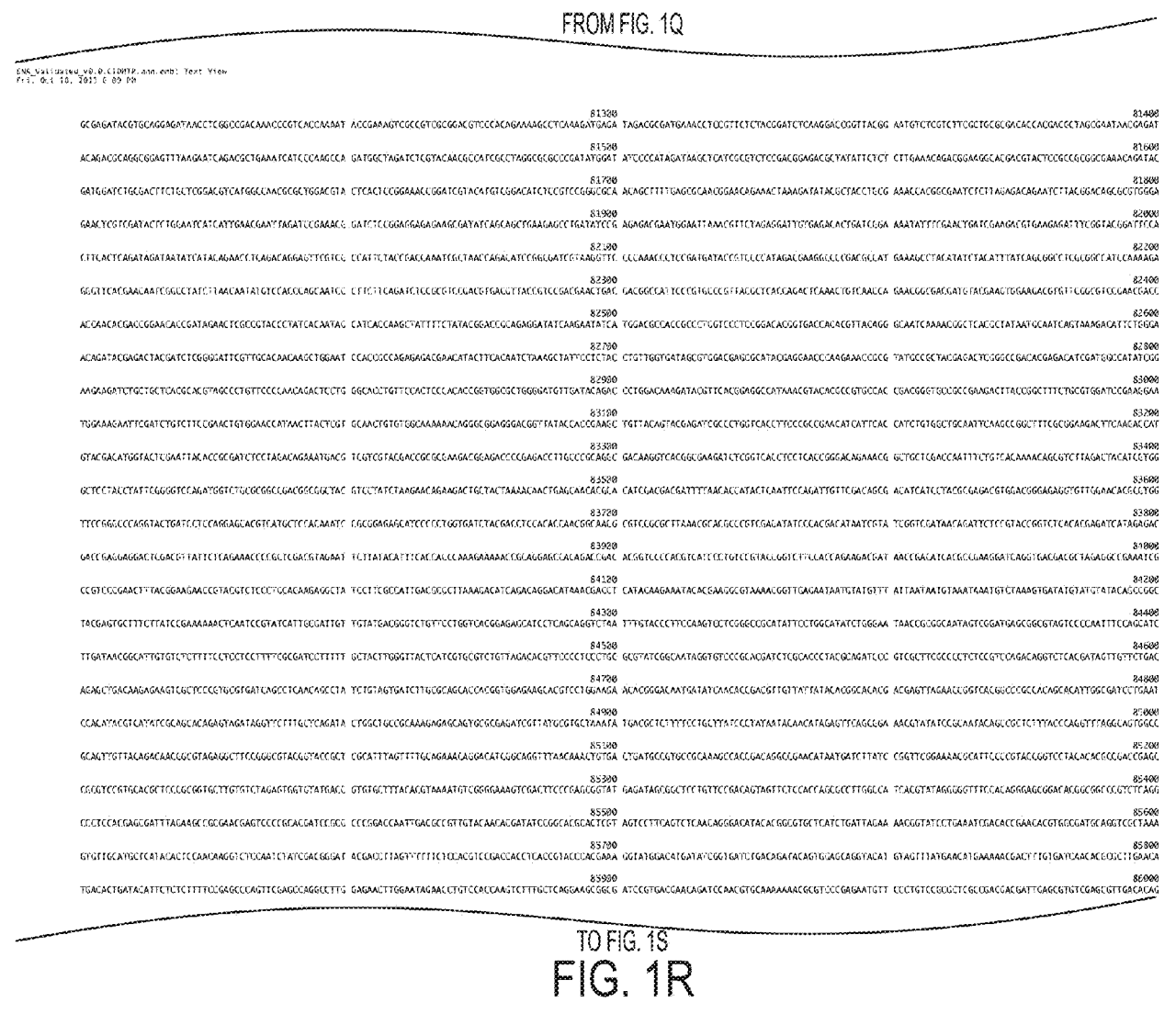
Figure 1S:
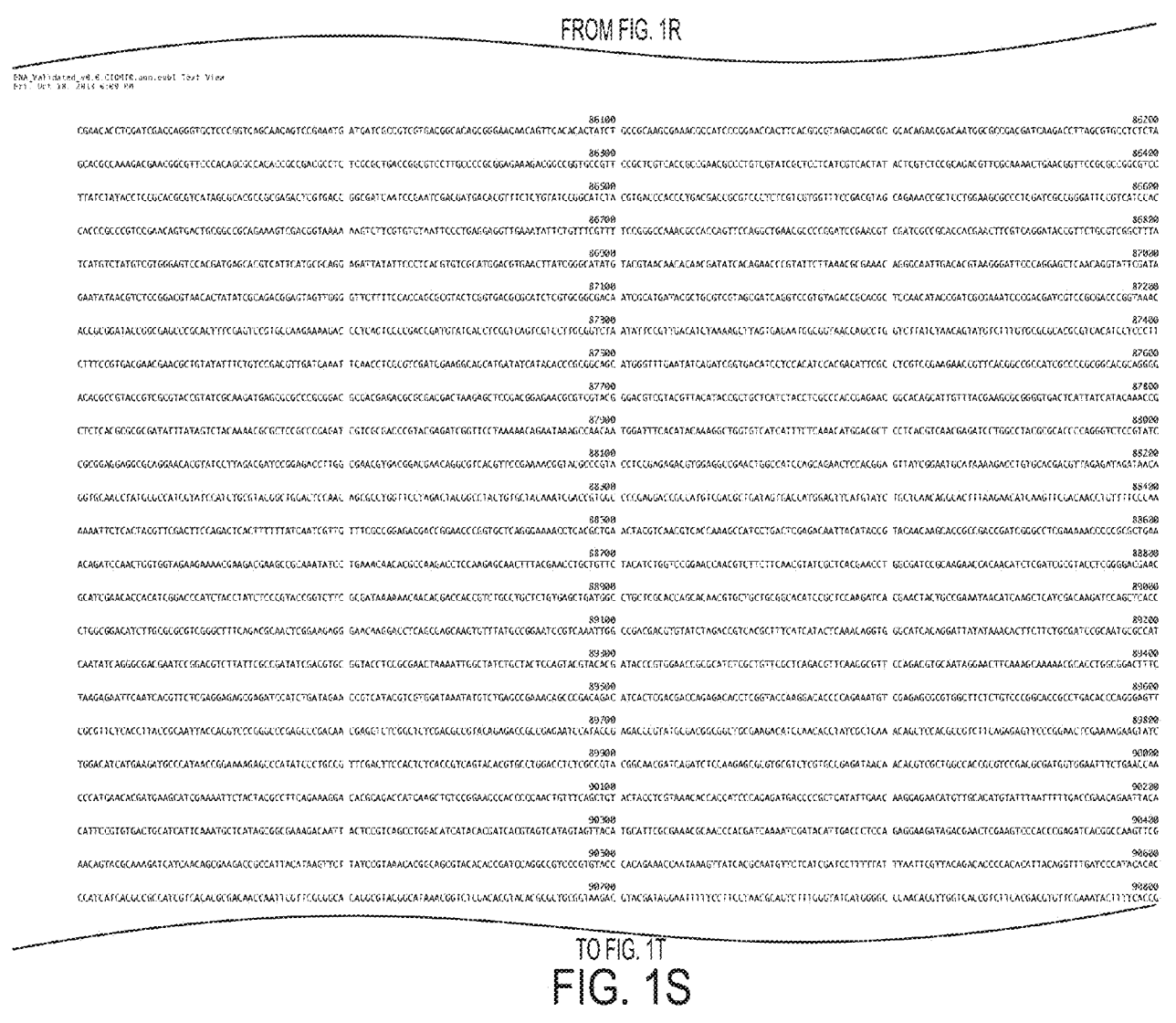
Figure 1T:
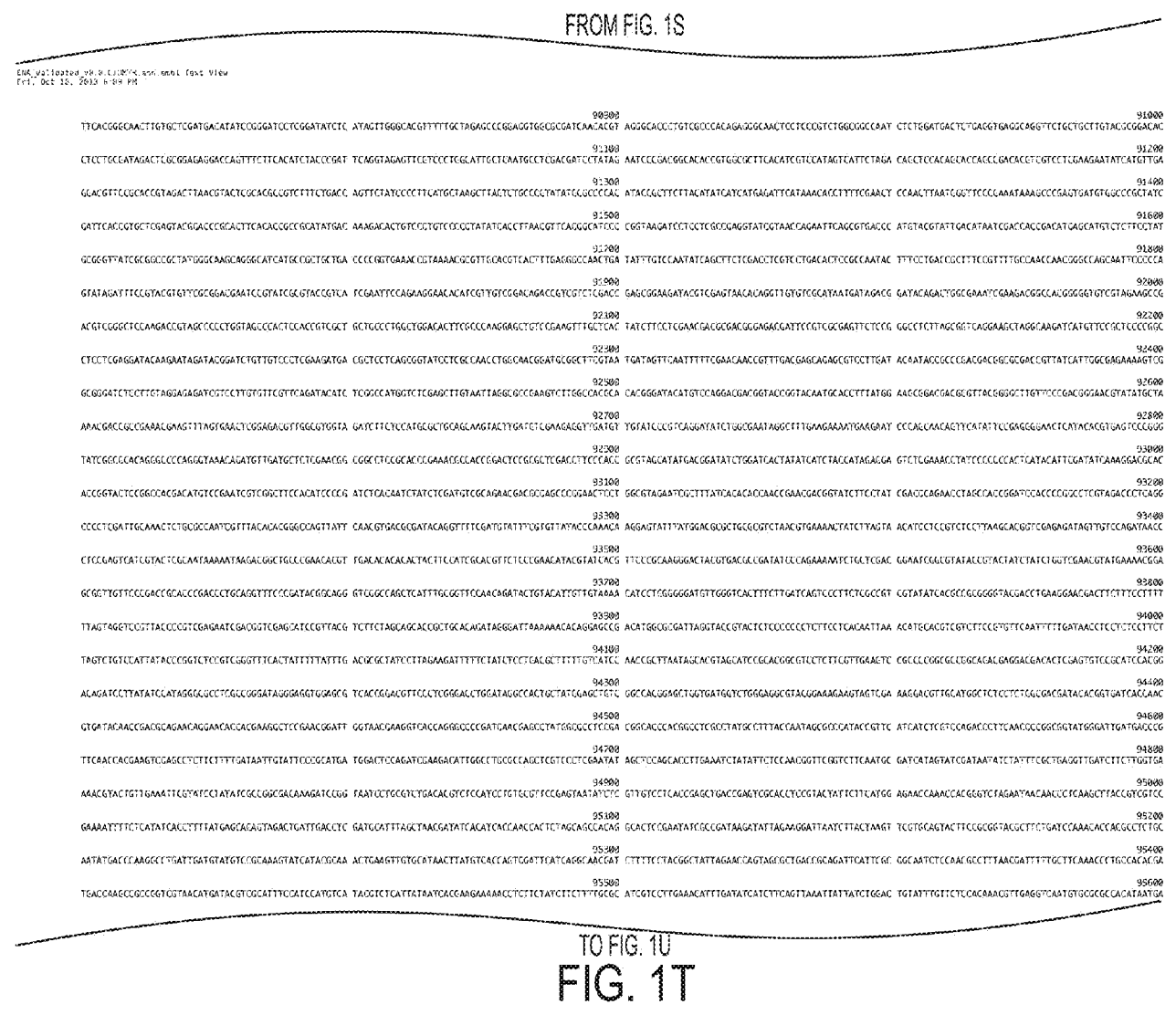
Figure 1U:
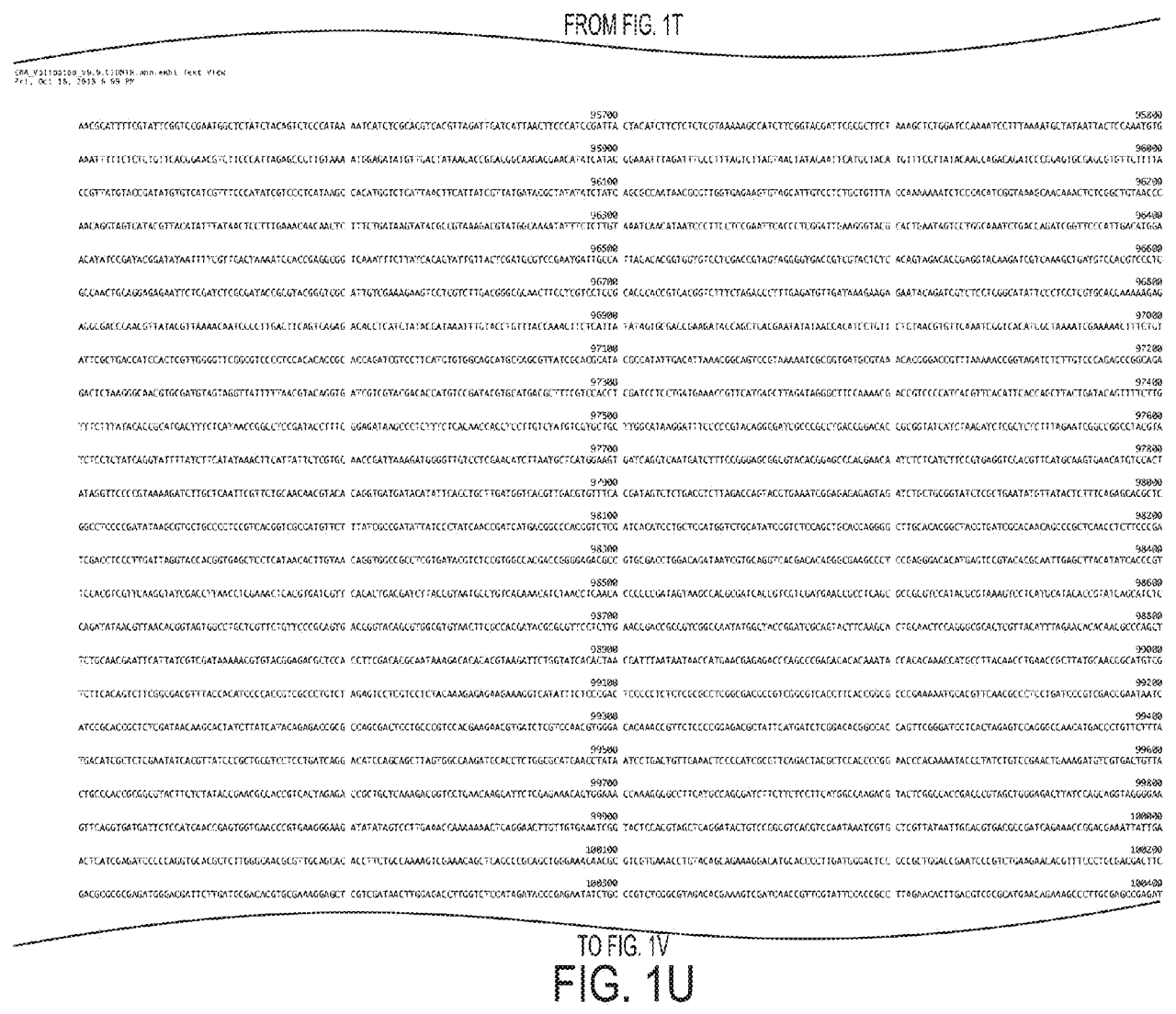
Figure 1V:
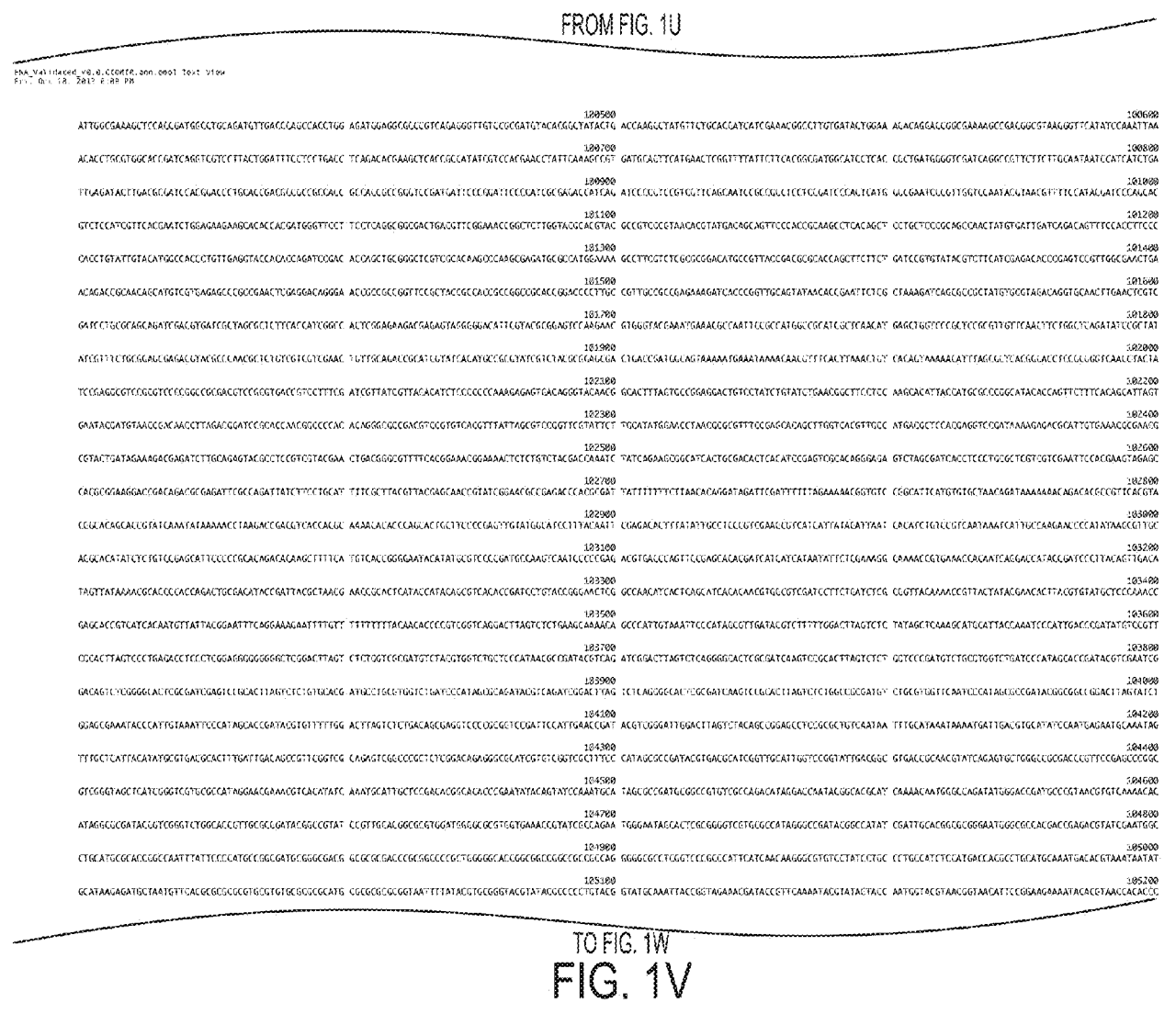
Figure 1X:
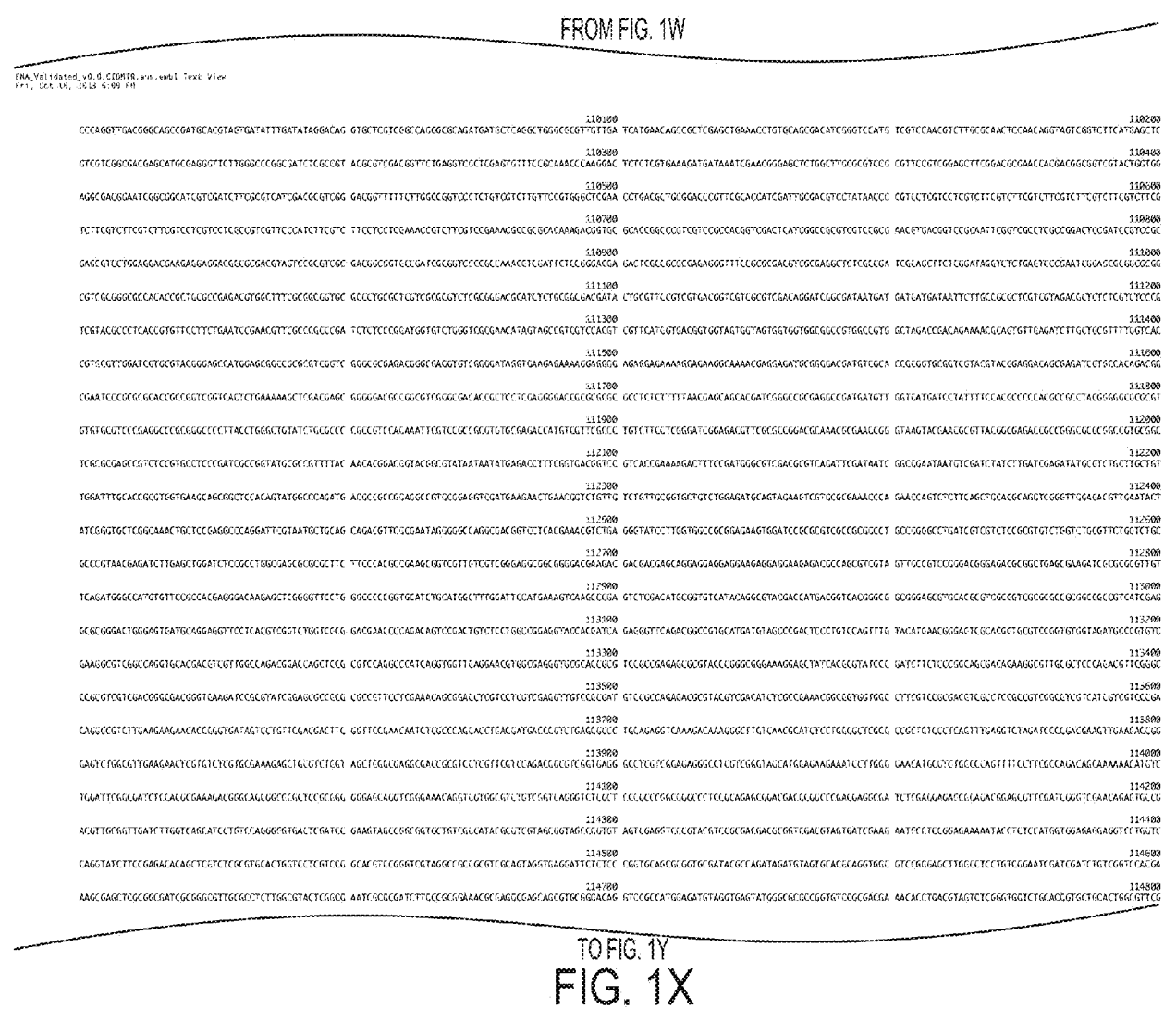
Figure 1Y:
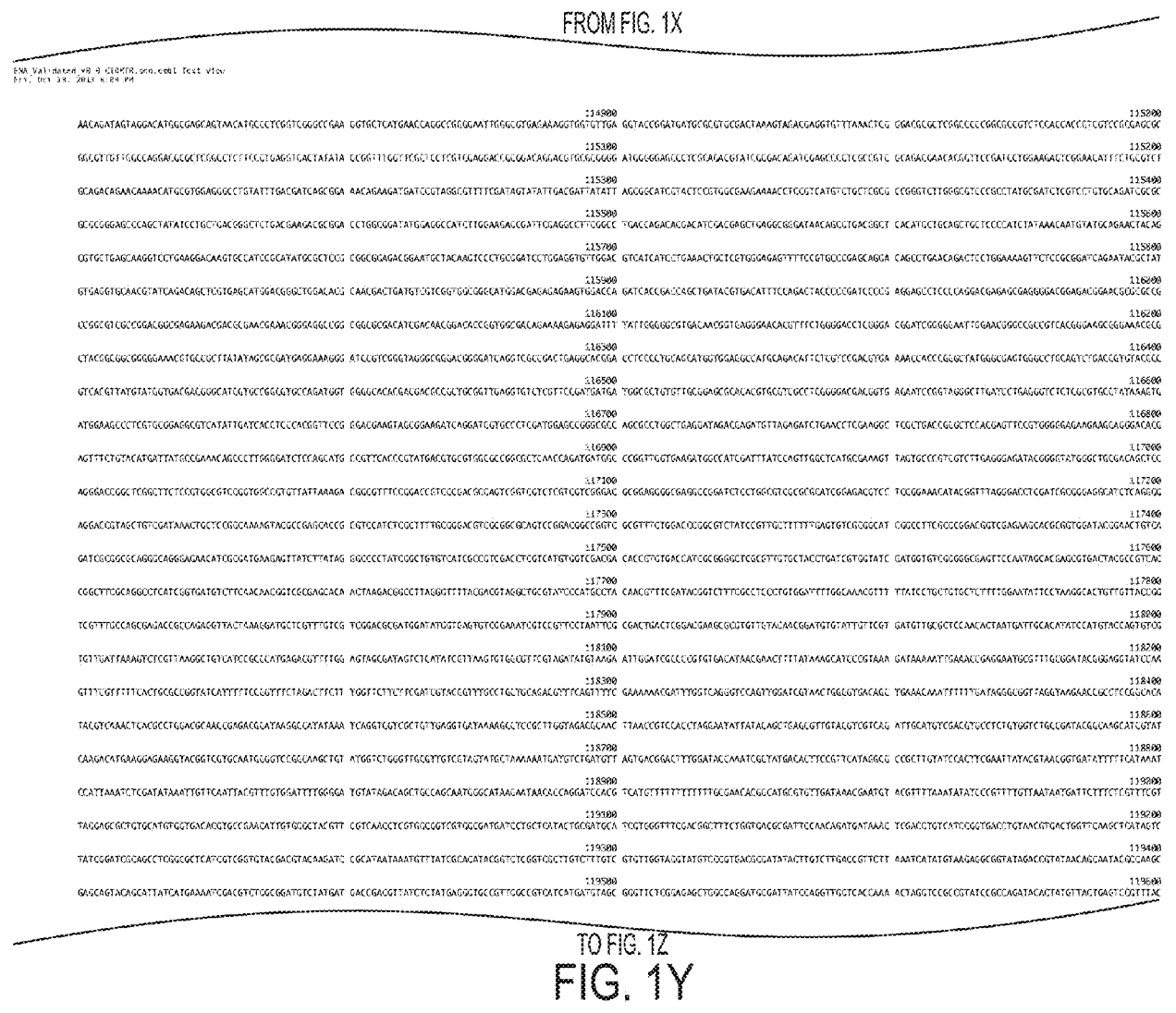

FIG. 1. Genomic sequence of guinea pig cytomegalovirus Strain CIDMTR (SEQ ID NO:1). The left terminal repeat spans nucleotides 1-842, and the right terminal repeat spans nucleotides 213938-232778.

FIG. 2 summarizes the predicted ORFs identified in the CIDMTR strain.

FIG. 4. Primer sequences (SEQ ID NOs: 11-18).

FIG. 5. Promoter sequence of CIDMTR (SEQ ID NO: 10).

DETAILED DESCRIPTION

GPCMV Strain CIDMTR

Figure 3A:
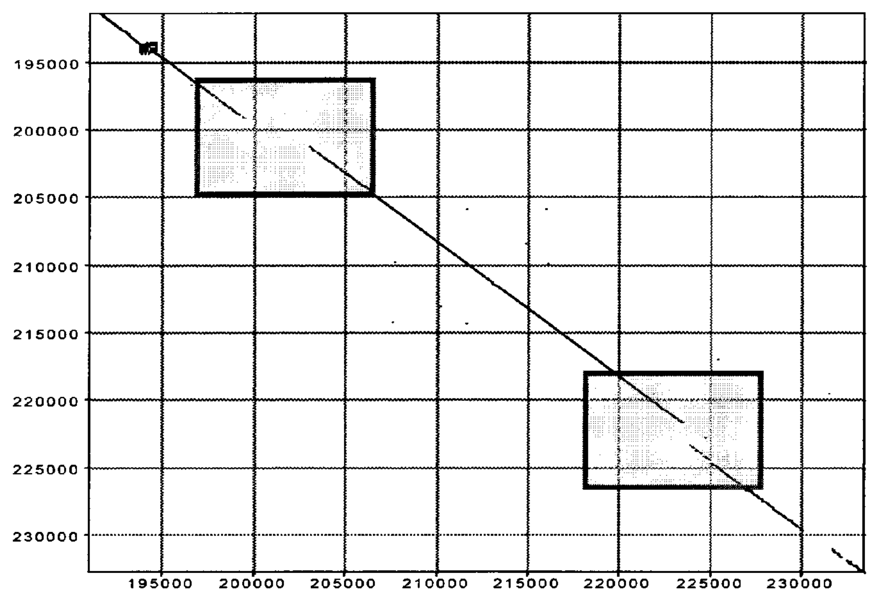
FIGS. 3A-3B. Strain-specific Genome Structure Differences between CIDMTR and 22122 strains. (a) Two genome regions demonstrating striking sequence variability at the (shaded boxes). These polymorphisms allow sequence-specific primers to differentiate reinfection with the novel strain from reactivation of the 22122 reference strain. X-axis, CIDMTR strain sequence; Y-axis, 22122 strain sequence. (b) Linear map comparison of the two major areas of genome discontinuity. Linear maps prepared using XPlasMap. Colored boxes in blue represent predicted function. Dotted arrow arrows indicate the positions where the sequences differ. See FIG. 2 for a full list of sequenced gene annotations.

In certain embodiments, the present invention provides a guinea pig cytomegalovirus (GPCMV) Strain CIDMTR, deposited with the American Type Culture Collection (ATCC®, 10801 University Boulevard, Manassas, Va. 20110-2209 USA) on Nov. 19, 2013 and given Patent Deposit Designation PTA-120714.

In certain embodiments, the present invention provides an isolated or purified guinea pig cytomegalovirus (GPCMV) Strain CIDMTR having at least 90% identity to SEQ ID NO:1 (i.e., from 90%-100% identity to SEQ ID NO:1). In certain embodiments, the GPCMV Strain CIDMTR has 95% identity, 98% identity, 99% identity, or even 100% identity with SEQ ID NO:1.

In certain embodiments, the present invention provides an isolated or purified guinea pig cytomegalovirus (GPCMV) Strain CIDMTR comprising a glycoprotein (GP), wherein the GP has having at least 75% sequence identity to GPCMV glycoprotein 129 (GP129), GPCMV glycoprotein 131 (GP131), GP74 (gO), GP75 (gH), GPCMV glycoprotein 55 (gB), GPCMV glycoprotein 73 (gN), or GPCMV glycoprotein 115 (gL). In certain embodiments, the GPCMV Strain CIDMTR comprises a GP that has at least 84% sequence identity to GPCMV glycoprotein 129 (GP129, SEQ ID NO:2), at least 94% sequence identity to GPCMV glycoprotein 131 (GP131, SEQ ID NO:3), at least 78% sequence identity to gpUL74 (gO, SEQ ID NO:4), or at least 82% sequence identity to gpUL75 (gH, SEQ ID NO:5). In certain embodiments, the GPCMV Strain CIDMTR GP has from 78% to 100% identity with the native GP sequence, such as 80%, 85%, 90%, 95% identity, 98% identity, 99% identity, or even 100% identity with the GP sequence.

GPCMV Strain CIDMTR Glycoproteins

In certain embodiments, the present invention provides an isolated or purified guinea pig cytomegalovirus (GPCMV) Strain CIDMTR glycoprotein (GP), wherein the GP has having at least 75% sequence identity to GPCMV glycoprotein 129 (GP129), GPCMV glycoprotein 131 (GP131), GP74 (gO), GP75 (gH), GPCMV glycoprotein 55 (gB), GPCMV glycoprotein 73 (gN), or GPCMV glycoprotein 115 (gL). In certain embodiments, the present invention provides an isolated or purified guinea pig cytomegalovirus (GPCMV) Strain CIDMTR glycoprotein (GP), wherein the GP has at least 84% sequence identity to GPCMV glycoprotein 129 (GP129, SEQ ID NO:2), at least 94% sequence identity to GPCMV glycoprotein 131 (GP131, SEQ ID NO:3), at least 78% sequence identity to gpUL74 (gO, SEQ ID NO:4), or at least 82% sequence identity to gpUL75 (gH, SEQ ID NO:5). In certain embodiments, the GPCMV Strain CIDMTR GP has from 78% to 100% identity with the native GP sequence, such as 80%, 85%, 90%, 95% identity, 98% identity, 99% identity, or even 100% identity with the GP sequence.

CIDMTR Strain gB (GP55) (SEQ ID NO: 6):

```
     MRPVRGIARSRILSCSWRGTWTSALTILYLGVYCESTTVTPTTVEDTTVSNGN
HSDASSNNTVIRNLTASVDFSQRKLYPYRICSMSMGTDLVRFARTIQCVPFNPRVNSE
EGIMLIYKRNILPYVFTAYTYQKELLFQRSYKYVTYDYLLGYSREFVALPMWEIFLV
NSRGQCYTSHQRVIGADRYIAYHNDNEVNETMWLMRDDMGNDDTYRYITVKEHA
RTPGSVWLYKETCSMNCIVTKTKGKSKFPYDMFVLPSGVIVNISPFYNGSNGKTFRE
QREKFHIWSNYSILKDFGSRALEARIVPKMAFYEREDVVIGWEVNDQSNVTCEMILW
ETVDRAIRTEYENAFHYVARTLTSTFVENKYSPDNNLTEDDIKCFKDDAQKKIEEVFL
RDYNETYDMDGNATYHVTTGGLVIVWQGLKQKSLKALEIAANESAVSATGSNSRR
KRSLPDESTGDISYAQLQFAYDTLRTYINQALGHIAEAWCLDQKRTAEVLHELSKINP
SNILSAIFGVPVAARVVGDVISLAKCIEVNQSTVLIKGDMRKFSDDGKLEGCYSRPVV
WFSMKNSTEVRLGQLGEDNEILLGTHRMETCQTQDYRIFVAGDIGYEFQQYVFTKKI
NLSEIDIIDTMIALKTEPLENIDFKVLELYSRDELAQANVFDLESIMREYNYQKKRLDF
VVERVINPIPPELKGLDEMMNGMGAIGKGIGEAVGAVGGAIGSFIGALVTFVTNPFG
AFVVFLFCVGCITLVITVYRRQRRAMQRPFDYFFPYASQTITSSVADSSIAVAYPGPEG
TSGDAPPPYPGEAPYGYKDLSVDADTRVSSSSAGAGADFNEEDAVRMLRAIKRLDD
KKRQEIEKSSKDSASNKNSETRRRPGIMDRLRRRGGYQKLNTEDDVHV*
```

CIDMTR Strain gH (GP75) (SEQ ID NO: 5):

```
     MSPAARFTVISCLVVSLITPSETSFSSWTYPDVNWTKSSLNMTCLNNHTGQRS
LTTEGLISFNFYEAPKTVRTYQVPKCIFMTTISKSIMQSVDLFESLESYKLRYYSYIIVP
VHAAFQIFIHELRTDLVPSTEELNVRADDTLPNITVWRTRSGSYVIPLLDVVTPEFEDC
NLFSNHTVVFDMKIPCSRELYLHQLGAHRFTIALTFTPNFFVLNIQTTRRSHTTEDDE
DTLLIFGDIQEIDVKAPYSKPVLTLRQSSRDDLLIVAKTSTVTTIYPFIQTQGFLKIELSN
NYLDFDRVYTEFSRLVTHNMMNGLCDAPPDNRTVSMVFSYAILIRALYHTANMTAR
LEDVTLRYVKLTLARTFLQQCFNIEPRYMRFPMIDGAVSVFLKLIRNSRDVDRAIKLS
LTFALIFGNNTNLTEERDIENALYEMKSIHRAGLVSPLSPRQRNLLYMMAYVMHHTA
AFPDIRREMLAMQTSLCSPQELYNWAPHVSSAGLTMQEMFTPCSGSGRRDYSEARIA
EIVQLNPLTTKTPADLYRILAHFDRSNLTNFPALSCISHLSGYVAVTLKDVTYVVSSN
VILKGTSYPVTNLAVDKTMIVTVSPAQQPCEQTEVAHATRSIPIVKNITIGNDCEYCKS
AIMEYDEVNGLSNIVYLADTADLVLVTNLDNRILASSPRTRYIMMTANGTLIEITSVII
DIRQTSIFMIMLYCSLGVLLLYGLYRLLHMI*
```

CIDMTR Strain gO (GP74) (SEQ ID NO: 4):

```
     MTWILVLFLCPLLAAVYTSPKSTNVIEQFISRFNGFMKNITVTYNSKWIQAAP
MNGSVIPIWYPKSVTNIRHHFLAYYDNATQTIQLAGPHCTTVPSPSCLDTMLAVSAD
HRGTSTCNLTTYNAQLYNIPRWTVKLRLPSGGFYHLNSDDLIYMALSVSVASRREFD
VCAGGGSYLTALSKNLFQLSPQLRSNWTLTKSFFRKLKRLQQANRTIEEEPKKSRNR
KNDTGAVKNETWIPPVSANAFLGFNFYLYGMLYKSSLCHTGRSNSYISTNATLNDM
RLSLLQNVSWADDSLNETLINTTLVHGYVQSLVLERNITNNTHPLYNTRFVRVSREL
GTDDFRHSPYPSRPTTNEHPLVTSGGLAGKRPVTTVP*
```

CIDMTR Strain gN (GP73) (SEQ ID NO: 7):

```
     MKSYLIGPLSAVSSPSTSSCGRRHRVTIAGLALCYLIVVSMVSGASSNSTSVTT
PSPASQASSVMSSTTVASTTKTALGFYDVGCVSHAYNVSIRSFASLWILANVFILLCSF
GIFLRHCCYRSFASETARGY*
```

CIDMTR Strain gL (GP115) (SEQ ID NO: 8):

```
     MFFSHRLTIGFYIPLIVLTTISSLSESLGERQKTACTVAAISCANSDTYNRTTVS
NHTFFYISDRWKYSELIRYEKPTWDLRHDKLIHVDREFLDIVSLLHNNENQLRTLLTIF
RSDSAPPWVKFMRGYSQCLDHPIIYTCVEEKCQQYNLEELPYGKDIFLENVVGFDLG
APPHNMSVLIAVSNTKPKITKVLRITSTSLTLFDALYNTVLTFFRSIGARNVDVVRRLI
LYQASLSGPHRDAPIHNYLNRDL*
```

CIDMTR Strain GP131 (SEQ ID NO: 3):

```
     MKRRLILLSWMMFCTSFGHAGRCYYPSTPIPKRFVKRVDTVRSLPECENDTV
AVLTLTNDAKLYVNMLNTWVDGYITTLQYVVPPTLSDIFTFIKRRIDRGSTGTAASTL
PSLTSVRTYFGDRDSSFLWHYTIRMKDGAKTLDCDVYVTSRVHFELNSYGAVQTVL
FEGGVIISRHPADSIACLLINWNWT*
```

CIDMTR Strain GP129 (SEQ ID NO: 2):

```
     MRVIVLLAMFCCTRPGMFDDPCCIYSSRDRLVQDFTTSNDTWRLIRCKDNLM
VAKRYTDSFCEFSLEENLFDSLALNVSRQELHTLAPECKFGPSVEVGINKQVKCIRYP
RMPKVPSKPEKPSILGVTYRVDYTVMIPTPHFPRDFNGLLCTFLEKNDTFYNTTVDVC
GSEFYSVDGNGK*
```

-continued

CISMTR Strain GP83 (pp65 phosphoprotein homolog) (SEQ ID NO: 9):

```
     MERYVGLGTTLHLALQVEGPFGPHETRFVHFDATFTVPRTPSVVIVAEEQVGS
HLPPSSPLRMKFRAIHSQEELDLLNLEVRNASDQPLPAKSFYDLNVVVFALPLPRVHA
APLHIFFNSALKPSRETFPTVSKTVVRRACGAIWGVRTALSNIAWTEGVGNRAHVDR
ALTVTVLLSVKPACMTHVDSLTEINVSHEDVQVFKAEVFQKGRPNVLGLTLQTTAKP
PPKKLTLFFQLLASHAQVVMRHNPYPALQSHPSNGFTIHCPGDIRLQSGQTYRLTLRN
GFDSTSHAALFFPADFPNADVSGGQWKARHNMDIVIRSHGETTVRKDEVLGTVHFF
DNDLFTFHRVAGVIDTCMMGKQFETRVRRVSESCQEQVFVKSGGRRTGNAARHRR
DRDGGDDDDDDENEDGEEGEEDGEEDVGDAKDDGSESSSESELGSGEDNDGDDDV
FECERPLAREDGASGSAERETLDESEDPSLRPRRVSEEIFPSVLFYPWALSIPTGFCAYI
HYNVVACSSEHSSGEVQDGSVWFDGVPTRPASHACSRTRRDDDGGAGTSRRSHRG
AQ*
```

Antibodies Specific for GPCMV Strain CIDMTR

In certain embodiments, the present invention provides a purified antibody that binds specifically to GPCMV Strain CIDMTR, or the GPs described above (i.e., gB, gH, gO, gN, GP129, GP131, GP133). As used herein the term "binds specifically" means that the antibody binds to a target agent, e.g., purified guinea pig cytomegalovirus (GPCMV) Strain CIDMTR or glycoproteins (GP) from GPCMV Strain CIDMTR, with a much higher degree of affinity than it binds to GPCMV ATCC/22122. In certain embodiments, the antibody binds to the target agent with a binding affinity of at least 2× greater than its affinity than to GPCMV ATCC/22122. As used herein the term "antibodies" includes monoclonal or polyclonal antibodies or an antibody fragments.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

Nucleic Acids

The present invention further provides nucleic acids that encode portions or all the GPCMV Strain CIDMTR genome. The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

"Genome" refers to the complete genetic material of an organism.

Promoters

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A general discussion of promoters is provided in U.S. Pat. No. 7,501,129, which is incorporated by reference herein.

As used herein, "biologically active" means that the promoter has at least about 0.1%, 10%, 25%, 50%, 75%, 80%, 85%, even 90% or more, e.g. 91%, 92%, 93%, 94%, 95%, 96%, 97%, 98%, 99% or 100% of the activity of the CCT promoter comprising SEQ ID NO:1 or SEQ ID NO:2. The activity of a promoter can be determined by methods well known to the art. For example, see Sambrook et al., Molecular Cloning: A Laboratory Manual (1989). Promoters of the present invention that are not identical to SEQ ID NO:1 or SEQ ID NO:2, but retain comparable biological activity, are called variant promoters. The nucleotide sequences of the invention include both naturally occurring sequences as well as recombinant forms.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

In certain embodiments, the present invention provides a promoters having at least about 70% to 100% identity with the sequence of SEQ ID NO: 10. In certain embodiments, the promoter has 75%, 80%, 85%, 90%, 95% or 99% identity to the sequence of SEQ ID NO: 10.

In certain embodiments, the present invention provides vectors and expression cassettes containing the promoters described above. A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

The selection and optimization of a particular expression vector for expressing a specific therapeutic composition (e.g., a protein) in a cell can be accomplished by obtaining the nucleic acid sequence encoding the protein, possibly with one or more appropriate control regions (e.g., promoter, insertion sequence); preparing a vector construct comprising the vector into which is inserted the nucleic acid sequence encoding the protein; transfecting or transducing cultured cells in vitro with the vector construct; and determining whether the protein is present in the cultured cells.

Nucleic acids encoding therapeutic compositions can be engineered into an AAV vector using standard ligation techniques, such as those described in Sambrook and Russell, Molecular Cloning: A Laboratory Manual, Cold Spring Harbor Laboratory Press Cold Spring Harbor, N.Y. (2001). For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration).

In certain embodiments, the present invention provides a vector containing an expression cassette comprising a promoter operably linked to a target sequence. "Expression cassette" as used herein means a nucleic acid sequence capable of directing expression of a particular nucleotide sequence in an appropriate host cell, which includes a promoter operably linked to the nucleotide sequence of interest that may be operably linked to termination signals. The coding region usually codes for a functional RNA of interest, for example an RNAi molecule. The expression cassette including the nucleotide sequence of interest may be chimeric.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Such expression cassettes will comprise the transcriptional initiation region linked to a nucleotide sequence of interest. Such an expression cassette may be provided with a plurality of restriction sites for insertion of the gene of interest to be under the transcriptional regulation of the regulatory regions. The expression cassette may additionally contain selectable marker genes.

The present disclosure also provides a mammalian cell containing a vector described herein.

Probes and Primers

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or is an atom or a molecule that permits the specific detection of a compound comprising the marker in the presence of similar compounds without a marker. Detectable markers include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The detectable labels used in the assays of the present invention to diagnose GPCMV, these labels are attached to the protein (e.g., antigen or antibody), can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^{3}$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where antibodies are contemplated to be detected in a clinical setting, the labels are preferably non-radioactive and readily detected without the necessity of sophisticated instrumentation. In certain embodiments, detection of the labels will yield a visible signal that is immediately discernible upon visual inspection. One example of detectable secondary labeling strategies uses an antigen linked to an enzyme (typically by recombinant or covalent chemical bonding). The antibody/antigen complex is detected when the enzyme reacts with its substrate, producing a detectable product. In certain embodiments, enzymes that can be conjugated to detection reagents of the invention include, e.g., β-galactosidase, luciferase, horseradish peroxidase, and alkaline phosphatase. The chemiluminescent substrate for luciferase is luciferin. One embodiment of a fluorescent substrate for β-galactosidase is 4-methylumbelliferyl-β-D-galactoside.

Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horseradish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

By “fragment” or “portion” of a sequence is meant a full length or less than full length of the nucleotide sequence encoding, or the amino acid sequence of a polypeptide or protein. As it relates to a nucleic acid molecule, sequence or segment of the invention when linked to other sequences for expression, “portion” or “fragment” means a sequence having, for example, at least 80 nucleotides, at least 150 nucleotides, or at least 400 nucleotides. If not employed for expressing, a “portion” or “fragment” means, for example, at least 9, 12, 15, or at least 20, consecutive nucleotides, e.g., probes and primers (oligonucleotides), corresponding to the nucleotide sequence of the nucleic acid molecules of the invention. Alternatively, fragments or portions of a nucleotide sequence that are useful as hybridization probes generally do not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides or more.

In certain embodiments, the present invention provides assays for determining the presence of GPCMV Strain CIDMTR. GPCMV Strain CIDMTR can be detected by any of a variety of means, including: 1) performing a hybridization reaction between the nucleic acid sample and a probe or probes that are capable of hybridizing to the GPCMV Strain CIDMTR; 2) sequencing at least a portion of the GPCMV Strain CIDMTR; or 3) determining the electrophoretic mobility of the GPCMV Strain CIDMTR or a component thereof. In one embodiment, the GPCMV Strain CIDMTR is subject to an amplification step, prior to or in conjunction with the performance of the detection step. In certain embodiments, amplification steps are by polymerase chain reaction (PCR), ligase chain reaction (LCR), strand displacement amplification (SDA), cloning, and variations of the above (e.g., RT-PCR and GPCMV Strain CIDMTR specific amplification). In one embodiment, the sample is hybridized with a set of primers, which hybridize 5' and 3' to a sense or antisense sequence of GPCMV Strain CIDMTR and is subject to PCR amplification.

In one embodiment, the detecting step is by GPCMV Strain CIDMTR specific hybridization followed by primer specific extension. In one embodiment, prior to or in conjunction with detection, the nucleic acid sample is subject to an amplification step. In one embodiment, the size analysis is preceded by a restriction enzyme digestion. In one embodiment, GPCMV Strain CIDMTR or a portion thereof is amplified. In one embodiment, at least one oligonucleotide probe is immobilized on a solid surface.

“Oligonucleotide probe” can refer to a nucleic acid segment, such as a primer, that is useful to amplify a sequence in the GPCMV Strain CIDMTR genome.

A “nucleic acid fragment” is a portion of a given nucleic acid molecule. Deoxyribonucleic acid (DNA) in the majority of organisms is the genetic material while ribonucleic acid (RNA) is involved in the transfer of information contained within DNA into proteins. The term “nucleotide sequence” refers to a polymer of DNA or RNA which can be single- or double-stranded, optionally containing synthetic, non-natural or altered nucleotide bases capable of incorporation into DNA or RNA polymers. The terms “nucleic acid,” “nucleic acid molecule,” “nucleic acid fragment,” “nucleic acid sequence or segment,” or “polynucleotide” may also be used interchangeably with gene, cDNA, DNA and RNA encoded by a gene, e.g., genomic DNA, and even synthetic DNA sequences. The term also includes sequences that include any of the known base analogs of DNA and RNA.

In one embodiment of the present invention, the method also involves contacting the sample with at least one oligonucleotide probe to form a hybridized nucleic acid and amplifying the hybridized nucleic acid. “Amplifying” utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. For example, in certain embodiments of the present invention, the GPCMV Strain CIDMTR, or a portion thereof, may be amplified by PCR. In another embodiment of the present invention, at least one oligonucleotide probe is immobilized on a solid surface.

Nucleic Acid Amplification Methods

According to the methods of the present invention, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or “3SR”), the Qβ replicase system, nucleic acid sequence-based amplification (or “NASBA”), the repair chain reaction (or “RCR”), and boomerang DNA amplification (or “BDA”).

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Various labels that can be incorporated into or operably linked to nucleic acids are well known in the art, such as radioactive, enzymatic, and florescent labels. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Methods of Use

In certain embodiments, the present invention provides a method of determining the effectiveness of a vaccine or therapeutic composition in preventing or ameliorating re-infection with cytomegalovirus comprising:

a. administering a first GPCMV to a guinea pig, b. administering a vaccine or therapeutic composition, c. administering a second GPCMV to the guinea pig, and d. determining the effectiveness of the vaccine or therapeutic composition in preventing or ameliorating re-infection. In certain embodiments, the first GPCMV is ATCC/22122 and the second GPCMV is GPCMV Strain CIDMTR. In certain embodiments, the first GPCMV is GPCMV Strain CIDMTR and the second GPCMV is ATCC/22122.

In certain embodiments, the present invention provides a method of determining the effectiveness of a vaccine or therapeutic composition in preventing or ameliorating infection with cytomegalovirus comprising:

a. administering a vaccine or therapeutic composition to a guinea pig seronegative for GPCMV, b. administering a GPCMV that is not ATCC/22122 to the guinea pig, and c. determining the effectiveness of the vaccine or therapeutic composition in preventing or ameliorating GPCMV infection.

In certain embodiments, the present invention provides a method of determining the effectiveness of a vaccine or therapeutic composition in preventing or ameliorating infection with cytomegalovirus comprising:

a. administering a vaccine or therapeutic composition to a first guinea pig seronegative for GPCMV and to a second guinea pig seronegative for GPCMV, b. administering a GPCMV that is not ATCC/22122 to the first guinea pig and GPCMV ATCC/22122 to the second guinea pig, and c. comparing the effectiveness of the vaccine or therapeutic composition in preventing or ameliorating infection by the GPCMV that is not ATCC/22122 or by GPCMV ATCC/22122.

In certain embodiments, the present invention provides a method of determining the effectiveness of a vaccine or therapeutic composition in preventing or ameliorating re-infection with cytomegalovirus comprising:

a. administering a vaccine or therapeutic composition to a guinea pig seropositive for GPCMV, b. administering a GPCMV that is not ATCC/22122 to the guinea pig, and c. comparing the effectiveness of the vaccine or therapeutic composition in preventing or ameliorating infection by the GPCMV that is not ATCC/22122.

In certain embodiments, the GPCMV that is not ATCC/22122 is GPCMV Strain CIDMTR.

In certain embodiments, an effective amount of the virus, vaccine or therapeutic composition is administered to the subject. "Effective amount" or "therapeutically effective amount" are used interchangeably herein, and refer to an amount of a compound, formulation, material, or composition, as described herein effective to achieve a particular biological result. Such results may include, but are not limited to the inhibition of virus infection as determined by any means suitable in the art.

In certain embodiments, an amount of the vaccine is administered in order to immunize to the subject. As used herein, "immunization" or "vaccination" are used interchangeably herein and are intended for prophylactic or therapeutic immunization or vaccination. "Therapeutic vaccination" is meant for vaccination of a patient with CMV infection.

"Isolated" means altered or removed from the natural state. For example, a nucleic acid or a peptide naturally present in a living animal is not "isolated." but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The terms “patient,” “subject,” “individual,” and the like are used interchangeably herein, and refer to any animal, or cells thereof whether in vitro or in situ, that can be infected with CMV. In certain non-limiting embodiments, the patient, subject or individual is a guinea pig. In certain embodiments, the patient, subject or individual is a human.

In certain embodiments, the vaccine, therapeutic composition or virus is administered via intramuscular, intradermal, or subcutaneous delivery. In certain embodiments, the vaccine, therapeutic composition or virus is administered via a mucosal surface, such as an oral, intranasal, or intravaginal surface. In certain embodiments, the vaccine, therapeutic composition or virus is administered via intrasternal injection, or by using infusion techniques.

In certain embodiments, “pharmaceutically acceptable” refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. “Pharmaceutically acceptable carrier” refers to a medium that does not interfere with the effectiveness of the biological activity of the active ingredient(s) and is not toxic to the host to which it is administered.

The term “therapeutic” as used herein means treatment and/or prophylaxis. A therapeutic effect is obtained by avoidance, delay, suppression, remission, or eradication of a disease state associated with CMV infection.

The term “treatment” as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises “treatment” of the disease. This includes for instance, prevention of CMV propagation to uninfected cells of an organism. The phrase “diminishing CMV infection” is sometimes used herein to refer to a treatment method that involves reducing the level of infection in a patient infected with CMV, as determined by means familiar to the clinician.

The invention will now be illustrated by the following non-limiting Example.

Example 1

The guinea-pig cytomegalovirus (GPCMV) provides a useful model system for testing “proof-of-concept” for vaccines and antivirals targeting prevention of congenital infection. One shortcoming of the model is the availability of only one strain of GPCMV, the ATCC/22122 strain. Originally isolated by Hartley in 1957, this strain underwent tissue culture-adaptation prior to deposit with ATCC, and is known to undergo deletions in cell culture that attenuate its in vivo replication. Thus, it is not clear whether this strain authentically recapitulates pathogenesis and immune response following experimental infection. Moreover, the availability of only one strain variant renders experimental evaluation of the process of re-infection problematic.

To address these deficiencies, sera from commercially purchased guinea pigs was examined by ELISA and western blot, toward the goal of identifying “naturally-infected” animals. Among a group of 24 guinea pigs, 5 (21%) were found to be GPCMV-seropositive. Western blot using purified viral particles demonstrated immunoreactivity with multiple virion-associated proteins including GP55 (GPCMV gB homolog) and GP131 (UL130 homolog). To further define the serological response of naturally seropositive guinea pigs to GP131 and another constituent of the epithelial/endothelial cell entry complex, GP129 (UL128 homolog), a series of GST fusion proteins were generated.

Sera from naturally seropositive animals, as well animals inoculated with salivary gland-adapted 22122, were highly immunoreactive with these GST fusions, providing evidence that GP129 and GP131 are targets of the humoral immune response in the context of natural infection. Next, efforts were undertaken to culture GPCMV from salivary gland homogenates from seropositive animals. A novel isolate of GPCMV, Strain CIDMTR, was propagated and successfully passaged, both in cell culture, and in vivo. In immune compromised strain 2 animals, disseminated infection was manifest as pneumonia, visceral organ disease, and viremia.

Next, DNA sequence analysis of Strain CIDMTR was performed for genes encoding GPCMV glycoproteins, and compared to reference strain 22122. There was striking sequence conservation of the gpUL55 (gB) homolog; although 13 SNPs were noted, only 2 coding changes were observed (overall identity of 99%). The gpUL100 (gM) homolog demonstrated a similar level of conservation, with 9 SNPs and one amino acid coding change (overall identity of 99%). Sequence of the gN (gpUL73), and gL (gpUL115) homologs demonstrated 93% and 99% identity, respectively. Protein coding variation for Strain CIDMTR as compared to 22122 was greater for GP129 (84% identity) than GP131 (94% identity). Sequence analysis of GP74 (gO) and GP75 (gH) demonstrated the greatest divergence from 22122 (78% and 82% identity, respectively).

In summary: 1) sera from naturally infected GPCMV-seropositive guinea pigs contain high levels of antibody to GP129 and GP131, supporting a role for testing these pentameric-complex proteins as vaccines in the GPCMV model; 2) sequence analysis of a newly isolated strain of GPCMV demonstrates the greatest divergence for the gO, gH, and UL128 homologs, suggesting that these proteins may be under substantial immunologic pressure in infected guinea pigs; 3) the availability of a new strain of GPCMV enables experimental modeling of congenital infection following maternal re-infection, a major and emerging issue in HCMV vaccine design and development.

Example 2

Development of a vaccine against human cytomegalovirus (HCMV) is a major public health priority. The suggestion that passively transferred antibody protects the fetus against infection and injury has driven efforts to develop recombinant targeting major envelope glycoproteins. Although clinical trials of recombinant gB vaccines have shown some degree of effectiveness in preventing CMV infection and disease in high risk populations, vaccine mediated protection with vaccines targeting this single envelope glycoprotein appears to be incomplete. Moreover, the effectiveness of natural immunity in preventing congenital CMV infection and its attendant sequelae is itself a matter of some controversy. A number of recent studies have described fetal CMV transmission in women with preconception immunity, due to re-infection with new strains of CMV. Such infections can produce sequelae identical to those observed in congenitally infected infants born to women with primary CMV infection in pregnancy. These observations certainly complicate CMV vaccine design, and suggest that: 1) for full protection, a CMV vaccine may need to enhance responses superior to those conferred by natural immunity; 2) there may be a strong rationale for vaccinating women of childbearing age who are already CMV seropositive, in addition to targeting and immunizing seronegative women, toward the goal of preventing re-infection with subsequent transmission of the "new" strain.

Several clinical studies have documented the phenomena of re-infection in women of childbearing age. In one prospective study performed at the University of Alabama-Birmingham, serum specimens from 46 women with preconceptional immunity against CMV obtained during a previous pregnancy and a new pregnancy were analyzed for antibodies against the strain-specific epitopes of CMV glycoprotein H (gH), and the nucleotide sequences of the gH gene from seven CMV isolates were determined. Ten of the 16 mothers with infected children (62%) acquired new antibody specificities against gH, as compared with only 4 of the 30 mothers of uninfected infants (13%), suggesting that acquisition of an infection with a virus expressing a novel strain-specific gH genotype during pregnancy was associated with congenital transmission. In another study in Brazil that followed 7,848 women prospectively, sera from 40 mothers of congenitally infected infants and 109 mothers of uninfected control newborns were analyzed for strain-specific anti-CMV antibodies, based not only on polymorphisms within gH binding sites, but also a second antibody reactivity site on gB. Seven of 40 (17.5%) study women, but only 5 of 109 (4.6%) controls acquired antibodies reactive with new CMV strains during pregnancy (p=0.002), suggesting that maternal reinfection by new strains of CMV is a major source of congenital infection in this population. In a study of re-infection (based on acquisition of new gB and/or gH antibody specificities) in 205 seropositive women performed by Ross and colleagues at UAB, approximately one-third of the study participants (59 of 205) were noted to have reinfection, using this definition, during follow-up. The molecular and immunological correlates of re-infection are unclear. There is some evidence that gB polymorphisms in clinical isolates may be less important for re-infection than polymorphisms in gH and other envelope glycoproteins. In a study in Brazil, infections in immunocompetent women with strains corresponding to more than one gB genotype were not common. Additionally, in a study of the CMV strains acquired longitudinally in women who developed infection in spite of being enrolled in the recombinant gB vaccine trial at UAB, there was no selection for or against any nonvaccine gB subtype, in spite of women being immunized only with gB protein corresponding to the Towne (gB1 subtype) strain. Other evidence suggests that the response (or lack thereof) to the envelope glycoprotein N (gN) may play a role in predisposing to re-infection with new CMV strains expressing heterologous gB and/or gH genotypes.

Irrespective of the mechanism(s) involved, the issue of re-infection is a major challenge in vaccine design. There is increasing evidence that congenital CMV infections after nonprimary maternal infections can lead to symptomatic disease and substantial long-term sequelae. Notably, recent evidence from a study at UAB indicated that the incidence of hearing loss in infants infected after nonprimary maternal infection was similar to that in infected infants born to women with primary infection, although significantly infants in the primary infection group had progressive and severe or profound hearing loss, compared to infants in the non-primary group. Since the consequences of re-infection with a new strain in a pregnant, seropositive woman can be similar to those that occur after primary infection in a CMV-seronegative woman, the study of re-infection in a small animal model of congenital transmission would be very useful for the modeling of vaccine strategies for this situation. Ideally, HCMV reinfection would be studied in an animal model prior to clinical vaccine trials. Unfortunately, the strict species-specificity of CMVs precludes preclinical testing of HCMV vaccines in animals. However, a number of rodent and primate CMVs are useful in modeling HCMV vaccines and therapies, given the conservation of many immunogenic structural proteins amongst the various viruses. Among the small animal models, the guinea pig CMV (GPCMV) is uniquely useful, since, in contrast to rodent models, transplacental infection of the fetus occurs following viral challenge during pregnancy. Hence, the GPCMV model is well-suited to the study of vaccines against congenital infection. However, to date it has not been feasible to study re-infection in the guinea pig model. In this report, we describe the isolation of a novel strain of GPCMV, the CIDMTR strain. This strain is the first GPCMV isolate reported since the originally 22122 strain isolated by Hartley in 1957. Although generally well conserved with the 22122 strain of GPCMV, this strain demonstrates some differences in genome structure, particularly in the right-hand end of the genome. There are also substantive differences in some protein coding sequences, including envelope glycoproteins, suggesting that these proteins have been the targets of immune selection during the evolution of GPCMV in the guinea pig. We describe in this paper the morphology and DNA sequence of this novel strain, and preliminary experiments regarding its pathogenesis in vivo. The availability of a second strain of GPCMV should enable the study of re-infection and, potentially, vaccination against re-infection in the guinea pig model of congenital CMV infection.

2. Results and Discussion 2.1 Isolation of the CIDMTR Strain

In the course of ongoing vaccine and pathogenesis studies, guinea pigs were screened at the time of purchase for GPCMV antibodies, using an ELISA-based assay (Schleiss, M. R.; Bourne, N.; Stroup, G.; Bravo, F. J.; Jensen, N. J.; Bernstein, D. I., Protection against congenital cytomegalovirus infection and disease in guinea pigs, conferred by a purified recombinant glycoprotein b vaccine. *J Infect Dis* 2004, 189, 1374-1381). Within a group of 24 guinea pigs purchased from a commercial source, 5 (21%) were found to be GPCMV-seropositive by ELISA. Western blot analysis was performed using sera from commercially purchased, ELISA-positive animals using purified virions as a target. These studies confirmed that sera from these animals were broadly cross-reactive with GPCMV virion-associated polypeptides, suggesting that these animals were infected with a CMV.

One of the seropositive animals identified in these preliminary experiments was immunosuppressed with cyclophosphamide, 100 mg/kg (Schleiss, M. R.; Bernstein, D. I.; McVoy, M. A.; Stroup, G.; Bravo, F.; Creasy, B.; McGregor, A.; Henninger, K.; Hallenberger, S., The non-nucleoside antiviral, bay 38-4766, protects against cytomegalovirus (cmv) disease and mortality in immunocompromised guinea pigs. *Antiviral Res* 2005, 65, 35-43), and seven days later the animal was sacrificed and salivary gland (SG) homogenates harvested. The SG homogenate was passaged in vivo by inoculation of two GPCMV seronegative inbred strain 2 guinea pigs, 1 ml by subcutaneous route in the dorsal neck. Three weeks following inoculation, these animals were also immunosuppressed with 100 mg/kg of cyclophosphamide. One week later, these animals were sacrificed and SG homogenates cultured on guinea pig fibroblast lung cells. Plaques from one of the salivary gland homogenates were noted 11 days later, and 3 days later (total of 14 days post-culture), this viral stock ($P_0$) was then subcultured into guinea pig lung fibroblasts and expanded to large-scale (20 flasks). These flasks were then incubated for an additional week prior to harvest of viral stock ($P_1$ stock). Some of these infected flasks were used for DNA purification for deep sequencing, as described below. The remainder of this stock was used for subsequent morphological Electron Microscopy (EM) studies) and for in vivo challenge experiments in guinea pigs, as described in section 2.4.

2.2 Morphological Analyses by EM

To confirm that the isolated virus had morphological characteristics of a CMV, EM was performed. Analysis of $P_1$ virus stock (section 2.1) revealed 20% of the cells showed cytopathic effect. Cells were enlarged with large intranuclear and intracytoplasmic basophilic inclusions visible upon examination by light microscopy on thick section of plastic preparation stained with Toluidine blue. Ultrastructurally, both intranuclear and intracytoplasmic inclusions represented nuclear and cytoplasmactic viral factories. The nuclear inclusion was typical for the center of replication and assembly characteristic of herpesviruses. These nuclear factories showed a large amount of fibrillary electron dense material admixed with moderate to large numbers of empty capsids and nucleocapsids containing electron dense core, features that were interpreted as representative of viral DNA. First envelopment was acquired at the inner nuclear membrane. De-envelopment of nucleocapsids took place at the outer nuclear membrane during the egress. The second envelopment and tegumentation was observed in the cytoplasm factory. Rearrangement of Golgi cisterns, Golgi vesicles, multivesicular body and endoplasmic reticulum in conjunction with formation of nucleocapsids produced large aggregations that were often mixed with electron dense material. Numerous dense bodies and enveloped particles were present in the intercellular space. On negative contrast preparation, a large number of non-infectious enveloped particles (220.24±48.15 nm) and dense bodies (357.83±97.85 nm) were observed. Infectious mature virions consisted of an envelope containing a 116.5±2.68 nm in diameter icosahedral capsid with capsomeres of approximately 11.66±1.87 nm. The CIDMTR strain of GPCMV presented similar cytopathic and pathogenetic effects as those demonstrated by ATCC strain 22122 (Fong, C. K.; Bia, F.; Hsiung, G. D., Ultrastructural development and persistence of guinea pig cytomegalovirus in duet cells of guinea pig submaxillary gland. *Arch Virol* 1980, 64, 97-108; Fong, C. K.; Bia, F.; Hsiung, G. D.; Madore, P.; Chang, P. W., Ultrastructural development of guinea pig cytomegalovirus in cultured guinea pig embryo cells. *J Gen Virol* 1979, 42, 127-140; Fong, C. K.; Brigati, D., Ultrastructural localization of viral antigen in nuclear inclusions of cytomegalovirus infected guinea pig cells. *Arch Virol* 1982, 74, 125-133). Nevertheless, some differences were noted between these two strains. The ATCC strain in contrast to the CIDMTR strain, demonstrated more efficient infection of fibroblasts, even at the same multiplicity of infection (MOI), with over 80% of fibroblastic cells exhibiting cytopathic effect. The nuclear and cytoplasmic factories were more pronounced, with generation of larger quantities of infectious and non-infectious enveloped viral particles and dense bodies.

2.3 Sequencing and Sequence Analysis

Viral DNA ($P_1$) was purified from the GPCMV-CIDMTR strain salivary gland homogenate isolate after passage in guinea pig lung fibroblast cells and subjected to sequence analysis using the MiSeq and PacBio platforms as described in section 3. FIG. 2 summarizes the predicted ORFs identified in the CIDMTR strain. ORFs with highly conserved ORFs with CMVs are noted in FIG. 2 in upper case/bold font (e.g., GP55). In contrast, ORFs appearing unique to GPCMV are noted in lower case (e.g., gp138). The "C" designation in FIG. 2 refers to complimentary strand. Splicing sites are predicted based on previously published reports (Kanai, K.; Yamada, S.; Yamamoto, Y.; Fukui, Y.; Kurane, I.; Inoue, N., Re-evaluation of the genome sequence of guinea pig cytomegalovirus. *J Gen Virol* 2011, 92, 1005-1020; Yang, D.; Tamburro, K.; Dittmer, D.; Cui, X.; McVoy, M. A.; Hernandez-Alvarado, N.; Schleiss, M. R., Complete genome sequence of pathogenic guinea pig cytomegalovirus from salivary gland homogenates of infected animals. *Genome Announc* 2013, 1, e0005413) and these need empiric confirmation in future studies; exons are described as coding exons. A notable observation is the codon, ATA, spanning nucleotides 191516-191518 (minus strand). This putative codon is ATG in the strain 22122 sequence, which was predicted to represent the start codon for both the IE2 homolog, GP122 (exons 3, 4 and 5) and the IE1 homolog, GP123 (exons 3, 4 and 6) of GPCMV (Yang, D.; Tamburro, K.; Dittmer, D.; Cui, X.; McVoy, M. A.; Hernandez-Alvarado, N.; Schleiss, M. R., Complet genome sequence of pathogenic guinea pig cytomegalovirus from salivary gland homogenates of infected animals. *Genome Announc* 2013, 1, e0005413; Yamada, S.; Nozawa, N.; Katano, H.; Fukui, Y.; Tsuda, M.; Tsutsui, Y.; Kurane, I.; Inoue, N., Characterization of the guinea pig cytomegalovirus genome locus that encodes homologs of human cytomegalovirus major immediate-early genes, ul128, and ul130. *Virology* 2009, 391, 99-106; Nozawa, N.; Yamamoto, Y.; Fukui, Y.; Katano, H.; Tsutsui, Y.; Sato, Y.; Yamada, S.; Inami, Y.; Nakamura, K.; Yokoi, M., et al., Identification of a 1.6 kb genome locus of guinea pig cytomegalovirus required for efficient viral growth in animals but not in cell culture. *Virology* 2008, 379, 45-54). Whether alternative splicing is occurring in the CIDMTR strain, or the start codon for the IE1/IE2 proteins is different between the two strains of GPCMV (in exon 4, not exon 3), requires further evaluation.

Figure 3B:
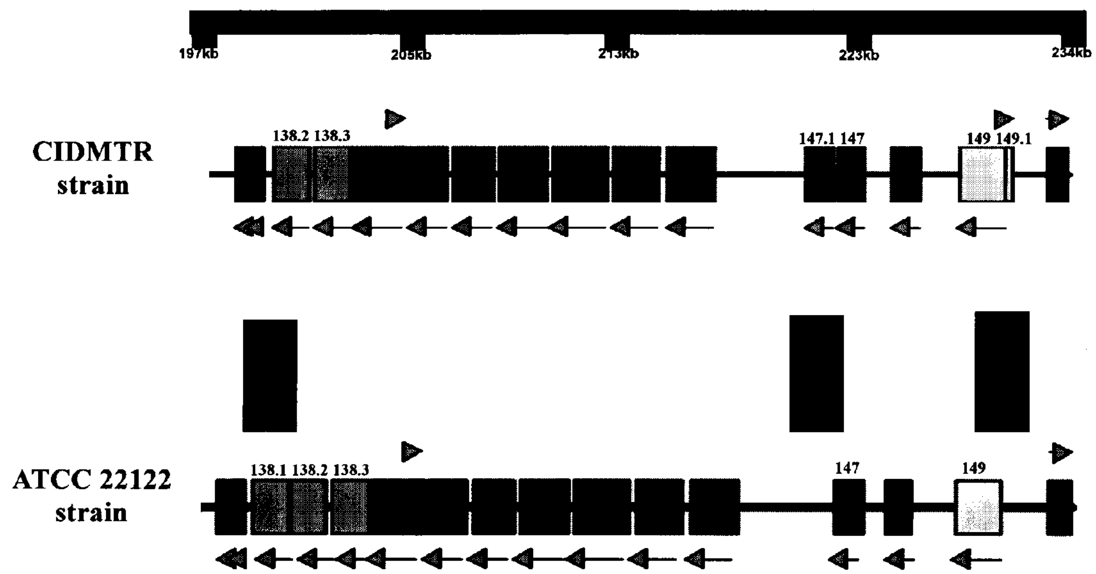

Sequence analysis demonstrated that the CR2P/CIDMTR strain was 232,778 nt in length. Comparison of the CIDMTR sequence with 22122 revealed two regions of striking discrepancy spanning nucleotides~198,780 to 201,300 of the CIDMTR sequence. A deletion of approximately 1.5 kb in this region in the CIDMTR strain resulted in the absence of one of the three gp138 ORFs previously annotated in 22122 (FIG. 3A). In contrast, a second region demonstrated an insertion, spanning coordinates 221,540 through 224,780. This region contained 1.45 kb of sequence that was not present in 22122, including a novel copy of a MHC class I homolog, annotated as gp147.1. Duplicate terminal repeat sequences were noted in the CIDMTR strain, as in the 22122 strain, but are slightly shorter (841 nt) than the repeats that are annotated in 22122 (953 nt). The CIDMTR strain putative coding sequences for genes encoding conserved envelope glycoproteins were compared to reference strain 22122. There was striking sequence conservation of the gB homolog; although 13 SNPs were noted, only 2 coding changes were observed (overall identity of 99%). In contrast, sequence analyses of GP74 (gO) demonstrated the greatest degree of sequence divergence, with 303/374 (81% identity) noted, followed by GP75 (gH), with 613/726 (84%) identity compared to the 22122 strain, (FIG. 3B). FIG. 3A highlights the regions of DNA sequence dissimilarity when the ATCC (22122) strain is compared to the CIDMTR strain (Yang, D.; Tamburro, K.; Dittmer, D.; Cui, X.; McVoy, M. A.; Hernandez-Alvarado, N.; Schleiss, M. R., Complete genome sequence of pathogenic guinea pig cytomegalovirus from salivary gland homogenates of infected animals. *Genome Announc* 2013, 1, e0005413; Kanai, K.; Yamada, S.; Yamamoto, Y.; Fukui, Y.; Kurane, I.; Inoue, N., Re-evaluation of the genome sequence of guinea pig cytomegalovirus. *The Journal of general virology* 2011, 92, 1005-1020). FIG. 3B illustrates in map format the regions of genomic discontinuity. To confirm that these large-scale rearrangements did not arise as a function of passage of virus in cell culture, PCR and sequence analysis was performed directly on both DNA purified from the original salivary gland homogenate (no tissue culture passage), and on DNA from the tissue culture-derived isolate, with identical results (see section 2.5). Sequence of the PCR-generated fragments was identical to that of the Illumina and PacBio sequenced virus, confirming that this genomic configuration did not arise as an artifact of tissue culture passage. Thus, these findings are compatible with a model whereby the "authentic" GPCMV sequence consists of a virus with 4 tandem copies of MHC Class I homologs, with the possible loss of one copy (with subsequent gene duplication event introducing a new gp138 homolog) having occurred in the ATCC/22122 virus. Further analysis of other primary virus isolates from "naturally infected" guinea pigs will be necessary to distinguish these two possibilities.

2.4 Sequence Characterization of DNA from Original SG Homogenate in Region of IE1/2 Start Codon A surprising finding from the DNA sequence analysis was the finding of an ATA codon as the putative start codon of the IE1/IE2 protein product (Yamada, S.; Nozawa, N.; Katano, H.; Fukui, Y.; Tsuda, M.; Tsutsui, Y.; Kurane, I.; Inoue, N., Characterization of the guinea pig cytomegalovirus genome locus that encodes homologs of human cytomegalovirus major immediate-early genes, ul128, and ul130. *Virology* 2009, 391, 99-106). To further examine this issue, sequence analyses of PCR amplified DNA from the original salivary gland homogenates, as well as salivary gland homogenates from further in vivo passages, was undertaken. In these experiments DNA from original seropositive guinea pig CR2P, in vivo passages 357 (F1) and 368 (F2), and DNA from GPL cells infected with CIDMTR were examined by PCR. The PCR was done with the primer pair designated IE splice 3' P1 (5'-TGCGAAGCGATCTCTCTCAAC-3' (SEQ ID NO: 19)) and IE splice 5' P1 (5'-GTGGTTGTACGTGTCGTCGTCA-3' (SEQ ID NO: 20)) which was predicted to produce an 864 bp product in CIDMTR strain. The PCR reaction was performed in a 25 μl of total volume using Vent (NEB) or Cloned Pfu (Agilent) polymerase, 1.0 μM primers and 200 μM dNTPs. The conditions of the for the PCR were: initial denaturation at 95° C. for 5 min, followed by 95° C. for 30 s, 55° C. for 30 s, 72° C. for 2 min for a total of 30 cycles, and elongation at 72° C. for 5 min. 1 unit of Taq polymerase was added to the reaction and incubated at 72° C. for 10 minutes. The PCR product was run in a 0.7% agarose gel. A band of the expected size was cut from the gel and purified using QIAquick Gel Extraction Kit (Qiagen). The purified DNA was cloned into pCR4-TOPO (Invitrogen) using the TOPO TA Cloning Kit for Sequencing (Invitrogen). Single colonies were grown in 3 ml of LB with ampicillin. The plasmids were purified using QIAprep Spin Miniprep Kit (Qiagen). The clones were analyzed for the present of the insert by digestion with EcoR I. Three of the clones with insert from each reaction were sequenced with T7 promoter, M13 forward (−20) and the PCR primers. From this analysis we can concluded that CR2P, the original seropositive animal, 357 (F1) and 368 (F2) contain an ATG codon in the putative start codon of the IE1/IE2 protein product but the CIDMTR strain that was passage in GPL cells contain an ATA codon.

To further examine splicing of the IE region from the CIDMTR strain (tissue culture derived) virus, reverse-transcriptase PCR was performed on RNA harvested at immediate early times post-infection using RNeasy mini kit (Qiagen) according to the manufacturer's instructions. RNA was treated with RNase-free DNase Set (Qiagen) while in column according to manufacturer's instructions. cDNA was synthesized from 1 μg of total RNA using Quantitect Reverse Transcription kit (Qiagen). Conventional PCR was carried out using cDNA as template and and goTaq (Promega). The PCR was done with primer pair IE splice 3' P1 (5'-TGCGAAGCGATCTCTCTCAAC-3' (SEQ ID NO: 21)) and IE splice 5' P1 (5'-GTGGTTGTACGTGTCGTCGTCA-3' (SEQ ID NO: 20)), and primer pair IE splice 3' P2 (5'- CTTGGACCATGGAACATGTCTG-3' (SEQ ID NO: 22)) and IE splice 5' P2 (5'-TCGCTATGCATATAACGTAGC-3' (SEQ ID NO: 23)). The splice 3' primers are in exon 5, whereas the splice 3' primers are localized in intron 2. Therefore the primers should produce up to 3 products, depending on different splice variants and the extent of splice product accumulation in the harvested RNA. A~850 bp product for immature mRNA (B1) and ~750 bp (B2) or ~650 bp (B3) products were noted, representing the splicing of 1 or 2 introns, respectively. These results suggest similar IE mRNA processing for the CIDMTR strain compared to strain 22122.

To further examine splicing of the IE region from the CIDMTR strain (tissue culture derived) virus, reverse-transcriptase PCR was performed on RNA harvested at immediate early times post-infection using RNeasy mini kit (Qiagen) according to the manufacturer's instructions. RNA was treated with RNase-free DNase Set (Qiagen) while in column according to manufacturer's instructions. cDNA was synthesized from 1 μg of total RNA using Quantitect Reverse Transcription kit (Qiagen). Conventional PCR was carried out using cDNA as template and and goTaq (Promega). The PCR was done with primer pair IE splice 3' P1 (5'-TGCGAAGCGATCTCTCTCAAC-3') and IE splice 5' P1 (5'-GTGGTTGTACGTGTCGTCGTCA-3'), and primer pair IE splice 3' P2 (5'-CTTGGACCATGGAACATGTCTG-3') and IE splice 5' P2 (5'-TCGCTATGCATATAACGTAGC-3'). The splice 3' primers are in exon 5, whereas the splice 3' primers are localized in intron 2. Therefore the primers should produce up to 3 products, depending on different splice variants and the extent of splice product accumulation in the harvested RNA. A ~850 bp product for immature mRNA (B1) and ~750 bp (B2) or ~650 bp (B3) products were noted, representing the splicing of 1 or 2 introns, respectively. These results suggest similar IE mRNA processing for the CIDMTR strain compared to strain 22122.

Sequence analysis was performed of RT-PCR products. The conditions of the PCR were: initial denaturation at 95° C. for 2 min, followed by 95° C. for 30 s, 55° C. for 30 s, 72° C. for 1 min for a total of 30 cycles, and elongation at 72° C. for 5 min. The PCR products were run in a 1.0% agarose gel. Three bands of the expected size were cut from the gel and purified using QIAquick Gel Extraction Kit (Qiagen). The purified DNA was cloned into pCR2.1 (Invitrogen) using the TA Cloning Kit (Invitrogen). Single colonies were grown in LB with ampicillin. The plasmids were purified using QIAprep Spin Miniprep Kit (Qiagen). The clones were analyzed for the present of the insert by digestion with EcoR I. Three of the clones with insert from each reaction were sequenced with T7 promoter, M13 Reverse and the PCR primers. Analysis of the DNA sequence indicated identical splice donor/acceptor sites as those identified for the 22122 strain. All of the clones were ATA in the putative start codon of IE1/IE2 gene for the RT-PCR products. It is unclear if: 1)

the ATA codons were selected for during the initial (limited) tissue culture passage and isolation of the CIDMTR strain in fibroblasts; 2) initiation of translation of the IE 1/IE2 protein products in exon 3 occurs at a non-ATG start site; 3) initiation of translation of the IE1/IE2 protein products occurs downstream at a conserved ATG in exon 4 for both the 22122 and CIDMTR strains. That the CIDMTR strain can replicate in cell culture and in vivo (section 2.6) indicates that, if there is a ATG→ATA mutation arising in tissue culture passage in fibroblasts, it does not render the virus replication incompetent. Further analysis is required to determine the precise start site of translation of the IE1 and IE2 proteins in the CIDMTR strain and to clarify the synthesis of the IE protein products in the CIDMTR strain.

2.5 PCR Confirmation of GPCMV-CIDMTR Structure and Development of a Real-Time PCR Assay To confirm the structure of the CIDMTR strain compared to the ATCC/22122 strain, PCR was performed on viral DNA from both strains, using primers spanning the mismatched regions observed in the sequence analysis comparisons (FIG. 3*a*, boxed/shaded regions). The PCR was done using primers pairs mismatch [1] F1/R1 and mismatch [1] F2/R2 which amplify a 4 kb region for the 22122 strain, but a 2.5 kb region for the CIDMTR strain. The amplification region using primer pairs mismatch [2] F1/R1 or mismatch [2] F2/R2 was predicted to be 2.2 kb for the 22122 strain and 3.7 kb for the CIDMTR strain. Primer sequences are indicated in FIG. 4.

To evaluate for DNAemia and end-organ infection in the course of in vivo studies (as described in section 3), a specific real-time PCR assay was developed in order to differentiate the GPCMV-CIDMTR strain from the 22122 (ATTC) strain. DNA was extracted from either 100 μl citrated blood, or from fresh frozen tissues samples, as described in the Methods section. For quantitative PCR, both previously validated primers for the GP83 gene [sequenced shared by both the ATCC/22122 strain] and novel primers for the GPCMV 147.1 gene [sequences only found in the CIDMTR strain] were used for real-time PCR assay. These comparisons demonstrated generally good concordance for the two primer sets as used in conventional PCR (data not shown). As a control, the GPCMV 147.1 primers were used in several PCR assays of ATCC/22122 DNA, with consistently negative results (data not shown).

2.6 Characterization of GPCMV-CIDMTR Infection in vivo

Twelve young, GPCMV-seronegative outbred Hartley guinea pigs were divided into two groups of six/group. Each group was challenge with CIDMTR strain virus (p1) at a dose of $1\times10^5$ pfu, administered subcutaneously, as described in section 3. Group 1 (n=6) was treated with 200 mg/kg cyclophosphamide on day −1 and 50 mg/kg on day +6 following viral challenge (Schleiss, M. R.; Bernstein, D. I.; McVoy, M. A.; Stroup, G.; Bravo, F.; Creasy, B.; McGregor, A.; Henninger, K.; Hallenberger, S., The non-nucleoside antiviral, bay 38-4766, protects against cytomegalovirus (cmv) disease and mortality in immunocompromised guinea pigs. *Antiviral Res* 2005, 65, 35-43); group 2 (n=6) was sham-treated (PBS only). Whole blood and sera samples were collected on day 0, 3, 7, and 21. Animals were humanely sacrificed on day 21 and tissue, including lung, liver, spleen, and brain, were collected for PCR analysis. In group 1, 5/6 animals were DNAemic, peaking at day 7 (mean, 3.2+/−0.3 $\log_{10}$ genomes/ml) while in group 2, the prevalence of DNAemia was lower (3/6 animals; 2.5+/−0.35 $\log_{10}$ genomes/ml, p=0.06 compared to group 1). Viral DNA was most readily recovered from spleen upon dissection at day 21 post-infection. All 6 animals from each group had recoverable CIDMTR strain DNA in the spleen. Total spleen viral load in group 1 was 2.4+/−0.07 copies/mg and was 2.4+/−0.1 copies/mg in group 2 (p=NS compared to group 1).

3. Experimental Section 3.1 Cells, Virus and DNA Preparation

GPCMV (strain 22122, ATCC VR682), and CPCMV/CIDMTR were propagated on guinea pig fibroblast lung cells (GPL; ATCC CCL 158) in F-12 medium supplemented with 10% fetal calf serum (FCS; Gibco-BRI), 10,000 IU of penicillin/liter, 10 mg of streptomycin/liter (Gibco-BRL), and 7.5% NaHCO3 (Gibco-BRL). When the P1 passaged CIDMTR virus exhibited >95 CPE in GPL cell culture, cells were pelleted. An aliquot of cells was fixed in phosphotungstic acid for EM studies (see below) and the remaining cells were washed in 10 mM Tris (pH 8.0)/1 mM EDTA (TE), and lysis buffer (200 mM NaCl, 2% SDS, 200 μg/ml proteinase K, in TE), was added. Cells were gently suspended, inverted, and incubated at 68° C. overnight. Following transfer to a 37° C. water bath, three successive phenol-chloroform extractions were performed, followed by ethanol precipitation.

3.2 Transmission Electron Microscopy

Cells were fixed in 1 ml of 2.5% glutaraldehyde in 0.1 M sodium cacodylate buffer and post fixed with 1% osmium tetroxide in 0.1M sodium cacodylate buffer (all reagents from Electron Microscopy Sciences, Hatfield, Pa., USA). Followed by three washes in distilled water, samples were dehydrated using a 25-100% ethyl alcohol gradient. Samples were then infiltrated with 2:1 ethanol: Embed 812 resin (Electron Microscopy Sciences, Hatfield, Pa., USA) for 1 hour and subsequently transferred to a 1:2 ethanol: Embed 812 resin mixture for 1 hour. Cells were further infiltrated with 100% resin and were embedded and incubated at 58° C. for 24 hours to polymerize the resin. Embedded samples were trimmed and sectioned on a Leica UC6 Ultramicrotome (Leica Microsystems, Vienna, Austria). Thin sections (60-70 nm) were obtained and collected on a 200 mesh copper grid (Electron Microscopy Sciences, Hatfield, Pa., USA) using a perfect loop. Grids were contrasted with 5% uranyl acetate for 20 minutes and Satos' lead citrate for 6 minutes. For negative contrast, virions and dense bodies were collected from $P_1$ supernatants of infected fibroblasts and transferred to airfuge tubes (Belkman-Coulter, Brea, Calif., USA) and centrifuged at 30 PSI using an airfuge (Belkman-Coulter, Brea, Calif., USA) for 20 minutes on parafilm and formvar coated copper grids (Electron Microscopy Sciences, Hatfield, Pa., USA). Excess liquid was wicked and the grids were stained with 1% phosphotungstic acid for one minute. All sections were observed under JEOL 1200 EX II transmission electron microscope (JEOL LTD, Tokyo, Japan). Images were obtained using a Veleta 2K×2K camera with iTEM software (Olympus SIS, Munster, Germany).

3.3 Deep Sequencing and Sequence Analyses

Viral DNA was purified as noted and subjected to deep sequencing. Genomic sequencing was performed using Illumina MiSeq and Pacific Biosciences PacBio RS platforms. Approximately 5.2 million 151 bp paired-end MiSeq reads were generated at the University of Minnesota's Biomedical Genomics Center with a nominal insert size of 400 bp. Removal of low quality reads and PhiX sequence resulted in a set of 4.0 million cleaned reads, approximately 11,000× coverage. Initial scaffolds were generated from the cleaned Illumina reads using the ABySS assembler (version 1.3.4) (Simpson, J. T.; Wong, K.; Jackman, S. D.; Schein, J. E.; Jones, S. J.; Birol, I., Abyss: A parallel assembler for short read sequence data. *Genome Res* 2009, 19, 1117-1123). Scaffold quality was assessed manually by comparison with the reference strain, 22122 (Yang, D.; Tamburro, K.; Dittmer, D.;

Cui, X.; McVoy, M. A.; Hernandez-Alvarado, N.; Schleiss, M. R., Complete genome sequence of pathogenic guinea pig cytomegalovirus from salivary gland homogenates of infected animals. *Genome Announc* 2013, 1, e0005413; Kanai, K.; Yamada, S.; Yamamoto, Y.; Fukui, Y.; Kurane, I.; Inoue, N., Re-evaluation of the genome sequence of guinea pig cytomegalovirus. *The Journal of general virology* 2011, 92, 1005-1020; Schleiss, M. R.; McGregor, A.; Choi, K. Y.; Date, S. V.; Cui, X.; McVoy, M. A., Analysis of the nucleotide sequence of the guinea pig cytomegalovirus (GPCMV) genome. *Virology journal* 2008, 5, 139), and by remapping the reads using Bowtie 2 and scrutinizing local coverage and consensus using Tablet (Milne, I.; Bayer, M.; Cardle, L.; Shaw, P.; Stephen, G.; Wright, F.; Marshall, D., Tablet—-next generation sequence assembly visualization. *Bioinformatics* 2010, 26, 401-402) and SAMtools (Li, H.; Handsaker, B.; Wysoker, A.; Fennell, T.; Ruan, J.; Homer, N.; Marth, G.; Abecasis, G.; Durbin, R., The sequence alignment/map format and samtools. *Bioinformatics* 2009, 25, 2078-2079). Special attention was paid to correct alignment and orientation of the paired ends. Regions of weak coverage and scaffold gaps were identified and closed either by manual local assembly (Waterhouse, A. M.; Procter, J. B.; Martin, D. M.; Clamp, M.; Barton, G. J., Jalview version 2—a multiple sequence alignment editor and analysis workbench. *Bioinformatics* 2009, 25, 1189-1191) or by Sanger sequencing. Independent validation of the pseudomolecule was performed using the longer PacBio RS reads. SMRT Analysis software produced 998 high quality ("corrected") reads ranging between 509-15,898 bp, median 6,257 bp (approximately 27× coverage), as well as another set of scaffolds. These data were used to evaluate the Illumina assembly, specifically its structural correctness, and to correct misassembled repeat regions.

3.4 GPCMV-CIDMTR Strain PCR Assay

For confirmation of viral genome structural differences noted by deep sequencing, PCR was performed for each virus using primers indicated in FIG. 4. The PCR reaction was performed in a 50 μl of total volume using GoTaq long PCR Master Mix from Promega and 1.0 μM primers. The DNA template was total genomic and viral DNA extracted from GPL cells infected with 22122 or CIDMTR tissue culture strain. The conditions for the PCR were: initial denaturation at 95° C. for 2 min, followed by 95° C. for 30 s, 53° C. for 30 s, 72° C. for 4 min for a total of 35 cycles, and elongation at 72° C. for 10 min. The PCR product (4 μl) were subjected to electrophoresis in a 0.7% agarose gel. The PCR product from mismatch 1 F2/R2 and mismatch 2 F2/R2 were purified from the gel using the Geneclean® II kit from MP Biomedicals following the manufacturer's instructions. The cleaned PCR product was then sequenced by Sanger sequencing (Functional Biosciences, Madison, Wis.). Purified PCR products were also subjected to restriction endonuclease comparisons.

The real-time PCR assay focused on the amplification of sequences corresponding to the CIDMTR strain GP147.1 ORF (FIG. 2), since this sequence is absent in the ATCC/22122 strain sequence. A GPCMV 147.1 specific real-time PCR primer pair, consisting of CIDMTR147.1_464F (5'-ATGCAACATAGCGTGCTGAC-3' (SEQ ID NO: 24)) and CIDMTR147.1_583R (5'-GGGACAAAAGCACGATGAAC-3' (SEQ ID NO: 25)) was designed and utilized for the real-time PCR assay. These primers amplified a 120 bp region of the 147.1 gene specific for the CIDMTR strain. The specific hydrolysis probe used for detection was CIDMTR147.1_494P (FAM-GTGTTCGTGTCCTTGATCGTACGCA-BHQ1 (SEQ ID NO: 26)). A second GPCMV 147.1 specific primer pair, CIDMTR147.1_225F (5'-AATGGTTCGCTACGGACATC-3' (SEQ ID NO: 27)) and CIDMTR147.1_368R (5'-CGGACAACGGAACATACTTG-3' (SEQ ID NO: 28))) was also utilized in real-time PCR assays. These primers amplified a 144 bp region of 147.1 specific for the CIDMTR strain. The specific hydrolysis probe used for detection with this primer pair was CIDMTR147.1_262P (FAM-TTCCTCGACGAAGCTCGCGGTATAAT-BHQ1 (SEQ ID NO: 29)). In each instance, the PCR reactions were performed in a 25 μl using LightCycler 480 Probes Master from Roche; as well as 0.4 μM primers, 0.1 μM probe and 0.4 u/μl of UNG. PCR was performed using the LightCycler 480 Real-Time PCR System (Roche) under the following conditions: initial denaturation at 95° C. for 10 min, followed by 95° C. for 10 s, 56° C. for 15 s, 72° C. for 10 s for a total of 45 cycles, then a final hold step at 40° C. The first primer pair (464F and 583R) was chosen for detection of viral genome for in vivo studies. Data were analyzed with the LightCycler Data Analysis Software (version 1.5; Roche) using standard curves generated using serial dilutions of plasmid pCR2.1 with 147.1 at known concentrations. Negative results were arbitrarily assigned a level of 50 for the purpose of statistical comparisons, based upon limit-of-detection analyses observed in other real-time PCR experiments (Crumpler, M. M.; Choi, K. Y.; McVoy, M. A.; Schleiss, M. R., A live guinea pig cytomegalovirus vaccine deleted of three putative immune evasion genes is highly attenuated but remains immunogenic in a vaccine/challenge model of congenital cytomegalovirus infection. *Vaccine* 2009, 27, 4209-4218).

3.5 Animal Challenge Studies

All animal studies were performed with the approval of the University of Minnesota Institutional Animal Care and Use Committee (IACUC). Some animals were immune suppressed at day −1 (200 mg/kg) and day +6 (50 mg/kg) with cyclophosphamide delivered by intraperitoneal route. Both cyclophosphamide-treated and untreated animals (n=6/group) were challenged with CIDMTR strain virus (P1 workpool) at a dose of 1×105 pfu by subcutaneous route. Blood samples were collected at day 0, 3, 7 and 21 post-inoculation and animals humanely sacrificed at day 21 for collection of tissue samples for PCR analyses.

4. Conclusions

In conclusion, we have isolated a new strain of GPCMV, which we designate as the CIDMTR strain. This isolate was obtained from a GPCMV seropositive guinea pig as a part of a longstanding commercial breeding colony; therefore, it is unclear if this strain represents a bona fide "wild-type" strain of GPCMV. However, this isolate was subjected to minimal passage (one passage in vivo; one passage in cell culture) prior to genomic characterization, making it more likely to represent a wild-type sequence than the highly passaged ATCC (22122) strain. Sequence comparison with the 22122 strain revealed generally good conservation of protein coding sequences, although two areas of substantial discontinuity compared to the reference (22122) strain were noted. One of these areas contains a copy of a MHC-1 homolog not found in the 22122 strain. Since these gene products appear to be of important for the in vivo pathogenesis of infection (Crumpler, M. M.; Choi, K. Y.; McVoy, M. A.; Schleiss, M. R., A live guinea pig cytomegalovirus vaccine deleted of three putative immune evasion genes is highly attenuated but remains immunogenic in a vaccine/challenge model of congenital cytomegalovirus infection. *Vaccine* 2009, 27, 4209-4218), further functional comparisons of the two strains are of interest. Studies in immune competent and immune compromised guinea pigs confirm the ability of the CIDMTR virus to disseminate and produce viremia (DNAemia). Variation in glycoprotein gene coding sequences were noted, particularly for the gH and gO proteins, suggesting that this virus may be a useful tool for the study of re-infection of immune guinea pigs in the guinea pig model of congenital CMV infection. Cross-neutralization studies of strain-specific immunity would enhance the usefulness of this new strain for the modeling of vaccine-mediated protection in this uniquely valuable model.

Example 3

The inventors have also determined the promoter region of CIDMTR virus (SEQ ID NO: 10), as indicated in FIG. 5.

All publications, patents and patent applications are incorporated herein by reference, While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for testing the effectiveness of a vaccine or therapeutic composition in preventing or ameliorating re-infection with cytomegalovirus comprising:

a. administering a first guinea pig cytomegalovirus (GPCMV) to a guinea pig, b. administering a vaccine or therapeutic composition, and c. administering a second GPCMV to the guinea pig, wherein the first GPCMV is strain ATCC/22122 and the second GPCMV is strain CIDMTR or wherein the first GPCMV is strain CIDMTR and the second GPCMV is strain ATCC/22122; and wherein (a) the CIDMTR strain is ATCC® deposit number PTA-120714;

(b) the CIDMTR strain has at least 99% identity to SEQ ID NO:1;

(c) the CIDMTR Strain comprises 1) a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5);

(d) the CIDMTR Strain comprises open reading frame gp147.1;

(e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5); or (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

2. The method of claim 1, wherein (i) the first GPCMV is strain ATCC/22122, and (ii) the second GPCMV is strain CIDMTR.

3. The method of claim 1, wherein (i) the first GPCMV is strain CIDMTR, and (ii) the second GPCMV is strain ATCC/22122.

4. The method of claim 1, wherein (a) the CIDMTR strain is ATCC® deposit number PTA-120714.

5. The method of claim 1, wherein (b) the CIDMTR strain has at least 99% identity to SEQ ID NO:1.

6. The method of claim 1, wherein (c) the CIDMTR Strain comprises 1)a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5).

7. The method of claim 1, wherein (d) the CIDMTR Strain comprises open reading frame gp147.1.

8. The method of claim 1, wherein (e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5).

9. The method of claim 1, wherein (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

10. A method for testing the effectiveness of a vaccine or therapeutic composition in preventing or ameliorating infection with cytomegalovirus comprising:

a. administering a vaccine or therapeutic composition to a guinea pig, and b. administering a GPCMV strain CIDMTR to the guinea pig, wherein (a) the CIDMTR strain is ATCC® deposit number PTA-120714;

(b) the CIDMTR strain has at least 99% identity to SEQ ID NO:1;

(c) the CIDMTR Strain comprises 1)a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5);

(d) the CIDMTR Strain comprises open reading frame gp147.1;

(e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5); or (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

11. The method of claim 10, wherein the guinea pig is seronegative for GPCMV.

12. The method of claim 10, wherein the guinea pig is seropositive for GPCMV.

13. The method of claim 12, wherein the GPCMV infection is not ATCC/22122.

14. The method of claim 10, wherein the vaccine, therapeutic composition or virus is administered via intramuscular, intradermal, subcutaneous delivery, or via a mucosal surface.

15. The method of claim 14, wherein the administration is via mucosal surface, and the mucosal surface is an oral, intranasal, or intravaginal surface.

16. The method of claim 10, wherein (a) the CIDMTR strain is ATCC® deposit number PTA-120714.

17. The method of claim 10, wherein (b) the CIDMTR strain has at least 99% identity to SEQ ID NO:1.

18. The method of claim 10, wherein (c) the CIDMTR Strain comprises 1) a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5).

19. The method of claim 10, wherein (d) the CIDMTR Strain comprises open reading frame gp147.1.

20. The method of claim 10, wherein (e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5).

21. The method of claim 10, wherein (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

22. A method for testing the effectiveness of a vaccine or therapeutic composition in preventing or ameliorating infection with cytomegalovirus comprising:

a. administering a vaccine or therapeutic composition to a first guinea pig seronegative for GPCMV and to a second guinea pig seronegative for GPCMV, and b. administering a GPCMV strain CIDMTR to the first guinea pig and GPCMV strain ATCC/22122 to the second guinea pig, wherein (a) the CIDMTR strain is ATCC® deposit number PTA-120714;

(b) the CIDMTR strain has at least 99% identity to SEQ ID NO:1;

(c) the CIDMTR Strain comprises 1)a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5);

(d) the CIDMTR Strain comprises open reading frame gp147.1;

(e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5); or (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

23. The method of claim 22, wherein the vaccine, therapeutic composition or virus is administered via intramuscular, intradermal, subcutaneous delivery, or via a mucosal surface.

24. The method of claim 22, wherein (a) the CIDMTR strain is ATCC® deposit number PTA-120714.

25. The method of claim 22, wherein (b) the CIDMTR strain has at least 99% identity to SEQ ID NO:1.

26. The method of claim 22, wherein (c) the CIDMTR Strain comprises 1) a glycoprotein (GP) having greater than 94% sequence identity to GPCMV glycoprotein 131 (GP131) (SEQ ID NO:3); and 2) a GP having greater than 84% sequence identity to GPCMV glycoprotein 129 (GP129) (SEQ ID NO:2), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7), greater than 99% sequence identity to glycoprotein 115 (gL) (SEQ ID NO:8), or greater than 82% sequence identity to GP75 (gH) (SEQ ID NO:5).

27. The method of claim 22, wherein (d) the CIDMTR Strain comprises open reading frame gp147.1.

28. The method of claim 22, wherein (e) the CIDMTR Strain comprises 1) a glycoprotein (GP) having greater than 93% sequence identity to glycoprotein 73 (gN) (SEQ ID NO: 7); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 99% sequence identity to glycoprotein 115 (gL) (SEQ ID NO:8), or greater than 82% sequence identity to GP75 (gH) (SEQ ID NO:5).

29. The method of claim 22, wherein (f) the CIDMTR Strain comprises 1) a glycoprotein (GP) having greater than 99% sequence identity to glycoprotein 115 (gL) (SEQ ID NO:8); and 2) a GP having greater than 84% sequence identity to GPCMV glycoprotein 129 (GP129) (SEQ ID NO:2), greater than 94% sequence identity to GPCMV glycoprotein 131 (GP131) (SEQ ID NO:3), greater than 78% sequence identity to GP74 (gO) (SEQ ID NO:4), greater than 99% sequence identity to glycoprotein 55 (gB) (SEQ ID NO:6), greater than 93% sequence identity to glycoprotein 73 (gN) (SEQ ID NO: 7) or greater than 82% sequence identity to GP75 (gH) (SEQ ID NO:5).

* * * * *